(12) United States Patent
Singh

(10) Patent No.: US 8,507,219 B2
(45) Date of Patent: *Aug. 13, 2013

(54) METHOD OF TREATING INFLAMMATION WITH STATINS

(75) Inventor: Inderjit Singh, Mt. Pleasant, SC (US)

(73) Assignee: MUSC Foundation for Research Development, Charleston, SC (US)

(*) Notice: Subject to any disclaimer, the term of this patent is extended or adjusted under 35 U.S.C. 154(b) by 333 days.

This patent is subject to a terminal disclaimer.

(21) Appl. No.: 13/117,675

(22) Filed: May 27, 2011

(65) Prior Publication Data

US 2011/0237662 A1 Sep. 29, 2011

Related U.S. Application Data

(60) Continuation of application No. 12/145,261, filed on Jun. 24, 2008, now abandoned, which is a continuation of application No. 11/204,288, filed on Aug. 15, 2005, now Pat. No. 7,396,659, which is a continuation of application No. 10/273,557, filed on Oct. 18, 2002, now Pat. No. 7,049,058, which is a division of application No. 09/579,791, filed on May 25, 2000, now Pat. No. 6,511,800, which is a continuation of application No. PCT/US98/25360, filed on Nov. 25, 1998.

(60) Provisional application No. 60/066,839, filed on Nov. 25, 1997.

(51) Int. Cl.
*C12Q 1/26* (2006.01)

(52) U.S. Cl.
USPC ........................................... 435/25; 435/69.2

(58) Field of Classification Search
USPC .................................. 435/25, 69.2
See application file for complete search history.

(56) References Cited

U.S. PATENT DOCUMENTS

| | | | |
|---|---|---|---|
| 5,118,601 A | 6/1992 | Gruber | |
| 5,130,333 A | 7/1992 | Pan et al. | |
| 5,286,895 A | 2/1994 | Harris et al. | |
| 5,498,536 A | 3/1996 | Khandke | |
| 5,498,539 A | 3/1996 | Harrison et al. | |
| 5,545,625 A | 8/1996 | Gross et al. | |
| 5,658,889 A | 8/1997 | Gruber et al. | |
| 5,695,761 A | 12/1997 | Denhardt et al. | |
| 5,730,992 A | 3/1998 | Savion et al. | |
| 5,912,019 A | 6/1999 | Singh | |
| 5,965,553 A | 10/1999 | Bell et al. | |
| 5,968,983 A * | 10/1999 | Kaesemeyer | 514/564 |
| 6,080,778 A | 6/2000 | Yankner et al. | |
| 6,147,109 A | 11/2000 | Liao et al. | |
| 6,204,248 B1 | 3/2001 | Demopoulos et al. | |
| 6,312,662 B1 | 11/2001 | Erion et al. | |
| 6,465,516 B1 * | 10/2002 | Kaesemeyer | 514/548 |
| 6,511,800 B1 * | 1/2003 | Singh | 435/4 |
| 6,552,075 B2 | 4/2003 | Gribble et al. | |
| 6,605,729 B1 | 8/2003 | Byrn et al. | |
| 6,673,831 B1 | 1/2004 | Tobert | |
| 7,030,152 B1 * | 4/2006 | Ridker et al. | 514/423 |
| 7,049,058 B2 * | 5/2006 | Singh | 435/4 |
| 7,396,659 B2 * | 7/2008 | Singh | 435/25 |

FOREIGN PATENT DOCUMENTS

| | | |
|---|---|---|
| WO | 93/14749 | 8/1993 |
| WO | 95/06470 | 3/1995 |
| WO | 98/09653 | 3/1998 |
| WO | 02/24194 | 3/2002 |

OTHER PUBLICATIONS

Pahan K. et al. Lovastatin and Phenylacetate Inhibit the Induction of Nitric Oxide Synthase . . . J Clinical Investigation 100(11)2671-9, Dec. 1, 1997.*
"Nymox pursuing new approaches to fighting Alzheimer's disease," Business Wire, Jul. 2, 2004.
"Statins—the next miracle drug? Beyond cholesterol lowering," Clinician Reviews, 14(6):84(3), Jun. 1, 2004.
Abud-Mendoza et al., "Therapy with statins in patients with refractory rheumatic diseases: a preliminary study," Lupus, 12(8):607-611 (2003).
Advisory Action in U.S. Appl. No. 12/145,261 dated Apr. 4, 2011.
Amendment after Notice of Allowance (Rule 312) in U.S. Appl. No. 11/204,288 dated May 23, 2008.
Amendment Submitted/Entered with Filing of CPA/RCE dated Mar. 21, 2011.
Amendment Submitted/Entered with Filing of CPA/RCE in U.S. Appl. No. 11/204,288 dated Jun. 14, 2007.
Amendment/Req. Reconsideration-After Non-Final Reject in U.S. Appl. No. 10/273,557 dated Aug. 24, 2004.
Amendment/Req. Reconsideration-After Non-Final Reject in U.S. Appl. No. 11/204,288 dated Jan. 25, 2008.
Amendment/Req. Reconsideration-After Non-Final Reject in U.S. Appl. No. 11/204,288 dated May 1, 2007.
Amendment/Req. Reconsideration-After Non-Final Reject in U.S. Appl. No. 11/204,288 dated Apr. 9, 2007.
Amendment/Req. Reconsideration-After Non-Final Reject in U.S. Appl. No. 12/145,261 dated Dec. 22, 2010.
Amerongen et al., "Simvastatin improves disturbed endothelial barrier function," Circulation, 102:2803-2809 (2000).
Appeal Brief in U.S. Appl. No. 10/273,557 dated Feb. 16, 2005.
Appel et al., "Lack of interaction between fluvastatin and oral hypoglycemic agents in healthy subjects and in patients with non-insulin-dependent diabetes mellitus," Am. J. Cardiol., 76:29A-32A (1995).
Azuma et al., "HMG-CoA reductase inhibitor attenuates experimental autoimmune myocarditis through inhibition of T cell activation," Cardiovascular Res., 64:412-420 (2004).
Baughman, "Dopamine-transporter densityin patients with ADHD," The Lancet, 355:1460-1461 (2000).

(Continued)

*Primary Examiner* — Ralph Gitomer
(74) *Attorney, Agent, or Firm* — Parker Highlander PLLC

(57) ABSTRACT

The current invention discloses novel methods for the inhibition of inducible nitric oxide synthesis (iNOS) and the production of NO. Methods of inhibiting the induction of proinflammatory cytokines are also described. Methods of treating various disease states, such as X-linked adrenoleukodystrophy, multiple sclerosis, Alzheimer's and septic shock using inhibitors of iNOS and cytokine induction are disclosed. The inhibitors include the exemplary compounds lovastatin, a sodium salt of phenylacetic acid (NaPA), FPT inhibitor II, N-acetyl cysteine (NAC), and cAMP.

17 Claims, 11 Drawing Sheets

(56) References Cited

OTHER PUBLICATIONS

Bedoya, "Pyrrolidine Dithiocarbamate Prevents IL-1 Induced Nitric Oxide Synthase mRNA, But Not Superoxide Dismutase mRNA, in Insulin Producing Cells," Biochem. Biophys. Res. Commun., 210(3):816-822 (1995).
Bellosta et al., "Direct vascular effects of HMG-CoA reductase inhibitors," Atheroscl., 137:S101-S109 (1998).
Bellosta et al., "Non-lipid related effects of statins," Ann. Med., 32:164-176 (2000).
Biesenbach et al., "Lovastatin in the treatment of hypercholesterolemia in nephrotic syndrome due to diabetic nephropathy state IV-V," Clin. Nephrology, 37:274-279 (1992).
Boese, "Effect of Cyclic GMP Dependent Vasodilators on the Expression of Inducible Nitric Oxide Synthase in Vascular Smooth Muscle Cells: Role of cAMP," Brit. J. Pharmacol., 119(4):707-715 (1996).
Bowen and Guyton, "Nonpharmacologic and pharmacologic treatment of patients with low levels of high-density lipoprotein cholesterol," Current Science, 2:58-63 (2000).
Buemi et al., "Effect of fluvastatin on proteinuria in patients with immunoglobin A nephropathy," Clin. Phar. & Therapeutics, 67:427-431 (2000).
Casey et al., "p21ras is modified by a farnesyl isoprenoid," Proc. Natl. Acad. Sci., 86:8323-8327 (1989).
Certificate of Correction in U.S. Appl. No. 10/273,557 dated Sep. 19, 2006.
Certificate of Correction in U.S. Appl. No. 11/204,288 dated Sep. 30, 2008.
Cetkovic-Cvrlje et al., "Nicotinamide and Dexamethasone Inhibit Interleukin-1-Induced Nitric Oxide Production by RINm5F Cells without Decreasing Messenger Ribonucleic Acid Expression for Nitric Oxide Synthase," Endocrinology, 133:1739-1743 (1993).
Co-pending U.S. Appl. No. 10/429,231, filed May 2, 2003.
Co-pending U.S. Appl. No. 60/531,828, filed Dec. 23, 2003.
Co-pending U.S. Appl. No. 60/559,112, filed Apr. 2, 2004.
Corsini et al., "Non-lipid-related effects of 3-hydroxy-3-methylgluataryl coenzyme A reductase inhibitors," Cardiology, 87:458-468 (1996).
Cuzzocrea et al., "Beneficial effects of n-acetylcystein on ischemic brain injury," British Journal of Pharmacology, 130:1219-1226 (2000).
Duval, "Effects of statins on ischemic stroke: neuroprotection and/or triggering of apoptotic damage?" Letters to the Editor, pp. 989-990, Stroke 2000 vol. 31:983-991.
Eizrik et al., "The inducible Form of Nitric Oxide Synthase in Insulin Producing Cells," Diabete & Metabolisme (Paris), 20(2):116-122 (1994).
Faggioto and Paoletti, "Stains and blockers of the renin-agiotensin system: vascular protection beyond their primary mode of action," Hypertension, 34:987-996 (1999).
Farmer, "Pleiotropic effects of statins," Curr. Atheroscl. Rpts., 2:208-217 (2000).
Fenyk-Melody et al., "Experimental autoimmune encephalomyelitis is exacerbated in mice lacking the NOS2 gene," J of Immunology, 160:2940-2946 (1998).
Final Rejection in U.S. Appl. No. 10/273,557 dated Sep. 15, 2004.
Final Rejection in U.S. Appl. No. 11/204,288 dated Feb. 22, 2008.
Final Rejection in U.S. Appl. No. 12/145,261 dated Jan. 21, 2011.
Frances et al., "Outcome of kidney transplant recipients with previous human herpesvirus-8 infection," Transplantation, 69:1776-1779 (2000).
Fukuo et al., "Effects of an HMG-CoA reductase inhibitor on cytokine production by human monocytes/macrophages," J. Nippon Med. Sch., 62:74-78 (1995).
Fukuzawa et al., "N-acetylcystein ameliorates reperfusion injury after warm hepatic ischemia," Transplantation, 59 (1):6-9 (1995).
Galinanes et al., "Sustained protection by acadesine against ischemia- and reperfusion-induced injury: Studies in the transplanted rat heart," Circulation, 86(2):589-611 (1992).
Garg, "Treatment of diabetic dyslipidemia," Am. J. Cardiol., 81:47B-51B (1998).
Giri et al., "5-aminoimidazole-4-carboxamide-1-beta-4-ribofuranoside inhibits proinflammatory response in glial cells: a possible role of AMP-activated protein kinase," J. Neuroscience, 24(2):479-487 (2004).
Gmerek et al., "A 4-Year, Placebo-Controlled Study of Atorvastatin as Prevention of CHD Endpoints in Patients with Non-Insulin Dependent Diabetes Melitus," Abstract Book, 57th Annual Meeting and Scientific Sessions, 336A (1997).
Goalstone et al., "Effect of insulin on farnesyltransferase activity in 3T3-L1 adipocytes," J. Biol. Chem., 271:27585-27589 (1996).
Goldberg et al., "Cardiovascular Events and Their Reduction With Pravastatin in Diabetic and Glucose-Intolerant Myocardial Infarction Survivors With Average Cholesterol Levels: Subgroup analyses in the cholesterol and recurrent events (CARE) trial," Circulation, 98:2513-2519 (1998).
Office Action mail date Oct. 22, 2011.
Office Action mail date Sep. 15, 2004.
Ongini et al., "Nitric oxide (NO)-releasing statin derivatives, a class of drugs showing enhanced antiproliferative and anti-inflammatory properties," Proc. Natl. Acad. Sci. USA, 101(22):8497-8502 (2004).
Ortego et al., "Atovastatin reduces NF-.kappa.K activation and chemokine expression in vascular smooth muscle cell and mononuclear cells," Atherosclerosis, 147:253-261 (1999).
Pahan et al., "Increasing cAMP Attenutates Induction of Inducible Nitric-oxide Synthase in Rat Primary Astrocytes," 272(12):7788-7791 (1997).
Pahan et al., "Lovastatin and Phenylacetate Inhibit the Induction of Nitric Oxide Synthase and Cytokines in Rat Primary Astrocytes, Microglia, and Macrophages," J. Clin. Invest, 100:2671-2679 (1997).
Pahan, "Increasing cAMP Attenuates Induction of Inducible Nitric Oxide Synthase in Rat Primary Astrocytes," J. Biol. Chem., 272(12):7786-7791 (1997).
Pahan, "Lovastatin and Phenyyacetate Inhibit the Induction of NOS and Cytokinase in Rat Primary Astrocytes," Microglia and Macrophages, J. Clinical Invest., 100(11):2671-2679 (1997).
Parving, "Cholesterol Lowering Therapy May Retard the Progression of Diabetic Nephropathy," Diabetologia, 39:367-373 (1996).
Paul, "Differential Regulation by Protein Kinase C Isoforms of Nitric Oxide Synthase Induction in RAW 264.7 Macrophages and Rat Aortic Smooth Muscle Cells," Brit. J. Pharmacol., 120(5):940-946 (1997).
Preliminary Amendment in U.S. Appl. No. 10/273,557 dated Nov. 24, 2003.
Preliminary Amendment in U.S. Appl. No. 10/273,557 dated Oct. 18, 2002.
Preliminary Amendment in U.S. Appl. No. 11/204,288 dated Aug. 15, 2005.
Preliminary Amendment in U.S. Appl. No. 11/204,288 dated Oct. 10, 2006.
Preliminary Amendment in U.S. Appl. No. 12/145,261 dated Aug. 7, 2009.
Preliminary Amendment in U.S. Appl. No. 12/145,261 dated Jun. 24, 2008.
Request for Continue Examination in U.S. Appl. No. 12/145,261 dated Apr. 21, 2011.
Request for Continued Examination in U.S. Appl. No. 11/204,288 dated Jun. 14, 2007.
Response to Amendment under Rule 312 in U.S. Appl. No. 11/204,288 dated Jun. 3, 2008.
Romano et al., "Inhibition of monocyte chemotactic protein-1 synthesis by statins," Lab. HMGInvestigation, 80:1095-1100 (2000).
Sacks et al., "The effect of pravastatin on coronary events after myocardial infarction in patients with average cholesterol levels," New Engl. J. Med., 335(14)1001-1009 (1996).
Sherman, "Pyrrolidine Dithiocarbamate Inhibits Induction of Nitric Oxide Synthase Activity in Rat Alveolar Macrophages," Biochem. Biophys. Res. Commun., 191(3):1301-1308 (1993).
Sinensky et al., "Differential inhibitory effects of lovastatin on protein isoprenylation and sterol synthesis," J. Biol. Chem., 265:19937-19941 (1990).

Sochman et al., "Infarct size limitation: acute N-acetylcystein defense (ISLAND trial): preliminary analysis and report after the first 30 patients," Clin. Cardiol., 19:94-100 (1996).
Sparks, "Coronary artery disease, hypertension, ApoE, and cholesterol: a link to Alzheimer's disease?" Ann. N.Y. Acad. Sci., 826:128-146 (1997).
Stuve et al., "The potential therapeutic role of statins in central nervous systems autoimmune disorders," Cell. Mol. Life Sci., 60:2483-2491 (2003).
Terkeltaub et al., "Role of the mevalonate pathway of isoprenoid synthesis IL-8 generation by activated monocytic cells," J. Leukoc. Biol., 55(6):749-755 (1994).
Terminal Disclaimers in U.S. Appl. No. 12/145,261 dated Dec. 22, 2010.
The Editors, "Statins & Alzheimer's," HealthNews, 6:1 (2000).
Thibault, "Phase I Study of Lovatatin, An Inhibitor of the Mevalonate Pathway, in Patients with Cancer," Clincal Cancer Research, 2:483-491 (1996).
Toledano and Patridge, "Statins: not just for cholesterol?" TEM vol. 11:255-256 (2000).
Van Doornum et al., "Atorvastatin reduces arterial stiffness in patients with rheumatoid arthritis," Ann. Rheum. Dis., 63:1571-1575 (2004).
Vaughan and Delanty, "Neuroprotective properties of statins in cerebral ischemia and stroke," Stroke, 30:1969-1973 (1999).
Vaughan et al., "Statins do more than just lower cholesterol," The Lancet, 348:1079-1082 (1996).
Weigland et al., "N-acetylcystein attenuates the increase in alpha-glutathione S-transferase and circulating ICAM-1 and VCAM-1 after reperfusion in humans undergoing liver transplantation," Transplantation, 72(4):694-698 (2001).
Wolozin et al., "Decreased prevalence of alzheimer disease associated with 3-Hydroxy-3-Methylglutaryl Coenzyme A reductase inhibitors," Arch. Neurol., 57:1439-1443 (2000).
Zamrini et al., "Association between statin use and Alzheimer's disease," Neuroepidemiology, 23:94-98 (2004).
Zhang et al., "Effects of pravastatin on lipid levels, in vitro oxidizability of non-HDL lipoproteins and microalbuminuria in IDDM patients," Diabetes Res. Clin. Practice, 29:189-194 (1995).
Griffith et al., "Design of Nitric Oxide Synthase Inhibitors and Their Use to Reverse Hypertension Associated with Cancer Immunotherapy," Advan. Enzyme Regul., 37:171-194 (1997).
Grip et al., "Pravastatin down-regulates inflammatory mediators in human monocytes in vitro," Eur. J. Pharmacol., 410:83-92 (2000).
Hadjidakis et al., "The Antidiabetic Action of Somatostatin-28 . . . ," Hormone and Metabolic Research, 19(11):574-578 (1987).
Hashimoto et al., "5-amino-4-imidazolecarboxamide riboside confers strong tolerance to glucose starvation in a 5'-AMP-activated protein kinase-dependent fashion," Biochem. Biophys. Res. Commun., 290:263-267 (2002).
Hibbs et al., "Evidence for cytokine-inducible nitric oxide synthesis from 1-arginine in patients receiving interleukin-2 therapy," J. Clin. Invest., 89:867-877 (1992).
Hirasawa et al., "Possible role of macrophage-derived soluble mediators in the pathogenesis of encephalomyocarditis virus-induced diabetes in mice," J. Virol., 71:4024-4031 (1997).
Hohmeier et al., "Stable expression of manganese superoxide dismutase (MnSOD) in insulinoma cells prevents IL-1beta-induced cytotoxicity and reduces nitric oxide production," J. Clin. Invest., 101:1811-1820 (1998).
Horwich et al., "Statin therapy is associated with improved survival in ischemic and non-ischemic heart failure," J. Am. College of Cardiol., 43(4):642-548 (2004).
Ikeda and Shumada, "Statins and monocytes," The Lancet, 353:2070 (1999).
Inoue et al., "Lipophilic HMG-CoA reductase inhibitor has an anti-inflammatory effect reduction of MRNA levels for interleukin-1β, interleukin-6, cyclooxygenase-2 and p22phox by regulation of peroxisome proliferator-activated receptor α (PPAR.alpha.) in preimary endothelial cells," Life Sciences, 67:863-876 (2000).
International Search Report in PCT/US98/25360 dated Mar. 12, 1999.

Issazadeh et al., "Interferon γ, interleukin 4 and transforming growth factor β in experimental autoimmune encephalomyelitis in lewis rats: dynamics of cellular MRNA expression in the central nervous system and lymphoid cells," J. Neuroscience Res., 40:579-590 (1995).
Issue Notification in U.S. Appl. No. 11/204,288 dated Jun. 18, 2008.
Izzat et al., "New molecular targets for cholestrol-lowering therapy," J. Pharmacol. & Exp. Therapeutics, 293:315-320 (2000).
Johnson, "Multi-Purpose Medicine," http://my.abcnews.go.com (2000).
Josefsen, "Statins may reduce risk of Alzheimer's disease," BMJ, 321:28 (2000).
Jukema et al., "Effects of lipid lowering by pravastatin on progression and regression of coronary artery disease in symptomatic men with normal to moderately elevated serum cholesterol levels," Circulation, 91:2528-2540 (1995).
Jungnickel et al., "Pravastatin: a new drug for the treatment of hypercholesterolemia," Clin. Pharm., 11:677-689 (1992).
Katznelson et al., "The effect of pravastatin on acute rejection after kidney transplantation—a pilot study," Transplantation, 61:1469-1474 (1996).
Kjaer, "Effect of simvastatin in patients with type I (insulin-dependent) diabetes mellitus and hypercholesterolemia," Acta Endocrin., 126:229-232 (1992).
Knuckey et al., "N-acetylcystein enhances hippocampal neuronal survival after transient forebrain ischemia in rats," Stroke, 26:305-311 (1995).
Kothe et al., "Hydroxymethylglutaryl coenzyme A reductase inhibitors modify the inflammatory response of human macrophages and endothelial cells infected with *Chlamydia pneumoniae*," Circulation, 101:1760-1763 (2000).
Kurakata et al., "Effects of different inhibitors of 3-hydroxy-3-methylglutaryl coenzyme A (HGM-CoA) reductase, prevastatin sodium and simvastatin, on sterol synthesis and immunological functions in human lymphocytes in vitro," Immunopharmacology, 34:51-61 (1996).
Kurakata, "Effects of Different Inhibitors of HMG-CoA Reductase," Immunopharmacology, 34:51-61 (1996).
Leung et al., "A novel anti-inflammatory role for simvastatin in inflammatory arthritis," J. Immunol., 170(3):1524-1530 (2003).
Limura, "HMG-CoA Reductase Inhibitors Induce Apoptosis in Mouse Proximal Tubular Cells in Primary Culture," Kidney International, 52(4):962-972 (1997).
Maggard et al., "Effects of pravastatin on chronic rejection of rat cardiac allografts," Transplantation, 65:149-155 (1998).
Maron et al., "Current perspectives on statins,"Circulation, 101:207-213 (2000).
Marz et al., "HMG-CoA reductase inhibition—anti-inflammatory effects beyond lipid lowering?", Herz, 25:117-125 (2000).
McCartney-Francis et al., "Suppression of arthritis by an inhibitor of nitric oxide synthase," J. Exp. Med., 178:749-754 (1993).
McCarty et al., "Suppression of dolichol synthesis with isoprenoids and statins may potentiate the cancer-retardant efficacy of IGF-I down-regulation," Medical Hypotheses, 56:12-17 (2001).
McDaniel et al., "Cytokines and nitric oxide in islet inflammation and diabetes," Proc. Soc. Exp. Biol. Med., 211:24-32 (1996).
Menasche et al., "Acadesine: a new drug that may improve myocardial protection in coronary artery bypass grafting," J. Thorac. Cardiovascular Surg., 110(4):1096-1106 (1995).
Miller et al., "Amelioration of chronic ileitis by nitric oxide synthase inhibition," J. Pharmacol. & Exp. Therapeutics, 264:11-16 (1992).
Miller et al., "The role of cholesterol and statins in Alzheimer's Disease," Annals of Pharmacotherpay, 38:91-98 (2004).
Napoli, "HMG-CoA reductase inhibitors (statins): a promising approach to stroke prevention," Neurology, 55:1066-1070 (2000).
Non-Final Rejection in U.S. Appl. No. 10/273,557 dated Mar. 1, 2004.
Non-Final Rejection in U.S. Appl. No. 11/204,288 dated Jul. 26, 2007.
Non-Final Rejection in U.S. Appl. No. 11/204,288 dated Mar. 12, 2007.
Non-Final Rejection in U.S. Appl. No. 12/145,261 dated Jun. 13, 2011.

Non-Final Rejection in U.S. Appl. No. 12/145,261 dated Jun. 30, 2010.
Notice of Allowance in U.S. Appl. No. 10/273,557 dated May 4, 2005.
Notice of Allowance in U.S. Appl. No. 10/273,557 dated Sep. 22, 2005.
Notice of Allowance in U.S. Appl. No. 11/204,288 dated May 13, 2008.
Notice of Appeal in U.S. Appl. No. 10/273,557 dated Dec. 20, 2004.
Oda et al., "Recent advances in statins and the kidney," Kidney Intl., 56:S-2-S-5 (1999).
Office Action mail date Jul. 26, 2007.
Office Action mail date Mar. 1, 2004.
Office Action mail date Mar. 12, 2007.
Office Action mail date May 18, 2007.

\* cited by examiner

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 1
ctccttcaaa gaggcaaaaa ta                                          22

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
cacttcctcc aggatgttgt                                             20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
cacttcctcc aggattggtg                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
accaccatgg agaaggctgg                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
ctcagtgtag cccaggatgc                                             20

<210> SEQ ID NO 6
<211> LENGTH: 25
<212> TYPE: DNA
<213> ORGANISM: Artificial Sequence
<220> FEATURE:
<223> OTHER INFORMATION: Synthetic Primer

<400> SEQUENCE: 6
gagagtgtgc aagtatttgt aggag                                       25

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
aaggtggctg agaagtttca                                             20
```

METHOD OF TREATING INFLAMMATION WITH STATINS

This application is a continuation of application Ser. No. 12/145,261, which was filed on Jun. 24, 2008 now abandoned, as a continuation application of U.S. application Ser. No. 11/204,288, which was filed on Aug. 15, 2005 (now issued as U.S. Pat. No. 7,396,659), which is a continuation application of U.S. application Ser. No. 10/273,557, filed on Oct. 18, 2002 (now issued as U.S. Pat. No. 7,049,058), which is a divisional of U.S. application Ser. No. 09/579,791 filed May 25 2000 (now issued as U.S. Pat. No. 6,511,800) which is a continuation of International Application No. PCT/US98/25360 filed Nov. 25, 1998, which claims the benefit of U.S. Provisional Application No. 60/066,839 filed Nov. 25, 1997. The entire text of the aforementioned applications is incorporated herein by reference in its entirety.

This invention was made with government support under Grant No. NS-22576 awarded by the National Institutes of Health. The government has certain rights in the invention.

BACKGROUND OF THE INVENTION

1. Field of the Invention

The present invention relates generally to the treatment of conditions involving undesired or pathological levels of inducible nitric oxide synthase (iNOS), e.g. septic shock or neuroinflammatory diseases. In one important aspect, the invention relates to methods of suppressing, inhibiting or preventing the accumulation of nitric-oxide induced cytotoxicity by using inhibitors that block or suppress the induction of cytokines and/or inducible nitric oxide synthase. Another aspect of the invention is the treatment of conditions involving undesired or pathological levels of proinflammatory cytokines (i.e. TNF-$\alpha$, IL-1$\beta$, IL-2, IL-6, IL-8 and/or IFN-$\gamma$) and/or iNOS. One important aspect of the invention relates to methods of suppressing, inhibiting, or preventing proinflammatory cytokines and/or iNOS induced or aggravated disorders including conditions involving the detrimental effects of inflammation (e.g. disorders such as lupus, rheumatoid arthritis, osteoarthritis, amyotrophic lateral sclerosis, and autoimmune disorders; ischemia/reperfusion; neuroinflammatory conditions such as Alzheimer's, stroke, multiple sclerosis, X-linked adrenoleukodystrophy; and the effects of aging).

2. Description of Related Art

Nitric Oxide and Proinflammatory Cytokines

Nitric oxide (NO) is a potent pleiotropic mediator of physiological processes such as smooth muscle relaxation, neuronal signaling, inhibition of platelet aggregation and regulation of cell mediated toxicity. It is a diffusible free radical which plays many roles as an effector molecule in diverse biological systems including neuronal messenger, vasodilation and antimicrobial and antitumor activities (Nathan, 1992; Jaffrey et al., 1995). NO appears to have both neurotoxic and neuroprotective effects and may have a role in the pathogenesis of stroke and other neurodegenerative diseases and in demyelinating conditions (e.g. multiple sclerosis, experimental allergic encephalopathy, X-adrenoleukodystrophy) and in ischemia and traumatic injuries associated with infiltrating macrophages and the production of proinflamatory cytokines (Mitrovic et al., 1994; Bo et al., 1994; Merrill et al., 1993; Dawson et al., 1991, Kopranski et al., 1993; Bonfoco et al., 1995). A number of pro-inflammatory cytokines and endotoxin (bacterial lipopolysaccharide, LPS) also induce the expression of iNOS in a number of cells, including macrophages, vascular smooth muscle cells, epithelial cells, fibroblasts, glial cells, cardiac myocytes as well as vascular and non-vascular smooth muscle cells. Although monocytes/macrophages are the primary source of iNOS in inflammation, LPS and other cytokines induce a similar response in astrocytes and microglia (Hu et al., 1995; Galea et al., 1992).

During inflammation, reactive oxygen species (ROS) are generated by various cells including activated phagocytic leukocytes; for example, during the neutrophil "respiratory burst", superoxide anion is generated by the membrane-bound NADPH oxidase. ROS are also believed to accumulate when tissues are subjected to inflammatory conditions including ischemia followed by reperfusion. Superoxide is also produced under physiological conditions and is kept in check by superoxide dismutates. Excessively produced superoxide overwhelms the antioxidant capacity of the cell and reacts with NO to form peroxynitrite, $ONOO^-$, which may decay and give rise to hydroxyl radicals, OH (Marietta, M., 1989; Moncada et al., 1989; Saran et al., 1990; Beckman et al. 1990). NO, peroxynitrite and OH are potentially toxic molecules to cells including neurons and oligodendrocytes that may mediate toxicity through modification of biomolecules including the formation of iron-NO complexes of iron containing enzyme systems (Drapier et al., 1988), oxidation of protein sulfhydryl groups (Radi et al., 1991), nitration of proteins and nitrosylation of nucleic acids and DNA strand breaks (Wink et al., 1991).

There is now substantial evidence that iNOS plays an important role in the pathogenesis of a variety of diseases. In addition, it is now thought that excess NO production may be involved in a number of conditions, including conditions that involve systemic hypotension such as septic and toxic shock and therapy with certain cytokines. Circulatory shock of various etiologies is associated with profound changes in the body's NO homeostasis. In animal models of endotoxic shock, endotoxin produces an acute release of NO from the constitutive isoform of nitric oxide synthase in the early phase, which is followed by induction of iNOS. NO derived from macrophages, microglia and astrocytes has been implicated in the damage of myelin producing oligodendrocytes in demyelinating disorders like multiple sclerosis and neuronal death during neuronal degenerating conditions including brain trauma (Hu et al., 1995; Galea et al., 1992; Koprowski et al., 1993; Mitrovic et al., 1994; Bo et al., 1994; Merrill et al., 1993).

NO is synthesized from L-arginine by the enzyme nitric oxide synthase (NOS) (Nathan, 1992). Nitric oxide synthases are classified into two groups. One type, constitutively expressed (cNOS) in several cell types (e.g., neurons, endothelial cells), is regulated predominantly at the post-transcriptional level by calmodulin in a calcium dependent manner (Nathan, 1992; Jaffrey et al., 1995). In contrast, the inducible form (iNOS), synthesized de novo in response to different stimuli in various cell types including macrophages, hepatocytes, myocytes, neutrophils, endothelial and messangial cells, is independent of calcium. Astrocytes, the predominant glial component of brain have also been shown to induce iNOS in response to bacterial lipopolysaccharide (LPS) and a series of proinflammatory cytokines including interleukin-1$\beta$ (IL-1$\beta$), tumor necrosis factor-$\alpha$ (TNF-$\alpha$), interferon-$\gamma$ (IFN-$\gamma$) (Hu et al., 1995; Galea et al., 1992).

Cytokines associated with extracellular signaling are involved in the normal process of host defense against infections and injury, in mechanisms of autoimmunity and in the pathogenesis of chronic inflammatory diseases. It is believed that nitric oxide (NO), synthesized by nitric oxide synthetase (NOS) mediates deleterious effects of the cytokines (Nathan, 1987; Zang et al., 1993; Kubes et al., 1991). For example, NO as a result of stimuli by cytokines (e.g., TNF-$\alpha$, IL-1 and interleukin-6 (IL-6) is implicated in autoimmune diseases such as multiple sclerosis, rheumatoid arthritis, osteoarthritis (Zang et al., 1993; McCartney-Francis et al., 1993). The NO produced by iNOS is associated with bactericidal properties of macrophages (Nathan, 1992; Stuehr et al., 1989). Recently, an increasing number of cells (including muscle cells, macrophages, keratinocytes, hepatocytes and brain cells) have been shown to induce iNOS in response to a series of proinflammatory cytokines including IL-1, TNF-α, interferon-γ (IFN-γ) and bacterial lipopolysaccharides (LPS) (Zang et al., 1993; Busse et al., 1990; Genge et al., 1995).

Signal Transduction Pathways

Mevalonate metabolites, particularly farnesyl pyrophosphate (FPP), are involved in post-translational modification of some G-proteins, including Ras (Goldstein et al., 1990; Casey et al., 1989). The inhibition of isoprenylation of Ras proteins by inhibitors of mevalonate pathway and their membrane association and transduction of signal from Ras to Raf/MAP kinase cascade (Kikuchi et al., 1994) indicates a role of mevalonate metabolites in the transduction of signal from receptor tyrosine kinases to Raf/MAP kinase cascade. Two enzymes that control the rate-limiting steps of the mevalonate pathway are 3-hydroxy-3-methylglutaryl coenzyme A (HMG-CoA) reductase, which catalyzes the formation of mevalonate from acetyl-CoA, and mevalonate pyrophosphate decarboxylase, which controls the use of mevalonate within the cell by converting 3-phospho-5-pyrophospho-mevalonate to isopentenyl pyrophosphate. Lovastatin, a potent inhibitor of HMG-CoA reductase, and sodium salt of phenylacetic acid (NaPA), an inhibitor of mevalonate pyrophosphate decarboxylase, are known to reduce the level of cellular isoprenoids (Castillo et al., 1991; Samid et al., 1994) and isoprenylated proteins (Repko and Maltese, 1989). No suppression of isoprenylated protein maturation in vitro by lovastatin treatment that produced 50% inhibition of sterol biosynthesis has been observed (Sinensky et al., 1991). The $IC_{50}$ for inhibition of sterol synthesis is 10 nM, whereas the $IC_{50}$ for inhibition of conversion of pro-p21$^{ras}$ to mature-p21$^{ras}$ is maximal at 2.6 µM (Sinensky et al., 1991). The pharmacologically attainable concentration for NaPA, however, is 1 to 5 mM (Thibault et al., 1995). HMG-CoA reductase can also be inhibited by 5-amino 4-imidazolecarboxamide ribotide (AICAR). AICAR stimulates AMP-activated protein kinase, an enzyme that inhibits acetyl-CoA carboxylase and HMG-CoA reductase (Henin et al., 1995)

LPS is shown to bind cell-surface receptor CD14 (Stefanova et al., 1993) and induce iNOS, probably via activation of NFkβ (Xie et al., 1994; Kwon et al., 1995). NFkβ is an ubiquitous multisubunit transcription factor that is activated in response to various stimuli including cytokines TNF-α, IL-1, IL-2, IL-6, viruses, LPS, DNA damaging agents and phorbol myristate acetate (PMA) (Schreck et al., 1992). Previous studies (Law et al., 1992) demonstrating the inhibition of NF-kβ activation by mevinolin and 5'-methylthioadenosine indicates a role of protein farnesylation and carboxyl methylation reactions in the activation of NF-kβ. Identification of the binding site of NF-kβ in the promoter region of the iNOS gene and that the activation of NFkβ in LPS-induced iNOS induction establishes a role of NFkβ activation in the induction of iNOS (Xie et al., 1994). Although the precise mechanism of NFkβ activation is not known at the present time, the inhibition of activation of NFkβ by inhibitors of tyrosine kinase and proteases indicates a role of phosphorylation and degradation of Ikβ in this process (Menon et al., 1993; Henkel et al., 1993).

Reactive oxygen (Schreck et al., 1992) and reactive nitrogen (Lander et al., 1993) species have been demonstrated to mediate the signal for NFkβ activation. The differential induction of NFkβ by protein phosphatase inhibitors in primary and transformed cell lines also indicates that induction of NFkβ is dependent on the dual processes of cellular redox and phosphorylation (Menon et al., 1993). The exact target of ROS that modulate cellular redox is unknown, and the lack of induction in cells in which activity of p21ras was blocked through expression of a dominant negative mutant or treatment with farnesyltransferase inhibitor indicate that direct activation of p21ras may be the central mechanism by which redox stress stimuli transmit its signal to the nucleus (Lander et al., 1995).

Ceramide Production and Apoptosis

Cytokine-mediated ceramide production is implicated in apoptosis of different cells including brain cells (Brugg et al., 1996; Wiesner and Dawson, 1996). Several studies support a role for hydrolysis of sphingomyelin as a stress-activated signaling mechanism in which ceramide plays a role in cell regulation, cell differentiation, growth suppression and apoptosis in various cell types including glial and neuronal cells (Hannun and Bell, 1989; Hannun, 1994; Kolesnick and Golde, 1994; Brugg et al., 1996; Wiesner and Dawson, 1996). Sphingomyelin is preferentially concentrated in the outer leaflet of the plasma membrane of most mammalian cells; it comprises sphingosine (a long chain sphingoid base backbone), a fatty acid, and a phosphocholine head group. Ceramide is composed of a sphingoid base with a fatty acid in amide linkage. Ceramide activates the proteases of the interleukin-converting enzyme (ICE) family (especially prICE/YAMA/CPP32), the protease responsible for cleavage of poly (A)DP-ribose polymerase (Martin et al., 1995), and that the activation of prICE by ceramide and induction of apoptosis are inhibited by overexpression of Bcl-2 (Zhang et al., 1996). Addition of exogenous ceramides or sphingomyelinase to cells induces stress-activated protein kinase-dependent transcriptional activity through the activation of c-jun (Latinis and Koretzky, 1996), and a dominant negative mutant of SEK1, the protein kinase responsible for phosphorylation and activation of stress-activated protein kinase, interferes with ceramide-induced apoptosis (Verheij et al., 1996). These observations also indicate that both Bcl-2 and stress-activated protein kinase function downstream of ceramide in the apoptotic pathway.

The signaling events in cytokine-mediated activation of sphingomyelin degradation to ceramide are poorly understood. Since the discovery of the sphingomyelin cycle, several inducers have been shown to be coupled to sphingomyelin-ceramide signaling events, including 1α,25-dihydroxyvitamin $D_3$, radiation, antibody cross-linking, TNF-α, IFN-γ, IL-1β, nerve growth factor, and brefeldin A (Hannun and Bell, 1989; Hannun, 1994; Kolesnick and Golde, 1994; Zhang and Kolesnick, 1995; Kantey et al., 1995; Linardic et al., 1996).

The sphingomyelin pathway-associated signal transduction pathway mediates the action of several extracellular stimuli that lead to important biochemical and cellular effects (Zhang and Kolesnick, 1995; Kantey et al., 1995; Yao et al., 1995; Hannun, 1996; Lozano et al., 1994). In the case of TNF-α, the pathway is initiated by the action of TNF-α on its 55-kDa receptor, leading to phospholipase $A_2$ activation, generation of arachidonic acid, and subsequent activation of sphingomyelinase (Jayadev et al., 1994). This pathway is initiated by the activation of two distinct forms of sphingomyelinase (SMase), a membrane-associated neutral sphingomyelinase (Chatterjee, 1993) and an acidic sphingomyelinase (Spence, 1993), which reside in the caveola and the endosomal-lysosomal compartment. Each type of SMase hydrolyzes the phosphodiester bond of sphingomyelin to yield ceramide and phosphocholine. Proinflammatory cytokines (tumor necrosis factor-α, TNF-α; interleukin-1β, IL-1β; interferon-γ, IFN-γ) and bacterial lipopolysaccharides have been shown as potent inducers of SMases. Ceramide has emerged as a second messenger molecule that is considered to mimic most of the cellular effects of cytokines and lipopolysaccharide in terminal differentiation, apoptosis, and cell cycle arrest (Zhang and Kolesnick, 1995; Kantey et al., 1995).

Sphingomyelin turnover and ceramide generation in response to TNF-α and IL-1β, occurs within minutes of stimulation; however, the sequence of events linking receptor stimulation and SMase activation remains largely unknown (Hannun, 1996; Lozano et al., 1994; Jayadev et al., 1994). In a number of cell systems, interaction of TNF-α with its membrane receptors (p75 and p55) has been found to activate phospholipase $A_2$ and to induce release of arachidonic acid from phosphatidylcholine and phosphatidylethanolamine pools. This arachidonic acid has been shown as a mediator of sphingomyelin hydrolysis in response to TNF-α (Jayadev et al., 1994). In addition, proteases have also been implicated in the pathway leading from TNF-α to the activation of SMase (Hannun, 1996; Dbaio et al., 1997) recently. On the other hand, IL-1β and TNF-α are known to induce the production of reactive oxygen species, a class of highly diffusible and ubiquitous molecules, which have been suggested to act as second messengers (Tiku et al., 1990; Lo and Cruz, 1995; Devary et al., 1991). ROS encompassing species such as superoxide, hydrogen peroxide, and hydroxyl radicals are known to regulate critical steps in the signal transduction cascade and many important cellular events including protein phosphorylation, gene expression, transcription factor activation, DNA synthesis, and cellular proliferation (Schreck et al., 1991; Sen and Packer, 1996). A recent observation has shown that glutathione or similar molecules inhibit the activity of magnesium-dependent neutral SMase in vitro (Liu and Hannun, 1997). However, surprisingly, the SH group of GSH was not required as S-methyl GSH and GSSG inhibited neutral SMase at lower concentrations than GSH (Liu and Hannun, 1997). On the other hand, N-acetylcysteine has also been found to inhibit the synthesis of ceramide in cultured rat hepatocytes through the inhibition of dihydroceramide desaturase (Michel et al., 1997).

Inflammatory Diseases

NO generated by iNOS has been implicated in the pathogenesis of inflammatory diseases. In experimental animals hypotension induced by LPS or TNF-alpha can be reversed by NOS inhibitors and reinitiated by L-arginine (Kilbourn et al., 1990). Conditions which lead to cytokine-induced hypotension include septic shock, hemodialysis (Beasley and Brenner, 1992) and IL-2 therapy in cancer patients (Hibbs et al., 1992). Studies in animal models have suggested a role for NO in the pathogenesis of inflammation and pain and NOS inhibitors have been shown to have beneficial effects on some aspects of the inflammation and tissue changes seen in models of inflammatory bowel disease (Miller et al., 1990) and cerebral ischemia and arthritis (Ialenti et al., 1993; Stevanovic-Racic et al., 1994).

Inflammation, iNOS activity and/or cytokine production has been implicated in a variety of diseases and conditions, including psoriasis (Ruzicka et al., 1994; Kolb-Bachofen et al., 1994; Bull et al., 1994); uveitis (Mandia et al., 1994); type 1 diabetes (Eisieik & Leijersfam, 1994; Kroncke et al., 1991; Welsh el al., 1991); septic shock (Petros et al., 1991; Thiemermann & Vane, 1992; Evans et al., 1992; Schilling et al., 1993); pain (Moore et al., 1991; Moore et al, 1992; Meller et al., 1992; Lee et al., 1992); migraine (Olesen et al., 1994); rheumatoid arthritis (Kaurs & Halliwell, 1994); osteoarthritis (Stadler et al., 1991); inflammatory bowel disease (Miller et al., 1993; Miller et al., 1993); asthma (Hamid et al., 1993; Kharitonov et al., 1994); Koprowski et al., 1993); immune complex diseases (Mulligan et al., 1992); multiple sclerosis (Koprowski et al., 1993); ischemic brain edema (Nagafuji et al., 1992; Buisson et al., 1992; Trifiletti et al., 1992); toxic shock syndrome (Zembowicz & Vane, 1992); heart failure (Winlaw et al., 1994); ulcerative colitis (Boughton-Smith et al., 1993); atherosclerosis (White et al., 1994); glomerulonephritis (Muhl et al., 1994); Paget's disease and osteoporosis (Lowick et al., 1994); inflammatory sequelae of viral infections (Koprowski et al., 1993); retinitis, (Goureau et al., 1992); oxidant induced lung injury (Berisha et al., 1994); eczema (Ruzica et al., 1994); acute allograft rejection (Devlin, J. et al., 1994); and infection caused by invasive microorganisms which produce NO (Chen, Y and Rosazza, J. P. N., 1994).

In the central nervous system, apoptosis may play an important pathogenetic role in neurodegenerative diseases such as ischemic injury and white matter diseases (Thompson, 1995; Bredesen, 1995). Both X-linked adrenoleukodystrophy (X-ALD) and multiple sclerosis (MS) are demyelinating diseases with the involvement of proinflammatory cytokines in the manifestation of white matter inflammation. The presence of immunoreactive tumor necrosis factor a (TNF-α) and interleukin 1 (IL-1β) in astrocytes and microglia of X-ALD brain has indicated the involvement of these cytokines in immunopathology of X-ALD and aligned X-ALD with MS, the most common immune-mediated demyelinating disease of the CNS in man (Powers, 1995; Powers et al., 1992; McGuiness et al., 1995; McGuiness et al., 1997). Several studies demonstrating the induction of proinflammatory cytokines at the protein or mRNA level in cerebrospinal fluid and brain tissue of MS patients have established an association of proinflammatory cytokines (TNF-α, IL-1β, IL-2, IL-6, and IFN-γ) with the inflammatory loci in MS (Maimone et al., 1991; Tsukada et al., 1991; Rudick and Ransohoff, 1992).

X-linked adrenoleukodystrophy (X-ALD), an inherited, recessive peroxisomal disorder, is characterized by progressive demyelination and adrenal insufficiency (Singh, 1997; Moser et al., 1984). It is the most common peroxisomal disorder affecting between 1/15,000 to 1/20,000 boys and manifests with different degrees of neurological disability. The onset of childhood X-ALD, the major form of X-ALD, is between the age of 4 to 8 and then death within the next 2 to 3 years. Although X-ALD presents as various clinical phenotypes, including childhood X-ALD, adrenomyeloneuropathy (AMN), and Addison's disease, all forms of X-ALD are associated with the pathognomonic accumulation of saturated very long chain fatty acids (VLCFA) (those with more than 22 carbon atoms) as a constituent of cholesterol esters, phospholipids and gangliosides (Moser et al., 1984) and secondary neuroinflammatory damage (Moser et al., 1995). The necrologic damage in X-linked adrenoleukodystrophy may be mediated by the activation of astrocytes and the induction of proinflammatory cytokines. Due to the presence of similar concentration of VLCFA in plasma and as well as in fibroblasts of X-ALD, fibroblasts are generally used for both prenatal and postnatal diagnosis of the disease (Singh, 1997; Moser et al., 1984).

The deficient activity for oxidation of lignoceroyl-CoA ligase as compared to the normal oxidation of lignoceroyl-CoA in purified peroxisomes isolated from fibroblasts of X-ALD indicated that the abnormality in the oxidation of VLCFA may be due to deficient activity of lignoceroyl-CoA ligase required for the activation of lignoceric acid to lignoceroyl-CoA (Hashmi et al., 1986; Lazo et al., 1988). While these metabolic studies indicated lignoceroyl-CoA ligase gene as a X-ALD gene, positional cloning studies led to the identification of a gene that encodes a protein (ALDP), with significant homology with the ATP-binding cassette (ABC) of the super-family of transporters (Mosser et al., 1993). The normalization of fatty acids in X-ALD cells following transfection of the X-ALD gene (Cartier et al., 1995) supports a role for ALDP in fatty acid metabolism; however, the precise function of ALDP in the metabolism of VLCFA is not known at present.

Similar to other genetic diseases affecting the central nervous system, the gene therapy in X-ALD does not seem to be a real option in the near future and in the absence of such a treatment a number of therapeutic applications have been investigated (Singh, 1997; Moser, 1995). Adrenal insufficiency associated with X-ALD responds readily with steroid replacement therapy, however, there is as yet no proven therapy for neurological disability (Moser, 1995). Addition of monoenoic fatty acid (e.g., oleic acid) to cultured skin fibroblasts of X-ALD patients causes a reduction of saturated VLCFA presumably by competition for the same chain elongation enzyme (Moser, 1995). Treatment of X-ALD patients with trioleate resulted in 50% reduction of VLCFA. Subsequent treatment of X-ALD patients with a mixture of trioleate and trieruciate (popularly known as Lorenzo's oil) also led to a decrease in plasma levels of VLCFA (Moser, 1995; Rizzo et al., 1986; Rizzo et al., 1989). Unfortunately, the clinical efficacy has been unsatisfactory since no proof of favorable effects has been observed by attenuation of the myelinolytic inflammation in X-ALD patients (Moser, 1995). Moreover, the exogenous addition of unsaturated VLCFA induces the production of superoxide, a highly reactive oxygen radical, by human neutrophils (Hardy et al., 1994). Since cerebral demyelination of X-ALD is associated with a large infiltration of phagocytic cells to the site of the lesion (Powers et al., 1992), treatment with unsaturated fatty acids may even be toxic to X-ALD patients. Bone marrow therapy also appears to be of only limited value because of the complexity of the protocol and of insignificant efficacy in improving the clinical status of the patient (Moser, 1995).

Experimental allergic encephalomyelitis (EAE) is an inflammatory demyelinating disease of the central nervous system (CNS) that serves as a model for the human demyelinating disease, multiple sclerosis (MS). Studies have shown that the majority of the inflammatory cells constitute of T-lymphocytes and macrophages (Merrill and Benveniste, 1996). These effector cells and astrocytes have been implicated in the disease pathogenesis by secreting number of molecules that act as inflammatory mediators and/or tissue damaging agents such as nitric oxide (NO). NO is a molecule with beneficial as well as detrimental effects. In neuroinflammatory diseases like EAE, high amounts of NO produced for longer durations by inducible nitric oxide synthase (iNOS) acts as a cytotoxic agent towards neuronal cells. Previous studies have shown NO by itself or it's reactive product ($ONOO^-$) may be responsible for death of oligodendrocytes, the myelin producing cells of the CNS, and resulting in demyelination in the neuroinflammatory disease processes (Merrill et al., 1993; Mitrovic et al., 1994).

Infiltrating T-lymphocytes in EAE produce pro-inflammatory cytokines such as IL-12, TNF-α and IFN-γ (Merrill and Benveniste, 1996). In addition to T-cells and macrophages, astrocytes have also been shown to produce TNF-α (Shafer and Murphy, 1997). Convincing evidence exists to support a role for both TNF-α and IFN-γ in the pathogenesis of EAE (Taupin et al., 1997; Villarroya et al., 1996; Issazadeh et al., 1995). Investigations with antibodies against TNF-α have shown that in mice these antibodies protect against active and adaptively transferred EAE disease (Klinkert et al., 1997). The expression of TNF-α and IFN-γ during EAE disease could result in the upregulation of iNOS in macrophage and astrocytes because TNF-α and IFN-γ have been shown to be potent inducers of iNOS in macrophages and astrocytes in culture (Xie et al., 1994). This induction of iNOS could result in the production of NO, which if produced in large amounts may lead to cytotoxic effects. Peroxynitrite ($ONOO^-$) has been identified in both MS and EAE CNS (Hooper et al., 1997; van der Veen et al., 1997). The role of peroxynitrite in the pathogenesis of EAE is supported by the beneficial effects of uric acid, a peroxynitrite scavenger, against EAE and by a subsequent survey documenting that MS patients had significantly lower serum uric acid levels than those of controls (Hooper et al., 1998). However, aggravation of EAE by inhibitors of NOS activity (Ruuls et al., 1996) and in an animal model of iNOS gene knockout (Fenyk-Melody et al., 1998) indicate that NO may not be the only pathological mediator in EAE disease process. In addition to NO other free radicals such as reactive oxygen intermediates ($O_2^-$, $H_2O_2$, and $OH^-$) can also be stimulated by cytokines (Merrill and Benveniste, 1996). Reactive oxygen intermediates (ROI) and NO are believed to be key mediators of pathophysiological changes that take place during inflammatory disease process. ROI's such as superoxide anion, hydroxy radicals and hydrogen peroxide can also be stimulated by TNF-α (Merrill and Benveniste, 1996). Therefore, it is likely that both the direct modulation of cellular functions by proinflammatory cytokines and toxicity of the ROI and reactive nitrogen species may play a role in the pathogenesis of EAE disease.

Several studies on protein and/or mRNA levels in plasma, cerebrospinal fluid (CSF), brain tissue, and cultured blood leukocytes from MS patients have established an association of proinflammatory cytokines (TNF-α, IL-1 and IFN-γ) with MS (Taupin et al., 1997; Villarroya et al., 1996; Issazadeh et al., 1995). The mRNA for iNOS has also been detectable in both MS as well as EAE brains (Bagasra et al., 1995; Koprowski et al., 1993). Semiquantitative RT-PCR™ for iNOS mRNA in MS brains shows markedly higher expression of iNOS mRNA in MS brains than control brains (Bagasra et al., 1995). Analysis of CSF from MS patients has also shown increased levels of nitrite and nitrate compared with normal control (Merrill and Benveniste, 1996). Peroxynitrite, ONOO— is a strong nitrosating agent capable of nitrosating tyrosine residues of proteins to nitrotyrosine. Increased levels of nitrotyrosine have been found in demyelinating lesions of MS brains as well as spinal cords of mice with EAE (Hooper et al., 1998; Hooper et al., 1997). A strong correlation exists between CSF levels of cytokines, disruption of blood-brain barrier, and high levels of circulating cytokines in MS patients (Villarroya et al., 1996; Issazadeh et al., 1995). Increase in TNF-α and IFN-γ levels seems to predict relapse in MS and the number of circulating IFN-γ positive blood cells correlates with severity of disability. These observations support the view that in both MS and EAE, induction of proinflammatory cytokines and production of NO through iNOS play roles in the pathogenesis of these diseases.

Alzheimer's disease (AD) is the most common degenerative dementia affecting primarily the elderly population. The disease is characterized by the decline of multiple cognitive functions and a progressive loss of neurons in the central nervous system. Deposition of beta-amyloid peptide has also been associated with AD. Over the last decade, a number of investigators have noted that AD brains contain many of the classical markers of immune mediated damage. These include elevated numbers of microglia cells, which are believed to be an endogenous CNS form of the peripheral macrophage, and astrocytes. Of particular importance, complement proteins have been immunohistochemically detected in the AD brain and they most often appear associated with beta-amyloid containing pathological structures known as senile plaques (Rogers et al., 1992; Haga et al., 1993).

These initial observations which suggest the existence of an inflammatory component in the neurodegeneration observed in AD has been extended to the clinic. A small clinical study using the nonsteroidal anti-inflammatory drug, indomethacin, indicated that indomethacin significantly slowed the progression of the disease (Neurology, 43(8):1609 (1993)). In addition, a study examining age of onset among 50 elderly twin pairs with onsets of AD separated by three or more years, suggested that anti-inflammatory drugs may prevent or delay the initial onset of AD symptoms (Neurology, 44:227 (1994)).

Over the years numerous therapies have been tested for the possible beneficial effects against EAE or MS disease but with mixed results (Cross et al., 1994; Ruuls et al., 1996). Though aminoguandine (AG) has been described as a competitive inhibitor of iNOS and a suppressor of its expression (Corbett and McDaniel, 1996; Joshi et al., 1996), to date few compounds which inhibit iNOS are of potential therapeutic value have been identified. This deficiency is particularly troubling given the significant cellular damage which can arise as a result of iNOS-mediated nitric oxide toxicity, especially in chronic inflammatory disease states. There is a present need for therapeutic agents which will inhibit or even prevent cytotoxic concentrations of NO from occurring in individuals suffering from diseases and conditions to which NO toxicity or an undesired production of proinflammatory cytokines is linked.

SUMMARY OF THE INVENTION

The invention generally provides methods of treating nitric oxide (NO) cytotoxicity comprising providing a biologically effective amount of an inducible nitric oxide synthase (iNOS) and/or proinflammatory cytokine induction suppressor and/or inhibitor. The invention provides a solution to the cytotoxicity induced or fostered by the presence of NO and/or proinflammatory cytokines which is observed in individuals suffering from autoimmune or inflammatory diseases, including stroke, neurodegenerative diseases, demyelinating conditions (e.g., multiple sclerosis, experimental allergic encephalopathy, X-adrenoleukodystrophy), brain trauma, ischemia-reperfusion, Alzheimer's disease, aging, Landry-Guillain-Barre-Strohl syndrome, rheumatoid arthritis, endotoxic shock, myocardial infarction, tissue injury or HIV-mediated NO neurotoxicity.

The invention first provides a method for suppressing the induction of inducible nitric oxide synthase and/or proinflammatory cytokines in a cell comprising contacting said cell with an effective amount of at least one induction suppressor and/or inhibitor of inducible nitric oxide synthase. Preferred cells throughout the various embodiments of the invention are lymphocytes, macrophages, endothelial cells, astrocytes, masengial cells, myocytes, Kuffer cells, epithelial cells, microglia, oligodendrocytes and neurons. Proinflammatory cytokines that are preferred include TNF-α, IL-1β, IL-2, IL-6, IL-8 and IFN-γ. As used herein certain embodiments "induction" may mean an increase in the overall rate of gene transcription and/or translation. Induction may also mean that the rate of gene message or protein product destruction is decreased, producing a net increase in the amount of a message or translated protein. As used herein certain embodiments, the phrase "inhibition of nitric oxide cytotoxicity" denotes any measurable decrease in the production of NO. Inhibition of nitric oxide cytotoxicity includes inhibition of iNOS activity, production of iNOS protein, production or translation of iNOS mRNA, inhibition of LPS- or cytokine-induced NF-kβ activation in a cell. As used herein certain embodiments, "inhibitors" refers to such compounds or agents that produce any measurable decrease in the activity, production, or secretion of a protein or biological compound, or the translation of mRNA, in, or in the case of secretion, from, a cell. Proteins and biological compounds that are specifically contemplated in the invention include iNOS and proinflammatory cytokines. As used herein certain embodiments, a "enhancer" or "stimulator" refers to such compounds or agents that produce any measurable increase in the activity, production, or secretion of a protein or biological compound, or the translation of mRNA, in, or in the case of secretion, from, a cell. As used herein certain embodiments, an "inducer" refers to such compounds or agents that produce any measurable increase in the content, production, translation, or secretion of a protein or biological compound, or the translation of mRNA, in, or in the case of secretion, from, a cell. As used herein certain embodiments, "a suppressor" refers to an agent or compound that produces any measurable reduction in the induction of a gene. Thus, a "suppressor" is a type of "inhibitor", that acts reduce the net rate of transcription or translation of a target gene.

In preferred aspects of the invention, the induction suppressor and/or inhibitor of inducible nitric oxide synthase and/or proinflammatory cytokines may be selected from the group including, but not limited to, lovastatin, mevastatin, FPT inhibitor II, forskolin, rolipram, phenylacetate (NaPA), N-acetyl cysteine (NAC), pyrrolidine dithiocarbamate (PDTC), 4-phenylbutyrate (4PBA), 5-aminoimmidazole-4-carboxamide ribonucleoside (AICAR), theophylline, papaverine, cAMP, 8-bromo-cAMP, (S)-cAMP, and salts, analogs, or derivatives thereof.

In some embodiments, the induction suppressor and/or inhibitor of inducible nitric oxide synthase and/or proinflammatory cytokines may be an inhibitor of the Ras/Raf/MAP kinase pathway. In certain embodiments the induction suppressor and/or inhibitor of inducible nitric oxide synthase and/or proinflammatory cytokines may be an inhibitor of NF-kB, such as for example an inhibitor of NF-kB activation, and/or a suppressor of its induction. In certain preferred embodiments the inhibitor of NF-kB activation includes, but is not limited to, lovastatin, NaPA, metastatin, 4-phenylbutyrate, FPT inhibitor II, AICAR and salts, analogs, or derivatives thereof. In some embodiments, the induction suppressor and/or inhibitor of inducible nitric oxide synthase and/or proinflammatory cytokines may be an inhibitor of mevalonate synthesis. In certain embodiments the inhibitor of mevalonate synthesis may be an inhibitor of the farnasylation of a protein. In certain preferred embodiments the inhibitor of mevalonate synthesis may be an inhibitor of HMG-CoA reductase and/or suppressor of its induction, including but not limited to, lovastatin or AICAR and salts, analogs, or derivatives thereof. In certain preferred embodiments the inhibitor of HMG-CoA reductase is a stimulator of AMP-activated protein kinase, including but not limited to, AICAR and salts, analogs, or derivatives thereof. In certain embodiments, the induction suppressor and/or inhibitor of inducible nitric oxide synthase and/or proinflammatory cytokines may be a stimulator of AMP-activated protein kinase. In certain other preferred embodiments the inhibitor of inducible nitric oxide synthase and/or proinflammatory cytokines may be an inhibitor of mevalonate pyrophosphate decarboxylase and/or suppressor of its induction, including but not limited to, phenylacetic acid, 4-phenylbutyrate and salts, analogs, or derivatives thereof. In certain preferred embodiments the inhibitor of mevalonate synthesis may be lovastatin, mevastatin, NaPA, AICAR, 4-phenylbutyrate and salts, analogs, or derivatives thereof. In certain aspects embodiments the inhibitor of inducible nitric oxide synthase and/or proinflammatory cytokines is an inhibitor of farnesyl pyrophosphate. Preferred inhibitors of farnesyl pyrophosphate include, but are not limited to 4-phenylbutyrate or NaPA.

In other embodiments the suppressor of inducible nitric oxide synthase and/or proinflammatory cytokines is an antioxidant. In preferred embodiments the antioxidant may be, but is not limited to, N-acetyl cysteine, PDTC, and salts, analogs, or derivatives thereof.

In certain other embodiments the inducible nitric oxide synthase and/or proinflammatory cytokines induction suppressor and/or inhibitor is an enhancer of intracellular cAMP, inhibitor of the Ras/Raf/MAP kinase pathway, and/or inhibitor of NF-kB, NF-kB activation and/or suppressor of NF-kB induction. In a preferred embodiment, the inhibitor of the Ras/Raf/MAP kinase pathway includes, but is not limited to, AICAR and salts, analogs, or derivatives thereof. The enhancer of intracellular cAMP may be an inhibitor of cAMP phosphodiesterase and/or suppressor of its induction. In preferred aspects of the invention, the inhibitor of cAMP phosphodiesterase may be, but is not limited to; rolipram and salts, analogs, or derivatives thereof. In certain other aspects of the invention, the induction suppressor and/or inhibitor of inducible nitric oxide synthase and/or proinflammatory cytokines is cAMP and salts, analogs, or derivatives thereof. Derivatives of cAMP include, but are not limited to, 8-bromo-AMP or (S)-cAMP. In other aspects of the invention, the enhancer of intracellular cAMP may be, but is not limited to, forskolin, rolipram, 8-bromo-cAMP, theophylline, papaverine, cAMP and salts, analogs, or derivatives thereof. In certain embodiments, the induction suppressor and/or inhibitor of inducible nitric oxide synthase and/or proinflammatory cytokines may be a enhancer of protein kinase A. In other aspects of the invention, the enhancer of protein kinase A may include, but is not limited to, forskolin, rolipram, 8-bromo-AMP, (S)-cAMP, cAMP and salts, analogs, or derivatives thereof. may be, but is not limited to, forskolin, rolipram, 8-bromo-cAMP, theophylline, papaverine, cAMP and salts, analogs, or derivatives thereof.

In yet another aspect of the invention, the induction suppressor and/or inhibitor of inducible nitric oxide synthase and/or proinflammatory cytokines may be a Ras farnesyl protein transferase inhibitor and/or induction suppressor, an inhibitor of the farnasylation of Ras, and/or an activator of G-proteins. In a preferred embodiment, the Ras farnesyl protein transferase inhibitor and/or induction suppressor includes, but is not limited to, a FPT inhibitor and salts, analogs, or derivatives thereof. In a preferred embodiment, the inhibitor of the farnasylation of Ras, includes, but is not limited to, a FPT inhibitor II and salts, analogs, or derivatives thereof.

In one embodiment of the invention, the inducible nitric oxide synthase and/or proinflammatory cytokines inhibitor and/or induction suppressor is selected from the group consisting of lovastatin, mevastatin, FPT inhibitor II, forskolin, rolipram, phenylacetate (NaPA), N-acetyl cysteine (NAC), PDTC, 4-phenylbutyrate (4PBA), 5-aminoimmidazole-4-carboxamide ribonucleoside (AICAR), theophylline, papaverine, cAMP, 8-bromo-cAMP, (S)-cAMP, and salts, analogs, or derivatives thereof. In a further embodiment of the invention, combinations of two or more inhibitors and/or induction suppressors are preferred for use in the methods described herein.

A "salt" is understood herein certain embodiments to mean a compound formed by the interaction of an acid and a base, the hydrogen atoms of the acid being replaced by the positive ion of the base. Salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases that form such base salts include ammonia, primary amines such as n-propylamine, n-butylamine, aniline, cyclohexylamine, benzylamine, p-toluidine, ethanolamine and glucamine; secondary amines such as diethylamine, diethanolamine, N-methylglucamine, N-methylaniline, morpholine, pyrrolidine and piperidine; tertiary amines such as triethylamine, triethanolamine, N,N-dimethylaniline, N-ethylpiperidine and N-methylmorpholine; hydroxides such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts.

As used herein, "derivatives" refers to chemically modified inhibitors or stimulators that still retain the desired effects on property(s) of iNOS or pro inflammatory gene, protein, and/or activity induction or suppression. Derivatives may also retain other desired properties described herein, such as suppressing the accumulation of very long chain fatty acids, defined herein as fatty acids with more than 22 carbon atoms. Such derivatives may have the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means described herein or known to those of skill in the art.

As used herein, "analogs" include structural equivalents or mimetics, described further in the detailed description.

In administering the inducible nitric oxide synthase and/or proinflammatory cytokines inhibitors and/or induction suppressors to a mammal, preferably a human, pig, cats, dogs, rodent, or cattle including but not limited to, sheep, goats and cows, the inhibitor is formulated in a pharmaceutically acceptable vehicle. The induction suppressor and/or inhibitor may be administered to a patient in a dose therapeutic to treat a diseases, conditions and disorders where there is an advantage in inhibiting the nitric oxide synthase enzyme and/or the production of proinflammatory cytokines.

A "patient", as used herein, may be an animal. Preferred animals are mammals, including but not limited to humans, pigs, cats, dogs, rodents, or cattle including but not limited to, sheep, goats and cows. Preferred patients are humans.

The induction suppressors, also known as "suppressing agents", and/or inhibitors of iNOS and/or proinflamrnatory cytokines, in pure form or in a pharmaceutically acceptable carrier, will find benefit in treating conditions and disorders, described below, where there is an advantage in inhibiting and/or suppression the induction of proinflammatory cytokines and/or the inducible isoform of nitric oxide synthase enzyme. These induction suppressors and/or inhibitors may also be used to treat conditions and disorders created, induced, enhanced and/or aggravated by the contact of a cell with bacterial endotoxin (LPS).

For example, the suppressing agents and/or inhibitors may be used to treat circulatory shock including its various aspects such as vascular and myocardial dysfunction, metabolic failure including the inhibition of mitochondrial enzymes and cytochrome P450-mediated drug metabolism, and multiple organ dysfunction syndrome including adult respiratory distress syndrome. Hypotension and/or circulatory shock may be a result of gram-negative and gram positive sepsis (a.k.a. septic shock), toxic shock, trauma, hemorrhage, burn injury, anaphylaxis, cytokine immunotherapy, liver failure, kidney failure or systemic inflammatory response syndrome. Suppressing agents and/or inhibitors also may be beneficial for patients receiving therapy, including cancer therapy, with cytokines such as TNF-α, IL-1β, IL-2, IL-6, IL-8 and/or IFN-γ, or therapy with cytokine-inducing agents, or as an adjuvant to short term immunosuppression in transplant therapy. In addition, the suppressing agents and/or inhibitors may be useful to inhibit NO synthesis in patients suffering from inflammatory conditions in which an excess of NO contributes to the pathophysiology of the condition, such as adult respiratory distress syndrome (ARDS) and myocarditis, for example.

There is also evidence that an NO synthase enzyme and/or proinflammatory cytokines may be involved in the pathophysiology of autoimmune and/or inflammatory conditions such as arthritis, rheumatoid arthritis and systemic lupus erythematosus (SLE) and in insulin-dependent diabetes, mellitus type 1 diabetes, and therefore, the suppressing agents may prove helpful in treating these conditions.

Furthermore, it is now clear that there are a number of additional inflammatory and noninflammatory diseases and/conditions that are associated with NO overproduction Examples of such physiological disorders include: inflammatory bowel diseases such as ileitis, ulcerative colitis and Crohn's disease; inflammatory lung disorders such as asthma, bronchitis, oxidant-induced lung injury and chronic obstructive airway disease; inflammatory disorders of the eye including corneal dystrophy, ocular hypertension, trachoma, onchocerciasis, retinitis, uveitis, sympathetic ophthalmitis and endophthalmitis; chronic inflammatory disorders of the gum including periodontitis; chronic inflammatory disorders of the joints including arthritis, septic arthritis and osteoarthritis, tuberculosis, leprosy, glomerulonephritis sarcoid, and nephrosis; disorders of the skin including sclerodermatitis, sunburn, psoriasis and eczema; inflammatory diseases of the central nervous system, including amyotrophic lateral sclerosis, chronic demyelinating diseases such as multiple sclerosis, dementia including AIDS-related neurodegeneration and Alzheimer's disease, encephalomyelitis and viral or autoimmune encephalitis; autoimmune diseases including immune-complex vasculitis, systemic lupus and erythematosis; and disease of the heart including ischemic heart disease, heart failure and cardiomyopathy. Additional disease that may benefit from the use of suppressing agents include adrenal insufficiency; hypercholesterolemia; atherosclerosis; bone disease associated with increased bone resorption, e.g., osteoporosis, pre-eclampsia, eclampsia, uremic complications; chronic liver failure, noninflammatory diseases of the central nervous system (CNS) including stroke and cerebral ischemia; and other disorders associated with inflammation and undesirable production of nitric oxide and/or proinflammatory cytokines such as cystic fibrosis, tuberculosis, cachexia, ischeimia/reperfusion, hemodialysis related conditions, glomerulonephritis, restenosis, inflammatory sequelae of viral infections, hypoxia, hyperbaric oxygen convulsions and toxicity, dementia, Sydenham's chorea, Parkinson's disease, Huntington's disease, amyotrophic lateral sclerosis (ALS), multiple sclerosis, epilepsy, Korsakoff's disease, imbecility related to cerebral vessel disorder, NO mediated cerebral trauma and related sequelae, ischemic brain edema (stroke), pain, migraine, emesis, immune complex disease, as immunosuppressive agents, acute allograft rejection, infections caused by invasive microorganisms which produce NO and for preventing or reversing tolerance to opiates and diazepines, aging, and various forms of cancer. All these nitric oxide and/or proinflammatory cytokine and/or endotoxin induced, mediated, enhanced, and/or aggravated diseases and disorders are contemplated as being treatable in a cell by contacting the cell with at least one suppressing agent and/or inhibitor of iNOS and/or proinflammatory cytokines. A patient with may also be treated by administering at least one suppressing agent and/or inhibitor of iNOS and/or proinflammatory cytokines. When administered to a patient, the at least one suppressing agent and/or inhibitor is formulated in a pharmaceutically acceptable vehicle.

In another aspect the present invention provides a method of identifying, or screening for, a candidate inducible nitric oxide synthase and/or proinflammatory cytokines inhibitor and/or induction suppressor, comprising preparing a cell capable of producing inducible nitric oxide synthase and/or proinflammatory cytokines activity and testing the candidate inhibitor and/or induction suppressor for the ability to inhibit the inducible nitric oxide synthase and/or proinflammatory cytokines activity, wherein the inhibition is indicative of a candidate inducible nitric oxide synthase and/or proinflammatory cytokines inhibitor and/or induction suppressor. These candidate inhibitor and/or induction suppressor are known herein as "candidate substances". A further aspect of this method is to identify an iNOS specific inhibitor and/or induction suppressor that does not inhibit or suppress one or more proinflammatory cytokines. Another aspect of this invention is to identify an inhibitor and/or induction suppressor that does not inhibit or suppress iNOS, but does inhibit or suppress one or more proinflammatory cytokines.

This method of identifying a candidate inducible nitric oxide synthase and/or proinflammatory cytokines induction suppressor and/or inhibitor comprising the steps of a) obtaining a cell comprising at least the capability of producing inducible nitric oxide synthase and/or proinflammatory cytokines activity; b) obtaining a candidate inducible nitric oxide synthase and/or proinflammatory cytokines induction suppressor and/or inhibitor; c) contacting the cell with the candidate inducible nitric oxide synthase and/or proinflammatory cytokines induction suppressor and/or inhibitor under conditions normally inducing, enhancing, and/or stimulating iNOS and/or proinflammatory cytokines; and d) determining the ability of the candidate inducible nitric oxide synthase and/or proinflammatory cytokines induction suppressor and/or inhibitor to inhibit the formation of nitric oxide in the presence of inducible nitric oxide synthase, wherein the inhibition of the formation of nitric oxide in the presence of inducible nitric oxide synthase is indicative of a candidate inducible nitric oxide synthase induction suppressor and/or inhibitor. In an aspect of the invention, decreased content or production of at least one proinflammatory cytokine by a cell is indicative of a candidate proinflammatory cytokine induction suppressor. In another aspect of the invention, decreased bioactivity of at least one proinflammatory cytokine is indicative of a candidate proinflammatory cytokine inhibitor and/or induction suppressor. In further aspects of this method, an induction suppressor and/or inhibitor is further identified by detecting the amount of iNOS and/or proinflammatory cytokine mRNA message and/or protein content and/or biological activity. In additional aspects of the invention, an induction suppressor and/or inhibitor is further identified by comparing the amount of iNOS and/or proinflammatory cytokine mRNA message and/or protein content and/or biological activity to another cell under conditions normally inducing, enhancing, and/or stimulating iNOS and/or proinflammatory cytokines in the absence of the candidate inhibitor and/or induction suppressor. The preferred conditions inducing, enhancing, and/or stimulating iNOS and/or proinflammatory cytokines is contacting a cell with endotoxin and/or at least one cytokine and/or at least one inducer or stimulator of at least one proinflammatory cytokine. Preferred cytokines are proinflammatory cytokines.

In preferred embodiments, a candidate induction suppressor and/or inhibitor of inducible nitric oxide synthase and/or proinflammatory cytokines is selected from agents that have certain traits or modes of action common to those of the suppressors and/or inhibitors identified herein. Preferred candidate substances would either inhibit the Ras/Raf/MAP kinase pathway, inhibit and/or suppress the induction and/or activation of NF-kB, inhibit mevalonate synthesis, be an enhancer of protein kinase A, and/or inhibit the farnasylation of proteins, including but not limited to Ras. In certain embodiments the inhibitor of mevalonate synthesis may be an inhibitor of HMG-CoA reductase or suppressor of its induction. In certain aspects the inhibitor of HMG-CoA reductase is a stimulator of AMP-activated protein kinase. In certain other embodiments the inhibitor of inducible nitric oxide synthase and/or proinflammatory cytokines may be an inhibitor of mevalonate pyrophosphate decarboxylase or suppressor of its induction. In other embodiments the candidate substance is an antioxidant. In other embodiments the candidate substance is an enhancer of intracellular cAMP. The enhancer of intracellular cAMP may be an inhibitor of cAMP phosphodiesterase and/or suppressor of its induction. In other embodiments the candidate substance is a farnesyl protein transferase inhibitor and/or induction suppressor.

Proinflammatory cytokine and/or iNOS RNA message, protein content, or activity can be detected by any method described herein or known to those of skill in the art (see for example, Sambrook et al., 1989), and include but are not limited to Northern analysis of iNOS and/or inflammatory cytokine message, PCR™ amplification of target message, immunodetection techniques including Western analysis of iNOS and/or proinflammatory cytokine content or production, and chemical or biological activity assays for iNOS or cytokine activity.

Candidate inhibitors and/or induction suppressors identified by the method of the invention are preferably purified. When administered to a mammal, the purified candidate inducible nitric oxide synthase inhibitor and/or induction suppressor is formulated in a pharmaceutically acceptable vehicle.

In another preferred embodiment, the invention provides a method of inhibiting nitric oxide cytotoxicity comprising contacting a cell capable of producing nitric oxide with a biologically effective amount of at least one inducible nitric oxide synthase induction suppressor and/or inhibitor identified by the screening assay of the invention. In preferred embodiments, the cell is in a patient.

In another preferred embodiment, the invention provides a method of inhibiting proinflammatory cytokine or endotoxin treated, induced or aggravated conditions and disorders, where there is an advantage in inhibiting and/or suppression the induction of proinflammatory cytokines. In certain embodiments, the method comprises contacting a cell with a biologically effective amount of at least one induction suppressor and/or inhibitor of: at least one proinflammatory cytokine and/or iNOS. In certain aspects of the invention, the at least one induction suppressor and/or inhibitor is identified by the screening assay of the invention. In preferred embodiments, the cell is in a patient.

The invention also provides a method of suppressing the accumulation of very long chain fatty acids in a cell, by contacting the cell with a biologically effective amount of at least induction suppressor and/or inhibitor of: inducible nitric oxide synthase and/or at least one proinflammatory cytokine. In certain aspects of the invention, the at least one induction suppressor and/or inhibitor is identified by the screening assay of the invention. In preferred embodiments, the cell is in a patient. Such methods have use in inflammatory conditions including, but not limited to, demyelinating diseases or neural trauma, and particularly in treating patients with X-ALD. In certain aspects of the invention, lignoceric acid β-oxidation is stimulated. In other aspects of the invention, the ratios of $C_{26:0}/C_{22:0}$ or $C_{24:0}/C_{22:0}$ fatty acids are lowered.

The invention provides a method of treating a nitric oxide and/or cytokine mediated disorder in a cell, by contacting the cell with a biologically effective amount of at least one induction suppressor and/or inhibitor of: inducible nitric oxide synthase and/or at least one proinflammatory cytokine. In certain aspects of the invention, the at least one induction suppressor and/or inhibitor is identified by the screening assay of the invention. In preferred embodiments, the cell is in a patient. In preferred aspects, the disorder is X-ALD, multiple sclerosis, Alzheimer's disease, amyotrophic lateral sclerosis, lupus, septic shock, stroke, ischemia/reperfusion, rheumatoid arthritis, osteoarthritis or aging. In other preferred aspects, the nitric oxide or cytokine mediated disorder is myelinolytic inflammation, a demyelinating condition or an inflammatory demyelinating disease, or a neuroinflammatory disease. The inflammatory disease is preferably X-ALD, multiple sclerosis, Landry-Guillain-Barre-Strohl syndrome, Alzheimer's disease and/or aging.

In another preferred embodiment, the invention provides a method of treating septic shock comprising contacting a cell capable of producing excess nitric oxide and/or at least one proinflammatory cytokine under conditions of septic shock with a biologically effective amount of an inducible nitric oxide synthase and/or proinflammatory cytokine induction suppressor and/or inhibitor. In certain aspects of the invention, the induction suppressor and/or inhibitor is identified by the screening assay of the invention. In preferred aspects of the invention, the cell is in a patient. Methods of treating septic shock with inhibitors of nitric oxide synthase activity are described in U.S. Pat. Nos. 5,028,627 and 5,296,466, each incorporated herein by reference in entirety.

The present invention is further directed to methods for inducing or suppressing apoptosis in the cells and/or tissues of individuals suffering from degenerative disorders characterized by inappropriate cell proliferation or inappropriate cell death, or in some cases, both. The method comprises contacting a cell capable of producing excess nitric oxide under conditions of degenerative disorders with a biologically effective amount of an inducible nitric oxide synthase and/or proinflammatory cytokines induction suppressor and/or inhibitor. In preferred aspects of the invention, the cell is in a patient. In certain aspects of the invention, the cytokines induction suppressor and/or inhibitor identified by the screening assay of the invention. Inappropriate cell proliferation will include the statistically significant increase in cell number as compared to the proliferation of that particular cell type in the normal population. Also included are disorders whereby a cell is present and/or persists in an inappropriate location, e.g., the presence of fibroblasts in lung tissue after acute lung injury, and cancer cells which exhibit the properties of invasion and metastasis and are highly anaplastic. Such cells include but are not limited to, cancer cells including, for example, tumor cells. Inappropriate cell death will include a statistically significant decrease in cell number as compared to the presence of that particular cell type in the normal population. Such underrepresentation may be due to a particular degenerative disorder, including, for example, viral infections such as AIDS (HIV), which results in the inappropriate death of T-cells, and autoimmune diseases which are characterized by inappropriate cell death. Autoimmune diseases are disorders caused by an immune response directed against self antigens. Such diseases are characterized by the presence of circulating autoantibodies or cell-mediated immunity against autoantigens in conjunction with inflammatory lesions caused by immunologically competent cells or immune complexes in tissues containing the autoantigens. Such diseases include systemic lupus erythematosus (SLE), rheumatoid arthritis. Standard reference works setting forth the heneral principles of immunology include Stites and Terr, 1991 and Abbas et al., 1991.

The invention particularly relates to the use of at least one iNOS and/or pro-inflammatory cytokine induction suppressor and/or inhibitors, preferably reductants such as NAC or other thiol compounds to reduce NO-mediated cytotoxicity as well as ceramide-mediated apoptosis in neuroinflammatory diseases and degenerative disorders. Suppressing agents in this class would be particularly preferred in treating diseases characterized by excessive or inappropriate cell death, including, for example, neuro-degenerative diseases and injury resulting from ischemia. Degenerative disorders characterized by inappropriate cell proliferation include, for example, inflammatory conditions, cancer, including lymphomas, such as prostate hyperplasia, genotypic tumors, etc. Degenerative disorders characterized by inappropriate cell death include, for example, autoimmune diseases, acquired immunodeficiency disease (AIDS), cell death due to radiation therapy or chemotherapy, neurodegenerative diseases, such as Alzheimer's disease, Parkinson's disease, Landry-Guillain-Barre-Strohl syndrome, multiple sclerosis, etc. In certain aspects of the invention, the at least one induction suppressor and/or inhibitor is identified by the screening assay of the invention.

The invention further provides a method for enhancing the production of an inducible nitric oxide synthatase or a proinflammatory cytokine in a cell comprising providing a biologically effective amount of a inducible nitric oxide synthatase and/or proinflammatory cytokine stimulator. In certain aspects of the invention, the at least one induction stimulator and/or enhancer is identified by the screening assay of the invention. A stimulator in this aspect of the invention is preferably an induction stimulator. Preferred stimulators include a PKA inhibitor or enhancer of intracellular cAMP. PKA inhibitors may include, but are not limited to, H-89, myristoylated PKI, (R)-cAMP and salts, analogs, or derivatives thereof. The enhancers of intracellular cAMP may also be selected from the group comprising forskolin, 8-bromo-cAMP and rolipram. In other preferred aspects of the invention, the enhancer of intracellular cAMP is an inhibitor of cAMP phosphodiesterase. A preferred inhibitor of cAMP phosphodiesterase is rolipram. In other aspects of this method, a biologically effective amount of LPS and/or one or more proinflammatory cytokine is administered to stimulate iNOS and/or proinflammatory cytokines' induction or activity. Preferred proinflammatory cytokine that are administered include TNF-α, IL-1β, IL-2, IL-6, IL-8 and/or IFN-γ.

Following long-standing patent law convention, the words "a" and "an," as used in this specification, including the claims, denotes "one or more." Specifically, the use of "comprising," "having," or other open language in claims that claim a combination or method employing "an object," denotes that "one or more of the object" may be employed in the claimed method or combination.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
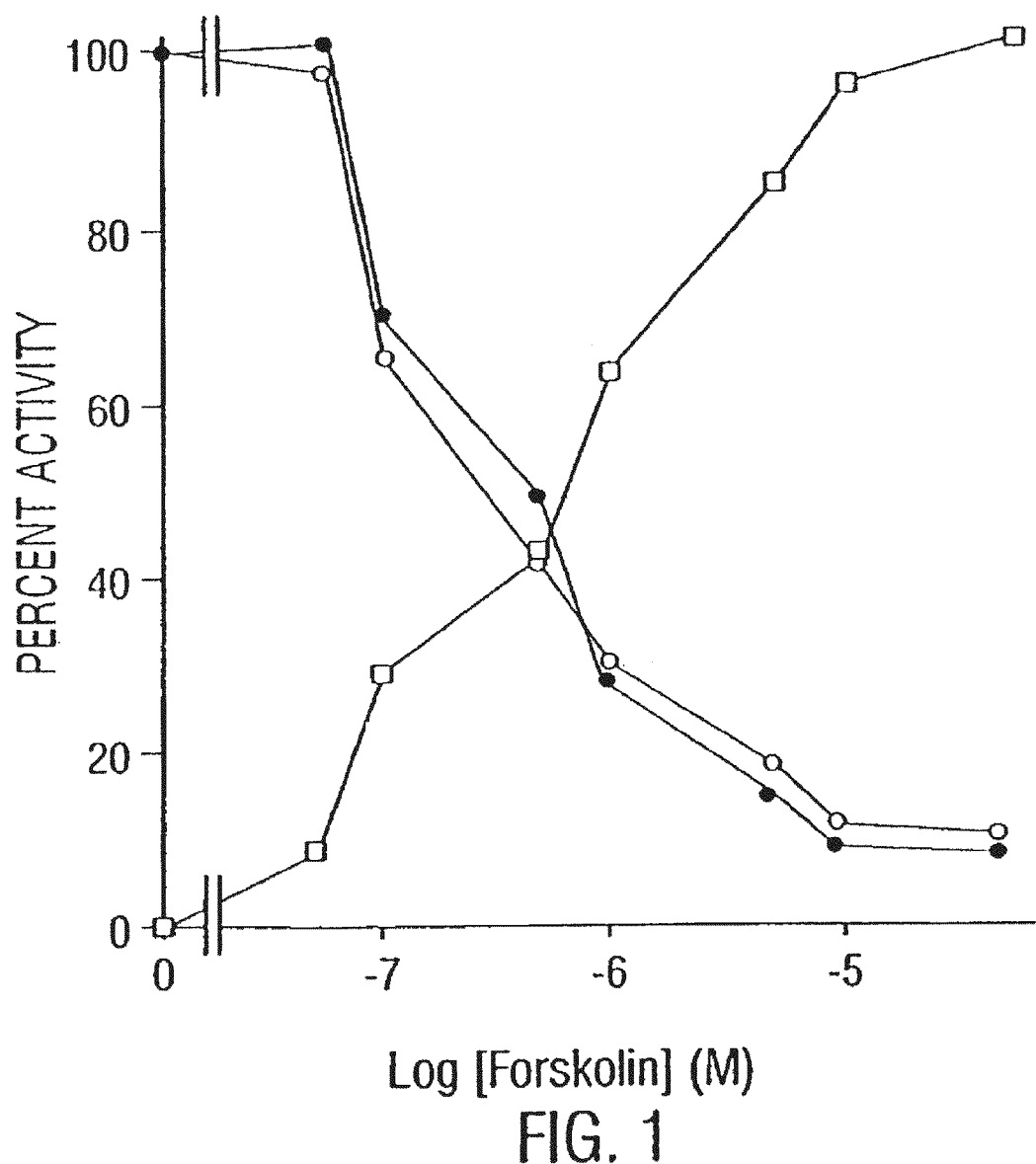
FIG. 1. Forskolin inhibits LPS-induced NO production and iNOS activity in a dose-dependent manner in rat primary astrocytes. Cells incubated in serum-free DMEM/F-12 received different concentrations of forskolin 15 min before the addition of 1.0 μg/ml LPS. The production of nitrite in supernatants (○) and activities of iNOS in cell homogenates (●) were measured after 24 h of incubation as described in Example 6. PKA activity was measured in cell homogenates (□) after 1 h of incubation. Nitrite production in supernatants (32.3±3.6 nmol/mg/24 h), and iNOS activity in homogenates (48.7±3.9 pmol/min/mg) found in cells stimulated with only LPS are considered as 100%. However, PKA activity found in extracts from cells stimulated with an optimal concentration of forskolin (74.4±9.4 pmol/min/mg) is considered as 100%. Values are mean of duplicate samples.

The invention discloses the novel uses of compounds which inhibit the induction of iNOS and/or proinflammatory cytokines and the production of NO and/or proinflammatory cytokines by cells, including lymphocytes, macrophages, endothelial cells, astrocytes and microglia in response to inflammatory cytokines for the therapeutic treatment of disease affecting the vascular and nervous systems. The therapeutic uses described herein utilizing these compounds provide protection against NO toxicity to including lymphocytes, macrophages, endothelial cells, astrocytes microglia, oligodendrocytes and neurons in neuroinflammatory disease, stroke, ischemia-reperfusion and tissue injury and HIV-mediated NO neurotoxicity for which there is no effective treatment presently available.

The present disclosure further describes the discovery of a novel role of the mevalonate pathway in controlling the expression of iNOS and different cytokines in lymphocytes, macrophages, endothelial cells, astrocytes and microglia. This discovery provides the basis for novel screening assays of previously unknown inhibitors of iNOS and the production of NO. An understanding of the cellular mechanisms involved in the induction of iNOS and cytokines allows identification of novel targets for the therapeutic intervention of NO-mediated, proinflammatory cytokine and/or endotoxin-mediated pathophysiology in inflammatory diseases.

The inventor demonstrates herein that LPS- and cytokine-induced production of NO can be blocked by antioxidants. Therefore maintenance of the thiol/oxidant balance appears to be crucial for protection against proinflammatory cytokine production and, at least, in NO cytotoxicity. The inventor has discovered that the use of reductants, such as N-acetyl cysteine (NAC) or other thiol compounds, is beneficial in restoring cellular redox and in inhibiting the production of proinflammatory cytokines and in reducing cytotoxic levels of NO. N-acetyl cysteine blocks the induction of TNF-α and iNOS and is a nontoxic drug that enters the cell readily and serves both as a scavenger of reactive oxygen species and a precursor of glutathione, the major intracellular thiol (Smilkstein et al., 1988; Aruoma et al., 1989). Therefore, the use of reductants such as NAC or other thiol compounds, may be beneficial in restoring cellular redox and in inhibition of production of proinflammatory cytokines and in reducing cytotoxic levels of NO.

The inventor investigated the cellular regulation of the induction of iNOS and cytokines by lovastatin and NaPA in rat primary lymphocytes, macrophages, endothelial cells, astrocytes and microglia. This investigation disclosed the first evidence that the induction of inducible nitric oxide synthase (iNOS) and cytokine (for example TNF-α, IL-1β and IL-6) gene expression are uniquely sensitive to the drugs lovastatin and the sodium salt of phenylacetic acid (NaPA) in astrocytes, glial cells and macrophages. The reversal of lovastatin-mediated inhibition of iNOS induction by mevalonate and FPP, and reversal of the inhibitory effect of NaPA by FPP, and inhibition of Ras farnesyl protein transferase by an inhibitor (FPT inhibitor II) demonstrated that the farnesylation reaction is a key step in the regulation of LPS-mediated induction of iNOS and production of NO and cytokines.

The inventor have discovered that lovastatin and NaPA, alone or in combination represent therapeutic agents directed against cytokine- and nitric oxide-mediated brain disorders, particularly in stroke, trauma, Alzheimer's Disease and in demyelinating conditions such as multiple sclerosis and X-adrenoleukodystrophy (X-ALD).

The inventor's results demonstrate that the inhibition iNOS expression by lovastatin, NaPA and FPT inhibitor II may be due to the inhibition of NF-kβ activation. Previous studies of Law et al. (1992) demonstrating the inhibition of NF-kβ activation by mevinolin and 5'-methylthioadenosine indicated a role of protein farnesylation and carboxyl methylation reactions in the activation of NF-kβ. The Ras protooncogene proteins function by binding to cytoplasmic surface of plasma membrane. Since mevalonate availability regulates the post-translational isoprenylation of many intracellular signaling proteins including Ras p21 (Goldstein et al., 1990), the observed inhibition of NF-kβ activation and induction of iNOS by lovastatin and NaPA appears to be due to decreased, or a lack of, isoprenylation of Ras that in turn leads to the lack of or abnormal signal transmission from receptor tyrosine kinase to Ras/Raf/MAP kinase cascade, activation of NF-kβ and induction of iNOS.

The inventor has also investigated the effect of other antioxidants on the induction of NO by LPS and/or cytokine-stimulated macrophages, C6 glioma cell lymphocytes, endothelial cells, astrocytes and microglia. These results clearly show that antioxidants (N-acetyl cysteine (NAC) and pyrrolidine dithiocarbamate (PDTC)) inhibit the LPS- and cytokine-induced production of NO, iNOS activity, production of iNOS protein and iNOS mRNA indicating a role of reactive oxygen species (e.g., $H_2O_2$, $O_2$ and OH) in iNOS induction. Superoxide ($O_2^-$) and hydroxyl radical (OH) are reported to be involved in the production of NO in brain cerebellum (Mittal, 1993) where the hydroxyl radical was indicated to hydroxylate L-arginine during its conversion to citrulline and NO (Mittal, 1993). The inventor has discovered through the inhibition of iNOS activity and induction of iNOS protein and mRNA in LPS- and cytokine-activated macrophages by NAC that reactive oxygen species (ROS) modulate the intracellular signal pathways for the induction of iNOS biogenesis.

Several lines of evidence disclosed herein clearly support the conclusion that inhibitors of HMG-CoA reductase (for example, lovastatin or mevastatin) and mevalonate pyrophosphate decarboxylase (NaPA) have an inhibitory effect on the induction of inflammatory mediators (iNOS, TNF-α, IL-1β and IL-6) in rat astrocytes, microglia and macrophages demonstrating the involvement of mevalonate metabolite(s), farnesyl pyrophosphate, in the induction of inflammatory mediators. This conclusion was based on the following observations. First, the LPS-induced expression of iNOS, TNF-α, IL-1β and IL-6, and activation of NF-kβ was inhibited by lovastatin and NaPA. Second, inhibitory effects of lovastatin and NaPA on LPS-mediated induction of iNOS and cytokines was not reversed by cholesterol and ubiquinone, end products of the mevalonate pathway, indicating that this inhibitory effect of lovastatin was not due to depletion of end products of mevalonate pathway. Third, the reversal of inhibitory effects of lovastatin by mevalonate and FPP and the reversal of inhibitory effects of NaPA by FPP, but not by mevalonate, indicates a role of farnesylation in LPS-mediated induction of iNOS. Fourth, the inhibition of LPS-induced activation of NF-kβ and induction of iNOS by FPT inhibitor II, an inhibitor of Ras farnesyl protein transferase, demonstrates that farnesylation of Ras is required for signal transduction in the LPS-induced expression of iNOS. Since the iNOS, TNF-α, IL-1β and IL-6 have been implicated in the pathogenesis of demyelinating and neurodegenerative diseases (Mitrovic et al., 1994; Bo et al, 1994; Merrill et al., 1993), these results provide an important mechanism whereby inhibitors of HMG-CoA reductase and mevalonate pyrophosphate decarboxylase can ameliorate neural injury.

Therapy For X-Adreno Leukodystrophy

Since X-ALD is a metabolic disorder of the very long chain fatty acids (VLCFA) that eventually leads to an inflammatory bilateral demyelination with marked activation of microglia and astrocytes and accumulation of proinflammatory cytokines (TNF-α and IL-1β) and extracellular matrix proteins (Powers et al., 1992; McGuinness et al., 1995), the inventor developed a therapy that should normalize the VLCFA and inhibit the induction of proinflammatory cytokines by astrocytes and microglia. Example 4 described herein demonstrates that the compounds that increase the intracellular levels of cAMP and the activity of protein kinase A (PKA) normalize the levels of VLCFA possibly by increasing the peroxisomal activity for β-oxidation of VLCFA. Moreover, the same compounds also inhibit the induction of TNF-α and IL-1β in lipopolysaccharide (LPS) stimulated astrocytes and microglia. These observations demonstrate the therapeutic potential of compounds that increase the activity of PKA in correction of the metabolic defect and inhibition of the neuroinflammatory disease process in X-ALD.

The inventor provides evidence that in X-ALD cultured skin fibroblasts, up regulation of PKA activity increased the β-oxidation of lignoceric acid, decreased the chain elongation of fatty acids and lowered cellular content of VLCFA to the normal level, despite the status (mutation or deletion) of the ALD gene. The detailed mechanism leading to the normalization of VLCFA in X-ALD is not known at the present, but is likely to involve cAMP-dependent protein kinase A. This conclusion is based on the following observations. First, cAMP analogs and rolipram, an inhibitor of cAMP phosphodiesterase, stimulated transport and β-oxidation of lignoceric acid and decreased the chain elongation of fatty acids in X-ALD as well as control skin fibroblasts whereas H-89 and myristoylated PKI, specific inhibitors of PKA, inhibited transport and β-oxidation of lignoceric acid, stimulated chain elongation of fatty acids and blocked the observed effects in normalization of VLCFA by cAMP analogs. Second, a long-term treatment of fibroblasts of X-ALD with cAMP analogs and rolipram although had no effect on protein and mRNA for X-ALD gene but lowered the accumulation of VLCFA to the control level that is also blocked by inhibitors of PKA. These results clearly indicate that increasing cAMP level in fibroblasts of X-ALD normalizes the VLCFA pathogen by a mechanism that is dependent on the activity of PKA but independent of the involvement of the ALD gene product.

Previous studies (Singh et al., 1984; Hashmi et al., 1986; Lageweg et al., 1991; Lazo et al., 1988; Lazo et al., 1989) have shown that VLCFA (lignoceric and cerotic acids) are preferentially β-oxidized in peroxisomes. The increased transport of lignoceric acid into cAMP-treated cells indicates that the observed increase in β-oxidation of lignoceric acid is due to higher availability of lignoceric acid in these cells. However, the increase in β-oxidation of lignoceric acid in cell-free extracts or permealized X-ALD cells, or cell homogenates demonstrate that normalization of VLCFA is due to increased activity of fatty acid β-oxidation system. In the cell, fatty acids are β-oxidized in mitochondria and peroxisomes (Singh, 1997). The lack of effect of etomoxir, an inhibitor of mitochondrial carnitine palmitoyl transferase-I (Mannaerts et al., 1979), on the cAMP-stimulated oxidation indicates that the higher lignoceric acid oxidation activity observed in cAMP-stimulated cells was due to increase in the activity of peroxisomal β-oxidation system. These observations provide the first evidence that peroxisomal β-oxidation of fatty acids is regulated by intracellular second messenger (cAMP).

The pathogenetic mechanism of X-ALD is poorly understood. The constant "hallmark" of X-ALD is an excessive accumulation of VLCFA with subsequent involvement of CNS with induction of proinflammatory cytokines (TNF-α and IL-1β) and extracellular matrix proteins by reactive astrocytes and microglia and demyelination/inflammatory dysmyelination and loss of oligodendrocytes (Powers et al., 1992; McGuinness et al., 1995; Powers, 1995). The documentation of immunoreactive TNF-α and IL-1β in astrocytes and microglia of X-ALD brain indicated the involvement of these cytokines in immunopathology of X-ALD and aligned X-ALD with multiple sclerosis (MS), the most common immune-mediated demyelinating disease of the CNS in man. However, apart from traditionally higher expression of cytokines by microglia than in astrocytes of MS and other neurodegenerative disorders, the expression of TNF-α and IL-1β is more prominent in astrocytes than microglia of X-ALD brain (Powers et al., 1992).

At present it is not known how the inherited metabolic abnormality of accumulation of VLCFA subsequently triggers a neuroinflammatory response in X-ALD brain. Since the metabolic defect appears prior to the detection of neuroinflammatory disease, the assumption is that these VLCFA, by themselves or as a constituent of complex lipid, act as a trigger for the inflammatory response that in turn becomes the basis for the observed demyelination and loss of oligodendrocytes in X-ALD. The data presented here indicate that cAMP may also inhibit the induction of proinflammatory cytokines in reactive astrocytes and microglia. The treatments of rat brain primary astrocytes or microglia with forskolin or rolipram inhibit the LPS-induced induction of TNF-α and IL-1β.

Previously it has been shown that cAMP derivatives and rolipram inhibit the cytokine-induced expression of inducible nitric oxide synthase and production of NO in astrocytes. The inventor's studies indicate that proinflammatory cytokines down regulate the peroxisomal function in the metabolism of VLCFA thereby aggravating the inherited metabolic abnormality by accumulating 4-times higher VLCFA and around the plaque than in normal looking X-ALD brain and these alterations by proinflammatory cytokines are mediated by NO toxicity (Khan et al., 1997). The inhibition of induction of cytokines as well as induction of iNOS by compounds that increase the activity of PKA (e.g., cAMP and rolipram) in astrocytes and microglia indicate that these compounds should be beneficial in terms of blocking the induction of proinflammatory cytokines in X-ALD These results provide the basis of a therapy to normalize the metabolic abnormality and block the neuroinflammatory process by inhibiting the induction of proinflammatory cytokines. The studies described in Example 4 clearly demonstrate that the compounds (e.g. forskolin, 8-Br-cAMP, rolipram) that increase cAMP and activate PKA meet both of these conditions. Moreover, recent reports showing the prevention of progression of autoimmune encephalomyelitis in mice (Sommer et al., 1995) as well as in marmoset by rolipram indicate that rolipram does cross the blood brain barrier and inhibit the cytokine-induced neuropathologies in these animal models.

The studies described in Example 5 demonstrate that lovastatin and sodium phenylacetate (NaPA), inhibitors of mevalonate pathway, normalize the levels of VLCFA in skin fibroblasts of X-ALD by increasing the peroxisomal activity for β-oxidation of VLCFA. In light of the fact that these compounds also inhibit the induction of proinflammatory cytokines and nitric oxide synthase in astrocytes and microglia, the inventor deduced that these drugs may have therapeutic potential in correction of the metabolic defect and inhibition of the neuroinflammatory disease process in X-ALD.

The inventor found that PD 98059, an inhibitor of MAP kinase (MEK), the kinase responsible for the activation of MAP kinase, inhibits the LPS-induced activation of NF-kB and the induction of iNOS in astrocytes indicating the possible involvement of the MAP kinase pathway in the induction of iNOS. MAP kinases exhibit dual-specificity, regulating both serine (Ser)/threonine (Thr) phosphorylation and Tyr autophosphorylation (Blenis, 1993; Rossomando et al., 1994; Her et al., 1993). In addition, MAP kinases themselves require concurrent Thr and Tyr phosphorylation for activation, and are, in turn, substrates for MEK (Blenis, 1993; Rossomando et al., 1994; Her et al., 1993). MEK is also a dual specificity kinase whose activation requires Ser/Thr phosphorylation (Blenis, 1993; Rossomando et al., 1994; Her et al., 1993). The inventor deduced form these observations that cellular regulation of this signaling pathway may utilize Ser/Thr phosphatases to modulate the phosphorylation state of critical phosphoproteins.

Since phosphoprotein phosphatases (PP) 1 and PP 2A are the two most abundant Ser/Thr phosphatases in the cell, the study presented in Example 6 was undertaken to investigate the cellular regulation of the induction of iNOS by PP 1 and PP 2A in rat primary astrocytes and macrophages. The results clearly demonstrate that calyculin A, microcystin, cantharidin and okadaic acid, inhibitors of PP 1 and PP 2A, stimulate the LPS- and cytokine-mediated expression of iNOS and production of NO in astrocytes and $C_6$ glial cells while the same inhibitors inhibit the LPS- and cytokine-mediated expression of iNOS and production of NO in macrophages and RAW 264.7 cells. Consistent with this observation, okadaic acid stimulates the iNOS promoter-derived chloramphenicol acetyl transferase (CAT) activity in LPS-treated astrocytes but inhibits the iNOS promoter-derived CAT activity in LPS-treated macrophages. This differential regulation of the induction of iNOS in astrocytes and macrophages by inhibitors of PP 1/2A indicates that, although PP 1/2A functions as a physiological inhibitor of the induction of iNOS in astrocytes, the induction of iNOS in macrophages requires the involvement of PP 1/2A. However, in spite of this differential regulation of the induction of iNOS in astrocytes and macrophages, inhibitors of PP 1/2A stimulate the activation of NF-kB and the production of TNF-α in both astrocytes and macrophages.

Transient modulation of protein phosphorylation and dephosphorylation is a major mechanism of intracellular signal transduction pathways triggered by different cytokines. Therefore, the inventor hypothesized that inhibition of protein phosphatase 1 and 2A (PP 1 and 2A) activities will influence cytokine induced signal transduction pathways for the induction of iNOS. The signaling events in cytokine-mediated induction of iNOS in astrocytes and macrophages are not well understood. An understanding of the cellular mechanisms involved in the induction of iNOS should identify novel targets for therapeutic intervention in NO-mediated neuroinflammatory diseases. Several lines of evidence presented in Example 6 support the conclusion that inhibition of PP 1/2A activity differentially modulates the LPS- and cytokine-induced expression of iNOS and production of NO in rat primary astrocytes and macrophages. The conclusion is based on the following observations. First, treatment of astrocytes and macrophages with LPS and/or cytokines induced the expression of iNOS and production of NO, and inhibitors of PP 2B (cypermethrin, deltamethrin and fenvalerate) had no effects on the LPS- and cytokine-mediated induction of iNOS and production of NO. Second, compounds (calyculin A, microcystin, okadaic acid and cantharidin) that inhibit PP 1/2A stimulated the LPS- and cytokine-mediated production of NO as well as expression of iNOS protein and mRNA in astrocytes and $C_6$ glial cells. However, in contrast, these inhibitors inhibited the LPS- and cytokine-mediated production of NO and expression of iNOS in rat resident macrophages and RAW 264.7 cells. Third, the inhibitors of PP 1/2A stimulated iNOS promoter-derived chloramphenicol acetyl transferase (CAT) activity in LPS-treated astrocytes but inhibited iNOS promoter-derived CAT activity in LPS-treated macrophages. These results indicate that the signaling events required for the induction of iNOS in astrocytes differ from those required for the induction of iNOS in macrophages.

Cytokines (TNF-α, IL-1β or IFN-γ) and LPS bind to their respective receptors and induce iNOS expression via activation of NF-kB (Xie et al., 1994, Kwon et al., 1995). The nuclear expression and biological function of the NF-kB transcription factor are tightly regulated through its cytoplasmic retention by the ankyrin-rich inhibitor IkBα (Beg et al., 1992). Activation of NF-kB by various cellular stimuli involves the proteolytic degradation of IkBα and the concomitant nuclear translocation of the liberated NF-kB heterodimer. Although the biochemical mechanism underlying the degradation of IkBα remains unclear, it appears that degradation of IkBα induced by various mitogens and cytokines occurs in association with the transient phosphorylation of IkBα on serines 32 and 36. Further the inventor has found that the 90 kDa ribosomal S6 kinase (a downstream candidate of the well characterized Ras-Raf-MEK-MAP kinase pathway), but not p70 S6 kinase or MAP kinase, phosphorylates the N-terminal regulatory domain of IkBα on serine 32. However, in vivo, only phorbol 12-myristate 13-acetate produced rapid activation of p90 RSK, other potent NF-kB inducers including TNF-α and the Tax transactivator of human T-cell lymphotrophic virus, type I, failed to activate p90 RSK indicating that more than a single IkBα kinase exists within the cell and that these IkBα kinases are differentially activated by different NF-kB inducers. By phosphorylation, IkBα which is still bound to NF-kB has apparently turned into a high affinity substrate for an ubiquitin-conjugating enzyme. Following this phosphorylation-controlled ubiquitination, IkBα is rapidly and completely degraded by the 20 S or 26 S proteosome.

Okadaic acid and other inhibitors of PP 1/2A have also been shown to induce the activation of NF-kB in monocytes, Jurkat T cells and Hela cells (Menon et al., 1993; Suzuke et al., 1994) due to the phosphorylation of IkBα at protein phosphatase 2A-sensitive phosphorylation sites which are different than cytokine-induced phosphorylation sites (Sun et al., 1995). However, according to Baeuerle and colleagues (Schmidt et al., 1995), okadaic acid-mediated activation of NF-kB in Hela cells requires the induction of oxidative stress. Identification of binding site of NF-kB in the promoter region of iNOS gene and the activation of NF-kB during cytokine-induced iNOS expression establishes the role of NF-kB activation in the induction of iNOS (Xie et al., 1994; Kwon et al., 1995). In contrast to the ability of okadaic acid on the activation of NF-kB in other cell types (Menon et al., 1993; Suzuke et al., 1994), okadaic acid by itself was unable to induce the activation of NF-kB in rat primary astrocytes. However, okadaic acid markedly stimulated LPS- or cytokine-mediated activation of NF-kB in astrocytes. Increase in the activation of NF-kB in LPS-stimulated astrocytes by okadaic acid paralleled the increase in induction of iNOS indicating that stimulation of iNOS expression in LPS-activated rat primary astrocytes by inhibitors of PP 1/2A is probably mediated via enhanced activation of NF-kB. However, consistent with the effect of okadaic acid on the activation of NF-kB in other cell types (Menon et al., 1993; Suzuke et al., 1994), okadaic acid by itself induced the activation of NF-kB in macrophages but this activation of NF-kB by okadaic acid did not result in the induction of iNOS indicating that activation of NF-kB by okadaic acid is not sufficient for the induction of iNOS in macrophages. Although similar to astrocytes, okadaic acid stimulated the LPS-mediated activation of NF-kB in rat peritoneal macrophages, yet in sharp contrast to the effect of okadaic acid on the induction of iNOS in astrocytes, the stimulation of NF-kB activation by okadaic acid in LPS-treated macrophages did not parallel with the expression of iNOS. Instead, consistent with a previous report, okadaic acid and other inhibitors of PP 1/2A markedly inhibited LPS- and cytokine-induced expression of iNOS in macrophages. However, the basis for this differential regulation of induction of iNOS in astrocytes and macrophages by inhibitors of PP 1/2A is not understood at the present time.

Earlier, the inventor observed that cAMP-dependent protein kinase A (PKA) also differentially modulates the induction of iNOS in astrocytes and macrophages. Inhibition of the activation of NF kB and the induction of iNOS with the increase in PKA activity, and stimulation of the activation of NF-kB and the induction of iNOS with the decrease in PP 1/2A activities in astrocytes indicate that both PKA (a serine-threonine protein kinase) and PP 1/2A (serine-threonine phosphoprotein phosphatases) function as inhibitory signals for the induction of iNOS in astrocytes modulating different steps of the signal transduction pathways. In contrast, in macrophages, inhibitors of PKA inhibited the LPS-mediated activation of NF-kB and induction of iNOS, and inhibitors of PP 1/2A stimulated the LPS-mediated activation of NF-kB but inhibited the induction of iNOS indicating that both PKA and PP 1/2A are necessary components of the LPS-mediated signaling pathways for the induction of iNOS. However, the molecular basis for the differential regulation of activation of NF-kB and expression of iNOS gene by inhibitors of PP 1/2A in rat peritoneal macrophages is not known. In light of the fact that NF-kB is necessary but not sufficient for the expression of iNOS gene and that many of the signal transduction events are cell type specific, the apparent stimulation of NF-kB and inhibition of iNOS gene expression by inhibitors of PP 1/2A clearly delineate that apart from the activation of NF-kB some other signaling pathway(s) sensitive to PP 1/2A is/are responsible for the expression of iNOS gene in macrophages.

The inventor examined the possible involvement of ROS in cytokine-mediated activation of sphingomyelin breakdown and ceramide formation and found that intracellular GSH plays a crucial role in the breakdown of SM to ceramide, in that low GSH levels are required for ceramide generation and high GSH levels inhibit production of ceramide. Inhibition of cytokine-mediated breakdown of SM to ceramide by antioxidants like N-acetyl cysteine (NAC) and pyrrolidine dithiocarbamate (PDTC) and induction of ceramide production by oxidants or pro-oxidants like hydrogen peroxide, aminotriazole, diamide and L-buthione (S,R)-sulfoximine clearly delineate a novel function of ROS and GSH in regulation of the first step of sphingomyelin signal transduction pathway. Moreover, decreased levels of GSH and increased levels of ceramide correlate with the DNA fragmentation in rat primary oligodendrocytes as well as in the banked human brains from patients with neuroinflammatory diseases (e.g. multiple sclerosis and X=adrenoleukodystrophy).

Changes in the cellular redox state toward either prooxidant or antioxidant conditions have profound effects on cellular functions. Several lines of evidence presented herein indicate that the first step of cytokine-induced sphingomyelin signal transduction pathway (i.e. breakdown of sphingomyelin to ceramide and phosphocholine) is redox sensitive. First, cytokines like TNF-α and IL-1β decreased intracellular GSH and induced the degradation of sphingomyelin to ceramide in rat primary astrocytes, oligodendrocytes, microglia and rat $C_6$ glial cells, and pretreatment of the cells with antioxidants like NAC restored the levels of GSH and blocked the degradation of sphingomyelin to ceramide. Second, depletion of endogenous glutathione by diamide or buthione sulfoximine alone induces the degradation of sphingomyelin to ceramide which is blocked by NAC. Third, the increase in intracellular $H_2O_2$ by the addition of exogenous $H_2O_2$ or by the inhibition of endogenous catalase by aminotriazole induced the degradation of sphingomyelin to ceramide which is also blocked by NAC. Fourth, besides NAC, pyrrolidine dithiocarbamate (PDTC), an amioxidant but not the precursor of GSH (Laight et al., 1997), also inhibited the TNF-α and IL-1β-induced hydrolysis of sphingomyelin to ceramide.

Several studies support a role for hydrolysis of sphingomyelin as a stress-activated signaling mechanism in which ceramide plays a role in growth suppression and apoptosis in various cell types including glial and neuronal cells (Brugg et al., 1996; Wiesner and Dawson, 1996). Ceramide activates the proteases of the interleukin converting enzyme (ICE) family, (especially prICE/YAMA/CPP32), the protease responsible for cleavage of poly-ADP-ribose polymerase (PARP) (Martin et al., 1995) and that the activation of prICE by ceramide and induction of apoptosis are inhibited by overexpression of Bcl-2 (Zhang et al., 1996). Addition of exogenous ceramides or sphingomyelinase to cells induces stress activated protein kinase (SAPK)-dependent transcriptional activity through the activation of c jun (Latinis and Koretzky, 1996) and a dominant negative mutant of SEK1, the protein kinase responsible for phosphorylation and activation of SAPK, interferes with ceramide-induced apoptosis (Verheij et al, 1996). These observations also indicate that both Bcl-2 and SAPK function downstream of ceramide in the apoptotic pathway.

The inventor has found that DNA fragmentation and increase in ceramide and decrease in GSH in primary oligodendrocytes and banked human brains with X-ALD and MS clearly indicate that intracellular redox (level of GSH) is an important regulator of apoptosis via controlling the generation of ceramide. This conclusion is based on following observations. First, treatment of oligodendrocytes with TNF-α decreased intracellular level of GSH, increased degradation of SM to ceramide and induced DNA fragmentation, however, pretreatment of oligodendrocytes with NAC blocked the TNF-α-mediated decrease in GSH level, increase in ceramide level and increase in DNA fragmentation. Second, treatment of oligodendrocytes only with diamide, a thiol-depleting agent, decreased intracellular level of GSH, increased level of ceramide and induced DNA fragmentation which are prevented by pretreatment of NAC, a thiol-replenishing agent. Third, the inventor found increased fragmentation of DNA in brains from patients with X-ALD and MS where the levels of GSH and ceramide were lower and higher respectively compared to those found in control human brains. These observations clearly indicate that maintenance of the thiol/oxidant balance is crucial for protection against cytokine-mediated ceramide production and thereby against ceramide-induced cytotoxicity.

Recent observation demonstrated that ceramide potentiates the cytokine-mediated induction of inducible nitric oxide synthase (iNOS) in astrocytes and $C_6$ glial cells. Although ceramide by itself did not induce the expression of iNOS and production of NO, it markedly stimulated the cytokine-induced expression of iNOS and production of NO indicating that sphingomyelin-derived ceramide generation may be an important factor in cytokine-mediated cytotoxicity in neurons and oligodendrocytes in neuroinflammatory diseases. The N-acetyl cysteine (NAC), which has been used to block the cytokine-induced ceramide production in this study and to inhibit cytokine-mediated induction of iNOS is a nontoxic pharmaceutical drug that enters the cell readily and serves both as a scavenger of ROS and a precursor of GSH, the major intracellular thiol (Smilkstein et al., 1988). Therefore, the use of reductants such as NAC or other thiol compounds, may be beneficial in restoring cellular redox and in inhibition of cytokine-mediated induction of iNOS and breakdown of sphingomyelin thus reducing NO-mediated cytotoxicity as well as ceramide-mediated apoptosis in neuroinflammatory diseases.

Inhibitors, Enhancers and Screening Assays

In still further embodiments, the present invention provides methods for identifying new iNOS and/or proinflammatory cytokine inhibitory compounds, which may be termed as "candidate substances." It is contemplated that such screening techniques will prove useful in the general identification of any compound that will serve the purpose of inhibiting iNOS and/or proinflammatory cytokines, and in preferred embodiments, will provide candidate therapeutic compounds. The present invention also provides methods for identifying new iNOS and/or proinflammatory cytokine stimulatory or enhancing compounds.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to inhibit or enhance iNOS and/or proinflammatory cytokine activity or transcription through a tight binding or other chemical interaction. Candidate substances may be obtained from libraries of synthetic chemicals, or from natural samples, such as rain forest and marine samples.

In preferred embodiments, a candidate induction suppressor and/or inhibitor of inducible nitric oxide synthase and/or proinflammatory cytokines is selected from agents that have certain traits or modes of action common to those of the suppressors and/or inhibitors identified herein. Preferred candidate substances would either inhibit the Ras/Raf/MAP kinase pathway, inhibit and/or suppress the induction and/or activation of NF-kB, inhibit mevalonate synthesis, be an enhancer of protein kinase A, and/or inhibit the farnasylation of proteins, including but not limited to Ras. In certain embodiments the inhibitor of mevalonate synthesis may be an inhibitor of HMG-CoA reductase or suppressor of its induction. In certain aspects the inhibitor of HMG-CoA reductase is a stimulator of AMP-activated protein kinase. In certain other embodiments the inhibitor of inducible nitric oxide synthase and/or proinflammatory cytokines may be an inhibitor of mevalonate pyrophosphate decarboxylase or suppressor of its induction. In other embodiments the candidate substance is an antioxidant. In other embodiments the candidate substance is an enhancer of intracellular cAMP. The enhancer of intracellular cAMP may be an inhibitor of cAMP phosphodiesterase and/or suppressor of its induction. In other embodiments the candidate substance is a farnesyl protein transferase inhibitor, and/or induction suppressor.

In other preferred embodiments, a candidate induction suppressor and/or inhibitor of inducible nitric oxide synthase and/or proinflammatory cytokines is selected from agents that have certain traits or modes of action common to those of the stimulators and/or enhancers identified herein. For example, a preferred candidate stimulators or enhancers would include a PKA inhibitor.

In other embodiments, the present invention provides methods for identifying new iNOS and/or proinflammatory cytokine inhibitory or stimulatory compounds. To determine whether a candidate substance has inhibitory, suppressor, stimulator, or enhancer activity for iNOS, and/or proinflammatory cytokines, assays may be employed to detect or measure the change in the message, content, and/or activity of iNOS, proinflammatory cytokines such as TNF-α, IL-1β, IL-2, IL-6, IL-8 and/or IFN-γ, proteins involved in second messenger pathways, or transcription factors such as NF-kβ.

Nucleic Acid Detection

Assays for the detection of iNOS, NF-kβ, and/or proinflammatory cytokines such as TNF-α, IL-1β, IL-2, IL-6, IL-8 and/or IFN-γ include detection of changes in the amount of nucleic acid message in a cell upon contact with a candidate inhibitor, suppressing agent, enhancer, and/or stimulator. Such assays are described in the specific examples. Additionally, gene sequences for known iNOS, NF-kβ, and/or proinflammatory cytokines in a database such as found in the National Center for Biotechnology Information (internet web site: http://www.ncbi.nlm.nih.gov) may be used as probes or primers in nucleic acid hybridization embodiments of such assays.

1. Hybridization

The use of a hybridization probe of between 17 and 100 nucleotides in length, or in some aspect of the invention even up to 1-2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

2. Amplification and PCR™

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to iNOS, NF-kβ, TNF-α, IL-1β, IL-2, IL-6, IL-8 and/or IFN-γ genes are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large. "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990, incorporated herein by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for changes in iNOS and/or proinflammatory cytokines in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification. Such kits generally will comprise, in suitable means, distinct containers for each individual reagent and enzyme as well as for each marker primer pair.

In another embodiment, such kits will comprise hybridization probes specific for iNOS, NF-k$\beta$, TNF-$\alpha$, IL-1$\beta$, IL-2, IL-6, IL-8 and/or IFN-$\gamma$. Such kits generally will comprise, in suitable means, distinct containers for each individual reagent and enzyme as well as for each marker hybridization probe.

Immunodetection Methods

In still further embodiments, the present invention concerns immunodetection methods for binding, purifying, removing, quantifying or otherwise generally detecting biological components such as iNOS, NF-k$\beta$, TNF-$\alpha$, IL-1$\beta$, IL-2, IL-6, IL-8 and/or IFN-$\gamma$ components. The antibodies specific for iNOS, NF-k$\beta$, TNF-$\alpha$, IL-1$\beta$, IL-2, IL-6, IL-8 and/or IFN-$\gamma$ may be prepared in accordance with the present invention may be employed to detect wild-type or mutant iNOS, NF-k$\beta$, TNF-$\alpha$, IL-1$\beta$, IL-2, IL-6, IL-8 and/or IFN-$\gamma$ proteins, polypeptides or peptides. The steps of various useful immunodetection methods have been described in the scientific literature, such as, e.g., Nakamura et al. (1987), incorporated herein by reference.

In general, the immunobinding methods include obtaining a sample suspected of containing an iNOS, NF-k$\beta$, TNF-$\alpha$, IL-1$\beta$, IL-2, IL-6, IL-8 and/or IFN-$\gamma$ protein, polypeptide or peptide, and contacting the sample with a first anti-iNOS, NF-k$\beta$, TNF-$\alpha$, IL-1$\beta$, IL-2, IL-6, IL-8 and/or IFN-$\gamma$ antibody in accordance with the present invention, as the case may be, under conditions effective to allow the formation of immunocomplexes.

These methods include methods for purifying wild-type or mutant iNOS, NF-k$\beta$, TNF-$\alpha$, IL-1$\beta$, IL-2, IL-6, IL-8 and/or IFN-$\gamma$ proteins, polypeptides or peptides as may be employed in purifying wild-type or mutant iNOS, NF-k TNF-$\alpha$, IL-1$\beta$, IL-2, IL-6, IL-8 and/or IFN-$\gamma$ proteins, polypeptides or peptides from patients' samples or for purifying recombinantly expressed wild-type or mutant iNOS, NF-k$\beta$, TNF-$\alpha$, IL-1$\beta$, IL-2, IL-6, IL-8 and/or IFN-$\gamma$ proteins, polypeptides or peptides. In these instances, the antibody removes the antigenic wild-type or mutant iNOS, NF-k$\beta$, TNF-$\alpha$, IL-1$\beta$, IL-2, IL-6, IL-8 and/or IFN-$\gamma$ protein, polypeptide or peptide component from a sample. The antibody will preferably be linked to a solid support, such as in the form of a column matrix, and the sample suspected of containing the wild-type or mutant iNOS, NF-k$\beta$, TNF-$\alpha$, IL-1$\beta$, IL-2, IL-6, IL-8 and/or IFN-$\gamma$ antigenic component will be applied to the immobilized antibody. The unwanted components will be washed from the column, leaving the antigen immunocomplexed to the immobilized antibody, which wild-type or mutant iNOS, NF-k$\beta$, TNF-$\alpha$, IL-1$\beta$, IL-2, IL-6, IL-8 and/or IFN-$\gamma$ antigen is then collected by removing the wild-type or mutant iNOS, NF-k$\beta$, TNF-$\alpha$, IL-1$\beta$, IL-2, IL-6, IL-8 and/or IFN-$\gamma$ from the column.

The immunobinding methods also include methods for detecting or quantifying the amount of a wild-type or mutant iNOS, NF-k$\beta$, TNF-$\alpha$, IL-1$\beta$, IL-2, IL-6, IL-8 and/or IFN-$\gamma$ protein reactive component in a sample, which methods require the detection or quantification of any immune complexes formed during the binding process. Here, one would obtain a sample suspected of containing a wild-type or mutant iNOS, NF-k$\beta$, TNF-$\alpha$, IL-1$\beta$, IL-2, IL-6, IL-8 and/or IFN-$\gamma$ protein, polypeptide or peptide, and contact the sample with an antibody against wild-type or mutant iNOS, NF-k$\beta$, TNF-$\alpha$, IL-1$\beta$, IL-2, IL-6, IL-8 and/or IFN-$\gamma$, and then detect or quantify the amount of immune complexes formed under the specific conditions.

In terms of antigen detection, the biological sample analyzed may be any sample that is suspected of containing a wild-type or mutant iNOS, NF-k$\beta$, TNF-$\alpha$, IL-1$\beta$, IL-2, IL-6, IL-8 and/or IFN-$\gamma$ protein-specific antigen, such as a lymphocytes, macrophages, endothelial cells, astrocytes, microglia, oligodendrocytes and/or neuron tissue section or specimen, a homogenized lymphocytes, macrophages, endothelial cells, astrocytes, microglia, oligodendrocytes and/or neuron tissue extract, or even any biological fluid that comes into contact with diseased lymphocytes, macrophages, endothelial cells, astrocytes, microglia, oligodendrocytes and neurons tissue, including blood and serum, although tissue samples and extracts are preferred.

Contacting the chosen biological sample with the antibody under conditions effective and for a period of time sufficient to allow the formation of immune complexes (primary immune complexes) is generally a matter of simply adding the antibody composition to the sample and incubating the mixture for a period of time lone enough for the antibodies to form immune complexes with, i.e., to bind to, any iNOS, NF-kβ, TNF-α, IL-1β, IL-2, IL-6, IL-8 and/or IFN-γ antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological or enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The iNOS, NF-kβ, TNF-α, IL-1β, IL-2, IL-6, IL-8 and/or IFN-γ antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

In the detection of an alteration in the levels of iNOS, NF-kβ, TNF-α, IL-1β, IL-2, IL-6, IL-8 and/or IFN-γ gene message, translation product, and/or activity in or from a biological sample, such as a cell, tissue, or organism, a comparison is made between a biological sample upon contact with a candidate suppressor, inhibitor, stimulator, and/or enhancer, to that of a similar or like biological sample that has not contacted with a candidate suppressor, inhibitor, stimulator, and/or enhancer. Reduced levels of iNOS, NF-kβ, TNF-α, IL-1β, IL-2, IL-6, IL-8 and/or IFN-γ gene message, translation product, and/or activity of a cell or patient is indictive of the candidate substance being a inhibitor or suppressor. An enhancer or stimulator would be identified by increased levels of iNOS, NF-kβ, TNF-α, IL-1β, IL-2, IL-6, IL-8 and/or IFN-γ gene message, translation product, and/or activity. Preferably, the biological sample has been contacted with a known inducer or enhancer, such as LPS and/or proinflammatory cytokines, or a suppressor or inhibitor, either before, during, and/or after contact with the candidate substance, to help measure the candidate substance's effect on the activity of the known inducer, suppressor, inhibitor, or enhancer. Those of skill in the art are very familiar with differentiating between significant differences in types or amounts of iNOS, NF-kβ, TNF-α, IL-1β, IL-2, IL-6, IL-8 and/or IFN-γ, which represent a positive identification, and low level or background changes of iNOS, NF-kβ, TNF-α, IL-1β, IL-2, IL-6, IL-8 and/or IFN-γ. Indeed, background expression levels are often used to form a "cut-off" above which increased detection will be scored as significant or positive. In this case, "background" levels may be the levels of iNOS, NF-kβ, TNF-α, IL-1β, IL-2, IL-6, IL-8 and/or IFN-γ seen after stimulation of a cell or patient with endotoxin and/or a cytokine, preferably a proinflammatory cytokine.

1. ELISAs

As detailed above, immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the anti-iNOS, NF-kβ, TNF-α, IL-1β, IL-2, IL-6, IL-8 and/or IFN-γ antibodies are immobilized onto a selected surface exhibiting protein affinity, such as a well in, a polystyrene microtiter plate. Then, a test composition suspected of containing the wild-type or mutant iNOS, NF-kβ, TNF-α, IL-1β, IL-2, IL-6, IL-8 and/or IFN-γ protein antigen, such as a clinical sample, is added to the wells. After binding and washing to remove non-specifically bound immune complexes, the bound wild-type or mutant iNOS, NF-kβ, TNF-α, IL-1β, IL-2, IL-6, IL-8 and/or IFN-γ protein antigen may be detected. Detection is generally achieved by the addition of another anti-iNOS, NF-kβ, TNF-α, IL-1β, IL-2, IL-6, IL-8 and/or IFN-γ antibody that is linked to a detectable label. This type of ELISA is a simple "sandwich ELISA". Detection may also be achieved by the addition of a second anti-iNOS, NF-kβ, TNF-α, IL-1β, IL-2, IL-6, IL-8 and/or IFN-γ antibody, followed by the addition of a third antibody that has binding affinity for the second antibody, with the third antibody being linked to a detectable label.

In another exemplary ELISA, the samples suspected of containing the wild-type or mutant iNOS, NF-kβ, TNF-α, IL-1β, IL-2, IL-6, IL-8 and/or IFN-γ antigen are immobilized onto the well surface and then contacted with the anti-iNOS, NF-kβ, TNF-α, IL-1β, IL-2, IL-6, IL-8 and/or IFN-γ antibodies of the invention. After binding and washing to remove non-specifically bound immune complexes, the bound anti-iNOS, NF-kβ, TNF-α, IL-1β, IL-2, IL-6, IL-8 and/or IFN-γ antibodies are detected. Where the initial anti-iNOS, NF-kβ, TNF-α, IL-1β, IL-2, IL-6, IL-8 and/or IFN-γ antibodies are linked to a detectable label, the immune complexes may be detected directly. Again, the immune complexes may be detected using a second antibody that has binding affinity for the first anti-iNOS, NF-kβ, TNF-α, IL-1β, IL-2, IL-6, IL-8 and/or IFN-γ antibody, with the second antibody being linked to a detectable label.

Another ELISA in which the wild-type or mutant iNOS, NF-kβ, TNF-α, IL-1β, IL-2, IL-6, IL-8 and/or IFN-γ proteins, polypeptides or peptides are immobilized, involves the use of antibody competition in the detection. In this ELISA, labeled antibodies against wild-type or mutant iNOS, NF-kβ, TNF-α, TNF-α, IL-1β, IL-2, IL-6, IL-8 and/or IFN-γ protein are added to the wells, allowed to bind, and detected by means of their label. The amount of wild-type or mutant iNOS, NF-kβ, TNF-α, IL-1β, IL-2, IL-6, IL-8 and/or IFN-γ protein antigen in an unknown sample is then determined by mixing the sample with the labeled antibodies against wild-type or mutant iNOS, NF-kβ, TNF-α, IL-1β, IL-2, IL-6, IL-8 and/or IFN-γ before or during incubation with coated wells. The presence of wild-type or mutant iNOS, NF-kβ, TNF-α, IL-1β, IL-2, IL-6, IL-8 and/or IFN-γ protein in the sample acts to reduce the amount of antibody against wild-type or mutant iNOS, NF-kβ, TNF-α, IL-1β, IL-2, IL-6, IL-8 and/or IFN-γ protein available for binding to the well and thus reduces the ultimate signal. This is also appropriate for detecting antibodies against wild-type or mutant iNOS, NF-kβ, TNF-α, IL-1β, IL-2, IL-6, IL-8 and/or IFN-γ protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by, incubation with a chromogenic substrate such as urea and bromocresol purple or 2,2'-azino-di-(3-ethyl-benzthiazoline-6-sulfonic acid (ABTS) and $H_2O_2$, in the case of peroxidase as the enzyme label. Quantification is then achieved by measuring the degree of color generation, e.g., using a visible spectra spectrophotometer.

2. Immunohistochemistry

The antibodies of the present invention may also be used in conjunction with both fresh-frozen and formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

Second Generation Inhibitors or Enhancers

In addition to the inhibitory compounds initially identified, the inventor also contemplates that other sterically similar compounds may be formulated to mimic the key portions of the structure of the inhibitors and/or enhancers. Such compounds, which may include peptidomimetics of peptide inhibitors and/or enhancer, may be used in the same manner as the initial inhibitors and/or enhancers.

Certain mimetics that mimic elements of protein secondary structure are designed using the rationale that the peptide backbone of proteins exists chiefly to orientate amino acid side chains in such a way as to facilitate molecular interactions. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as is well known to the skilled artisan. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of computer-based chemical modeling is now well known. Using such methods, a chemical that specifically inhibits iNOS and/or proinflammatory cytokines can be designed, and then synthesized, following the initial identification of a compound that inhibits iNOS and/or proinflammatory cytokines activity and/or induction, but that is not specific or sufficiently specific to inhibit iNOS activity in individuals suffering from demylenating diseases or neural trauma. Also using such methods, a chemical that specifically enhances iNOS and/or proinflammatory cytokines can be designed, and then synthesized, following the initial identification of a compound that enhances iNOS and/or proinflammatory cytokines activity and/or induction. It will be understood that all such sterically similar constructs and second generation molecules fall within the scope of the present invention.

Optimization in Therapy

A compound identified as having the ability to inhibit or enhance the induction of iNOS and/or cytokines can be assayed its optimum therapeutic dosage alone or in combination with another anti-iNOS, anti-cytokine or anti-inflammatory agent. Such assays are well known to those of skill in the art, and include tissue culture or animal models for various disorders that are treatable with such agents.

Examples of such assays include those described herein and in U.S. Pat. No. 5,696,109, the disclosure of which is incorporated herein by reference in its entirety. For instance, an assay to determine the therapeutic potential of molecules in brain ischemia (stroke) evaluates an agent's ability to prevent irreversible damage induced by an anoxic episode in brain slices maintained under physiological conditions. An animal model of Parkinson's disease involving iatrogenic hydroxyl radical generation by the neurotoxin MPTP (Chiueh et al., 1992, incorporated herein by reference) may be used to evaluate the protective effects of iNOS or pro-inflammatory cytokine induction inhibitors. The neurotoxin, MPTP, has been shown to lead to the degeneration of dopaminergic neurons in the brain, thus providing a good model of experimentally induced Parkinson's disease (e.g. iatrogenic toxicity). An animal model of ischemia and reperfision damage is described using isolated iron-overloaded rat hearts to measure the protective or therapeutic benefits of an agent. Briefly, rats receive an intramuscular injection of an iron-dextran solution to achieve a significant iron overload in cardiac tissue. Heart are then isolated and then subjected to total global normothermic ischemia, followed by reperfusion with the perfusion medium used initially. During this reperfusion, heart rate, and diastolic and systolic pressures were monitored. Cardiac tissue samples undergo the electron microscopy evaluation to measure damage to mitochondria such as swelling and membrane rupture, and cell necrosis. Comparison of measured cardiac function and cellular structural damage with or without the agent or iron-overloading after ischemia/reoxygenation is used to determine the therapeutic effectiveness of the agent. Another assay measures acute lung injury (ALI) in sepsis and endotoxemia. LPS/endotoxin-induced ALI in pigs may be used as a model to measure the effectiveness of an agent for the treatment of sepsis-induced ALI in humans. After infusion of LPS/endotoxin, changes in lung wet-to-dry weight ratio, lung lipid peroxidation, pulmonary arterial hypertension, arterial hypoxemia and decreased dynamic pulmonary compliance is measured to determine the effectiveness of an agent in preventing LPS/endotoxin induced damage.

One of skill in the art will recognize that there are other assays and models for disease states available, including testing in humans. These assays may be used to measure the effectiveness of iNOS and/or pro-inflammatory cytokine induction suppressor and/or inhibitor agent for a particular disease or condition, determine the best agent or combination of agents to be used, and determine the dosages for administration, with routine experimentation.

Combination Therapy

The suppressor agents of the invention may also be used in combination with other therapeutic agents, for example, anti-inflammatory agents, particularly non-steroidal anti-inflammatory drugs (NSAIDs), vasodilator prostaglandins including prostacyclin and prostaglandin E sub 1, cancer chemotherapeutic agents including cisplatin, NO donors or NO inhalation therapy, or PAF-receptor antagonists.

Pharmaceutical Compositions

A further aspect of the invention are compositions comprising a first iNOS and/or proinflammatory cytokine inhibitor and/or induction suppressor in a pharmaceutically-acceptable excipient. In a preferred embodiment, the iNOS and/or proinflammatory cytokine inhibitor and/or induction suppressor is selected from the group consisting of lovastatin, mevastatin, FPT inhibitor II, forskolin, rolipram, phenylacetate (NaPA), N-acetyl cysteine (NAC), PDTC, 4-phenylbutyrate (4PBA), 5-aminoimmidazole-4-carboxamide ribonucleoside (AICAR), theophylline, papaverine, cAMP, 8-bromo-cAMP, (S)-cAMP, and salts, analogs, or derivatives thereof.

A further aspect of the invention is a composition which comprises at least two iNOS and/or proinflammatory cytokine inhibitor and/or induction suppressor in a pharmaceutically-acceptable excipient. In a preferred embodiment, at least one of the iNOS and/or proinflammatory cytokine inhibitors or suppressors is selected from the group consisting of lovastatin, mevastatin, FPT inhibitor II, forskolin, rolipram, phenylacetate (NaPA), N-acetyl cysteine (NAC), PDTC, 4-phenylbutyrate (4PBA), 5-aminoimmidazole-4-carboxamide ribonucleoside (AICAR), theophylline, papaverine, cAMP, 8-bromo-cAMP, (S)-cAMP, and salts, analogs, or derivatives thereof.

A further aspect of the invention are compositions comprising a first iNOS and/or proinflammatory cytokine stimulator, enhancer, or inducer in a pharmaceutically-acceptable excipient. A further aspect of the invention is a composition which comprises at least two iNOS and/or proinflammatory cytokine stimulator, enhancer, or inducer in a pharmaceutically-acceptable excipient. In another embodiment, the enhancer, stimulator or inducer of iNOS or proinflammatory cytokines is H-89, myristoylated PKI, (R)-cAMP, forskolin, 8-bromo-cAMP, rolipram and salts, analogs, or derivatives thereof. Inducers, stimulators or enhancers of iNOS and/or proinflammatory cytokines may be tissue specific, and such tissues include microglia cells.

In certain embodiments, the suppressors, inhibitors, stimulators, enhancers and/or inducers of iNOS and/or proinflammatory cytokines may be administered of from about 0.001 mg per kg body weight per day (mg/kg/day) to about 20 mg/kg/day. Of course it is understood that of from about 0.001 mg/kg/day to about 20 mg/kg/day includes doses of from about 0.001, about 0.002, about 0.003, about 0.004, about 0.005, about 0.006, about 0.007, about 0.008, about 0.009, about 0.01, about 0.011, about 0.012, about 0.013, about 0.014, about 0.015, about 0.016, about 0.017, about 0.018, about 0.019, about 0.02, about 0.021, about 0.022, about 0.023, about 0.024, about 0.025, about 0.026, about 0.027, about 0.028, about 0.029, about 0.03, about 0.032, about 0.034, about 0.036, about 0.038, about 0.04, about 0.042, about 0.044, about 0.046, about 0.048, about 0.05, about 0.055, about 0.06, about 0.065, about 0.07, about 0.075, about 0.08, about 0.085, about 0.09, about 0.095, about 0.10, about 0.11, about 0.12, about 0.13, about 0.14, about 0.15, about 0.16, about 0.17, about 0.18, about 0.19, about 0.20, about 0.21, about 0.22, about 0.23, about 0.24, about 0.25, about 0.26, about 0.27, about 0.28, about 0.29, about 0.30, about 0.31, about 0.32, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.65, about 0.70, about 0.75, about 0.80, about 0.85, about 0.90, about 0.95, about 1.00, about 1.05, about 1.10, about 1.15, about 1.20, about 1.25, about 1.30, about 1.35, about 1.40, about 1.45, about 1.50; about 1.55, about 1.60, about 1.65, about 1.70, about 1.75, about 1.80, about 1.85, about 1.90, about 1.95, about 2.00, about 2.10, about 2.20, about 2.30, about 2.40, about 2.50, about 2.60, about 2.70, about 2.80, about 2.90, about 3.00, about 3.10, about 3.20, about 3.30, about 3.40, about 3.50, about 3-60, about 3.70, about 3.80, about 3.90, about 4.00, about 4.10, about 4.20, about 4.30, about 4.40, about 4.50, about 4.60, about 4.70, about 4.80, about 4.90, about 5.00, about 5.25, about 5.5, about 5.75, about 6.00, about 6.25, about 6.5, about 6.75, about 7.0, about 7.25, about 7.5, about 7.75, about 8.00, about 8.25, about 8.5, about 8.75, about 9.0, about 9.25, about 9.5, about 9.75, about 10.00, about 10.5, about 11.0 about 11.5, about 12.00, about 12.5, about 13, about 13.5, about 14.00, about 14.5, about 15, about 15.5, about 16, about 16.5, about 17.0, about 17.5, about 18.00, about 18.5, about 19.0, about 19.5, and about 20.00 mg/kg/day. One may select any dosages described herein as a range of dosage administration, such as a range of about 1.45 mg/kg/day to about 11 mg/kg/day, or about 0.24 mg/kg/day to about 14 mg/kg/day, etc., as well as any values within such ranges that are not specifically recited.

One of skill in the art will recognize that the toxicity for different suppressors, inhibitors, enhancer, stimulator and/or inducers of iNOS and/or proinflammatory cytokines either alone, in combination with each other, or in combination with other pharmaceuticals may limit the maximum dose administered to a patient. Dosage optimization for maximum benefits with minimal toxicity in a patient may be optimized by those of skill in the art without undue experimentation using any method to determine optimum dosage in a patient as is known to those of the art, or using the methods described herein. Additionally, the suppressors, inhibitors, enhancer, stimulator and/or inducers of the present invention may be obtained from commercial vendors and administered in any of the methods or dosages described in exemplary texts, such as "Remington's Pharmaceutical Sciences" 8th and 15th Editions; the "Physicians' Desk Reference", 1998 Edition, the Merck Index, 11th Edition, each incorporated herein in their entirety).

In certain preferred embodiments, lovastatin or mevastatin is taken orally with food once daily at about 0.01 mg per kg body weight per day (mg/kg/day) to about 0.24 mg/kg/day. Of course it is understood that about 0.01 mg/kg/day to about 0.24 mg/kg/day includes doses of about 0.01, about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, about 0.20, about 0.21, about 0.22, about 0.23, to about 0.24 mg/kg or so per day. In a preferred embodiment, lovastatin or mevastatin is taken orally with food once daily at about 0.25 mg per kg body weight per day (mg/kg/day) to about 0.55 mg/kg/day. Of course it is understood that about 0.25 mg/kg/day to about 0.55 mg/kg/day includes doses of about 0.25, about 0.26, about 0.27, about 0.28, about 0.29, about 0.30, about 0.31, about 0.32, about 0.33, about 0.33, about 0.34, about 0.35, about 0.36, about 0.37, about 0.38, about 0.39, about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, to about 0.55 mg/kg or so per day. When two or more iNOS and/or proinflammatory cytokine inhibitors and/or induction suppressors are administered, the combined dose of two or more iNOS and/or proinflammatory cytokine inhibitors and/or induction suppressors is preferably about 0.25 mg/kg/day to about 0.55 mg/kg/day. It is also specifically contemplated by the inventor that a patient may be treated with about 0.55 mg/kg/day to about 5 mg per day or more of lovastatin and/or mevastatin, including about 0.60, about 0.65, about 0.70, about 0.75, about 0.80, about 0.85, about 0.90, about 0.95, about 1.00, about 1.05, about 1.10, about 1.15, about 1.20, about 1.25, about 1.30, about 1.35, about 1.40, about 1.45, about 1.50, about 1.55, about 1.60, about 1.65, about 1.70, about 1.75, about 1.80, about 1.85, about 1.90, about 1.95, about 2.00, about 2.05, about 2.10, about 2.15, about 2.20, about 2.25, about 2.30, about 2.35, about 2.40, about 2.45, about 2.50, about 2.55, about 2.60, about 2.65, about 2.70, about 2.75, about 2.80, about 2.85, about 2.90, about 2.95, about 3.00, about 3.10, about 3.20, about 3.30, about 3.40, about 3.50, about 3.60, about 3.70, about 3.80, about 3.90, about 4.00, about 4.10, about 4.20, about 4.30, about 4.40, about 4.50, about 4.60, about 4.70, about 4.80, about 4.90, to about 5.00 mg/kg or more per day. Compositions for such treatment are described in, for example U.S. Pat. Nos. 3,983,140, and 4,231,938, the disclosures of which are incorporated herein by reference in their entirety.

In yet another preferred embodiment of the invention nitric oxide induced cytotoxicity may be prevented or reduced in a patient by treatment with from about 0.01 mg/kg/day to about 2.0 mg/kg/day of rolipram, including about 0.01, about 0.02, about 0.04, about 0.06, about 0.08, about 0.10, about 0.12, about 0.14, about 0.16, about 0.18, about 0.20, about 0.22, about 0.24, about 0.26, about 0.28, about 0.30, about 0.32, about 0.34, about 0.36, about 0.38, about 0.40, about 0.42, about 0.44, about 0.46, about 0.48, about 0.50, about 0.52, about 0.54, about 0.56, about 0.58, about 0.60, about 0.62, about 0.64, about 0.66, about 0.68, about 0.70, about 0.72, about 0.74, about 0.76, about 0.78, about 0.80, about 0.82, about 0.84, about 0.86, about 0.88, about 0.90, about 0.92, about 0.94, about 0.96, about 0.98, about 1.00, about 1.01, about 1.02, about 1.04, about 1.06, about 1.08, about 1.10, about 1.12, about 1.14, about 1.16, about 1.18, about 1.20, about 1.22, about 1.24, about 1.26, about 1.28, about 1.30, about 1.32, about 1.34, about 1.36, about 1.38, about 1.40, about 1.42, about 1.44, about 1.46, about 1.48, about 1.50, about 1.52, about 1.54, about 1.56, about 1.58, about 1.60, about 1.62, about 1.64, about 1.66, about 1.68, about 1.70, about 1.72, about 1.74, about 1.76, about 1.78, about 1.80, about 1.82, about 1.84, about 1.86, about 1.88, about 1.90, about 1.92, about 1.94, about 1.96, about 1.98, to about 1.00 or more mg/kg/day. Preferably 0.1 mg/kg/day to about 0.7 mg/kg/day is used and most preferably about 0.5 mg/kg/day. Compositions for such treatment have been described in, for example, U.S. Pat. No. 5,672,622, specifically incorporated herein by reference in its entirety.

In yet another preferred embodiment of the invention, nitric oxide induced cytotoxicity may be prevented or reduced in a patient by treatment with about 0.01 mg/kg/day to about 1.0 mg/kg/day of forskolin, including about 0.01, about 0.02, about 0.04, about 0.06, about 0.08, about 0.10, about 0.12, about 0.14, about 0.16, about 0.18, about 0.20, about 0.22, about 0.24, about 0.26, about 0.28, about 0.30, about 0.32, about 0.34, about 0.36, about 0.38, about 0.40, about 0.42, about 0.44, about 0.46, about 0.48, about 0.50, about 0.52, about 0.54, about 0.56, about 0.58, about 0.60, about 0.62, about 0.64, about 0.66, about 0.68, about 0.70, about 0.72, about 0.74, about 0.76, about 0.78, about 0.80, about 0.82, about 0.84, about 0.86, about 0.88, about 0.90, about 0.92, about 0.94, about 0.96, about 0.98, and about 1.0 or more mg/kg/day. Compositions for such treatment have been described in, for example, U.S. Pat. No. 5,371,104, incorporated herein by reference in its entirety.

In still yet another preferred embodiment of the invention, nitric oxide induced cytotoxicity may be prevented or reduced in a patient by treatment with about 0.1 mg/kg/day to about 20 mg/kg/day of a farnesyl protein transferase inhibitor, for example, FPT II. Specifically contemplated is any dose within this range, including about 0.1, about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5; about 10.0, about 10.5, about 71.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5 and 20.0 or more mg/kg/day. Preferably about 0-5 mg/kg/day to 10 mg/kg/day is used. Compositions for such treatment are described in, for example, U.S. Pat. No. 5,420,157, specifically incorporated herein by reference in its entirety.

In still yet another preferred embodiment of the invention, nitric oxide induced cytotoxicity may be prevented or reduced in a patient by treatment with up to about 50 mg/kg/day of N-acetyl cysteine. Of course, it will be understood that up to about 50 mg/kg/day includes all dosages described above generically for the iNOS and/or proinflammatory cytokine inhibitors and/or induction suppressors of the present invention, and dosages of from about 20 mg/kg/day to about 50 mg/kg/day, including of from about 20, about 20.5, about 21, about 21.5, about 22.0, about 22.5, about 23, about 23.5, about 24, about 24.5, about 25, about 25.5, about 26, about 26.5, about 27, about 27.5, about 28, about 28.5, about 29, about 29.5, about 30, about 30.5, about 31.5, about 32, about 32.5, about 33, about 33.5, about 34, about 34.5, about 35, about 35.5, about 36, about 36.5, about 37, about 37.5, about 38, about 38.5, about 39, about 39.5, about 40, about 40.5, about 41, about 41.5, about 42, about 42.5, about 43, about 43.5, about 44, about 44.5, about 45, about 45.5, about 46, about 46.5, about 47, about 47.5, about 48, about 48.5, about 49, about 49.5, and about 50.0 or more mg/kg/day. Specific compositions for such treatment are disclosed in, for example, U.S. Pat. No. 5,080,960, incorporated herein by reference in its entirety.

TABLE 1

Contemplated Ranges for Dose Administration in the Methods of the Invention

| | | |
|---|---|---|
| Lovastatin | Range | About 0.001 mg/kg/day to about 20.00 mg/kg/day |
| | Preferred Range | About 0.01 to about 5.00 mg/kg/day |
| | More Preferred Range | About 0.25 to about 0.55 mg/kg/day |
| Mevastatin | Range | About 0.001 mg/kg/day to about 20.00 mg/kg/day |
| | Preferred Range | About 0.01 to about 5.00 mg/kg/day |
| | More Preferred Range | About 0.25 to about 0.55 mg/kg/day |
| Phenyl Acetic Acid | Range | About 0.001 mg/kg/day to about 20.00 mg/kg/day |
| N-acetyl Cysteine | Range | About 0.001 mg/kg/day to about 50.00 mg/kg/day |
| | Preferred Range | About 0.1 to about 5.0 mg/kg/day |
| PTDC | Range | About 0.001 mg/kg/day to about 20.00 mg/kg/day |
| Forskolin | Range | About 0.001 mg/kg/day to about 20.00 mg/kg/day |
| | Preferred Range | About 0.01 to about 1.0 mg/kg/day |
| Rolipram | Range | About 0.001 mg/kg/day to about 20.00 mg/kg/day |
| | Preferred Range | About 0.01 to about 2.0 mg/kg/day |
| | More Preferred Range | About 0.1 to about 0.7 mg/kg/day |
| | Even More Preferred Range | About 0.5 mg/kg/day |
| cAMP | Range | About 0.001 mg/kg/day to about 20.00 mg/kg/day |
| 8-bromo-cAMP | Range | About 0.001 mg/kg/day to about 20.00 mg/kg/day |
| FTP inhibitor II | Range | About 0.001 mg/kg/day to about 20.00 mg/kg/day |
| | Preferred Range | About 0.1 to about 20.0 mg/kg/day |
| | More Preferred Range | About 0.5 to about 10.0 mg/kg/day |
| H-89 | Range | About 0.001 mg/kg/day to about 20.00 mg/kg/day |
| Myristoylated PKI | More Preferred Range | About 0.001 mg/kg/day to about 20.00 mg/kg/day |
| (R)-cAMP | More Preferred Range | About 0.001 mg/kg/day to about 20.00 mg/kg/day |
| (S)-cAMP | Range | About 0.001 mg/kg/day to about 20.00 mg/kg/day |
| 4-phenylbutyrate (4PBA) | Range | About 0.001 mg/kg/day to about 20.00 mg/kg/day |
| 5-amino-immidazole-4-carboxamide ribonucleoside (AICAR) | Range | About 0.001 mg/kg/day to about 20.00 mg/kg/day |
| theophylline | Range | About 0.001 mg/kg/day to about 20.00 mg/kg/day |
| papaverine | Range | About 0.001 mg/kg/day to about 20.00 mg/kg/day |

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained. It will be understood to one of skill in the art that the actual amount of active ingredient used may vary depending on a number of variables such as the symptoms of the patient, the size of the patient and the age of the patient.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally e.g. intraperitoneally or intravascularly. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention; of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or other untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Therapeutic Kits

In one aspect, the invention provides a therapeutic kit comprising, in suitable container means, a therapeutically-effective amount of one or more iNOS inhibitors and/or proinflammatory cytokine inhibitors and/or induction suppressors selected from the group consisting of lovastatin, mevastatin, FPT inhibitor II, forskolin, rolipram, phenylacetate (NaPA), N-acetyl cysteine (NAC), PDTC, 4-phenylbutyrate (4PBA), 5-aminoimmidazole-4-carboxamide ribonucleoside (AICAR), theophylline, papaverine, cAMP, 8-bromo-cAMP, (S)-cAMP, and salts, analogs, or derivatives therefrom, and if desired, a pharmaceutically acceptable excipient. The compositions may be formulated such that they are suitable for oral or parenteral administration.

In another aspect, the invention provides a therapeutic kit comprising, in suitable container means, a therapeutically-effective amount of one or more iNOS inhibitors and/or proinflammatory cytokine inhibitors and/or induction suppressors selected from agents that have certain traits or modes of action common to those of the suppressors and/or inhibitors identified herein. Preferred substances would either inhibit the Ras/Raf/MAP kinase pathway, inhibit and/or suppress the induction and/or activation of NF-kB, inhibit mevalonate synthesis, be an enhancer of protein kinase A, and/or inhibit the farnasylation of proteins, including but not limited to Ras. In certain embodiments the inhibitor of mevalonate synthesis may be an inhibitor of HMG-CoA reductase or suppressor of its induction. In certain aspects the inhibitor of HMG-CoA reductase is a stimulator of AMP-activated protein kinase. In certain other embodiments the inhibitor of inducible nitric oxide synthase and/or proinflammatory cytokines may be an inhibitor of mevalonate pyrophosphate decarboxylase or suppressor of its induction. In other embodiments the substance is an antioxidant. In other embodiments the substance is an enhancer of intracellular cAMP. The enhancer of intracellular cAMP may be an inhibitor of cAMP phosphodiesterase and/or suppressor of its induction. In other embodiments the substance is a farnesyl protein transferase inhibitor and/or induction suppressor.

In other preferred embodiments, a preferred stimulators or enhancers would include a PKA inhibitor.

The other preferred embodiments, the inhibitors, suppressors stimulators or enhancers would be identified by the screening assay described herein.

The diagnostic/therapeutic kits comprising the pharmaceutical compositions disclosed herein will generally contain, in suitable container means, a therapeutically-effective amount of an iNOS and/or proinflammatory cytokine inhibitor and/or induction suppressor in a pharmaceutically acceptable excipient. The kit may have a single container means that contains the iNOS and/or proinflammatory cytokine inhibitor and/or induction suppressor and a suitable excipient or it may have distinct container means for each compound.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

When the components of the kit are provided in one or more liquid solutions, the liquid solution is an aqueous solution, with a sterile aqueous solution being particularly preferred. The iNOS and/or proinflammatory cytokine inhibitor(s) and/or induction suppressor(s) may also be formulated into a syringeable composition. In which case, the container means may itself be a syringe, or other such like apparatus, from which the formulation may be administered into the body, preferably by injection or even mixed with the other components of the kit prior to injection. The iNOS and/or proinflammatory inhibitor and/or induction suppressor to be administered may be a single inhibitor, or a composition comprising two or more inhibitors in a single or multiple dose for administration. Alternatively, one or more inhibitors may be administered consecutively or concurrently with other agents as deemed appropriate by the clinician. Dosage of each of the compositions will vary from subject to subject depending upon severity of conditions, size, body weight, etc. The calculation and adjustment of dosages of pharmaceutical compositions is well-known to those of skill in the art.

In an alternate embodiment, components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the iNOS and/or proinflammatory cytokin inhibitor and/or induction suppressor may be placed, preferably, suitably allocated. Where two or more inhibitors and/or supressors are provided, the kit will also generally contain a second vial or other container into which this additional inhibitors and/or suppressors may be formulated. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained. Alternatively, the vials may be prepared in such a way as to permit direct introduction of the composition into an intravenous drug delivery system.

Irrespective of the number or type of containers, the kits of the invention may also comprise, or be packaged with, an instrument for assisting with the injection/administration or placement of the ultimate iNOS and/or proinflammatory cytokine inhibitor and/or induction suppressor composition within the body of an animal. Such an instrument may be a syringe, pipette, forceps, measured spoon, eye dropper or any such medically approved delivery vehicle.

The term "iNOS and/or proinflammatory cytokine inhibitor and/or induction suppressor" and also includes derivatives of the compounds disclosed herein which exhibit at least some biological activity in common with the unmodified compound. In general these compounds are inhibitors of inducible nitric oxide synthase and/or proinflammatory cytokines.

The following examples are included to demonstrate new and inventive methods of the inventor and preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Inhibition of iNOS and Cytokines

Reagent Recombinant rat IFN-γ, DMEM/F-12 medium, RPMI 1640 medium, fetal bovine serum and Hanks' balanced salt solution (HBSS) were obtained from GIBCO. Human IL1-β was obtained from Genzyme, USA. Mouse recombinant TNF-α was obtained from Boehringer Mannheim, Germany. Lovastatin, mevastatin and farnesyl pyrophosphate were obtained from Biomol, USA and CalBiochem, USA. Cholesterol, ubiquinone, arginase, N-Acetyl cystein (NAC), pyrrolidine dithiocarbamate (PDTC), NADPH, FAD, tetrahydrobiopterin, Dowen-50W and LPS (*Escherichia coli*) were obtained from Sigma (St. Louis, Mo.). $N^G$-methyl-L-arginine (L-NMA), FPT inhibitor II and antibodies against mouse macrophage iNOS were obtained from Calbiochem, USA. Immunoassay kits for TNF-α, IL-1β and IL-6 were obtained from R&D, USA. NF-kβ DNA binding protein detection kit was obtained from GIBCO/BRL, USA. [γ-$^{32}$P] ATP (3000 Ci/mmol) and L-[2,3,4,5-$^3$H] arginine were obtained from Amersham, USA. Sodium salt of phenylacetic acid (NaPA) was prepared from phenylacetic acid (Sigma) and NaOH as described (Samid et al., 1992).

Induction of NO Production in Rat Astrocytes, Microglia and C6 Glial Cells Astrocytes were prepared from rat cerebral tissue as described by McCarthy et al. (1980). Cells were maintained in DMEM/F-12 medium containing 10% fetal bovine serum (FBS). After 10 days in culture, astrocytes were separate from microglia and oligodendrocytes by shaking for 24 h in an orbital shaker at 240 rpm. To ensure the complete removal of all oligodendrocytes and microglia, the shaking was repeated twice after a gap of one or two days before subculturing. The microglial contamination was checked by non-specific esterase staining and oligodendrocytes were examined by immunofluorescence using antibodies against GC (McCarthy et al., 1980). Cells were trypsinized, subcultured and stimulated with LPS or different cytokines in serum-free DMEM/F-12 medium.

Microglial cells were isolated from mixed glial cultures according to the procedure of Guilian et al. (1986). Briefly, on day 7 to 9 the mixed glial cultures were washed 3 times with DMEM/F-12 and subjected to a shake at 240 rpm for 2 h at 37° C. on a rotary shaker. The floating cells were washed and seeded on to plastic tissue culture flasks and incubated at 37° C. for 2 h. The attached cells were removed by trypsinization and seeded on to new plates for further studies. Ninety to ninety-five percent of this preparation was found to be positive for non-specific esterase, a marker for macrophages and microglia. For the induction of NO production, cells were stimulated with LPS or cytokines in serum-free condition.

C6 glial cells, obtained from ATCC, were also maintained and induced with different stimuli as indicated above.

Treatment of Cells With iNOS Inhibitors Cells in culture were treated with these compounds by addition of these compounds to the cell culture media. Dose ranges are provided in the accompanying figures and tables.

Isolation of Rat Macrophages and Induction of NO Production Resident macrophages were obtained from rats by peritoneal lavage with sterile RPMI 1640 medium containing 1% fetal bovine serum and 100 µg/ml gentamicin (Wang et al., 1995). Cells were washed three times with RPMI 1640 at 4° C. All cell cultures were maintained at 37° C. in a humidified incubator containing 5% $CO_2$ in air. Macrophages, at a concentration of 2×10$^6$/ml in RPMI 1640 medium containing L-glutamine and gentamicin, were added in volumes of 800 µl to a 35 mm plate. After 1 h, nonadherent cells were removed by washing and 800 µl of serum-free RPMI 1640 medium with various stimuli were added to the adherent cells. After 24 h incubation in 5% $CO_2$ in air at 37° C., the culture supernatants were transferred to measure NO production (Geng et al., 1995; Wang et al., 1995).

Assay of the Viability of Cells Treated with Lovastatin, Mevastatin, NaPA, TNF-α, IL-1β, IFN-γ, or LPS The cytotoxic effects of the compounds used in various studies disclosed herein were determined by measuring the cell viability by trypan blue exclusion.

It was found that none of the compounds lovastatin, mevastatin, NaPA, TNF-α, IL-1β, IFN-γ, or LPS had a significant effect on the viability of astrocytes, microglia or macrophages. Changes in cell viability can therefore be ruled out as a cause for the disclosed findings.

Assays of NO synthesis and NOS Activity Synthesis of NO was determined by assay of culture supernatants for nitrite, a stable reaction product of NO with molecular oxygen. Briefly, 400 µl of culture supernatant was allowed to react with 200 µl of Griess reagent (Feinstein et al., 1994a; Wang et al., 1995) and incubated at room temperature for 15 min. The optical density of the assay samples was measured spectrophotometrically at 570 nm. Fresh culture media served as the blank in all experiments. Nitrite concentrations were calculated from a standard curve derived from the reaction of $NaNO_2$ in the assay. Protein was measured by the procedure of Bradford (1976).

NOS activity was measured directly by production of L-[2,3,4,5-$^3$H]citrulline from L-[2,3,4,5-$^3$H] arginine (Feinstein et al., 1994a). In these studies, 50 µl of macrophage homogenate was incubated at 37° C. in presence of 50 mM Tris-HCl (pH 7.8), 0.5 mM NADPH, 5 µM FAD, 5 µM tetrahydrobiopterin and 12 µM L-[2,3,4,5-$^3$H]arginine (118 mCi/mmol) in a total volume of 200 µl. Assays were carried out for 30 to 40 min and the production of L-[2,3,4,5-$^3$H] citrulline was linear. The reactions were stopped by addition of 800 µl of ice-cold 20 mM HEPES (pH 5.5) followed by addition of 2 ml of Dowex-50W equilibrated in the same buffer. The samples were then centrifuged and the concentration of L-[$^3$H]citrulline was determined in the supernatant by liquid scintillation counting. Protein was measured by the procedure of Bradford (1976).

Immunoblot analysis for iNOS Following 24 h incubation in the presence or absence of stimuli by different cytokines or LPS, macrophages were scraped off, washed with Hank's buffer, and homogenized in 50 mM Tris-HCl (pH 7.4) containing protease inhibitors (1 nM PMSF, 5 µg/ml aprotinin, 5 µg/ml pepstatin A, and 5 µg/ml leupeptin). After electrophoresis the proteins were transferred onto a nitrocellulose membrane, and the iNOS band was visualized by immunoblotting with antibodies against mouse macrophage iNOS and [$^{125}$I]-labeled protein A (Singh et al., 1988).

Cells pre-incubated in serum-free media with different concentrations of lovastatin (5 or 10 µM) or NaPA (2 or 5 mM) or a combination of 2 µM lovastatin and 2 mM NaPA for 8 h received 1.0 µg/ml of LPS. Cell homogenates were electrophoresed, transferred on nitrocellulose membrane and immunoblotted with antibodies against mouse macrophage iNOS as described in Example 7. Western blot analysis for iNOS protein of LPS-stimulated astrocytes clearly showed that both lovastatin and NaPA significantly inhibited the LPS-mediated induction of iNOS protein. A combination of lovastatin and NaPA at dose lower than the one used individually almost completely inhibited LPS-induced production of NO and expression of iNOS.

RNA isolation, Northern blot analysis, and reverse-transcriptase coupled polymerase chain reaction (RT-PCR) Stimulated peritoneal macrophages were taken out from culture dishes directly by adding Ultraspec-II RNA reagent (Biotecx Laboratories Inc.) and total RNA was isolated according to the manufacturer's protocol. For northern blot analyses, 20 μg of total RNA was electrophoresed on 1.2% denaturing formaldehyde-agarose gels, electrotransferred to Hybond-Nylon Membrane (Amersham) and hybridized at 68° C. with $^{32}$P-labeled cDNA probe using Express Hyb hybridization solution (Clontech) as described by the manufacturer. The cDNA probe was made by PCR™ amplification using two primers (forward primer: 5'-CTCCTTCAAAGAG-GCAAAAATA-3' (SEQ ID NO:1); reverse primer: 5'-CACT-TCCTCCAGGATGTTGT-3' (SEQ ID NO:2)) (Geller et al., 1993). After hybridization filters were washed two to three times in solution I (2×SSC, 0.05% SDS) for 1 h at room temperature followed by solution II (0.1×SSC, 0.1% SDS) at 50° C. for another hour. The membranes were then dried and exposed to X-ray film (Kodak). The same filters were stripped and rehybridized with probes for GAPDH. The relative mRNA content for iNOS was measured after scanning the bands with a Biorad (Model GS-670) imaging densitometer.

Five micrograms of total RNA was reverse transcribed by using oligo-dT by using 1 mM of each dNTP, 40 U of RNase inhibitor (Promega), 50 U of Moloney murine leukemia virus (M-MLV) reverse transcriptase (Stratagene) and reverse transcription buffer (Stratagene) in a 50 μl reaction volume. The integrity of the RNAs was checked by running an alkaline RNA gel. The first strand cDNA synthesis was carried out at 37° C. for 1 h. To check the quality of cDNAs for iNOS (730 bp) and for GAPDH (528 bp), the same cDNA was used as a control to amplify 1.5 kb fragment of a iNOS gene. Five microliters of this 1st strand cDNA was used to amplify by PCR™ in 100 μl reaction volume containing 0.2 μM of each primer, 200 μM of each dNTP, manufacturer-supplied 1× buffer containing 1.5 mM $MgCl_2$ and 2.5 U of Taq DNA polymerase (Stratagene). A total of 30 cycles were run with each cycle having denaturation at 91° C. for 1 min, annealing at 54° C. for 1 min and extension at 72° C. for 2 min. Final extension was carried out 72° C. for 10 min. Oligonucleotide primers for iNOS (forward primer: 5'-CTCCTTCAAAGAG-GCAAAAATA-3' (SEQ ID NO:1); reverse primer: 5'-CACT-TCCTCCAGGATTGGTG-3' (SEQ ID NO:3)) were synthesized based on the sequences described by Geller et al. (1993). The PCR™ amplified products were flirter confirmed by restriction mapping. Oligonucleotide primers for glyceraldehyde 3-phosphate dehydrogenase (GAPDH) (forward primer: 5'-ACCACCATGGAGAAGGCTGG-3' (SEQ ID NO:4); reverse primer: 5'-CTCAGTGTAGCCCAGGAT GC-3' (SEQ ID NO:5)) were used as control. PCR™ products were visualized by electrophoresis in 1.5% agarose gel containing 0.5 μg/ml ethidium bromide and photographed with a DS-34 type camera. The relative mRNA content for iNOS was measured after scanning the bands with a Biorad (Model GS-670) imaging densitometer.

After 5 h of incubation, cells were taken out directly by adding ultraspec-II RNA reagent (Biotecx Laboratories Inc., Houston, Tex.) to the plates for isolation of total RNA, and northern blot analysis for iNOS mRNA was carried out as described in Example 7. The Northern blot analysis for iNOS mRNA of LPS-stimulated astrocytes clearly showed that both lovastatin (5 or 10 μM) and NaPA (2 or 5 mM) significantly inhibited the LPS-mediated induction of iNOS mRNA. A combination of lovastatin and NaPA, at 2 μM and 2 mM respectively, at a dose lower than the one used individually almost completely inhibited LPS-induced production of NO and expression of iNOS.

Determination of TNF-α, IL-1β and IL-6 in culture supernatants Macrophages were stimulated with LPS and IFN-γ in serum-free RPMI 1640 media for 24 h in the presence or absence of NAC, PDTC, lovastatin or NaPA, and concentrations of TNF-α, IL-1β and IL-6 were measured in culture supernatants by using a high-sensitivity enzyme-linked immunosorbent assay (ELISA; Genzyme, Cambridge, Mass.; R&D Systems, USA) according to the manufacturer's instructions.

Preparation of Nuclear Extracts and Electrophoretic Mobility shift assay Nuclear extracts from stimulated or unstimulated astrocytes ($1 \times 10^7$ cells) were prepared using the method of Dignam et al. (1983) with slight modification. Cells were harvested, washed twice with ice-cold phosphate-buffered saline and lysed in 400 μl of buffer A (10 mM HEPES, pH 7.9, 10 mM KCl, 2 mM $MgCl_2$, 0.5 mM DTT, 1 mM PMSF, 5 μg/ml aprotinin, 5 μg/ml pepstatin A, and 5 μg/ml leupeptin (Sigma, St. Louis, Mo.) containing 0.1% Nondet P-40 for 15 min on ice, vortexed vigorously for 15 s, and centrifuged at 14,000 rpm for 30 s. The pelleted nuclei were resuspended in 40 μl of buffer B (20 mM HEPES, pH 7.9, 25% (v/v) glycerol, 0.42 M NaCl, 1.5 mM $MgCl_2$, 0.2 mM EDTA, 0.5 mM DTT, 1 mM PMSF, 5 μg/ml aprotinin, 5 μg/ml pepstatin A, and 5 μg/ml leupeptin). After 30 min on ice, lysates were centrifuged at 14,000 rpm for 10 min. Supernatants containing the nuclear proteins were diluted with 20 μl of modified buffer C (20 mM HEPES, pH 7.9, 20% (v/v) glycerol, 0.05 M KCl, 0.2 mM EDTA, 0.5 mM DTT, and 0.5 mM PMSF) and stored at −70° C. until use. Nuclear extracts were used for the electrophoretic mobility shift assay using the NF-kβ DNA binding protein detection system kit (GIBCO/BRL), according to the manufacturer's protocol.

Inhibition Of LPS- And Cytokine-Induced Production Of NO By Lovastatin To examine whether cytokine-induced NO production is inhibited by lovastatin, rat primary astrocytes were stimulated with different combinations of LPS, TNF-α, IL-1β and IFN-γ (i.e. LPS+TNF-α, LPS+IFN-γ, TNF-α+IL-1β, TNF-α+IFN-γ) for 24 h and the production of NO was measured as described above. Cells, pre-incubated in serum-free media with 10 μM lovastatin for 8 h, received different combinations of LPS and cytokines. Concentration of different stimuli were: LPS, 0.5 μg/ml; TNF-α, 20 ng/ml; IL-1β, 50 ng/ml; IFN-γ, 50 U/ml. After 24 h of incubation, the production of nitrite was measured in supernatants. Data was taken as the mean±S.D. of three different studies. All the combinations of LPS and cytokines significantly induced the production of NO, however, the addition of 10 μM lovastatin to astrocytes inhibited the NO production and induction of iNOS protein. Cell homogenates were analyzed for iNOS protein by immunoblotting as described. Under similar conditions lovastatin was also found to inhibit LPS- and cytokine-induced NO production in rat C6 glial cells.

Inhibition of LPS-Induced Expression of iNOS by Lovastatin, NaPA and Mevastatin An examination was made of the effect of lovastatin, mevastatin and mevalonate pyrophosphate decarboxylase (NaPA) on the induction of iNOS and production of NO. As shown in Table 1, it was found that bacterial LPS at a concentration of 1.0 μg/ml induced the production of NO by about 8-fold. The inhibition of NO production by arginase, an enzyme that degrades the substrate (L-arginine) of NOS and L-NMA, a competitive inhibitor of NOS, indicate that LPS-induced NO production in astrocytes is dependent on NOS-mediated arginine metabolism (Table 2). Lovastatin or mevastatin alone was neither stimulatory nor inhibitory to nitrite production in control astrocytes. However, both the inhibitors, when added 8 h before the addition of LPS, inhibited LPS-mediated induction of nitrite production in astrocytes. Only 25% inhibition in LPS-induced NO production was found when lovastatin was added to the cells along with LPS; however, the degree of inhibition increased with the increase in time of preincubation with lovastatin reaching about 90% inhibition of NO production within 8 to 10 h of preincubation. Lovastatin (5 or 10 µM) or NaPA (2 or 5 mM) or a combination of 2 µM lovastatin and 2 mM NaPA also inhibited the induction of NO production in rat primary astrocytes. After 24 h, supernatants were used for nitrite assay as described above. Data was the mean±S.D. of three different studies.

TABLE 2

Inhibition of LPS-induced NO production in rat primary astrocytes by lovastatin and mevastatin

| Stimuli | Nitrite (nmol/mg/24 h) | % Inhibition |
|---|---|---|
| Control | 2.9 ± 0.5 | — |
| LPS | 25.3 ± 3.2 | — |
| LPS + Arginase | 5.9 ± 0.8 | 87 |
| LPS + L-NMA | 5.5 ± 0.7 | 88 |
| Lovastatin | 2.9 ± 0.3 | — |
| Mevastatin | 2.8 ± 0.4 | — |
| LPS + Lovastatin | 5.2 ± 0.5 | 90 |
| LPS + Mevastatin | 5.5 ± 0.5 | 88 |

Astrocytes were cultured for 24 h in serum-free DMEM/F-12 with the listed reagents; and nitrite concentration in the supernatants were measured as described. Arginase (100 units/ml) and L-NMA (0.1 mM) were added to the cells together with LPS (1.0 µg/ml). Data are mean±standard deviation (S.D.) of three different studies.

Inhibition of LPS-Induced Activation of NF-kβ and Expression of iNOS by Lovastatin and NaPA The effect of lovastatin (5 or 10 µM) or NaPA (2 or 5 mM) on LPS-induced activation of NF-kβ in astrocytes was examined by gel-shift DNA-binding assay. Cells incubated in serum-free media received 1.0 µg/ml of LPS. After 1 h of incubation, cells were taken out to prepare nuclear extracts and nuclear proteins were used for the electrophoretic mobility shift assay of NF-kβ as described in Example 10. Lanes were run containing control, LPS, LPS-treated nuclear extract with 25-fold excess of unlabelled probe, and LPS-treated nuclear extract with 50-fold excess of unlabelled probe. Treatment of rat primary astrocytes with 1.0 µg/ml of LPS resulted in the activation of NF-kβ. This gel shift assay detected a specific band in response to LPS that was competitively removed by an unlabelled probe. Lovastatin or NaPA alone at different concentrations failed to induce NF-kβ. However, cells preincubated in serum-free media with lovastatin or NaPA for 8 h were markedly inhibited for the LPS-induced activation of NF-kβ, indicating that the inhibition of iNOS expression by lovastatin and NaPA is due to the inhibition of NF-kβ.

To evaluate the possible mechanism of the effect of lovastatin and NaPA or to determine whether reduced concentrations of end products as opposed to intermediate products of the mevalonate pathway were responsible for the effects of lovastatin and NaPA, the inventor performed rescue experiments with cholesterol, ubiquinone, mevalonate and farnesyl pyrophosphate (FPP). Cells preincubated in serum-free media with 10 µM of lovastatin or 5 mM of NaPA for 8 h received 1.0 µg/ml of LPS along with 100 µM mevalonate or 200 µM farnesyl pyrophosphate. After 24 h, supernatants were used for a nitrite assay as described in Example 6. Combinations that were tested included control, LPS alone, LPS+lovastatin, LPS+lovastatin+mevalonate, LPS+lovastatin+FPP, LPS+NaPA, LPS+NaPA+mevalonate, and LPS+NaPA+FPP. Data was measured as the mean±S.D. of three different studies. After 5 h of incubation, cells were analyzed for iNOS mRNA by northern blotting technique as described. GAPDH mRNA was also measured. After 1 h of incubation, cells were taken out to prepare nuclear extracts and nuclear proteins were used for the electrophoretic mobility shift assay of NF-kβ as described in Example 10. Addition of 10 µM ubiquinone or cholesterol to astrocytes did not prevent the inhibitory effect of lovastatin and NaPA. These observations support the conclusion that the depletion of intermediary products rather than end products of mevalonate pathway are responsible for the observed inhibitory effect of lovastatin or NaPA on LPS-induced iNOS expression. On the other hand, mevalonate of FPP substantially reversed the inhibitory effect of lovastatin on iNOS expression and NF-kβ activation. However, FPP not mevalonate reversed the inhibitory effect of NaPA indicating that the utilization of mevalonate rather than its synthesis is the prime target of the NaPA.

Inhibition of LPS-Induced Expression of iNOS in Rat Primary Astrocytes by FPT inhibitor II An examination was made of the effect of FPT inhibitor II, an inhibitor of enzymes that transfers farnasyl group to proteins (e.g. Ras), on LPS-mediated expression of iNOS and activation of NF-kβ in rat primary astrocytes. Cells pre-incubated in serum-free media with 100 µM or 200 µM FPT inhibitor II for 1 h received 1.0 µg/ml of LPS. Samples assayed included control, LPS, LPS+FPT inhibitor II (100 µM or 200 µM). After 24 h of incubation, supernatants were used for nitrite assay as described in Example 6. Data was measured as the mean±S.D. of three different studies. After 5 h of incubation, cells were analyzed for iNOS mRNA by northern blotting technique as described. After 1 h of incubation, cells were taken out to prepare nuclear extracts and nuclear proteins were used for the electrophoretic mobility shift assay of NF-kβ as described in Example 10. A preincubation of cells for 1 h with 100 or 200 µM FPT inhibitor II inhibited LPS-induced activation of NF-kβ, expression of iNOS and production of NO; thus, demonstrating the importance of farnesylation of Ras in LPS-mediated activation of NF-kβ and induction of iNOS in astrocytes.

Lovastatin and NaPA inhibit the LPS-induced expression of Cytokines An examination was made of the effect of NaPA and lovastatin on LPS-induced expression of TNF-α, IL-1β and IL-6. Rat primary astrocytes pre-incubated in serum-free media with different concentrations of lovastatin (5 or 10 µM) or NaPA (2 or 5 mM) or a combination of 2 µM of lovastatin and 2 mM of NaPA for 8 h received 1.0 µg/ml of LPS. Combinations that were tested included control, LPS, LPS+lovastatin (5 µM), LPS+lovastatin (10 µM), NaPA (2 µM), LPS+NaPA (5 µM), and LPS+lovastatin (2 µM)+NaPA (2 µM). Concentrations of TNF-α, IL-1β and IL-6 were measured in the supernatants after 24 h of incubation (Table 3) and the mRNA expression of these cytokines was examined in the cells after 5 h of LPS stimulation as described. Bacterial LPS markedly induced the mRNA expression and production of respective cytokines in astrocytes. Although lovastatin or NaPA alone had no effect on the production of cytokines, these two compounds strongly inhibited the LPS-induced production of TNF-α, IL-1β and IL-6 in the supernatants (Table 3). Additionally, 2 mM NaPA and 2 µM lovastatin worked more effectively to inhibit LPS-induced production of TNF-α, IL-1β and IL-6 than 5 mM NaPA or 5 µM lovastatin alone. The decrease in cytokine production was also accompanied by an inhibition of their mRNA expression demonstrating that lovastatin and NaPA down-regulate the expression of all the inflammatory mediators (iNOS, TNF-α, IL-1β and IL-6) in astrocytes. No adverse effects on the viability of astrocytes, as measured by trypan blue exclusion, were observed.

TABLE 3

Inhibition of LPS-induced production of NO, TNF-α, IL-1β and IL-6 in rat primary astrocytes, microglia and macrophages by lovastatin and NaPA

| Cells | Production of NO or cytokines | LPS only | Treatments LPS + Lovastatin | LPS + NaPA |
|---|---|---|---|---|
| Astrocytes | NO | 25.3 ± 3.2 | 5.2 ± 0.4 | 5.4 ± 0.6 |
|  | TNF-α | 5.3 ± 0.8 | 0.3 ± 0.05 | 0.4 ± 0.06 |
|  | IL-1β | 10.4 ± 1.5 | 0.8 ± 0.1 | 1.1 ± 0.2 |
|  | IL-6 | 136.5 ± 16.8 | 6.9 ± 0.9 | 7.6 ± 0.8 |
| Microglia | NO | 81.2 ± 6.9 | 5.9 ± 0.4 | 6.9 ± 0.9 |
|  | TNF-α | 14.5 ± 2.1 | 0.9 ± 0.1 | 1.3 ± 0.2 |
|  | IL-1β | 28.2 ± 3.4 | 2.1 ± 0.3 | 2.4 ± 0.2 |
|  | IL-6 | 295.6 ± 33.5 | 7.8 ± 1.1 | 9.3 ± 1.2 |
| Macrophages | NO | 118.5 ± 12.5 | 7.2 ± 0.9 | 9.5 ± 0.7 |
|  | TNF-α | 18.6 ± 2.3 | 1.2 ± 0.1 | 1.7 ± 0.2 |
|  | IL-1β | 34.6 ± 4.5 | 2.3 ± 0.3 | 3.1 ± 0.4 |
|  | IL-6 | 350.0 ± 27.6 | 8.3 ± 0.6 | 10.2 ± 1.4 |

Cells preincubated with 10 μM lovastatin or 5 mM NaPA for 8 h in serum-free condition was stimulated with 1.0 μg/ml of LPS. After 24 h of incubation, concentrations of NO, TNF-α, IL-1β and IL-6 were measured in supernatants as described above. NO is expressed as nmol/24 h/mg protein whereas TNF-α, IL-1β and IL-6 are expressed as ng/24 h/mg protein. Data are expressed as the mean±S.D. of three different experiments.

Inhibition Of LPS-Induced Production Of NO and Cytokines In Rat Primary Microglia And Macrophages By Lovastatin Both macrophages and microglia, important sources of NO and cytokines, actively participate in the pathophysiologies of different inflammatory disorders. Since lovastatin and NaPA inhibited the LPS-induced production of NO, TNF-α, IL-1β and IL-6 in astrocytes, a determination of the effect of lovastatin and NaPA on LPS-stimulated production of NO, TNF-α, IL-1β and IL6 in rat primary microglia and macrophages was made (Table 3). It was found that the rate of production of NO and cytokines after LPS stimulation was much higher in both macrophages and microglia than in astrocytes. Similar to astrocytes, lovastatin or NaPA alone had no effect on the production of NO and cytokines in macrophages and microglia. However, both of these compounds strongly inhibited the LPS-induced production of NO, TNF-α, IL-1β and IL-6 in macrophages and microglia (Table 3). These results demonstrate the importance of these compounds in controlling iNOS produced NO and production of proinflammatory cytokines (TNF-α, IL-1β and IL-6 and IFN-γ) in microglia and macrophages. It is important to note that under the conditions used, no adverse effects on the viability of microglia or macrophages, as measured by trypan blue exclusion, were observed.

EXAMPLE 2

NAC Inhibits LPS-Induced NO Synthesis in Resident Peritoneal Macrophages

Reagents Reagents were as given in Example 1. Rat macrophages, astrocytes and C6 glial cells were prepared as described in Example 1. Assays to measure the induction of NO synthesis, NOS activity, immunoblot analyses for iNOS, RNA isolation, RT-PCR and determination of TNF-α in culture supernatants were as described in Example 1.

The effect of NAC on LPS-induced NO-synthesis was examined in resident peritoneal macrophages. Resident macrophages were cultured in RPMI medium without serum in presence of different concentrations of LPS and NAC. The concentration of NO as nitrite was measured in cultured supernatants after 24 h. As shown in Table 4, in rat resident macrophages, LPS (1 μg/ml) induced the production of nitrite, the soluble product of NO in the culture medium (Wang et al., 1995), by more than ten fold. LPS-induced production of nitrite was concentration dependent with maximal induction at 1-5 μg/ml of LPS (data not shown). NAC itself was neither stimulatory nor much inhibitory to nitrite production in control resident macrophages. However, NAC, when added 2 h before the addition of LPS, inhibited LPS-mediated induction of nitrite production in macrophages. Over 90% inhibition was observed when NAC was used at a concentration of 20 mM. Both L-NMA, a competitive inhibitor of NOS, and arginase suppressed LPS-mediated nitrite secretion, indicating that LPS-induced nitrite release in rat peritoneal macrophages is dependent on NOS-mediated arginine metabolism (Table 4).

TABLE 4

Inhibition of Arginine-Dependent Nitrite Accumulation in LPS-Stimulated Resident Macrophages by NAC

| Stimuli | Nitrite (nmol/mg Protein$^{24h}$) | Inhibition (%) |
|---|---|---|
| Control | 9.8 ± 1.5 |  |
| NAC | 6.2 ± 0.8 |  |
| lps | 124.2 ± 9.7 |  |
| LPS + NAC | 11.6 ± 1.5 | 91 |
| LPS + NMA | 15.8 ± 2.2 | 87 |
| LPS + arginase | 22.5 ± 3.1 | 82 |

Resident macrophages were cultured for 24 h in serum-free RPMI 1640 with the listed reagents; nitrite concentration in the supernatants was then measured as described in the methods section. Concentration of reagents were: LPS, 1.0 μg/ml; NAC, 20 mM; NMA, 0.1 mM; arginase, 100 units/ml. NMA and arginase were added to the cells together with LPS whereas NAC was added 2 h before the addition of LPS. Data are mean±S.D. of three different experiments.

Kinetics of inhibition of NO synthesis by NAC in rat macrophages To determine whether inhibition of LPS-induced NO synthesis by NAC was simply due to delayed induction, nitrite concentrations were measured in LPS-stimulated cultures maintained up to 48 h. Rat resident macrophages were stimulated with 1.0 μg/ml LPS alone or together with 20 mM NAC, where NAC was added 2 h before the addition of LPS. Supernatants were harvested at different time intervals (6 to 48 h) to measure concentrations of nitrite as described. Data was measured as the mean±S.D. of three different studies. When cells were stimulated in the absence of NAC, nitrite was detected in culture supernatants after 8 h and the concentration of nitrite increased progressively thereafter for 48 h. However, when 20 mM NAC was added 2 h before the addition of LPS, nitrite production was significantly inhibited. From the onset of detectable NO release until 24 h, nitrite accumulated at a rate of 5.2 nmol/mg/h in the absence of NAC and at 0.5 nmol/mg/h in the presence of NAC.

To study the Effect of decreasing or increasing the time interval between addition of LPS and NAC on LPS-stimulated macrophage NO production, resident macrophages were incubated with 1.0 μg/ml LPS. NAC (20 mM) was added to cultures 2 h or 1 h before, simultaneously or 1 h, 3 h, 5 h, or 7 h after the addition of LPS. Supernatants were collected 24 h after the addition of LPS. Each value was determined as the mean±S.D. of three different studies. Culture supernatants were collected after 24 h of incubation to measure the concentration of nitrite. Maximal suppression of nitrite production was observed when NAC was added 2 h before the addition of LPS. When NAC was added after the addition of LPS, the extent of inhibition progressively decreased. Only 20% inhibition was observed when NAC was added 7 h after the addition of LPS, indicating that inhibition of nitrite production by NAC is due to the inhibition of oxygen radical-mediated signaling reactions.

NAC and PDTC inhibit LPS-mediated induction of iNOS in rat resident macrophages To understand the mechanism of inhibition of LPS-induced nitrite production in resident macrophages by antioxidants, an examination was made of the effect of NAC and PDTC on the formation of L-citrulline from L-arginine, the reaction which is catalyzed by NOS in homogenates of macrophages. Homogenates were prepared from macrophages that had been incubated for 24 h with 1.0 μg/ml LPS in the presence or absence of 20 mM NAC. NAC was added to the cells 2 h before the addition of LPS. Production of L-[2,3,4,5-$^3$H]citrulline from L-[2,3,4,5$^3$-H]arginine was determined at different time points. Data was determined as the mean of two separate studies. The formation of L-citrulline from L-arginine was linear up to 40 min in LPS-activated macrophages in the absence of NAC whereas in the presence of NAC, formation of L-citrulline was strongly inhibited.

In another study, cells received different concentrations of NAC and PDTC, 2 h before the addition of 1.0 μg/ml LPS. Samples that were tested included control, LPS, 5 mM NAC+ LPS, 10 mM NAC+LPS, 20 mM NAC+LPS, 50 μM PDTC+ LPS, and 100 μM PDTC+LPS. After 24 h of incubation, cells were washed, scraped off, and homogenized. NOS activity was measured in cell homogenates as described. Data was determined as the mean±S.D. of three different studies. Cell homogenates were electrophoresed, transferred on nitrocellulose membrane, and immunoblotted with antibodies against mouse macrophage iNOS as described. After 6 h of incubation, cells were taken out from culture dishes directly by adding ultraspec-II RNA reagent (Biotecx Laboratories Inc.). Total RNA of each sample was prepared, reverse-transcribed and amplified by using specific primers for iNOS and glyceraldehyde-3-phosphate dehydrogenase (GAPDH) mRNA. PCR™ products were electrophoresed in 1.5% agarose gel containing 0.5 μg/ml ethidium bromide and photographed with a DS-34 type polaroid camera.

Both NAC and PDTC inhibited LPS-induced NOS activity as evidenced by L-citrulline formation, and PDTC at a concentration of 100 μM was as potent as NAC at 20 mM. Immunoblot analysis with antibodies against murine macrophage iNOS and RT-PCR for iNOS mRNA analysis of LPS-stimulated macrophages incubated in the presence or absence of NAC or PDTC show that both the antioxidants inhibited LPS-mediated induction of iNOS protein and mRNA, indicating that LPS induced induction of iNOS protein in macrophages via oxygen radicals signal pathway.

Inhibition Of LPS- And/Or Cytokine-Induced NO Production By NAC Peritoneal macrophage iNOS can be induced not only by LPS but also by IFN-γ, in combination with either IL-1β or TNF-α (Mehta et al., 1994). To determine whether cytokine-induced NO synthesis is also inhibited by NAC, resident macrophages were cultured with TNF-α, IL-1β or IFN-γ separately or in several combinations, in the presence or absence of NAC. IL-1β or IFN-α when added alone was not able to induce nitrite production; whereas, IFN-γ alone significantly increased NOS-mediated nitrite production (Table 5). Additionally, different combinations of cytokines and LPS induced high level of nitrite production and NOS activity (Table 5). However, NAC, when added 2 h before the addition of cytokines, potentially inhibited the induction of nitrite production. This inhibition of nitrite production was associated with the inhibition of NOS activity as measured by the formation of L-citrulline (Table 5).

NAC and PDTC inhibit LPS/cytokines stimulated induction of iNOS in rat macrophages Cells received 20 mM NAC 2 h before the addition of different cytokines. After 24 h of incubation with different cytokines, cells were scraped off, washed, and homogenized. Homogenates were immunoblotted with antibodies against mouse macrophage iNOS as described in Example 7. After 6 h of incubation with different stimuli, cells were taken out from culture dishes directly by adding ultraspec-II RNA reagent (Biotecx Laboratories Inc.). Total RNA of each sample was prepared, reverse-transcribed, and amplified by using specific primers for iNOS and GAPDH mRNA. PCR™ products were electrophoresed in 1.5% agarose gel containing 0.5 μg/ml ethidium bromide and photographed with a DS-34 type polaroid camera. Bands were scanned with a Biorad (Model GS-670) imaging densitometer. The ratio of iNOS gene product to the internal standard, glyceraldehyde 3-phosphate dehydrogenase (GAPDH) was used to quantitate the message level. Results were measured as the mean±S.D. of three different studies. Assays were done for control, LPS+TNF-α, LPS+IL-1β, LPS+IFN-γ, TNF-α+IL-1β, TNF-α+IFN-γ, NAC+LPS+TNF-α, NAC+LPS+IL-1β, NAC+LPS+IFN-γ, NAC+TNF-α+IL-1β, and NAC+TNF-α+IFN-γ. Concentrations of different stimuli were 0.2 μg/ml for LPS, 50 U/ml for IFN-γ, 20 ng/ml for TNF-α, and 25 ng/ml for IL-1β. The LPS and cytokine combinations stimulated nitrite production, while NAC in combination with LPS and/or cytokines inhibited nitrite production. This inhibition was associated with the inhibition of NOS activity as measured as well as the inhibition of expression of the iNOS protein and mRNA, indicating with the results described above for Table 5 that LPS- and cytokines-mediated expression of iNOS involves oxygen radicals signal pathway.

TABLE 5

Inhibition nitrite production and NOS activity by NAC in stimulated rat resident macrophages

| Stimuli | NAC (20 mM) | Nitrite (nmol/ mg/24 h) | Inhibition (%) | L-citrulline (pmol/ min/mg) | Inhibition (%) |
|---|---|---|---|---|---|
| Control | − | 9.8 ± 1.5 | | 13.5 ± 1.8 | |
|  | + | 6.2 ± 0.8 | 37 | 10.2 ± 0.9 | 25 |
| LPS | − | 124.2 ± 9.7 | | 156.4 ± 21.2 | |
|  | + | 11.6 ± 1.5 | 91 | 14.2 ± 2.3 | 91 |
| IL-1β | − | 21.4 ± 1.9 | | 22.5 ± 3.2 | |
|  | + | 9.2 ± 0.7 | 57 | 12.9 ± 2.1 | 43 |
| TNF-α | − | 27.9 ± 3.5 | | 32.8 ± 2.9 | |
|  | + | 10.1 ± 1.6 | 64 | 12.9 ± 2.3 | 61 |
| IFN-γ | − | 87.9 ± 10.2 | | 132.4 ± 11.6 | |
|  | + | 9.9 ± 1.8 | 89 | 13.2 ± 2.4 | 90 |
| TNF-α + IL-1β | − | 136.9 ± 15.8 | | 182.6 ± 20.2 | |
|  | + | 22.8 ± 2.7 | 83 | 28.2 ± 4.3 | 85 |
| TNF-α + IFN-γ | − | 145.9 ± 17.4 | | 201.6 ± 22.5 | |
|  | + | 29.6 ± 4.2 | 79 | 36.9 ± 3.4 | 82 |
| LPS + TNF-α | − | 168.2 ± 19.4 | | 232.7 ± 20.6 | |
|  | + | 13.6 ± 2.6 | 92 | 19.7 ± 2.7 | 91 |
| LPS + IFN-γ | − | 162.3 ± 15.2 | | 218.5 ± 23.6 | |
|  | + | 25.2 ± 3.9 | 84 | 32.3 ± 4.6 | 83 |

TABLE 5-continued

Inhibition nitrite production and NOS activity by NAC in stimulated rat resident macrophages

| Stimuli | NAC (20 mM) | Nitrite (nmol/mg/24 h) | Inhibition (%) | L-citrulline (pmol/min/mg) | Inhibition (%) |
|---|---|---|---|---|---|
| LPS + IL-1β | − | 149.6 ± 11.2 | | 204.3 ± 17.6 | |
| | + | 28.4 ± 3.7 | 81 | 44.9 ± 6.1 | 78 |

Nitrite accumulation in the supernatants and NOS activity in the cells were measured as described. When different stimuli were used alone, their concentrations were: LPS, 1.0 μg/ml; TNF-α, 100 ng/ml; IL-1β, 200 ng/ml; IFN-γ, 200 U/ml. When stimuli were used in different combinations their concentrations were: LPS, 0.2 μg/ml; TNF-α, 20 ng/ml; IL-1β, 25 ng/ml; IFN-γ, 50 U/ml. Cells received NAC 2 h before the addition of different stimuli. Data are mean±S.D. of three different experiments.

NAC Inhibits LPS And/Or Cytokine-Mediated NO Production In Rat Astrocytes And C6 Glial Cells A study was carried out to determine if NAC inhibits LPS and/or cytokine-mediated NO production in rat astrocytes and glial cells. Both astrocytes and C6 glial cells are reported to express iNOS in the presence of different stimuli (Feinstein et al., 1994a; Hu et al., 1995). Similar to previous reports (Feinstein et al., 1994a; Feinstein et al., 1994b), incubation of C6 cells with LPS, TNF-α, IFN-γ or IL-1β alone did not stimulate nitrite production whereas addition of several combinations of either LPS or cytokines induced the production of NO (Table 6). In contrast to the induction of NO production found in C6 glial cells, either LPS or cytokines alone induced the production of NO in cultured rat astrocytes (Table 6). However, similar to macrophages, addition of NAC at 20 mM concentration 2 h prior to the addition of several cytokines blocked the induction of NO production in both C6 glial cells and astrocytes (Table 6).

TABLE 6

Inhibition of nitrite production by NAC in stimulated astrocytes and C6 glial cells

| | | Astrocytes | | C6 glial cells | |
|---|---|---|---|---|---|
| Stimuli | NAC (20 mM) | Nitrite (nmol/mg/24 h) | Inhibition (%) | Nitrite (nmol/mg/24 h) | Inhibition (%) |
| Control | − | 4.3 ± 1.2 | | 3.1 ± 0.4 | |
| | + | — | | — | |
| LPS | − | 27.8 ± 5.2 | | 3.5 ± 0.4 | |
| | + | 5.6 ± 1.6 | 80 | — | |
| TNF-α | − | 23.4 ± 3.9 | | 3.6 ± 0.2 | |
| | + | 10.5 ± 2.3 | 55 | — | |
| IL-1β | − | 30.1 ± 2.6 | | 3.8 ± 0.5 | |
| | + | 7.8 ± 1.8 | 74 | — | |
| IFN-γ | − | 22.3 ± 4.2 | | 5.3 ± 1.1 | |
| | + | 4.4 ± 1.2 | 80 | — | |
| LPS + TNF-α | − | 41.8 ± 2.8 | | 33.9 ± 4.2 | |
| | + | 15.2 ± 1.5 | 64 | 7.1 ± 1.1 | 79 |
| LPS + IL-1β | − | 21.7 ± 2.9 | | 22.8 ± 3.4 | |
| | + | 4.5 ± 2.8 | 79 | 5.8 ± 1.2 | 75 |
| LPS + IFN-γ | − | 50.7 ± 6.8 | | 32.1 ± 4.2 | |
| | + | 23.5 ± 1.4 | 54 | 8.2 ± 1.4 | 74 |
| TNF-α + IL-1β | − | 36.4 ± 4.5 | | 20.7 ± 3.1 | |
| | + | 5.2 ± 0.7 | 86 | 4.2 ± 0.8 | 80 |
| TNF-α + IFN-γ | − | 38.4 ± 2.6 | | 30.9 ± 5.1 | |
| | + | 14.1 ± 2.04 | 63 | 8.4 ± 2.1 | 73 |

Astrocytes and C6 glial cells were cultured for 24 h in serum-free DMF-12 medium with the listed stimuli, and nitrite accumulation in the supernatants was measured as described previously. Concentrations of different stimuli were the same as described in the legend of Table 4. Data are mean±S.D. of three different experiments.

Inhibition of LPS-mediated TNF-α production by NAC and PDTC in macrophages LPS stimulates a variety of cell types including macrophages to induce the production of TNF-α. To study whether antioxidants effect the production of TNF-α, rat resident macrophages were cultured in serum-free RPMI 1640 medium. They were either treated with antioxidants (NAC and PDTC) 2 h before the addition of LPS or IFN-γ alone or in combination (Table 7). LPS alone at a concentration of 1.0 μg/ml induced appreciable amounts of TNF-α production (20.3±3.6 ng/mg/24 h) and the addition of IFN-γ augments the action of LPS (Table 7). However, IFN-γ alone, was ineffective in inducing TNF-α from macrophages. Pre-incubation of cells with either NAC or PDTC almost completely eliminated the induction of TNF-α production by LPS and IFN-γ. These results indicate that similar to the induction of iNOS, the production of TNF-α by LPS and IFN-γ involves oxygen radicals signal pathway.

TABLE 7

Effect of NAC and PDTC on TNF-α production in rat resident macrophages stimulated with LPS and IFN-γ

| Reagents | TNF-α (ng/24 h/mg protein) | Inhibition (%) |
|---|---|---|
| Control | 0.7 ± 0.1 | |
| NAC | 0.6 ± 0.2 | |
| PDTC | 0.7 ± 0.2 | |
| LPS | 20.3 ± 3.6 | |
| IFN-γ | 1.3 ± 0.4 | |
| LPS + IFN-γ | 31.6 ± 2.9 | |
| LPS + NAC | 1.6 ± 0.3 | 92 |
| LPS + PDTC | 0.9 ± 0.1 | 95 |
| LPS + IFN-γ + NAC | 2.3 ± 0.2 | 93 |
| LPS + IFN-γ + PDTC | 1.4 ± 0.3 | 96 |

Resident macrophages cultured in serum-free RPMI 1640 medium received 20 mM NAC or 100 μM PDTC 2 h before the addition of stimuli. When stimuli were used separately their concentrations were: LPS, 1.0 μg/ml; IFN-γ, 200 U/ml, and when they were used together, their concentrations were: LPS, 0.2 μg/ml; IFN-γ, 50 U/ml. Supernatants were collected 24 h after the addition of stimuli to measure TNF-α concentration using ELISA as described.

EXAMPLE 3

Modulation of LPS-induced NO Production and Expression of iNOS in Rat Primary Astrocytes by Compounds that Modulate Intracellular Levels of cAMP The activation of PKA correlates with the inhibition of LPS-induced iNOS expression in rat primary astrocytes. Primary astrocytes in serum-free DMEM/F-12 received 10 μM forskolin, 500 μM 8-Br-cAMP, 5 μM ($S_p$)-cAMP, 0.2 μM H-89, or 20 μM ($R_p$)-cAMP 15 min before the addition of 1.0 μg/ml LPS. Nitrite concentrations were measured in supernatants after 24 h; and NOS activities were measured in cell homogenates as described herein. Cell homogenates were electrophoresed, transferred on nitrocellulose membrane, and immunoblotted with antibodies against mouse macrophage iNOS. After 6 h of incubation, cells were taken out from culture dishes directly by adding Ultraspec-II RNA reagent (Biotecx Laboratories Inc.) to isolate total RNA, and Northern blot analyses for iNOS mRNA were carried out as described in Examples 7 and 8. After 30 min of incubation, PKA activities were measured in cells by phosphorylation of Kemptide in the presence or absence of the inhibitor peptide PKI. Results were determined as the mean±S.D. of three different studies. Assay were conducted for control, LPS, LPS+forskolin, LPS+8-bromo-cAMP, LPS+($S_p$)-cAMP, LPS+H-89, and LPS+($R_p$)-cAMP.

The compounds forskolin, 8-bromo-cAMP, and ($S_p$)-cAMP, known to increase intracellular cAMP, inhibited the LPS-stimulated NO production as nitrite, iNOS activity as conversion of arginine to citrulline, expression of iNOS protein and iNOS mRNA, and activated PKA activity. The inactive forskolin analogue, 1,9-dideoxyforskolin (10 μM), neither inhibited the LPS induced iNOS activity nor stimulated the PKA activity (Table 8). Other PKA activators like β-adrenergic receptor agonist, isoproterenol (10 μM), and cAMP phosphodiesterase inhibitor, 3-isobutyl-1-methylxanthine (1 mM), also inhibited LPS-stimulated NO production and iNOS activity (Table 8). On the other hand, LPS-stimulated NO production, iNOS activity, and expression of iNOS protein and mRNA were increased by PKA inhibitors (H-89 and ($R_p$)-cAMP). However, in the absence of LPS neither PKA activators nor PKA inhibitors had any effect on the production of NO. This inhibition of NO production by cAMP was not only confined to astrocytes, but forskolin was also found to inhibit LPS, and cytokine-induced NO production in rat $C_6$ glial cells $C_6$ glial cells incubated in serum-free DMEM/F-12 received 10 μM forskolin 15 min before the addition of LPS and cytokines. Nitrite concentrations were measured in supernatants after 24 h of incubation as described in Example 6. Concentrations of different stimuli were included LPS, 0.5 μg/ml; TNF-α, 20 ng/ml; IL-1β, 50 ng/ml; and IFN-γ, 50 units/ml. Data were measured as the mean±S.D. of three different studies. Assay were conducted for control, LPS, LPS+TNF-α, LPS+IFN-γ, LPS+IL-1β, LPS+TNF-α+forskolin, LPS+forskolin+IFN-γ, and LPS+forskolin+IL-1β.

The decrease in LPS-induced iNOS expression with the increase in cAMP level and the increase in LPS-induced iNOS expression with the decrease in cAMP level clearly delineate cAMP and cAMP-dependent protein kinase as important regulators of iNOS biosynthesis in glial cells.

TABLE 8

Inhibition Of LPS-Induced Nitrite Accumulation In Rat Primary Astrocytes By Different cAMP Agonists

| Stimuli | Nitrite nmol/mg/24 h | Inhibition % |
|---|---|---|
| Control | 3.2 ± 0.4 | |
| LPS | 31.4 ± 3.6 | 0 |
| LPS + forskolin | 4.7 ± 1.2 | 85 |
| LPS + dideoxyforskolin | 31.2 ± 4.1 | — |
| LPS + isoproterenol | 8.1 ± 2.3 | 74 |
| LPS + IBMX | 6.8 ± 1.3 | 78 |
| LPS + Rolipram | 6.2 ± 1.2 | 80 |

Primary astrocytes were cultured for 24 h in serum-free DMEM/F-12 with the listed reagents; nitrite concentration in the supernatants was then measured as described above. Concentration of reagents were: LPS, 1.0 μg/ml; forskolin, 10 μM; 1,9-dideoxyforskolin, 10 μM; isoproterenol, 10 μM; 1-isobutyl-1-methylxanthine (IBMX), mM; Rolipram, 10 μM. All the cAMP agonists were added to the cells 15 min prior to the addition of LPS. Data are mean±S.D. of three different studies.

Dose Dependence of Forskolin Inhibition of the LPS Stimulation of iNOS Astrocytes were incubated with different concentrations of forskolin 15 min before the addition of 1 μg/ml LPS, and after 24 h the iNOS activity was measured as nitrite concentrations in the supernatant and conversion of arginine to citrulline in the cellular homogenates (FIG. 1). The level of nitrite and iNOS activity were inhibited to a similar degree at all the concentrations of forskolin tested. The lowest does of forskolin found to inhibit iNOS activity and NO production significantly (by 30%) was 0.1 μM. At 10 μM forskolin, NO production and iNOS activity were inhibited by about 90%. Higher doses of forskolin (50-100 μM) did not result in further significant inhibition of iNOS. This may be due to the fact that PKA was already completely activated in extracts of cells incubated with 10 μM forskolin. The PKA activity increased with the increase in forskolin concentration. The reciprocal relationship of production of NO and iNOS activity with PKA activity supports the conclusion that PKA plays a pivotal role in the regulation of iNOS expression in astrocytes.

Modulation of LPS- and/or Cytokine-mediated iNOS Expression by Compounds Modulating Intracellular Levels of cAMP in Rat Primary Astrocytes Primary astrocytes were stimulated with TNF-α, IL-1β, and IFN-γ alone or in different combinations for 24 h and iNOS was measured. TNF-α, IL-1β, and IFN-γ individually were able to induce iNOS activity, protein, and mRNA, however, when tested in combinations between them or with LPS, the magnitude of induction was significantly higher. Cells incubated in serum-free DMEM/F-12 received 10 μM forskolin or 0.2 μM H-89 15 min before the addition of the different cytokines (TNF-α, 100 ng/ml; IL-1β, 200 ng/ml; IFN-γ, 200 units/ml). Assay were conducted for control, TNF-α, IL-1β, IFN-γ, TNF-α+H-89, IL-1β+H-89, IFN-γ+H-89, TNF-α+forskolin, IL-1β+forskolin, IFN-γ+forskolin. Activities for iNOS were measured in cell homogenates after 24 h as described. Results are expressed as means±S.D. of three different studies. Cell homogenates were immunoblotted with antibodies against mouse macrophage iNOS as described. After 6 h of incubation, cells were taken out from culture dishes directly by adding Ultraspec-II RNA reagent (Biotecx Laboratories Inc.) to isolate total RNA and northern blot analyses for iNOS mRNA were carried out as described. Forskolin, the activator of PKA, completely inhibited the cytokine-induced expression of iNOS, whereas H-89, a specific inhibitor of PKA, stimulated the cytokine-induced expression of iNOS.

Similarly, the induction of iNOS by several combinations of cytokines and LPS were also inhibited by forskolin in rat primary astrocytes, indicating that augmentation of the cellular levels of cAMP and the activation of cAMP-dependent protein kinase represents a general counter-regulatory mechanism for down-regulation of iNOS expression in astrocytes. Cells in this study were incubated in serum free DMEM/F-12 received 10 μm forskolin (FOR) for 15 min before the addition of different combinations of LPS and cytokines. After 24 h of incubation, cell homogenates were analyzed for: iNOS activity, and iNOS protein by immunoblotting. After 6 h of incubation, cells were taken out and northern blot analyses for iNOS mRNA were carried out as described. Concentrations of different stimuli were: LPS, 0.5 μg/ml; TNF-α, 20 ng/ml; IL-1β, 50 ng/ml; IFN-γ, 50 units/ml. Assay were conducted for control, TNF-α+IFN-γ, TNF-α+IL-1β, LPS+IL-1β, LPS+TNF-α, LPS+IFN-γ, TNF-α+IFN-γ+forskolin, TNF-α+IL-1β+forskolin, LPS+IL-1β+forskolin, and LPS+IFN-γ+forskolin.

EXAMPLE 4

Therapy for X-Adrenoleukodystrophy:
Normalization of Very Long Chain Fatty Acids and
Inhibition of Induction of Cytokines by cAMP Materials and Methods Reagents DMEM and bovine calf serum were from GIBCO. Forskolin, 1,9-dideoxyforskolin, 8-Br cAMP, S(p)-cAMP, H-89, rp-cAMP and rolipram were obtained from Biomol, USA. $C_{18:0}$-CoA, NADPH and N-ethylmaleimide were from Sigma (USA). [2-$^{14}$C]Malonyl-CoA and K$^{14}$CN (52 mCi/mmol) were purchased from DuPont-New England Nuclear. [1-$^{14}$C]Lignoceric acid was synthesized by treatment of n-tricosanoyl bromide with K$^{14}$CN as described previously (Hoshi and Kishimoto, 1973).

Enzyme assay for β-oxidation of lignoceric acid The enzyme activity of [1-$^{14}$C]lignoceric acid β-oxidation to acetate was measured in intact cells suspended in Hank's Buffered Salt Solution (HBSS). Briefly, the reaction mixture in 0.25 ml of HBSS contained 50-60 µg of protein and 6 µM [1-$^{14}$C]lignoceric acid. Fatty acids were solubilized with α-cyclodextrin and β-oxidation of [1-$^{14}$C]lignoceric acid was carried out as described previously (Singh et al., 1984; Hashmi et al., 1986; Lageweg et al., 1991; Lazo et al., 1988). The reaction was stopped after 1 h with 0.625 ml of 1 M KOH in methanol, and the denatured protein was removed by centrifugation. The supernatant was incubated at 60° C. for 1 h, neutralized with 0.125 ml of 6 N HCl, and partitioned with chloroform and methanol. Radioactivity in the upper phase is an index of [1-$^{14}$C]lignoceric acid oxidized to acetate.

Transport of lignoceric acid into cultured skin fibroblasts Cells were incubated for 15 min at 37° C. under isotonic conditions in HBSS with [1-$^{14}$C]lignoceric acid (6 µM) solubilized with α-cyclodextrin as described earlier (Singh et al., 1984; Hashmi et al., 1986; Lageweg et al., 1991). Then cells were separated from the incubation medium by centrifugation through an organic layer of brominated hydrocarbons (Cornell, 1980). This was performed in micro tubes (1.5 ml) containing 50 µl of 0.25 M sucrose in HBSS (as cushion), an organic layer (400 µl) consisting of a mixture of bromododecane and bromodecane (7:4, v/v), and an upper layer (500 µl) of cells in HBSS.

Protein kinase A assay Cell extracts were assayed for PKA activity as described (Graves et al., 1993) and herein by measuring the phosphorylation of kemptide (0.17 mM) in the presence or absence of PKI peptide (15 µM). PKA activity was calculated as the amount of kemptide phosphorylated in the absence of PKI peptide minus that phosphorylated in the presence of PKI peptide.

Enzyme assay for fatty acid elongation The fatty acid elongation activity was assayed by the method of Tsuji et al. (Tsuji et al., 1984). Briefly, the assay mixture contained 100 mM potassium phosphate (pH 7.2), 0.5 mM NADPH, 0.05 mM [2-$^{14}$C]malonyl-CoA, 1 mM N-ethyl maleimide and 50-60 µg of protein in a total volume of 0.25 ml. The concentrations of $C_{18:0}$-CoA was 1 mM. The reaction was started at 37° C. by the addition of total homogenate and stopped by the addition of 1.25 ml of 10% (w/v) KOH after 30 min incubation. After saponification at 100° C. for 30 min, the solutions were acidified with 1 ml of 4N HCl and fatty acids were extracted with 2.5 ml of n-pentane three times. The radioactivities incorporated into fatty acids were measured with a liquid scintillation counter.

Measurement of VLCFA in Fibroblasts Fatty acid methyl ester (FAME) was prepared as described previously by Lepage and Roy (1986) with modifications. Fibroblast cells, suspended in HBSS, were disrupted by sonication to form a homogeneous solution. An aliquot (200 µl) of this solution was transferred to a glass tube and 5 g heptacosanoic (27:0) acid was added as internal standard and lipids were extracted by Folch partition. Fatty acids were transesterified with acetyl chloride (200 µl) in the presence of methanol and benzene (4:1) for 2 h at 100° C. The solution was cooled down to room temperature followed by addition of 5 ml 6% potassium carbonate solution at ice-cooled temperature. Isolation and purification of FAME were carried out as detailed by Dacremont et al. (1995). Purified FAME, suspended in chloroform, were analyzed by gas chromatograph GC-15A attached with chromatopac C-R3A integrator from Schimadzu Corporation.

Preparation of post-nuclear membrane and western blot analysis The Membranes were prepared as described previously (Contreras et al., 1996). Briefly, the post-nuclear fraction was diluted with an ice-cold solution of 0.1 M sodium carbonate, 30 mM iodoacetamide, pH 11.5. After 30 min of incubation at 4° C., the membranes were sedimented by ultracentrifugation. The sedimented membranes were electrophoresed in 7.5% sodium dodecylsulfate-polyacrylamide gel, transferred to PVDF membranes and immunoblotted with antibodies against ALDP as described (Contreras et al., 1996).

RNA isolation and Northern blot analysis Cultured skin fibroblasts were taken out from culture flasks directly by adding Ultraspec-II RNA reagent (Biotecx Laboratories Inc.) and total RNA was isolated according to the manufacturer's protocol. Twenty micrograms of RNA from each sample were electrophoretically resolved on 1.2% denaturing formaldehyde-agarose gel, transferred to nylon membrane, and cross-linked using UV Stratalinker (Stratagene, USA). Full length ALDP cDNA was obtained from Dr. Patrick Aubourg, INSERM, Hospital Saint-Vincent-de-Paul, Paris, France. $^{32}$P-labeled cDNA probes were prepared according to the instructions provided with Ready-To-Go DNA labeling kit (Pharmacia Biotech). Northern blot analysis was performed essentially as described for Express Hyb Hybridization solution (Clontech) at 68° C. Actin cDNA probe was used as standard for comparing hybridization signals.

Isolation of rat primary astrocytes and microglia Astrocytes were prepared from rat cerebral tissue as described (McCarthy and De Vellis, 1980) and herein. Microglial cells were isolated from mixed glial cultures according to the procedure of Guilian and Baker (1986). For the induction of cytokine production, cells were stimulated with LPS in serum-free condition.

Determination of TNF-α and IL-1β in culture supernatants Cells were stimulated with LPS in serum-free media for 24 h in the presence or absence of forskolin or rolipram, and concentrations of TNF-α and IL-1β were measured in culture supernatants by using high-sensitivity enzyme-linked immunosorbent assay (R&D Systems, USA) according to the manufacturer's instructions.

Results

Figure 2A:
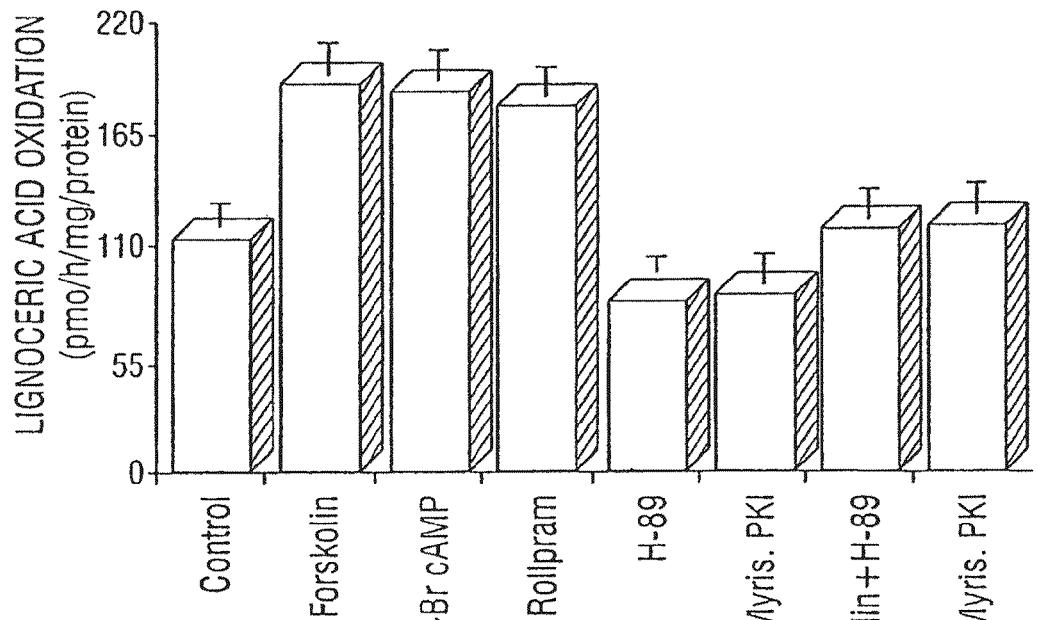
FIG. 2. Activation of PKA correlates with the stimulation of β-oxidation and inhibition of fatty acid chain elongation in cultured skin fibroblasts of X-ALD. Cells were treated for 72 h serum-containing DMEM with the listed reagents; β-oxidation of lignoceric acid (FIG. 2A), fatty acid chain elongation (FIG. 2B) and PKA (FIG. 2C) activities were measured as described in Example 4. Media was replaced after every 24 h with the addition of fresh reagents. Concentrations of reagents were: forskolin, 4 μM; 8-Br-cAMP, 50 μM; rolipram, 10 μM; H-89, 1 μM; myristoylated PKI, 0.2 μM. Data are mean±S.D. of three different experiments.

Compounds that modulate the intracellular cAMP also modulate the β-oxidation of lignoceric acid and fatty acid chain elongation in X-ALD fibroblasts: First, the effect of cAMP derivatives on lignoceric acid β-oxidation in control human fibroblasts was examined. Cultured skin fibroblasts were treated with different activators and inhibitors of protein kinase A (PKA) and tested for β-oxidation of lignoceric acid. It is apparent from Table 9 that compounds known to increase cAMP (forskolin and 8-Br-cAMP) stimulated lignoceric acid β-oxidation whereas compounds known to decrease cAMP (H-89 and myristoylated PKI) inhibited lignoceric acid β-oxidation in control skin fibroblasts. The inactive analogue of forskolin, 1,9-dideoxyforskolin, was ineffective in stimulating β-oxidation (Table 9). These results indicate that PKA has a positive modulatory role on lignoceric acid β-oxidation. Since the β-oxidation of lignoceric acid is impaired in X-ALD patients, the inventor studied the effect of different activators and inhibitors of PKA on lignoceric acid β-oxidation in cultured skin fibroblasts of X-ALD. FIG. 2 shows that the compounds (forskolin, 8-bromo cAMP and rolipram) known to increase intracellular cAMP stimulated lignoceric acid β-oxidation (FIG. 2A) and activated the PKA activity (FIG. 2C). On the other hand, β-oxidation of lignoceric acid was inhibited by PKA inhibitors (H-89 and myristoylated PKI). A combination of forskolin (activator of PKA) and H-89 or myristoylated PKI (inhibitors of PKA) had relatively little effect on the activation of PKA as well as on the β-oxidation of lignoceric acid. These observations indicate that β-oxidation of lignoceric acid is modulated by cAMP and PKA.

Figure 2B:
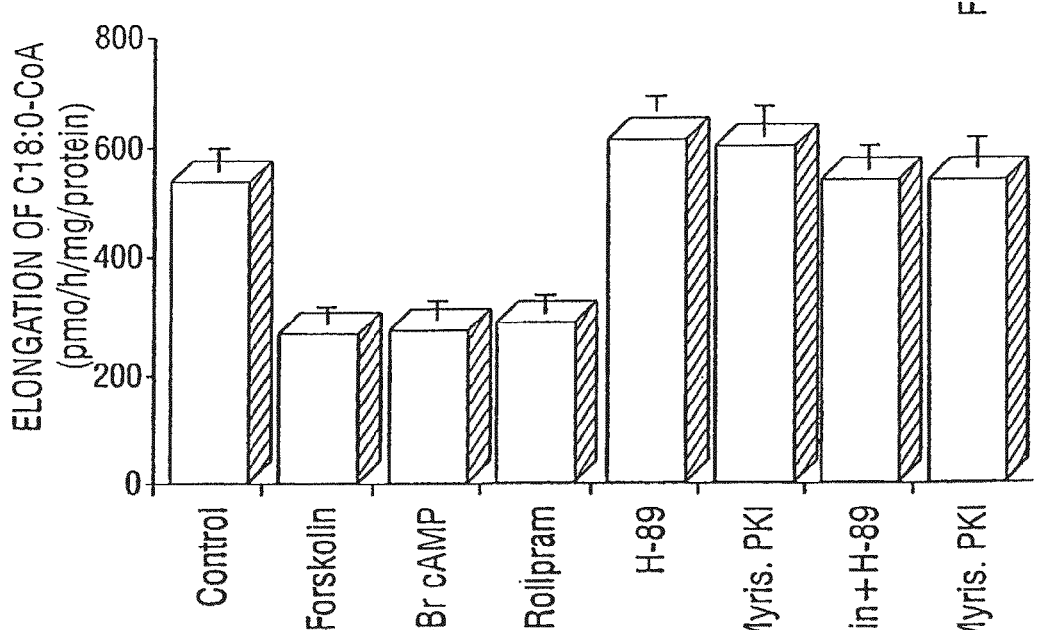
Figure 2C:
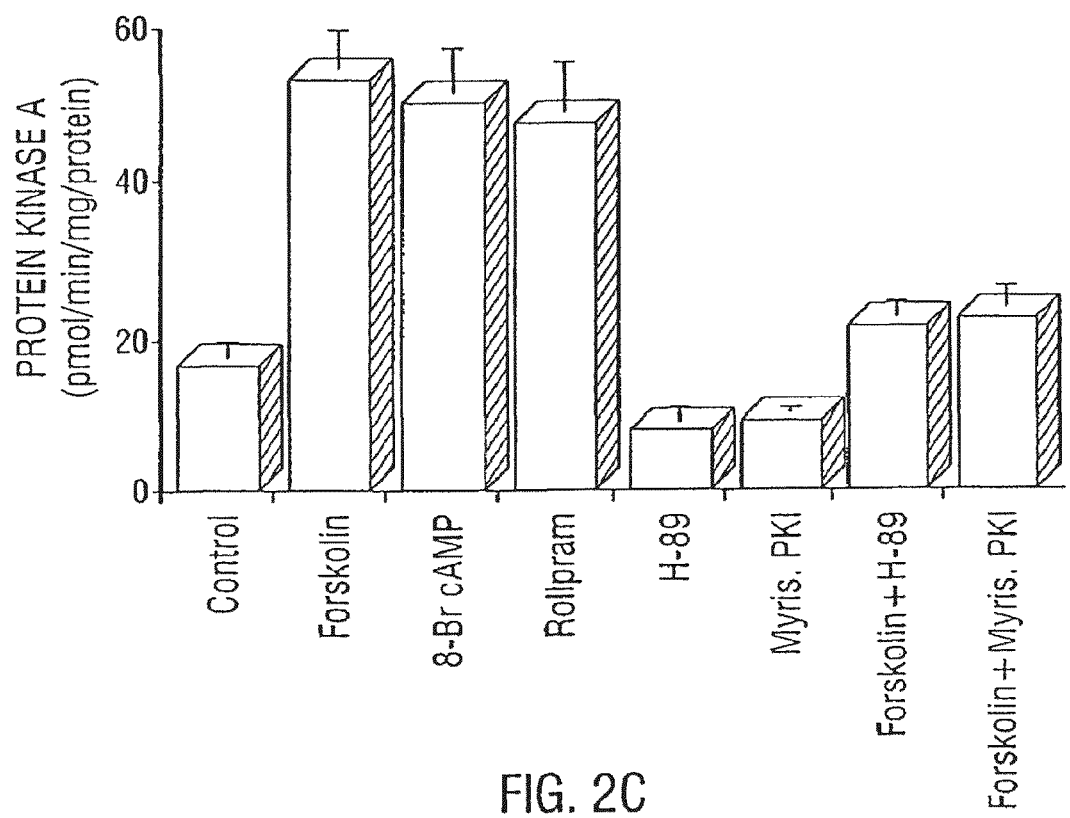

However, in contrast to the effects on β-oxidation of lignoceric acid, activators of PKA inhibited the fatty acid chain elongation and inhibitors of PKA stimulated this activity in X-ALD fibroblasts (FIG. 2B). The increase in β-oxidation of lignoceric acid by forskolin and it's inhibition by H-89 were dose-dependent. Cells in this experiment were incubated in serum-containing DMEM with different concentrations of forskolin (0-10 µM) or H-89 (0-4 µM) for 72 h. After every 24 h, media was replaced with the addition of fresh reagents. β-oxidation of lignoceric acid (pmol/h/mg protein) was measured in cell-suspension as described in the methods section.

To understand the mechanism of cAMP-mediated stimulation of lignoceric acid β-oxidation, fibroblasts of X-ALD were treated with cAMP analogs, and the transport of lignoceric acid into intact cells and β-oxidation of lignoceric acid in cell homogenates of X-ALD were measured. Similar to the modulation of lignoceric acid β-oxidation, activators of PKA also stimulated the transport of lignoceric acid into ALD cells by more than two fold whereas inhibitors of PKA inhibited the transport of lignoceric acid by 40 to 50 percent. Stimulation of lignoceric acid β-oxidation in cell homogenates of ALD fibroblasts as well as in cell suspension (FIG. 2A) indicates that increase in β-oxidation is not due to an intracellular increase of substrate concentration but by stimulation of enzyme system for oxidation of lignoceric acid. In the cell, fatty acids are oxidized by mitochondrial and peroxisomal β-oxidation enzyme. Etomoxir, an inhibitor of mitochondrial β-oxidation of fatty acids (Mannaerts et al., 1979), had no effect on cAMP-mediated stimulation of lignoceric acid β-oxidation indicating that the observed stimulation of lignoceric acid was a peroxisomal function. The increase in β-oxidation and transport of lignoceric acid but the decrease in fatty acid chain elongation with the increase in cAMP level and PKA activity, and the decrease in β-oxidation and transport of lignoceric acid but the increase in fatty acid chain elongation with the decrease in cAMP level and PKA activity clearly delineate cAMP and cAMP-dependent protein kinase A as important regulators of the metabolism of VLCFA.

TABLE 9

Effects of different agonists and antagonists of PKA on
β-oxidation of lignoceric acid in control human fibroblasts

| Treatments | Lignoceric acid β-oxidation (pmol/h/mg protein) |
| --- | --- |
| Control | 565.2 ± 48.3 |
| Forskolin | 885.3 ± 62.1 |
| 1,9 dideoxy forskolin | 571.4 ± 39.6 |
| 8-Br-cAMP | 872.0 ± 53.7 |
| H-89 | 405.6 ± 44.1 |
| Myristoylated PKI | 432.3 ± 46.5 |

Cells were treated for 72 h serum-containing DMEM with the listed reagents; β-oxidation of lignoceric acid was measured as described under "Material and Methods". Media was replaced after every 24 h with the addition of fresh reagents. Concentrations of reagents were: forskolin, 4 and µM; 1,9 dideoxy forskolin, 4 µM; 8-Br-cAMP, 50 µM; H-89, 1 µM; myristoylated PKI, 0.2 µM. Data are mean±S.D. of three different experiments.

Figure 3A:
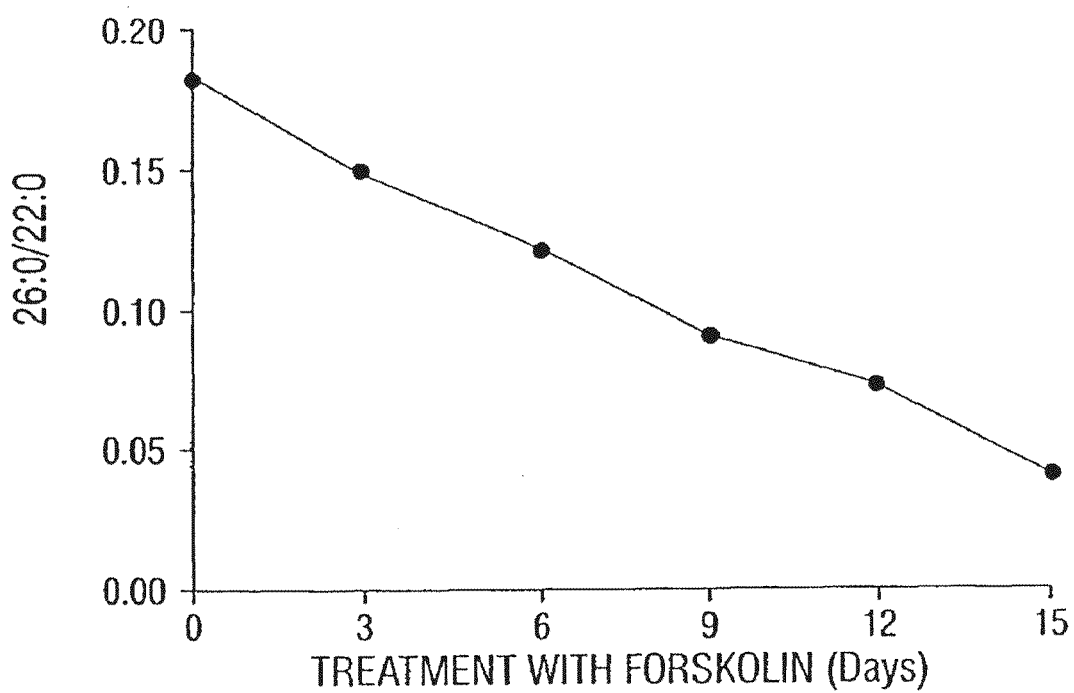
FIG. 3. Time-dependent effect of forskolin on the ratios of VLCFA ($C_{26:0}/C_{22:0}$ and $C_{24:0}/C_{22:0}$) and β-oxidation of lignoceric acid in cultured skin fibroblasts of X-ALD. Cells were incubated in serum-containing DMEM with 4 μM forskolin for different days, and the ratios of $C_{26:0}/C_{22:0}$ (FIG. 3A) and $C_{24:0}/C_{22:0}$ (FIG. 3B), and β-oxidation of lignoceric acid (FIG. 3C) were measured as described in Example 4 (O, experiment 1; O, experiment 2).
Figure 3B:
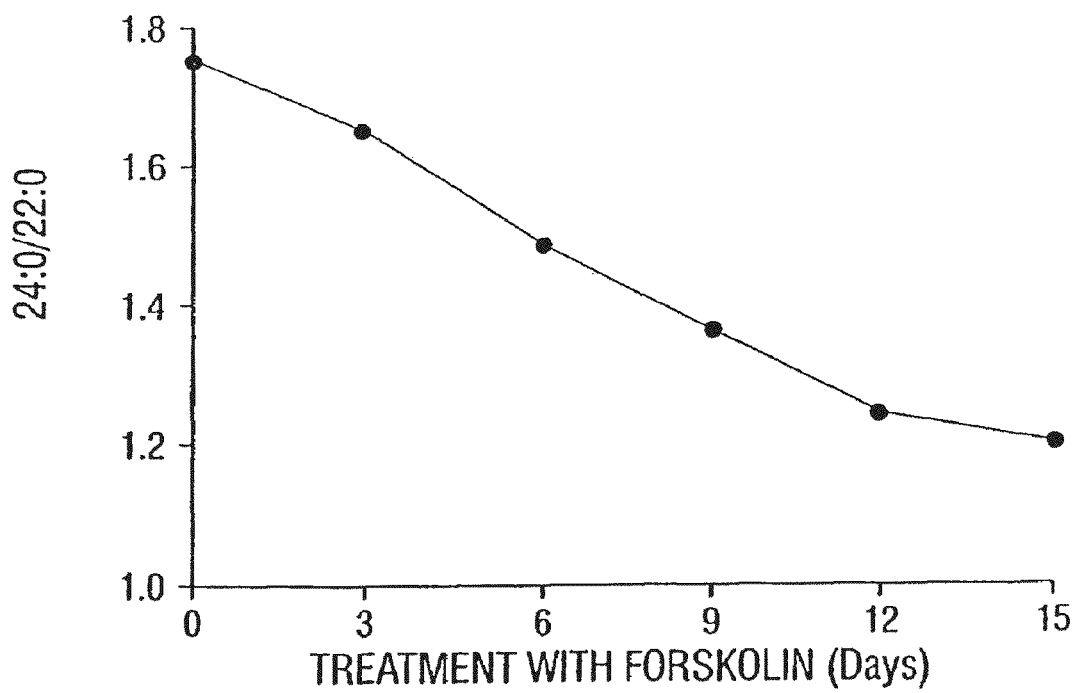
Figure 3C:
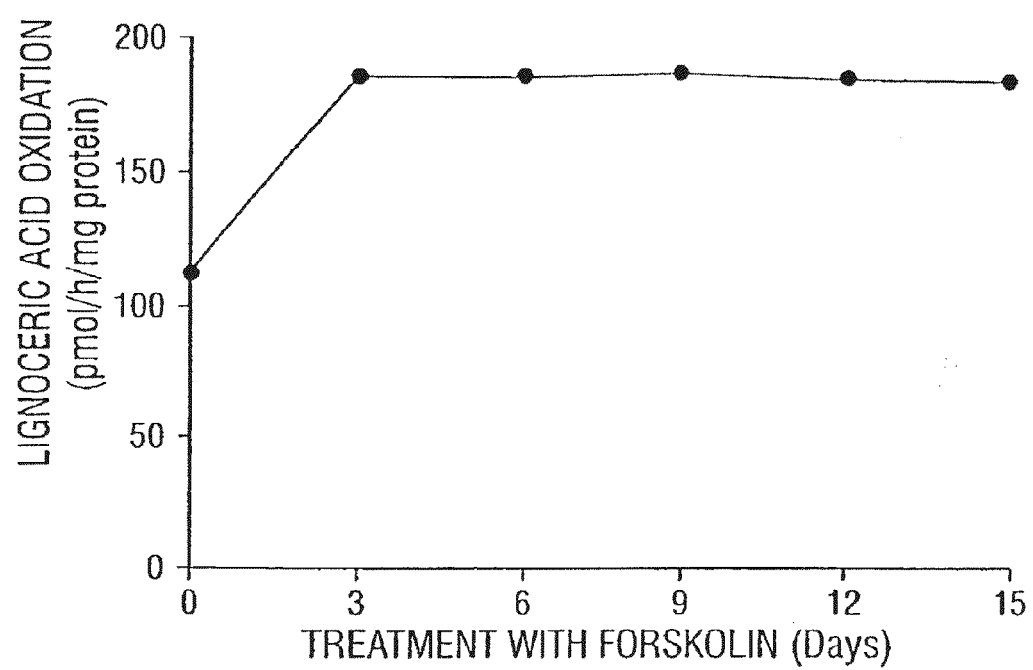

Modulation of cellular content of VLCFA in X-ALD and AMN fibroblasts by compounds modulating intracellular levels of cAMP Since cAMP derivatives increase β-oxidation of lignoceric acid and decrease fatty acid chain elongation, the effect of cAMP derivatives on the level of VLCFA in X-ALD fibroblasts was examined. Treatment of X-ALD fibroblasts with 4 µM of forskolin for different time periods (days) resulted in a time-dependent increase in oxidation of lignoceric acid and a time-dependent decrease $C_{22:0}$ in the ratios of $C_{26:0}/C_{22:0}$ and $C_{24:0}/C_{22:0}$ as shown in FIG. 3A-3C. Within 12 to 15 days of treatment, the ratios of $C_{26:0}/C_{22:0}$ and $C_{24:0}/C_{22:0}$ in X-ALD fibroblasts decreased to the normal level. This decrease in the ratios of $C_{26:0}/C_{22:0}$ and $C_{24:0}/C_{22:0}$ was also associated with the decrease in the absolute amounts of $C_{24:0}$ and $C_{26:0}$ whereas no significant change was observed in the levels of $C_{22:0}$ (behenoic acid). To decipher the possible mechanism of this dramatic decrease of VLCFA, X-ALD fibroblasts were treated with different activators of PKA (forskolin, 8-Br-cAMP and rolipram) for 15 days and analyzed the level of VLCFA. The treatment of X-ALD cultured skin fibroblasts with compounds known to increase intracellular cAMP lowered the ratios of $C_{26:0}/C_{22:0}$ and $C_{24:0}/C_{22:0}$ to the normal level. Cells were incubated in serum-containing DMEM for 15 days with control, forskolin, 8-Br-cAMP, rollpram, forskolin+H-89, H-89, and IFN-β, and the ratios of $C_{26:0}/C_{22:0}$ and $C_{24:0}/C_{22:0}$ were measured as described in Example 4. Concentrations of reagents were: forskolin, 4 µM; 8-Br-cAMP, 50 µM; rolipram, 10 µM; H-89, 1 µM; myristoylated PKI, 0.2 µM; IFN-β, 50 U/ml. Data are mean±S.D. of three different experiments. The inactive forskolin analogue, 1,9-dideoxyforskolin, had no effect on the ratios of $C_{26:0}/C_{22:0}$ and $C_{24:0}/C_{22:0}$. However, compared to X-ALD fibroblasts, forskolin marginally lowered the ratios of $C_{26:0}/C_{22:0}$ and $C_{24:0}/C_{22:0}$ in control skin fibroblasts. A two weeks treatment with forskolin lowered the ratio of $C_{26:0}/C_{22:0}$ from 0.04 to 0.029 and the ratio of $C_{24:0}/C_{22:0}$ from 1.23 to 1.12. Consistent with the effect of H-89 and myristoylated PKI on the β-oxidation of lignoceric acid, these two compounds blocked the observed effect of forskolin on the level of VLCFA when added along with forskolin indicating that cAMP analogs lower the level of VLCFA in X-ALD fibroblasts via activation of PKA. On the other hand, interferon-β, which has been indicated as a possible therapy for X-ALD based on favorable effects found in multiple sclerosis (Moser, 1995), was ineffective in lowering the ratios of $C_{26:0}/C_{22:0}$ and $C_{24:0}/C_{22:0}$ in skin fibroblasts of X-ALD.

Normalization of the levels of VLCFA by forskolin or rolipram in different X-ALD cells with or without deletion of the X-ALD gene Although the precise function of ALDP, an X-ALD gene product, in the metabolism of VLCFA is not known at the present time, accumulation of VLCFA in X-ALD cells with loss or mutations of ALDP and their normalization following transfection of cDNA for ALDP indicate a role of ALDP in the metabolism of VLCFA (Cartier et al., 1995). Therefore, the inventor examined whether decrease in VLCFA in X-ALD fibroblasts by activators of PKA is mediated through the involvement of the ALD gene. ALDS1, ALDS5 and ALDS6 are X-ALD skin fibroblasts with deletion of the X-ALD gene, whereas ALDS2, ALDS3 and ALDS4 are X-ALD skin fibroblasts with mutation of the X-ALD gene. These cell lines were incubated in serum-containing DMEM with 4 µM forskolin for 15 days or control medium, and the ratios of $C_{26:0}/C_{22:0}$ and $C_{24:0}/C_{22:0}$, β-oxidation of lignoceric acid and elongation of fatty acids were measured as described in Example 4. X-ALD cells with mutation or deletion of the ALD gene were treated with forskolin for two weeks and tested for the levels of ALDP protein and it's mRNA, levels of VLCFA. Results were measured as the mean±S.D. of three different experiments.

It was apparent that treatment of X-ALD fibroblasts with forskolin for two weeks had no effect on the steady state levels of ALDP and its mRNA in X-ALD cells. However, forskolin normalized the level of VLCFA in X-ALD fibroblasts by decreasing the rate of fatty acid chain elongation and increasing the rate of β-oxidation of lignoceric acid despite the status of mRNA and protein of ALDP. Treatment of X-ALD fibroblasts with rolipram for two weeks also increased the oxidation of lignoceric acid between 50 to 65 percent and normalized the levels of VLCFA in these cell lines indicating that rolipram, an inhibitor of cAMP phosphodiesterase, has same effect on the metabolism of VLCFA in X-ALD cells with nonfunctional ALDP due to a mutation or with absence of ALDP due to a deletion of the X-ALD gene.

Figure 4A:
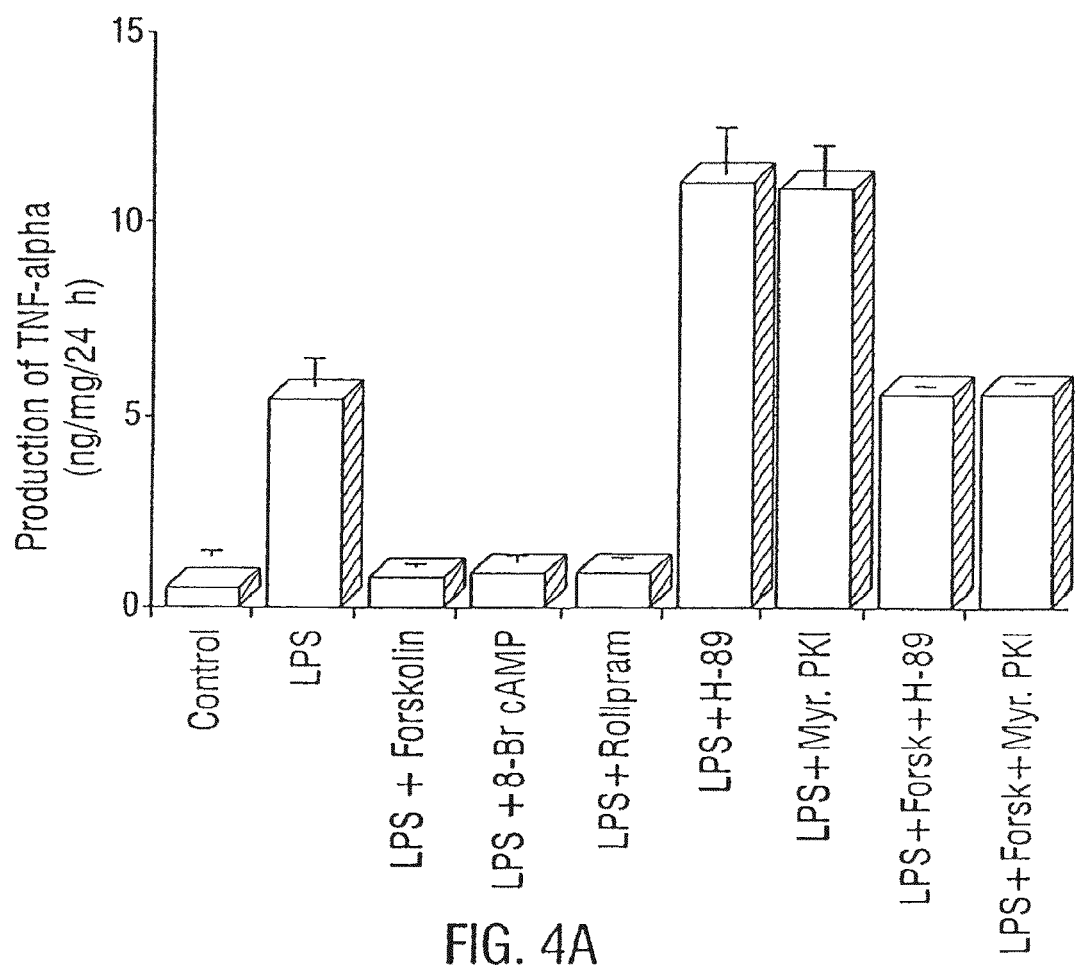
FIG. 4. Modulators of PKA modulate the induction of TNF-α and IL-1β in rat primary astrocytes. Cells preincubated with the listed reagents for 15 min in serum-free condition was stimulated with 1.0 μg/ml of LPS. After 24 h of incubation, concentrations of TNF-α (FIG. 4A) and IL-1β (FIG. 4B) were measured in supernatants as described in the methods section. After 1 h of incubation, activity of PKA (FIG. 4C) was measured in cell extracts as described in Example 4. TNF-α and IL-1β are expressed as ng/24 h/mg protein. Data are expressed as the mean±S.D. of three different experiments. Concentrations of reagents were: forskolin, 10 µM; 8-Br-cAMP, 100 µM; rolipram, 20 µM; H-89, 2 µM; myristoylated PKI, 0.4 µM. Data are mean±S.D. of three different experiments.
Figure 4B:
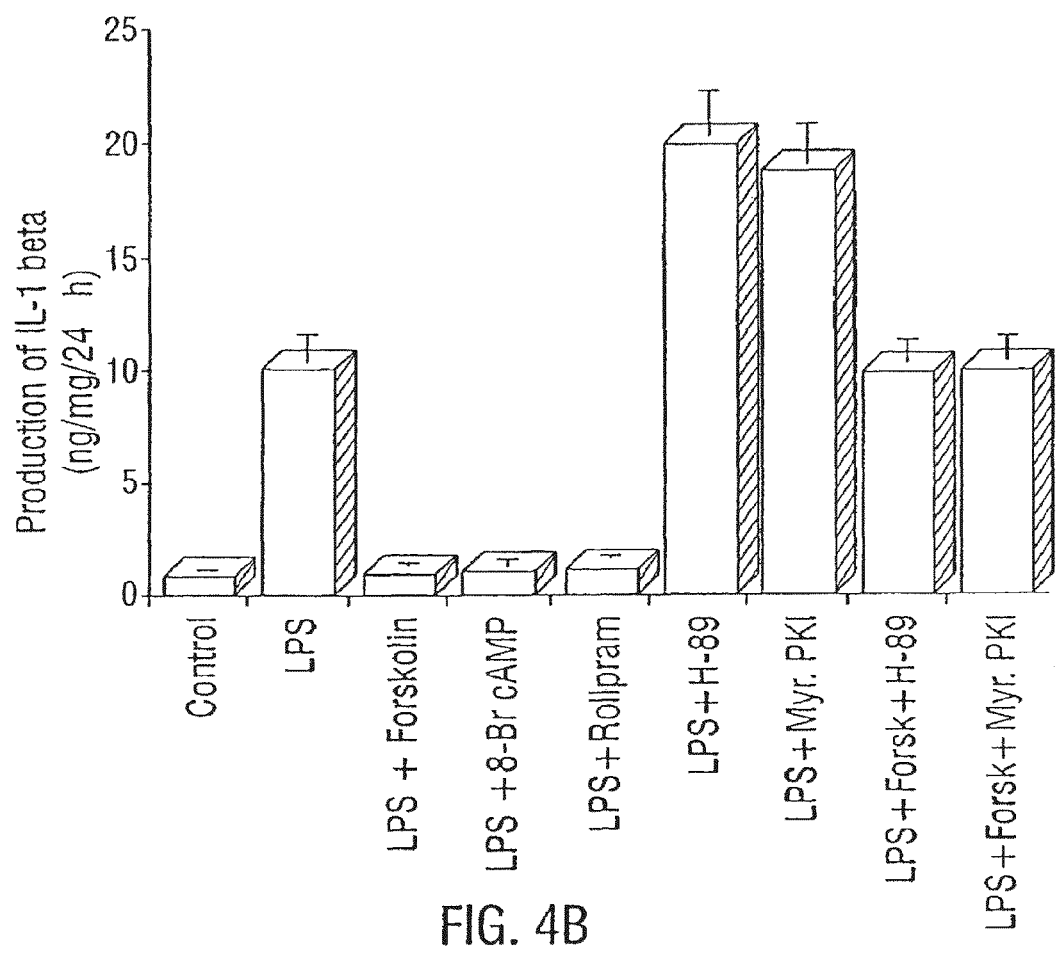
Figure 4C:
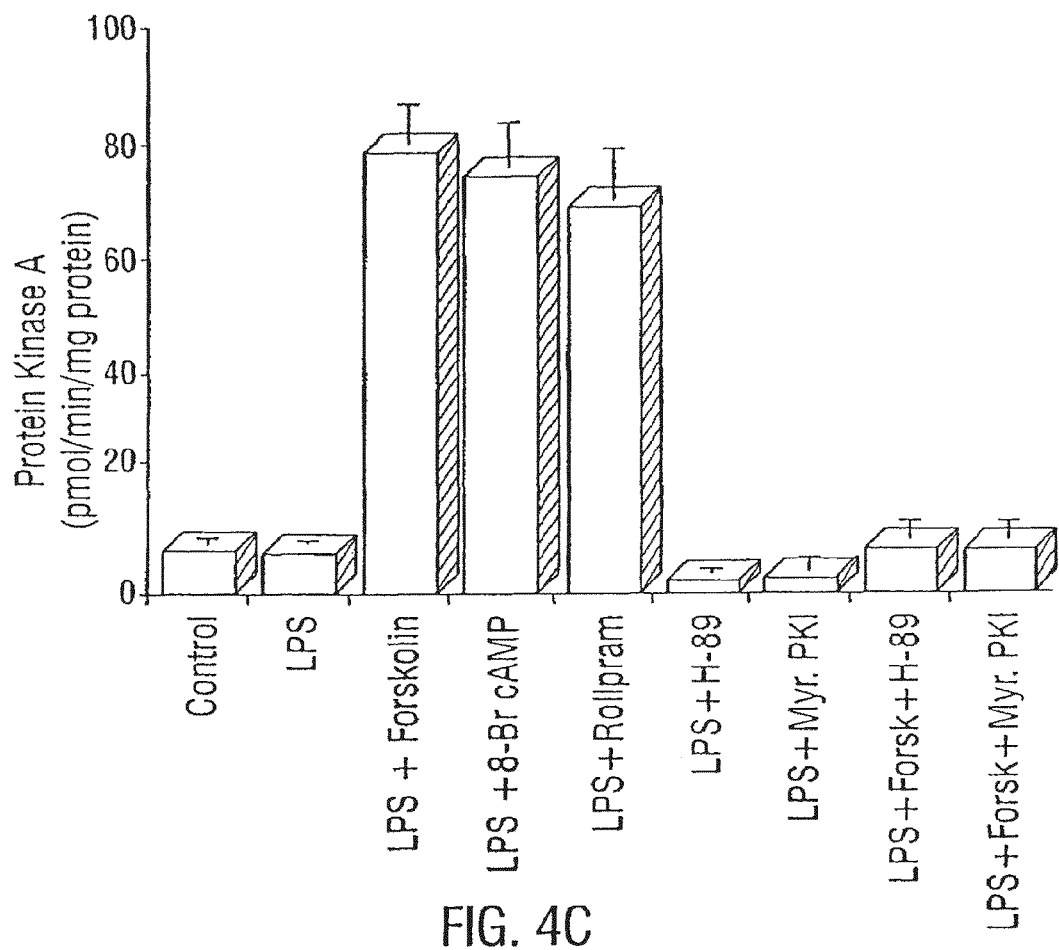

Forskolin and rolipram inhibit the induction of cytokine production in rat primary astrocytes and microglia Since both astrocytes and microglia, reactive glial cells, in the demyelinating lesions of ALD brain, are reported to express TNF-α and IL-1β (Powers et al., 1992; McGuinness et al., 1995), the effect of cAMP derivatives on the induction of cytokine production in astrocytes and microglia was studied. Primary astrocytes in serum-free DMEM/F-12 were treated with different activators and inhibitors of PKA 15 min before the addition of 1 µm of lipopolysaccharide (LPS). FIG. 4 shows that the compounds (forskolin, 8-bromo-AMP, and rolipram) known to increase intracellular cAMP inhibited the LPS-stimulated production of TNF-α (FIG. 4A) and IL-1β (FIG. 4B), and activated PKA activity (FIG. 4C). On the other hand, LPS-stimulated production of TNF-α and IL-1β were increased by inhibitors of PKA (H-89 and myristoylated PKI). The reciprocal relationship of induction of TNF-α and IL-1β with PKA activity supports the conclusion that PKA plays a pivotal role in the regulation of proinflammatory cytokines in astrocytes. Similar to astrocytes, forskolin or rolipram also inhibited the LPS-induced production of TNF-α and IL-1β, and H-89 stimulated the production of these proinflammatory cytokines in rat primary microglia (Table-10).

TABLE 10

Inhibition of LPS-induced production of TNF-α and IL-1β in rat primary microglia by forskolin and rolipram

| Production of cytokines | Treatments | | |
|---|---|---|---|
| | LPS only | LPS + Forskolin | LPS + Rolipram |
| TNF-α | 14.1 ± 2.1 | 0.9 ± 0.1 | 1.2 ± 0.09 |
| IL-1β | 20.8 ± 2.8 | 1.9 ± 0.2 | 2.3 ± 0.3 |

Cells preincubated with 10 µM forskolin or 20 µM of rolipram for 15 min in serum-free condition was stimulated with 1.0 µg/ml of LPS. After 24 h of incubation, concentrations of TNF-α and IL-β were measured in supernatants as described in the methods section. TNF-α and IL-β are expressed as ng/24 h/mg protein. Data are expressed as the mean±S.D. of three different experiments.

EXAMPLE 5

Lovastatin and Sodium Phenylacetate Normalize the Level of Very Long Chain Fatty Acids in Skin Fibroblasts of X-Adrenoleukodystrophy Materials and Methods Reagents DMEM, bovine calf serum and Hank's Buffered Salt Solution (HBSS) were from GIBCO. [1-$^{14}$C]Lignoceric acid was synthesized by treatment of n-tricosanoyl bromide with K$^{14}$CN as described previously.

Enzyme assay for β-oxidation of lignoceric acid The enzyme activity of [1-$^{14}$C]lignoceric acid β-oxidation to acetate was measured in intact cells suspended in HBSS. Briefly, the reaction mixture in 0.25 ml of HBSS contained 50-60 µg of protein and 6 µM [1-$^{14}$C]lignoceric acid. Fatty acids were solubilized with α-cyclodextrin and β-oxidation of [1-$^{14}$C]lignoceric acid was carried out as described previously (Singh et al., 1984; Lazo et al., 1988).

Measurement of VLCFA in Fibroblasts Fatty acid methyl ester (FAME) was prepared as described previously (Lepage and Roy, 1986) with modifications. Fibroblast cells, suspended in HBSS, were disrupted by sonication to form a homogeneous solution. An aliquot (200 µl) of this solution was transferred to a glass tube and 5 µg heptacosanoic (27:0) acid was added as internal standard and lipids were extracted by Folch partition. Fatty acids were transesterified with acetyl chloride (200 µl) in the presence of methanol and benzene (4:1) for 2 h at 100° C. The solution was cooled down to room temperature followed by addition of 5 ml 6% potassium carbonate solution at ice-cooled temperature. Isolation and purification of FAME were carried out as detailed by Dacremont et al. (1995). Purified FAME, suspended in chloroform, were analyzed by gas chromatograph GC-15A attached with chromatopac C-R3A integrator from Shimadzu Corporation.

Preparation of post-nuclear membrane and western blot analysis The Membranes were prepared as described previously (Contreras et al., 1996). Briefly, the post-nuclear fraction was diluted with an ice-cold solution of 0.1 M sodium carbonate, 30 mM iodoacetamide, pH 11.5. After 30 min of incubation at 4° C., the membranes were sedimented by ultracentrifugation. The sedimented membranes were electrophoresed in 7.5% sodium dodecylsulfate-polyacrylamide gel, transferred to PVDF membranes and immunoblotted with antibodies against ALDP as described (Contreras et al., 1996).

RNA isolation and Northern blot analysis Cultured skin fibroblasts were taken out from culture flasks directly by adding Ultraspec-II RNA reagent (Biotecx Laboratories Inc.) and total RNA was isolated according to the manufacturer's protocol. Twenty micrograms of RNA from each sample were electrophoretically resolved on 1.2% denaturing formaldehyde-agarose gel, transferred to nylon membrane, and cross-linked using UV Stratalinker (Stratagene, USA). Full length ALDP cDNA was obtained from Dr. Patrick Aubourg, INSERM, Hospital Saint-Vincent-de-Paul, Paris, France. $^{32}$P-labeled cDNA, probes were prepared according to the instructions provided with Ready-To-Go DNA labeling kit (Pharmacia Biotech). Northern blot analysis was performed essentially as described for Express Hyb Hybridization solution (Clontech) at 68° C. GAPDH cDNA probe was used as standard for comparing hybridization signals.

Results

Inhibitors of mevalonate pathway stimulate the β-oxidation of lignoceric acid in X-ALD fibroblasts First, the effect of mevalonate inhibitors (lovastatin, mevastatin and NaPA) on the β-oxidation of lignoceric acid in control human fibroblasts was examined. It is apparent from Table 11 that lovastatin, mevastatin and NaPA stimulated the β-oxidation of lignoceric acid in control human fibroblasts. Since the β-oxidation of lignoceric acid is impaired in X-ALD patients, the effect of these compounds on lignoceric acid β-oxidation was studied in cultured skin fibroblasts of X-ALD.

TABLE 11

Lovastatin and NaPA stimulate the β-oxidation of lignoceric acid in control human skin fibroblasts

| Treatments | Lignoceric acid β-oxidation (pmol/h/mg protein) |
|---|---|
| Control | 570.2 ± 52.3 |
| Lovastatin (5 μM) | 945.7 ± 105.6 |
| Mevastatin (5 μM) | 889.6 ± 78.4 |
| NaPA (5 mM) | 826.2 ± 87.2 |

Cells were treated for 72 h in serum-containing DMEM with the listed reagents; β-oxidation of lignoceric acid was measured as described in the methods section. Media was replaced after every 24 h with the addition of fresh reagents. Data are mean±S.D. of three different studies.

Similar to control fibroblasts, these compounds also stimulated lignoceric acid β-oxidation in X-ALD skin fibroblasts. Cells were incubated in serum-containing DMEM with different concentrations of lovastatin (0-10 μM) or NaPA (0-5 mM). After every 24 h, media was replaced with the addition of fresh reagents. Lignoceric acid β-oxidation was measured (pmol/h/mg protein) after 72 h in cell-suspension as described in the methods section. Values were determined as the mean±S.D. of three different studies. Both lovastatin and NaPA dose-dependently stimulated lignoceric acid β-oxidation in X-ALD fibroblasts. The highest dose of lovastatin found to stimulate lignoceric acid β-oxidation (by 70%) was 5 μM whereas the highest dose of NaPA found to stimulate lignoceric acid β-oxidation (by 40%) was 5 mM. However, greater degree of stimulation (more than two fold) was observed by a combination of lovastatin and NaPA even at a dose lower than the one used individually. Higher doses of lovastatin (10-20 μM) or NaPA (10-20 mM) were cytotoxic to the X-ALD fibroblasts and did not result in further significant stimulation. In the cell, fatty acids are oxidized by mitochondrial and peroxisomal β-oxidation enzyme. Etomoxir, an inhibitor of mitochondrial β-oxidation of fatty acids (Mannaerts et al., 1979), had no effect on lovastatin- or NaPA-mediated stimulation of lignoceric acid β-oxidation indicating that the observed stimulation of lignoceric acid β-oxidation was a peroxisomal function.

Modulation of cellular content of VLCFA in X-ALD fibroblasts by lovastatin and NaPA Since mevalonate inhibitors increased β-oxidation of lignoceric acid in control as well as X-ALD fibroblasts, the inventor examined the effect of these compounds on the level of VLCFA in X-ALD fibroblasts. Treatment of X-ALD cultured skin fibroblasts with 5 μM of lovastatin for different time periods (days) resulted in a time-dependent decrease in the ratios of $C_{26:0}/C_{22:0}$ and $C_{24:0}/C_{22:0}$. Cells were incubated in serum-containing DMEM with 5 μM lovastatin, 5 mM NaPA or the combination of 4 μM lovastatin and 2 mM NaPA for 0-15 days, and the ratios of $C_{26:0}/C_{22:0}$ (24A) and $C_{24:0}/C_{22:0}$ (24B) were measured every 3 days as described in the methods section. Values are mean of two different studies. Within 12 to 15 days of treatment, the ratios of $C_{26:0}/C_{22:0}$ and $C_{24:0}/C_{22:0}$ in X-ALD fibroblasts decreased to the normal level. Similar to lovastatin, NaPA also lowered the ratios of $C_{26:0}/C_{22:0}$ and $C_{24:0}/C_{22:0}$ in X-ALD fibroblasts almost to the normal level after 15 days of treatment. However, consistent with the higher degree of stimulation of lignoceric acid β-oxidation by a combination of lovastatin and NaPA, the same combination lowered the ratios of $C_{26:0}/C_{22:0}$ and $C_{24:0}/C_{22:0}$ to the normal level within 7 days. This decrease in the ratios of $C_{26:0}/C_{22:0}$ and $C_{24:0}/C_{22:0}$ was also associated with the decrease in the absolute amounts of $C_{24:0}$ and $C_{26:0}$ whereas no significant change was observed in the levels of $C_{22:0}$ (behenoic acid).

Normalization of the levels of VLCFA by lovastatin or NaPA in different X-ALD cells with or without deletion of the X-ALD gene Although the precise function of ALDP, X-ALD gene product, in the metabolism of VLCFA is not known at the present time, however, accumulation of VLCFA in X-ALD cells with loss or mutations of ALDP and their normalization following transfection of cDNA for ALDP indicate a role of ALDP in the metabolism of VLCFA (Cartier et al., 1995). Therefore, the inventor examined whether lovastatin or NaPA were able to lower the level of VLCFA in different X-ALD fibroblasts with mutation or deletion of the X-ALD gene. The status of ALDP mRNA or protein and the rate of β-oxidation of lignoceric acid (Table 12) in different X-ALD fibroblasts indicates that ALDS2, ALDS3 and ALDS4 are X-ALD skin fibroblasts with mutation of the X-ALD gene, whereas ALDS5 and ALDS6 are X-ALD skin fibroblasts with deletion of the X-ALD gene. It is apparent from Table 3 that treatment of X-ALD fibroblasts with lovastatin or NaPA or the combination of these two stimulated the β-oxidation of lignoceric acid (55-80%) and normalized the ratios of $C_{26:0}/C_{22:0}$ and $C_{24:0}/C_{22:0}$ indicating that these drugs are capable of lowering the level of VLCFA in X-ALD fibroblasts to the normal level, irrespective of mutation or deletion of the X-ALD gene, the candidate gene for X-ALD.

TABLE 12

Effect of lovastatin-and NaPA on (A) β-oxidation of lignoceric acid and (B)
the ratios of $C_{26:0}/C_{22:0}$ and $C_{24:0}/C_{22:0}$ in cultured skin fibroblasts of X-ALD

A

| | Lignoceric acid β-oxidation (pmol/h/mg protein) | | | |
|---|---|---|---|---|
| | Control | Lovastatin | NaPA | Lovastatin + NaPA |
| ALDS2 | 142.7 ± 15.7 | 223.5 ± 24.1 | 202.5 ± 17.4 | 274.6 ± 30.5 |
| ALDS5 | 154.2 ± 14.2 | 248.2 ± 26.2 | 211.5 ± 22.6 | 296.2 ± 25.6 |
| ALDS6 | 132.4 ± 15.9 | 218.3 ± 19.8 | 189.7 ± 21.2 | 250.1 ± 28.3 |
| ALDS3 | 122.3 ± 11.7 | 201.3 ± 22.3 | 183.2 ± 17.3 | 248.6 ± 29.6 |
| ALDS4 | 118.5 ± 12.6 | 192.8 ± 20.5 | 178.9 ± 18.3 | 238.7 ± 21.1 |

B

| | $C_{26:0}/C_{22:0}$ | | | $C_{24:0}/C_{22:0}$ | | |
|---|---|---|---|---|---|---|
| Cell Lines | Control | Lovastatin | Lovastatin + NaPA | Control | Lovastatin | Lovastatin + NaPA |
| ALDS2 | 0.17 ± 0.022 | 0.049 ± 0.01 | 0.04 ± 0.008 | 1.84 ± 0.25 | 1.25 ± 0.15 | 1.14 ± 0.15 |
| ALDS5 | 0.18 ± 0.025 | 0.055 ± 0.008 | 0.04 ± 0.007 | 1.94 ± 0.29 | 1.28 ± 0.21 | 1.18 ± 0.12 |
| ALDS6 | 0.22 ± 0.034 | 0.058 ± 0.01 | 0.045 ± 0.008 | 2.01 ± 0.3 | 1.31 ± 0.18 | 1.21 ± 0.14 |
| ALDS3 | 0.16 ± 0.024 | 0.045 ± 0.06 | 0.03 ± 0.005 | 1.88 ± 0.21 | 1.26 ± 0.16 | 1.19 ± 0.25 |
| ALDS4 | 0.19 ± 0.028 | 0.052 ± 0.07 | 0.036 ± 0.006 | 1.96 ± 0.23 | 1.29 ± 0.02 | 1.22 ± 0.15 |

Cells were incubated in serum-containing DMEM with 5 μM lovastatin, 5 mM NaPA or the combination of 4 μM forskolin and 2 mM NaPA for 15 days, and the β-oxidation of lignoceric acid (A) and the ratios of $C_{26:0}/C_{22:0}$ and $C_{24:0}/C_{22:0}$ (B) were measured as described in the methods section. Results are mean±S.D. of three different studies. ALDS2, ALDS3 and ALDS4 are X-ALD skin fibroblasts with mutation of the X-ALD gene, whereas ALDS5 and ALDS6 are X-ALD skin fibroblasts with deletion of the X-ALD gene.

The results of the preceding Examples 1-4 that lovastatin and NaPA inhibit the induction of nitric oxide synthase and proinflammatory cytokines (TNF-α, IL-1β and IL-6) in rat primary astrocytes, microglia and macrophages indicates that these drugs, alone or in combination, represent a novel approach for therapeutics directed against cytokine- and NO-mediated brain disorders, particularly in demyelinating conditions. Lovastatin and NaPA have already been approved for medication/drug trials on human diseases. Therefore, normalization of VLCFA by lovastatin and NaPA in X-ALD fibroblasts indicates that these drugs may be used to lower the level of VLCFA and ameliorate the myelinolytic inflammation in X-ALD patients.

EXAMPLE 6

Inhibitors of Phosphatase 1 and 2A Differentially Regulate Expression of iNOS

Materials and Methods

Reagents Recombinant rat IFN-γ, DMEM/F-12 medium, fetal bovine serum, Hanks' balanced salt solution (HBSS) and NF-kB DNA binding protein detection kit were from GIBCO. Human IL1-β was from Genzyme. Mouse recombinant TNF-α was obtained from Boehringer Mannheim, Germany. LPS (*Escherichia coli*) was from Sigma. $N^G$-methyl-L-arginine (L-NMA), okadaic acid, calyculin A, cantharidin and antibodies against mouse macrophage iNOS were obtained from Calbiochem, USA. Deltamethrin and fenvalerate were obtained from Biomol, USA. [γ-$^{32}$P]ATP (3000 Ci/mmol) were from Amersham, USA.

Induction of NO production in astrocytes and $C_6$ glial cells Astrocytes were prepared from rat cerebral tissue as described by McCarthy and DeVellis (McCarthy and DeVellis, 1980). Cells were maintained in DMEM/F-12 medium containing 10% fetal bovine serum (FBS).

After 10 days of culture astrocytes were separated from microglia and oligodendrocytes by shaking for 24 h in an orbital shaker at 240 rpm. The shaking was repeated two more times after a gap of one or two days time before subculturing to ensure the complete removal of all the oligodendrocytes and microglia. Cells were trypsinized, subcultured and stimulated with LPS or different cytokines in serum-free DMEM/F-12. $C_6$ glial cells obtained from ATCC was also maintained and induced with different stimuli as above.

Isolation of rat macrophages and induction of NO production Resident macrophages were obtained from rat by peritoneal lavage with sterile RPMI 1640 medium containing 1% fetal bovine serum and 100 μg/ml gentamicin as described herein. Cells were washed three times with RPMI 1640 at 4° C. All cell cultures were maintained at 37° C. in a humidified incubator containing 5% $CO_2$ in air. Macrophages at a concentration of $2 \times 10^6$/ml in RPMI 1640 medium containing L-glutamine and gentamicin were added in volumes of 800 μl to a 35 mm plate. After 1 h, nonadherent cells were removed by washing and 800 μl of serum-free RPMI 1640 medium with various stimuli were added to the adherent cells. After incubation in 5% $CO_2$ in air at 37° C., culture supernatants were transferred to measure NO production.

Assay for NO synthesis Synthesis of NO was determined by assay of culture supernatants for nitrite, a stable reaction product of NO with molecular oxygen. Briefly, 400 μl of culture supernatant was allowed to react with 200 μl of Griess reagent and incubated at room temperature for 15 min. The optical density of the assay samples was measured spectrophotometrically at 570 nm. Fresh culture media served as the blank in all studies. Nitrite concentrations were calculated from a standard curve derived from the reaction of $NaNO_2$ in the assay.

In vitro PP1/2A assay The extraction and assay for PP1/2A were performed as described (Begum and Ragolia, 1996). Control and treated cells were scraped off the dishes with 0.3 ml of phosphatase extraction buffer containing 20 mM imidazole-HCl, 2 mM EDTA, 2 mM EGTA, pH 7.0, with 10 μg/ml each of aprotinin, leupeptin, antipain, soybean trypsis inhibitor, 1 mM benzamide, and 1 mM PMSF. The cells were sonicated for 10 s and centrifuged at 2000×g for 5 min, and the supernatants were used for the assay of phosphatase activities using the protein phosphatase assay kit (Life Technologies, Inc.) according to the manufacturer's protocol.

Immunoblot analysis for iNOS Following 24 h incubation in the presence or absence of different stimuli, cells were scraped off, washed with Hank's buffer, and homogenized in 50 mM Tris-HCl (pH 7.4) containing protease inhibitors. After electrophoresis the proteins were transferred onto a nitrocellulose membrane, and the iNOS band was visualized by immunoblotting with antibodies against mouse macrophage iNOS and [$^{125}$I]-labeled protein A.

RNA isolation and Northern blot analysis Cells were taken out from culture dishes directly by adding Ultraspec-II RNA reagent (Biotecx Laboratories Inc.) and total RNA was isolated according to the manufacturer's protocol. For Northern blot analyses, 20 μg of total RNA was electrophoresed on 1.2% denaturing formaldehyde-agarose gels, electrotransferred to Hybond-Nylon Membrane (Amersham) and hybridized at 68° C. with $^{32}$P-labeled cDNA probe using Express Hyb hybridization solution (Clontech) as described by the manufacturer. The cDNA probe was made by PCR™ amplification using two primers (forward primer: 5'-CTCCT-TCAAAGAGGCAAAAATA-3' (SEQ ID NO:1); reverse primer: 5'-CACTTCCTCCAGGATGTTGT-3' (SEQ ID NO:2) (Geller et al., 1993). After hybridization filters were washed two or three times in solution I (2×SSC, 0.05% SDS) for one hour at room temperature followed by solution II (0.1×SSC, 0.1% SDS) at 50° C. for another hour. The membranes were then dried and exposed with X-ray films (Kodak). The same filters were stripped and rehybridized with probes for GAPDH. The relative mRNA content for iNOS was measured after scanning the bands with a Biorad (Model GS-670) imaging densitometer.

Preparation of nuclear extracts and electrophoretic mobility shift assay Nuclear extracts from stimulated or unstimulated astrocytes (1×107 cells) were prepared as described (Dignam et al., 1983) with slight modification. Cells were harvested, washed twice with ice-cold phosphate-buffered saline and lysed in 400 μl of buffer A (10 mM HEPES, pH 7.9, 10 mM KCl, 2 mM MgCl$_2$, 0.5 mM DTT, 1 mM PMSF, 5 μg/ml aprotinin, 5 μg/ml pepstatin A, and 5 μg/ml leupeptin) containing 0.1% Nonidet P40 for 15 min on ice, vortexed vigorously for 15 s, and centrifuged at 14,000 rpm for 30 s. The pelleted nuclei were resuspended in 40 μl of buffer B (20 mM HEPES, pH 7.9, 25% (v/v) glycerol, 0.42 M NaCl, 1.5 mM MgCl$_2$, 0.2 mM EDTA, 0.5 mM DTT, 1 mM PMSF, 5 μg/ml aprotinin, 5 μg/ml pepstatin A, and 5 μg/ml leupeptin). After 30 min on ice, lysates were centrifuged at 14,000 rpm for 10 min. Supernatants containing the nuclear proteins were diluted with 20 μl of modified buffer C (20 mM HEPES, pH 7.9, 20% (v/v) glycerol, 0.05 M KCl, 0.2 mM EDTA, 0.5 mM DTT, and 0.5 mM PMSF) and stored at −70° C. until use. Nuclear extracts were used for the electrophoretic mobility shift assay using the NF-kB DNA binding protein detection system kit (GIBCO/BRL), according to the manufacturer's protocol.

Construction of reporter plasmid, transfection and assay of chloramphenicol acetyl transferase activity The CAT (chloramphenicol acetyl transferase) under the control of nitric oxide synthase promoter (iNOS) was created by subcloning 1.5 kb promoter from pGEM-NOS at Sph I and Sal I restriction sites of pCAT-basic vector (Promega). Full length promoter (Eberhardt et al., 1996) was amplified by using two primers (Forward: 5'-GAGAGTGTGCAAGTATTTGTAG-GAG-3' (SEQ ID NO:6) and reverse: 5'-AAGGTGGCT-GAGAAGTTTCA-3' (SEQ ID NO:7)) from rat genomic DNA and cloned in pGEM-T vector (Promega) to produce pGEM-NOS. The clone was confirmed by restriction mapping and sequencing. The cells were transfected by using the lipofectin (Life Technologies Inc., USA) method, as has been described in manufacturer's protocol, with 2 μg of reporter plasmid. They were then stimulated 24 h after transfection and harvested after 14 h of stimulation. CAT activity was measured as has been described.

Cell viability: Cytotoxic effects of all the inhibitors were determined by the MTT assay measuring the metabolic activity of cells.

Results

Inhibitors of PP1/2A stimulate LPS-induced production of NO in rat primary astrocytes: Rat primary astrocytes were cultured in serum-free DMEM/F-12 in the presence of LPS and inhibitors of different protein phosphatases. The concentration of NO as nitrite (a stable reaction product of NO with molecular oxygen) was measured in culture supernatants after 24 h. It is evident from Table 13 that bacterial LPS at a concentration of 1.0 μg/ml induced the production of NO as nitrite by about 8 fold. L-NMA, a competitive inhibitor of NOS suppressed LPS-mediated nitrite secretion indicating that LPS-induced nitrite release in rat primary astrocytes is dependent on NOS-mediated arginine metabolism (Table 13). Inhibitors of protein phosphatase (PP) 1/2A (calyculin A and microcystin), PP 2B (deltamethrin and fenvalerate) or protein tyrosine phosphatase (dephostin and orthovanadate) alone was neither stimulatory nor inhibitory to nitrite production in control astrocytes. However, calyculin A and microcystin, when added with the addition of LPS, potentially stimulated LPS-mediated induction of nitrite production in astrocytes. In contrast, inhibitors of PP 2B (cypermethrin, deltamethrin and fenvalerate) had no effect on LPS-induced nitrite production in astrocytes indicating that stimulation of LPS-induced production of NO in astrocytes is specific for the inhibitors of PP 1/2A.

To understand the mechanism of stimulatory effect of inhibitors of PP 1/2A on the LPS-mediated nitrite production in astrocytes, the effect of these inhibitors on the protein and mRNA level of inducible nitric oxide synthase (iNOS) was examined. Rat primary astrocytes were incubated in serum-free DMEM/F-12 received calyculin A, microcystin or cantharidin along with 1.0 μg/ml of LPS. After 24 h, concentration of nitrite was measured in the supernatants as described in Example 6. Data were taken as the mean±S.D. of three different experiments. Cell homogenates were electrophoresed, transferred on nitrocellulose membrane and immunoblotted with antibodies against mouse macrophage iNOS as described in Example 6. After 6 h of incubation, cells were taken out directly by adding ultraspec-11 RNA reagent (Biotecx Laboratories Inc) to the plates for isolation of total RNA, and northern blot analysis for iNOS mRNA was carried out as described. Assays were conducted for control, LPS, LPS+calyculin A (1 nM), LPS+calyculin A (2 nM), LPS+microcystin (1 nM), LPS+microcystin (2 nM), LPS+cantharidin (200 nM), and LPS+cantharidin (400 nM). Consistent with the production of nitrite, western blot analysis with antibodies against murine macrophage iNOS and northern blot analysis for iNOS mRNA of LPS-stimulated astrocytes clearly showed that inhibitors of PP 1/2A (calyculin A, microcystin and cantharidin) enhanced the LPS-mediated induction of iNOS protein and mRNA.

Since the inhibitors of PP 1/2A stimulated the LPS-mediated induction of iNOS, the inventor examined whether these inhibitors inhibited the activities of PP 1/2A in LPS-treated astrocytes. The activities of PP 1/2A were measured in homogenates after 30 min of incubation. Cells incubated in serum-free DMEM/F-12 received different concentrations of okadaic acid (0-20 nM) along with 1.0 µg/ml of LPS. After 30 min of incubation, protein phosphatase activity was measured (nmol PI/mln/mg). Data was measured as the mean±S.D. of three different experiments. Cells incubated in serum free DMEM/F-12 received different concentrations of okadaic acid in the presence or absence of 1.0 µg/ml of LPS. After 24 h of incubation, nitrite concentrations (nmol/mg/24 h) were measured in supernatants. Data are mean±S.D. of three different experiments. Okadaic acid dose-dependently inhibited the activities of PP 1/2A and stimulated the LPS-mediated induction of iNOS protein and production of NO in astrocytes. In a similar manner, calyculin A also inhibited the activities of PP 1/2A.

Cells incubated in serum-free DMEM/F-12 received different concentrations of okadaic acid (0, 1, 2, 4, 8, 15, and 20 nM) along with 1.0 µg/ml of LPS. After 24 h of incubation, cell homogenates were electrophoresed, transferred on nitrocellulose membrane and immunoblotted with antibodies against mouse macrophage iNOS as described before.

TABLE 13

Effect of inhibitors of different protein phosphatases on LPS-induced production of NO in rat primary astrocytes

| Stimuli | Nitrite (nmol/rag/24 h) |
|---|---|
| Control | 3.1 ± 0.3 |
| LPS | 28.2 ± 3.1 |
| LPS + L-NMA (0.1 mM) | 5.2 ± 0.4 |
| LPS + Cypermethrin (1 nM) | 27.6 ± 2.7 |
| LPS + Deltamethrin (1 nM) | 26.8 ± 2.9 |
| LPS + Fenvalerate (20 nM) | 27.1 ± 2.1 |
| LPS + Calyculin A (2 nM) | 67.8 ± 7.3 |
| LPS + Microcystin (2 nM) | 64.8 ± 7.2 |

Astrocytes preincubated in serum-free DMEM/F-12 for 30 min with L-NMA and different inhibitors of protein phosphatases received LPS (1.0 µg/ml). After 24 h of incubation, nitrite concentration in the supernatants were measured as described under "Materials and Methods". Data are expressed as the mean±S.D. of three different experiments.

Stimulation of LPS- and cytokine-induced production of NO by calyculin A in $C_6$ glial cell Similar to primary astrocytes, proinflammatory cytokines and LPS induce the production of nitrite as well as the expression of iNOS in rat $C_6$ glial cells (Feinstein et al., 1994a, Dobashi et al., 1997). Unlike astrocytes, neither LPS or cytokine(s) alone was not a sufficient inducer of NO production in rat $C_6$ glial cells (Feinstein et al., 1994a; Dobashi et al., 1997). A combination of LPS and cytokines was required to induce the production of NO in C6 glial cells (Feinstein et al., 1994a; Dobashi et al., 1997).

However, the addition of 2 nM calyculin A along with LPS and cytokines to $C_6$ cells stimulated the expression of iNOS protein and the production of NO (nmol/mg/24 hr) by more than three fold in $C_6$ glial cells. Samples tested included control, LPS+TNF-α, TNF-α+IFN-γ, TNF-α+IL-1β, LPS+TNF-α+calyculin A, TNF-α+IFN-γ+calyculin A, and TNF-α+IL-1β+calyculin A. After 24 h, concentration of nitrite was measured in the supernatants as described. Data was measured as the mean±S.D. of three different experiments. Cells incubated in serum-free DMEM/F-12 received calyculin A along with LPS and cytokines. Cell homogenates were electrophoresed, transferred on nitrocellulose membrane and immunoblotted with antibodies against mouse macrophage iNOS as described. These results indicate that both in primary astrocytes and C6 glial cells the inhibitors of PP 1/2A up regulate the cytokine-induced expression of iNOS and the production of NO.

Inhibition of LPS- and cytokine-induced NO production by inhibitors of PP1/2A in rat peritoneal macrophages: Since inhibitors of PP 1/2A stimulated the LPS- and cytokine-induced NO production in rat primary astrocytes and C6 glial cells, the effect of these inhibitors on NO production and expression of iNOS in rat resident macrophages was examined. Similar to astrocytes, inhibitors of PP 1/2A alone had no effect on the induction of NO production. However, in contrast to the stimulation of NO production in astrocytes (Table 13), all three inhibitors of PP1/2A (calyculin A, microcystin and cantharidin) inhibited the LPS-induced NO production in rat peritoneal macrophages. Cells in this study were incubated in serum-free DMEM/F-12 and received calyculin A, microcystin or cantharidin along with 1.0 µg/ml of LPS. Samples tested included control, LPS, LPS+calyculin A (1 nM), LPS+calyculin A (2 n), LPS+microcystin (1 nM), LPS+microcystin (2 nM), LPS+cantharidin (200 nM), and LPS+cantharidin (400 nM). After 24 h, concentration of nitrite was measured (nmol/mg/24 h) in the supernatants as described in Example 6. Data was measured as the mean±S.D. of three different experiments. Cell homogenates were electrophoresed, transferred on nitrocellulose membrane and immunoblotted with antibodies against mouse macrophage iNOS as described. After 6 h of incubation, cells were analyzed for iNOS mRNA by northern blotting technique as described earlier. This decrease in NO production was accompanied by a decrease in iNOS protein and iNOS mRNA.

Okadaic acid, another very specific and potent inhibitor of PP 1/2A, also dose-dependently inhibited the LPS-mediated production of NO and expression of iNOS protein in astrocytes. Cells incubated in serum-free DMEM/F-12 received different concentrations of okadaic acid (0, 5, 10, 15, and 20 nM in the presence or absence of 1.0 µg/ml of LPS. After 24 h of incubation, nitrite concentrations were measured in supernatants. Data was determined as the mean±SD. of three different studies. Cells incubated in serum-free DMEM/F-12 received different concentrations of okadaic acid along with 1.0 µg/ml of LPS. Samples tested included control, LPS, LPS+okadaic acid (1 nM), LPS+okadaic acid (2 nM), LPS+okadic acid (4 nM), LPS+okadic acid (8 nM), LPS+okadic acid (15 nM), LPS+okadic acid (20 nM). After 24 h of incubation, cell homogenates were electrophoresed, transferred on nitrocellulose membrane and immunoblotted with antibodies against mouse macrophage iNOS as described in Example 6.

Similar to macrophages, calyculin A was also found to inhibit the LPS- and cytokine-induced production of NO and the expression of iNOS protein in the murine macrophage cell line RAW 264.7. Cells in this study were incubated in serum-free DMEM/F-12 received calyculin A along with LPS and cytokines. Samples tested included control, LPS+TNF-α, TNF-α+IFN-γ, TNF-α+IL-1β, LPS+TNF-α+calyculin A, TNF-α+IFN-γ+calyculin A, and TNF-α+IL-1β+calyculin A. After 24 h, concentration of nitrite (nmol/mg/24 h) was measured in the supernatants as described in Example 6. Data are mean±S.D. of three different studies. Cell homogenates were electrophoresed, transferred on antibodies against mouse macrophage iNOS as described. Taken together, these results indicate that PP 1/2A activities are required to induce iNOS gene expression in macrophages.

Figure 5A:
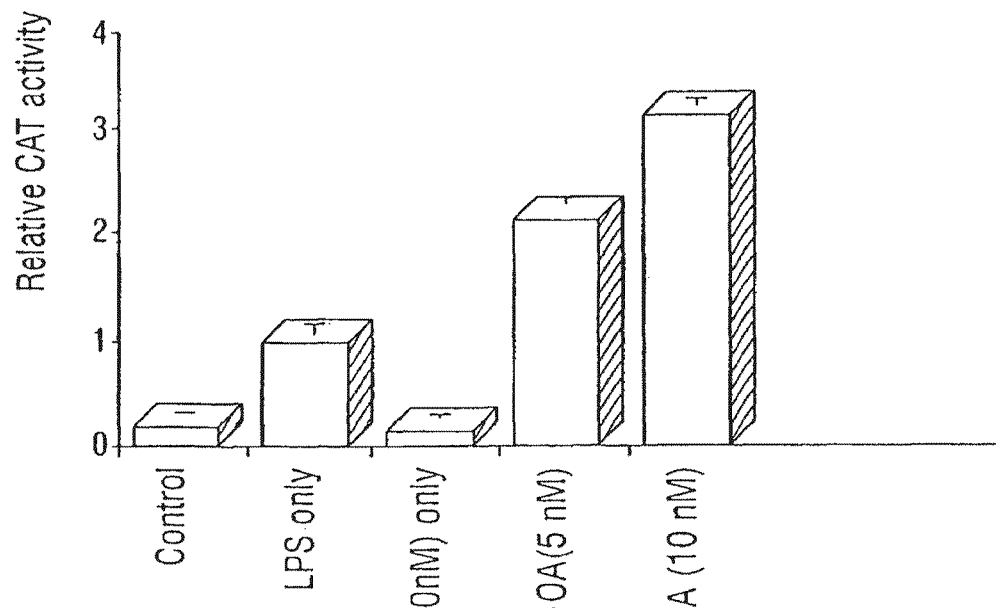
FIG. 5. Effect of okadaic acid on iNOS promoter-derived CAT activity in rat primary astrocytes and macrophages. Astrocytes (FIG. 5A) macrophages (FIG. 5B) were transfected with the construct containing the iNOS promoter fused to the CAT gene using lipofectamine. Twenty four hour after transfection, cells received okadaic acid with or without 1.0 µg/ml of LPS and after 14 h of stimulation, CAT activity was measured. Data are mean±S.D. of three different experiments.
Figure 5B:
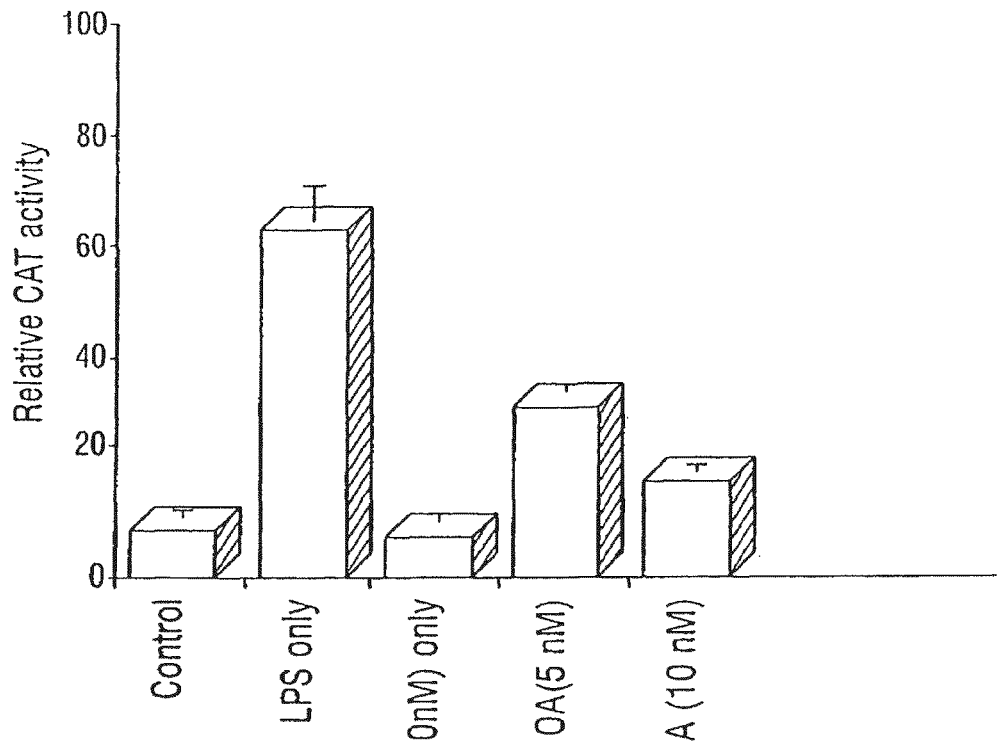

Differential effect of okadaic acid on iNOS promoter-derived chloramphenicol acetyl transferase (CAT) activity in LPS-stimulated rat primary astrocytes and macrophages Differential regulation of the induction of iNOS mRNA and protein in astrocytes and macrophages by the inhibitors of PP 1/2A indicates that these inhibitors regulate the transcription of iNOS gene differentially in these two different cell lines. Therefore, to understand the effect of okadaic acid on the transcription of iNOS gene, astrocytes and macrophages were transfected with a construct containing the iNOS-promoter fused to the CAT gene, and activation of this promoter was measured after stimulating the cells with LPS in the presence or absence of okadaic acid. Consistent with the effect of okadaic acid on the production of NO and the expression of iNOS in two different cell types, okadaic acid stimulated the LPS-induced CAT activity in astrocytes but inhibited the LPS-induced CAT activity in macrophages (FIG. 5) indicating that okadaic acid differentially regulates the transcription of iNOS gene in astrocytes and macrophages.

Effect of okadaic acid on the activation of NF-kB in rat primary astrocytes and macrophages Inhibitors of PP 1/2A stimulated the induction of iNOS in astrocytes but inhibited the induction of iNOS in macrophages indicating that PP 1/2A transduce different signals in two different cell types for the differential regulation of iNOS. Since the activation of NF-kB is necessary for the induction of iNOS, to understand the basis of this differential regulation of induction of iNOS by inhibitors of PP 1/2A, the effect of okadaic acid on the LPS-induced activation of NF-kB in astrocytes and macrophages was examined. Astrocytes and macrophages incubated in serum-free DMEM/F-12 were treated with okadaic acid alone or together with LPS (1.0 µg/ml), and nuclear proteins were isolated. After 1 h of incubation, cells were taken out to prepare nuclear extracts and nuclear proteins were used for the electrophoretic mobility shift assay as described in Example 6. Samples assayed included nuclear extract of control cells, nuclear extract of LPS-treated cells, nuclear extract of LPS-treated cells incubated with 100-fold excess of unlabelled oligonucleotide, nuclear extract of cells treated with okadaic acid (5 nM) alone, nuclear extract of cells treated with okadaic acid (10 nM) alone, nuclear extract of LPS and okadaic acid (5 nM) treated cells, and nuclear extract of LPS and okadaic acid (10 nM) treated cells. Activation of NF-kB was evaluated by the formation of a distinct and specific complex in a gel-shift DNA-binding assay. Treatment of astrocytes or macrophages with 1.0 µg/ml of LPS resulted in the activation of NF-kB.

This gel shift assay detected a specific band in response to LPS that was competed off by an unlabelled probe. Although okadaic acid alone at different concentrations failed to induce the activation NF-kB in astrocytes yet okadaic acid alone induced the activation of NF-kB in macrophages. However, in both astrocytes and macrophages, okadaic acid stimulated the LPS-induced activation of NF-kB.

Inhibitors of PP 1/2A stimulate the LPS-induced production of TNF-α in rat primary astrocytes and macrophages: Okadaic acid stimulated the transcription of iNOS in astrocytes and attenuated the transcription of iNOS in macrophages. However, in contrast, okadaic acid stimulated the activation of NF-kB in both astrocytes and macrophages. Since the induction of TNF-α also depends on the activation of NF-kB, the effect of okadaic acid on the LPS-induced production of TNF-α in astrocytes and macrophages was studied. Consistent with the stimulatory effect of okadaic acid on the LPS-induced activation of NF-kB, okadaic acid stimulated the LPS-induced production of TNF-α in both astrocytes and macrophages (Table 14).

TABLE 14

Effect of inhibitors of PP 1 and PP 2A on LPS-induced production of TNF-α in rat primary astrocytes and macrophages

| Stimuli | TNF-α (ng/24 h/mg protein) | |
|---|---|---|
| | Astrocytes | Macrophages |
| Control | 0.3 ± 0.03 | 0.5 ± 0.06 |
| LPS | 5.8 ± 0.7 | 18.9 ± 52.3 |
| LPS + Calyculin A (1 nM) | 12.5 ± 1.6 | 27.5 ± 3.1 |
| LPS + CalyculinA(2 nM) | 16.9 ± 2.1 | 31.2 ± 3.6 |
| LPS + Okadaic acid (5 nM) | 10.8 ± 1.2 | 24.3 ± 1.9 |
| LPS + Okadaic acid (10 nM) | 14.6 ± 1.8 | 28.9 ± 3.4 |

Cells preincubated in serum-free DMEM/F-12 with different concentrations of okadaic acid for 30 min was stimulated with 1.0 jig/ml of LPS. After 24 h of incubation, concentration of TNF-α was measured in supernatants as described under "Materials and Methods". Data are expressed as the mean±S.D. of three different experiments.

Effect of inhibitors of PP1/2A on cell viability Astrocytes or macrophages were incubated with different inhibitors of PP1/2A for 24 h and their viability was determined as measured by the MTT assay. None of the inhibitors at the concentrations used in this study decreased or increased the viability of the cells. Therefore, stimulation of the expression of iNOS in astrocytes and inhibition of the expression of iNOS in macrophages by inhibitors of PP 1/2A are not due to any change in viability of either astrocytes or macrophages.

EXAMPLE 7

Cytokine-Mediated Induction of Ceramide Production is Redox-Sensitive

Materials and Methods

Reagents DMEM/F-12 and fetal bovine serum (FBS) were from GIBCO. Human IL1β was from Genzyme. Mouse recombinant TNF-α was obtained from Boehringer Mannheim, Germany. Diamide, buthione (S,R)-sulfoximine, N-acetyl cysteine, pyrrolidine dithiocarbamate were from Sigma.

Isolation and maintenance of rat primary microglia, oligodendrocytes and astrocytes Microglial cells were isolated from mixed glial cultures according to the procedure of Guilian and Baker (1986). Briefly, after 7 days the mixed glial cultures were washed 3 times with DMEM/F-12 containing 10% FBS and subjected to a shake at 240 rpm for 4 h at 37° C. on a rotary shaker. The floating cells were washed and seeded onto plastic tissue culture flasks and incubated at 37° C. After 30 min the non-attached cells (mostly oligodendrocytes) were removed by repeated washes and the attached cells were used as microglia. These cells were seeded onto new plates for further studies. Ninety to ninety-five percent of this preparation was positive for nonspecific esterase, a marker for macrophages and microglia.

After 4 h shaking, the flasks were washed three times to remove the floating cells. Medium with 10% FBS was added and flasks were subjected to another cycle of shaking for 24 h at 250 rpm. The suspended cells were spun at 200 g and incubated for 30 min in tissue culture dish. The non-attached or weakly attached cells (mostly oligodendrocytes) were removed and seeded onto polylysine coated dishes and cultured in medium containing 1% FBS. Ninety-five to ninety-seven percent of these cells were positive for galactocerebroside immunostaining.

Astrocytes were prepared from rat cerebral tissue as described by McCarthy and DeVellis (1980). After 10 days of culture astrocytes were separated from microglia and oligodendrocytes by shaking for 24 h in an orbital shaker at 240 rpm. To ensure the complete removal of all oligodendrocytes and microglia, the shaking was repeated twice after a gap of one or two days. Attached cells were trypsinized (1 mM EDTA and 0.05% trypsin in 10 mM tris-buffer saline, pH 7.4) and distributed into culture dishes. These cells when checked for the astrocyte marker glial fibrillar acidic protein (GFAP), were found to be 95 to 100% positive. C6 glial cells obtained from ATCC were also maintained in DMEM/F-12 containing 10% FBS as indicated above.

Brain tissue Frozen and fixed X-adrenoleukodystrophy and multiple sclerosis brain tissues were obtained from Brain and Tissue Banks for Developmental Disorders, University of Maryland, Baltimore, Md. 21201.

Lipid extraction Approximately $1.0 \times 10^6$ cells were exposed to different cytokines in the presence or absence of antioxidants for different periods and lipids were extracted according to the methods described by Welsh (1996).

Quantification of sphingomyelin by HPTLC and densitometry Sphingomyelin was separated from total lipid extracts by HPTLC (LPK-plates from Whatman Labsales, USA) as described (Ganser et al., 1988) for phospholipids with the modification, that the plate was overrun for 30 min during its development and was dried overnight in vacuum desicator. Sphingomyelin was quantitated by densitometric scanning using Imaging Densitometer (Model GS-670; Bio-Rad, USA) and software provided with the instrument by the manufacturer.

Quantification of ceramide levels by diacylglycerol kinase assay Ceramide content was quantified essentially according to Priess et al. using diacylglycerol (DAG) kinase and $[\gamma-^{32}P]$ ATP (Priess et al., 1986). Briefly, dried lipids were solubilized in 20 μl of an octyl β-D-glucoside/cardiolipin solution (7.5% octyl β-D-glucoside, 5 mM cardiolipin in 1 mM DTPA) by sonication in a sonicator bath. The reaction was then carried out in a final volume of 100 μl containing the 20 μl sample solution, 50 mM imidazole HCl, pH 6.6, 50 mM NaCl, 12.5 mM $MgCl_2$, 1 mM EGTA, 2 mM dithiothreitol, 6.6 μg of DAG kinase, and 1 mM $[\gamma-^{32}P]ATP$ (specific activity of 1-5× $10^5$ cpm/nmol) for 30 min at room temperature. The labeled ceramide 1-phosphate was resolved with a solvent system consisting of methyl acetate: n-propanol:chloroform:methanol:0.25% KCl in water:acetic-acid (100:100:100:40:36:2). A standard sample of ceramide was phosphorylated under identical conditions and developed in parallel. Both standard and samples had identical $R_F$ value (0.46). Quantification of ceramide 1-phosphate was carried out by autoradiography and densitometric scanning using Imaging Densitometer (Model GS-670; Bio-Rad, USA). Values are expressed either as arbitrary units (absorbance) or as percent change.

Measurement of reduced glutathione (GSH) concentration in rat primary astrocytes Concentration of intracellular GSH was measured using a colorimetric assay kit for GSH from RandD, USA. Briefly, $2 \times 10^6$ cells were homogenized in 500 μl of ice-cold 5% metaphosphoric acid and centrifuged at 3000 g for 10 min. Supernatants were used to assay GSH using 4-chloro-1-methyl-7-trifluoromethyl-quinolinium methylsulfate and 30% NaOH at 400 nm.

Detection of DNA fragmentation Cells ($1 \times 10^6$) were pelleted in an eppendorf tube by centrifugation at 1,000 rpm for 5 min, washed with PBS (pH 7.4), resuspended gently in 50 μl of a lysis buffer [200 mM NaCl, 10 mM Tris-HCl (pH 8.0), 40 mM EDTA (pH 8.0), 0.5% SDS, 400 ng RNase A/μl] and incubated at 37° C. for 1 h. The lysate received 200 μl of the digestion buffer [200 mM NaCl, 10 mM Tris-HCl (pH 8.0), 0.5% SDS, 125 ng proteinase K/μl]. The contents were mixed by inversion several times and then incubated at 50° C. for 2 h. An equal volume of a mixture phenol (pH 8.0), chloroform and isoamyl alcohol (25:24:1, v/v) was added, gently mixed for 10 min, and stored at room temperature for 2 min. The two phases were separated by centrifugation at 3,000 rpm for 10 min. The viscous aqueous phase was transferred to a fresh tube and the phenol/chloroform extraction was repeated. The aqueous phase was extracted with an equal volume of chloroform and 1.0 M $MgCl_2$ was added to the aqueous phase to a final concentration of 10 mM. The total DNA was precipitated by the addition of 2 vols. of absolute ethanol with several inversions. DNA was pelleted by centrifugation at 3,000 rpm for 15 min, washed with 70% ethanol and air-dried. The pellet was dissolved in 25 μl of 10 mM Tris-HCl containing 1.0 mM EDTA (pH 8.0) and electrophoresed in 1.8% agarose gel at 4° C. The gel was stained with ethidium bromide and DNA-intercalated ethidium fluorescence was photographed on Polaroid film 665 (P/N) using an orange filter. To study DNA fragmentation in banked human brain tissues, brain tissues were gently homogenized in 0.85 M sucrose buffer and nuclei were purified according to the procedure described previously (Lazo et al., 1991). Total genomic DNA was isolated from the nuclei and electrophoresed as described.

Fragment end labeling of DNA on paraffin-embedded tissue sections of MS and X-AID brains Fragmented DNA was detected in situ by the terminal deoxynucleotidyl transferase (TDT)-mediated binding of 3'-OH ends of DNA fragments generated in response to apoptotic signals, using a commercially available kit (TdT FragEL™) from Calbiochem, USA. Briefly, paraffin-embedded tissue slides were deparaffinized, rehydrated in graded ethanol, treated with 20 μg/ml proteinase K for 15 min at room temperature, and washed prior to TdT staining. After TdT staining, sections were lightly counterstained with methyl green.

Results

N-Acetyl-L-cysteine (NAC) and pyrrolidine dititiocarbamate (PDTC) block TNF-α- and IL-1β-induced degradation of sphingomyelin to ceramide in primary rat astrocytes Rat primary astrocytes were cultured in serum-free media with TNF-α or IL-1β for different times to quantify the production of ceramide using diacylglycerol (DAG) kinase. Since DAG kinase phosphorylates both DAG and ceramide using $[\gamma-^{32}P]ATP$ as substrate, both lipids can be quantified in the same assay. Cells were exposed to TNF-α (50 ng/ml) for different time intervals (0, 5, 15, 30, 45, and 60 minutes). Lipids were extracted, and DAG and ceramide contents were determined as described (i.e. optical density) in Example 7. Results were measured as the mean±S.D. of three different studies. It was found that in astrocytes, the DAG content was much higher than the ceramide content.

Figure 6A:
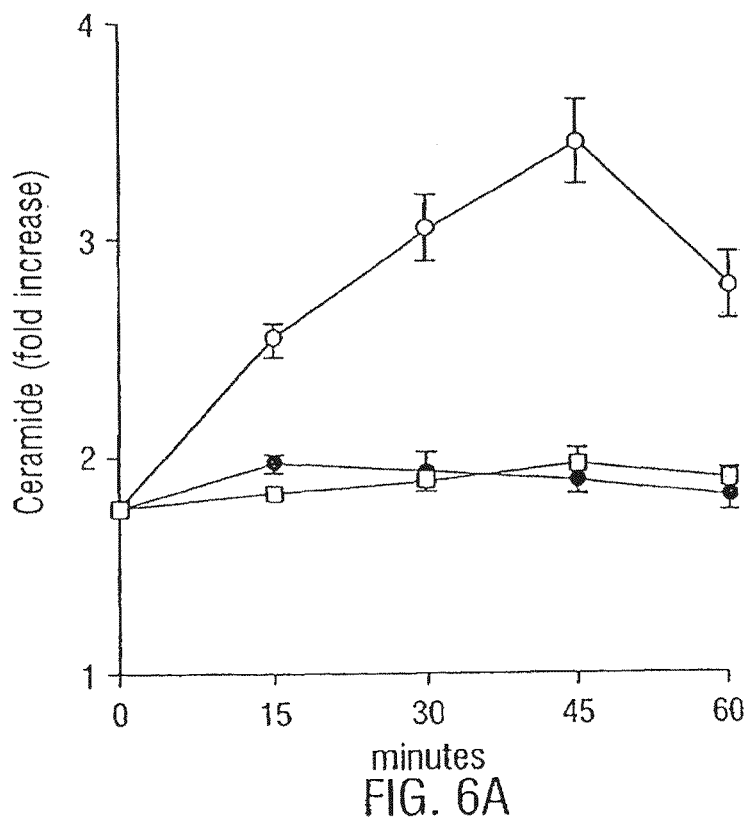
FIG. 6. Inhibition of TNF-α-induced degradation of sphingomyelin to ceramide by NAC and PDTC in rat primary astrocytes. Cells preincubated with either 10 mM NAC or 100 µM PDTC for 1 h in serum-free DMEM/F-12 received TNF-α (50 ng/ml). At different time intervals, cells were washed with HBSS and scrapped off Lipids were extracted, and levels of ceramide (FIG. 6A) and sphingomyelin (FIG. 6B) were measured as described in Example 7. Ceramide levels are expressed as -fold change over the level at 0 min. Results are mean±S.D. of three different studies.
Figure 6B:
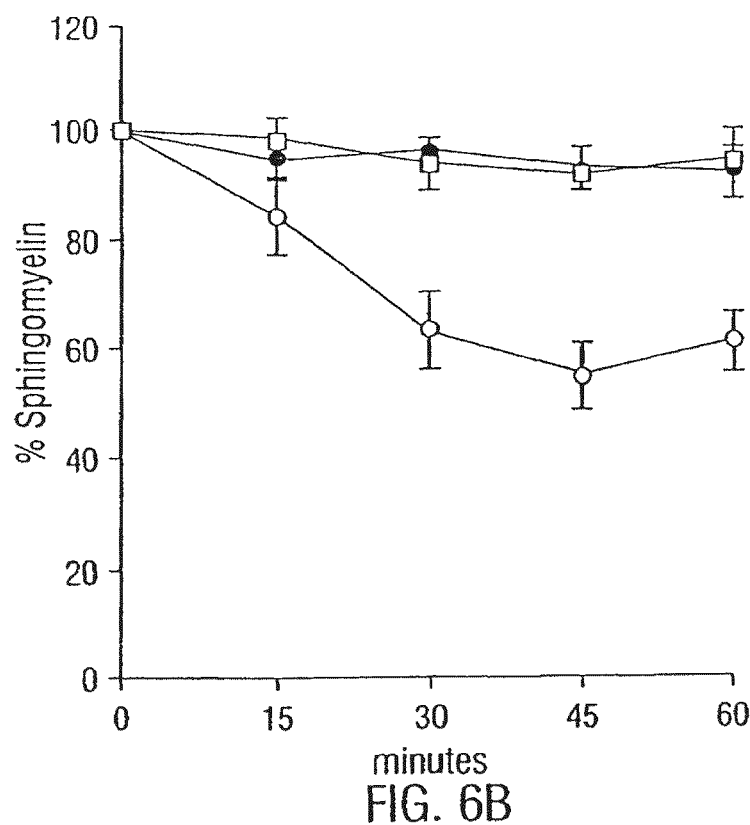
Figure 7A:
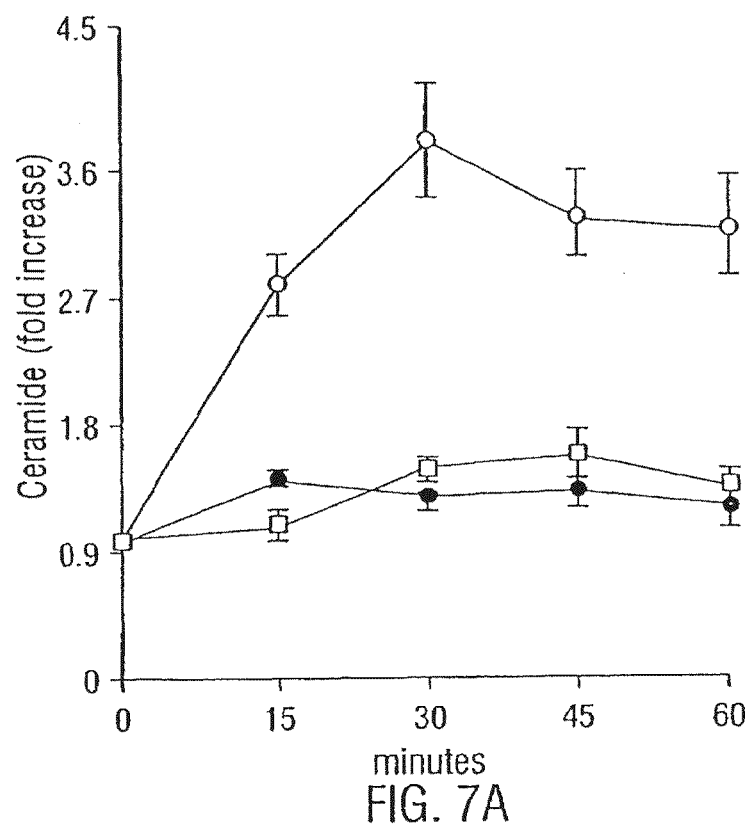
FIG. 7. NAC and PDTC inhibit IL-1β-mediated degradation of sphingomyelin to ceramide in rat primary astrocytes. Cells preincubated with either 10 mM NAC or 100 µM PDTC for 1 h in serum-free DMEM/F-12 received IL-1β (50 ng/ml). At different time intervals, cells were washed with HBSS and scrapped off Lipids were extracted, and levels of ceramide (FIG. 7A) and sphingomyelin (FIG. 7B) were measured as described in Example 7. Ceramide levels are expressed as -fold change over the level at 0 min. Results are mean±S.D. of three different studies.
Figure 7B:
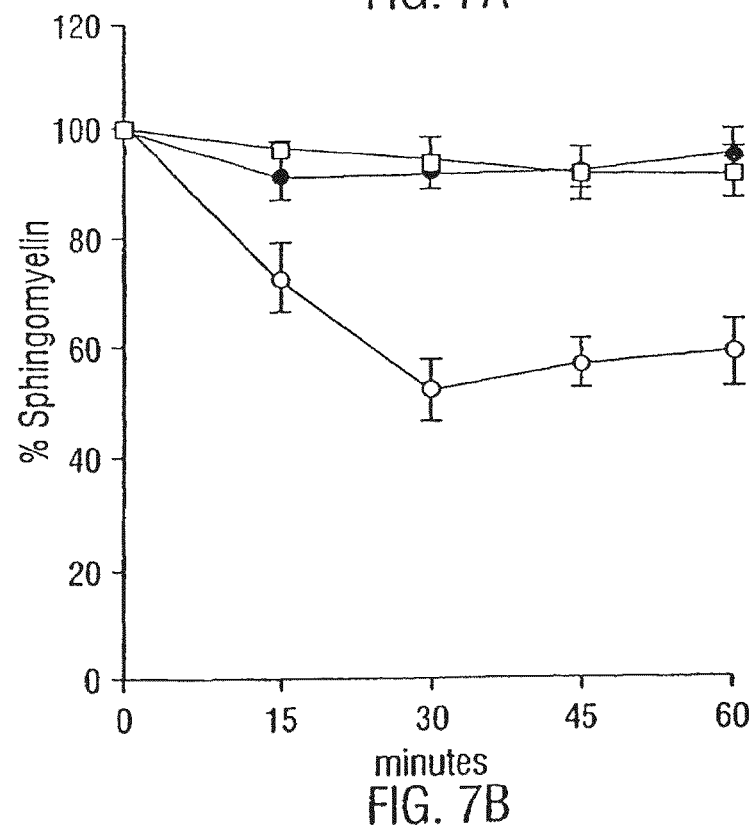

Stimulation of cells with TNF-α resulted in a time-dependent increase in the production of ceramide (about 3 fold after 45 min). In contrast to induction of ceramide production, the level of DAG, an activator of protein kinase C and acidic sphingomyelinase, was unchanged at different time points of stimulation. Similar to TNF-α (FIG. 6), stimulation of astrocytes with IL-1β for different times also induced a significant increase in the ceramide content (FIG. 7). Almost three to four fold increase in ceramide production was found in astrocytes after 30 or 45 min of exposure with TNF-α or IL-1β. This increase in ceramide was paralleled by TNF-α- and IL-1β-induced decrease in sphingomyelin (FIG. 6 and FIG. 7). Sphingomyelin concentration decreases of approximately 18 to 25% could be observed as early as 15 min following treatment of astrocytes (FIG. 6 and FIG. 7) and maximal effects of up to 45 to 50% SM hydrolysis were observed after 30 to 45 min of treatment with TNF-α or IL-1β. These results indicate that both TNF-α and IL-1β modulate the degradation of sphingomyelin to produce ceramide, the putative second messenger of the sphingomyelin signal transduction pathway, in rat primary astrocytes within a short time. Interestingly, it was found that treatment of astrocytes with antioxidants like NAC or PDTC 1 h before the addition of TNF-α or IL-1β potentially blocked the decrease in sphingomyelin as well as the increase in ceramide (FIG. 6 and FIG. 7) indicating that reactive oxygen species (ROS) are possibly involved in cytokine-induced degradation of SM to ceramide.

TNF-α and IL-I~decrease intracellular level of reduced glutathione (GSH) in rat primary astrocytes and NAC blocks this decrease Since intracellular level of GSH is an important regulator of the redox state of a cell, to understand the relationship between induction of ceramide production and intracellular level of GSH in cytokine-stimulated astrocytes, rat primary astrocytes were stimulated with TNF-α or IL-1β and the level of GSH was measured at different times. Cells preincubated with 10 mM NAC for 1 h received either TNF-α (50 ng/ml) or IL-1β (50 ng/ml). At different time intervals (0, 15, 30, 45, 60, 75, and 90 minutes), cells were scrapped off and GSH concentrations (100% value is 210±18.5 nmol/mg protein) were measured as described Example 7. Measurements were done in duplicate. The stimulation of cells with TNF-α or IL-1β resulted in an immediate decrease in intracellular level of GSH with the maximal decrease (66 to 70% of control) found within 15 to 30 min of initiation of stimulation and with a further increase in time of incubation, the level of GSH was found to be almost normalized (88 to 95% of control at 90 min). These results show that cytokine stimulation induces rapid, short-term production of oxidants which transiently deplete GSH. However, intracellular level of GSH did not decrease when cells were stimulated with cytokines in presence of NAC indicating that NAC inhibited the cytokine-induced degradation of SM to ceramide by maintaining the normal levels of GSH.

Thiol-depleting agents induce the production of ceramide in rat primary astrocytes Since NAC, a thiol antioxidant, blocked cytokine-mediated depletion of intracellular level of GSH and breakdown of SM to ceramide, the effect of a thiol-depleting agents [diamide and buthione (S,R)-sulfoximine] on ceramide production was examined. Diamide reduces the intracellular level of GSH by its oxidation to GSSG whereas buthione (S,R)-sulfoximine does so by blocking the synthesis of GSH (Shertzer et al., 1995; Akamatsu et al., 1997). Rat primary astrocytes were preincubated with 10 mM NAC for 1 h received diamide (0.5 mM). At different time intervals (0, 15, 30, 45, and 60) cells were washed with HBSS and scrapped off. Lipids were extracted, and level of ceramide was measured as described in the methods section. Ceramide levels were expressed as -fold change over the level at 0 minutes in this study. Results were measured as the mean±S.D. of three different studies. At different time intervals, intracellular level of GSH (100% value was 210±18.5 mmol/mg protein) was measured as described in Example 7. Measurements were done in duplicate. Stimulating rat primary astrocytes with diamide resulted in an immediate decrease in intracellular level of GSH due to rapid consumption of intracellular GSH through its nonenzymatic conversion to the oxidized dimer, GSSG (Shertzer et al., 1995) and marked induction of ceramide production (about 7 fold after 30 min of stimulation) indicating that intracellular level of GSH is the important regulator of degradation of SM to ceramide. Consistent with this conclusion, treatment of cells with NAC blocked diamide-mediated decrease in GSH level and induction of ceramide production. Similar to diamide, buthione (S,R)-sulfoximine also decreased the level of GSH and induced the production of ceramide. Thus the low GSH and/or high intracellular oxidant (ROS) levels induced by cytokines and thiol-depleting agents facilitated the induction of ceramide production, while the normal levels of GSH and/or low ROS induced or maintained by the addition of NAC blocked the hydrolysis of sphingomyelin to ceramide. Taken together, these results demonstrate that the intracellular levels of GSH and/or ROS regulate the extent to which sphingomyelin is degraded to ceramide and ceramide-mediated signaling cascades are transduced.

Aminotriazole and hydrogen peroxide induce the production of ceramide in rat primary astrocytes Inhibition of cytokine-mediated induction of ceramide production by antioxidants and induction of ceramide production by thiol-depleting agents alone indicate the involvement of ROS in the induction of ceramide production. Therefore, the effect of exogenous addition of an oxidant, like $H_2O_2$, or endogenously produced $H_2O_2$ on inhibition of catalase with aminotriazole (ATZ), which inhibits endogenous catalase to increase the level of $H_2O_2$, on the induction of ceramide production. Rat primary astrocytes were incubated with 5 mM aminotriazole or 0.5 mM $H_2O_2$ in presence or absence of 10 mM NAC. At different time intervals (0, 15, 30, 45, and 60 minutes), cells were washed with HBSS and scrapped off. Lipids were extracted, and level of ceramide was measured as described in Example 7. Ceramide levels were expressed as -fold change over the level at 0 minutes in these studies. Results are measured as the mean±S.D. of three different studies. The time course of ceramide production in rat primary astrocytes following the addition of ATZ. Approximately 45 min following the addition of ATZ, ceramide generation increased more than 5-fold over baseline. However, pretreatment of cells with NAC blocked the ATZ-mediated increase in ceramide production. Consistent with the increase in ceramide production by ATZ, addition of exogenous $H_2O_2$ to astrocytes also induced the production of ceramide with the maximum increase of about 7-fold after 15 min. These results clearly indicate that intracellular levels of ROS regulate the production of ceramide.

Inhibition of cytokine-mediated production of ceramide in rat primary microglia, oligodendrocytes and C6 glial cells by NAC Since NAC inhibited the cytokine-mediated production of ceramide in rat primary astrocytes, the inventor examined the effect of NAC on cytokine-mediated induction of ceramide production in rat primary oligodendrocytes, microglia and $C_6$ glial cells was examined. Rat primary microglia, oligodendrocytes and $C_6$ glial cells were preincubated with 10 mM NAC for 1 h in serum-free DMEM/F-12 received TNF-α (50 ng/ml). Cells were washed with HBSS and scrapped off at different intervals (0, 15, 30, 45, and 60 minutes). Lipids were extracted, and ceramide content was measured as described in Example 7. Ceramide levels were expressed as -fold change over the level at 0 minutes in these studies. Results are mean±S.D. of three different studies. The addition of TNF-α to oligodendrocytes, microglia or $C_6$ glial cells induced the production of ceramide. The increase in ceramide in these cells ranges from 2.5 to 4-fold with highest increase in glial cells and lowest in oligodendrocytes. The ceramide levels peaked in glial cells at 30 min following stimulation and 45 min of stimulation in oligodendrocytes and $C_6$ glial cells. These results show that similar to astrocytes, the SM cycle is also present in microglia, oligodendrocytes and $C_6$ glial cells. Consistent with the effect of NAC on the production of ceramides in astrocytes, this antioxidant also potently blocked the TNF-α-induced production of ceramide in microglia, oligodendrocytes and $C_6$ glial cells indicating that ROS are also involved in cytokine-mediated ceramide production in these cells was examined.

NAC inhibits TNF-α- and diamide-mediated apoptosis in rat primary oligodendrocytes by increasing the intracellular level of GSH and decreasing the production of ceramide: Since cytokine-mediated ceramide production is implicated in apoptosis of different cells including brain cells (Brugg et al., 1996; Wiesner and Dawson, 1996), the effect of NAC on TNF-α- as well as diamide-mediated apoptosis in rat primary oligodendrocytes, as evidenced by electrophoretical detection of hydrolyzed DNA fragments ("laddering") was investigated. To understand the role of intracellular level of GSH in inducing apoptosis, rat primary oligodendrocytes were treated with TNF-α or with diamide, a thiol-depleting agent. Cells preincubated with 10 mM NAC for 1 h received either diamide (0.5 mM) or TNF-α (50 ng/ml). Samples were prepared for control cells, diamide, diamide+NAC, TNF-α, and TNF-α+NAC. After 12 h of incubation, cells were harvested and washed with PBS, and genomic DNA was extracted and run on agarose gels as described in the methods section. Ten micrograms of DNA was loaded in each lane. Levels of ceramide and GSH were measured in homogenates as described in Example 7. Results were determined as the mean±S.D. of three different studies. Both TNF-α and diamide decreased the intracellular level of GSH, increased the level of ceramide and induced internucleosomal DNA fragmentation as evident from the typical ladder pattern that was generated. Interestingly, blocking of diamide- as well as TNF-α-mediated decrease in intracellular level of GSH by pre-treatment with NAC inhibited the induction of ceramide formation and DNA fragmentation indicating that intracellular level of GSH regulate apoptosis in oligodendrocytes through ceramide formation.

DNA fragmentation in banked human brains with X-adrenoleukodystrophy (X-ALD) and multiple sclerosis (MS) In the CNS, apoptosis may play an important pathogenetic role in neurodegenerative diseases such as ischemic injury, and white matter diseases (Thompson, 1995; Bredesen, 1995). Both X-adrenoleukodystrophy (X-ALD) and MS are demyelinating diseases with the involvement of proinflammatory cytokines in the manifestation of white matter inflammation. Several studies demonstrating the induction of proinflammatory cytokines at the protein or mRNA level in MS patients' cerebrospinal fluid and brain tissue have established an association of proinflammatory cytokines (TNF-α, IL-1β, IL-2, IL-6 and IFN-γ) with the inflammatory loci in MS (Maimone et al., 1991; Tepper et al., 1995; Rudick and Ransohoff, 1992). Recent documentation of the presence of TNF-α, IL-1β and IFN-γ in X-ALD brain have revealed the neuroinflammatory character of this disease (Powers et al., 1992; McGuiness et al., 1997).

Therefore, to understand the underlying relationship among intracellular level GSH, level of ceramide and DNA fragmentation in cytokine-inflamed CNS of X-ALD and MS, the inventor measured the levels of GSH and ceramide in homogenates was measured and the DNA fragmentation in nuclei from brains of patients with X-ALD and MS was also studied. Genomic DNA isolated from nuclei of banked human brains was run on agarose gel and photographed as described Example 7. Ten micrograms of DNA was loaded in each lane. Levels of ceramide (optical density) and GSH (nmol/mg protein) were measured in homogenates as described. Results were determined as the mean±S.D. of three different studies. In both X-ALD and MS brain homogenates, the level of GSH was lower (55 to 70% of control) and the level of ceramide was higher (2 to 3 fold) compared to those found in control brains. Consistent with a lower level of GSH and a higher level of ceramide, genomic DNA isolated from nuclei of X-ALD and MS brains when run on agarose gels formed the typical ladder pattern which was absent in both of the normal brains. To confirm apoptosis in brain tissues of X-ALD and MS, paraffin-embedded tissue sections of X-ALD and MS were stained with TdT-mediated fragment end labeling. Terminal deoxynucleotidyl transferase (TdT)-mediated end labeling of 3'-OH ends of DNA fragments on paraffin-embedded tissue sections for control, X-ALD and MS samples was carried out using a commercially available kit from Calbiochem, USA. Consistent with increased DNA fragmentation in isolated nuclei of X-ALD and MS, increased TdT staining on brain sections of X-ALD and MS was observed as compared to those of controls. These observations indicate that intracellular level of GSH are an important factor in cytokine-mediated degradation of SM to ceramide and apoptosis in inflammatory demyelinating diseases like X-ALD and MS.

EXAMPLE 8

Lovastatin and Phenylacetate Inhibit the Induction of Nitric Oxide Synthase and Cytokines in Rat Primary Astrocytes, Microglia, and Macrophages This study explores the role of mevalonate inhibitors in the activation of NF-kβ and the induction of inducible nitric oxide synthase (iNOS) and cytokines (TNF-α, IL-1β, and IL-6) in rat primary astrocytes, microglia, and macrophages.
Materials and Methods Reagents Recombinant rat IFN-γ, DMEM/F-12 medium, FBS, and HBSS were from GIBCO-BRL (Gaithersburg, Md.). Human IL-1β was from Genzyme Corp. (Boston, Mass.). Mouse recombinant TNF-α was obtained from Boehringer Mannheim (Mannheim, Germany). Lovastatin, mevastatin, and farnesyl pyrophosphate were from BIO-MOL Res. Labs Inc. (Plymouth Meeting, Pa.). Mevalonate, cholesterol, ubiquinone, arginase and LPS (*Escherichia coli*, serotype 0111:B4) were from Sigma Chemical Co. (St. Louis, Mo.). $N^G$-methyl-L-arginine (L-NMA), FPT inhibitor II, and antibodies against mouse macrophage iNOS were obtained from Calbiochem Corp. (La Jolla, Calif.). Immunoassay kits for TNF-α, IL-1β, and IL-6 were obtained from R&D Systems, Inc. (Minneapolis; MN). NF-kβ DNA binding protein detection kit was from GIBCO-BRL. [γ-$^{32}$P]ATP (3,000 Ci/mmol) was from Amersham Corp. (Arlington Heights, Ill.). [2-$^{14}$C]acetate was purchased from ICN Biomedicals Inc. (Irvine, Calif.). NaPA was prepared from phenylacetic acid (Sigma Chemical Corp.) and NaOH as described (Samid et al., 1992).

Induction of NO production in rat astrocytes, microglia, and $C_6$ glial cells Astrocytes were prepared from rat cerebral tissue as described by McCarthy and DeVellis (McCarthy and DeVellis, 1980). Cells were maintained in DMEM/F-12 medium containing 10% FBS. After 10 d of culture, astrocytes were separated from microglia and oligodendrocytes by shaking for 24 h in an orbital shaker at 240 rpm. To ensure complete removal of the oligodendrocytes and microglia, the shaking was repeated twice after a gap of 1 or 2 d. Cells were trypsinized, subcultured, and stimulated with LPS or different cytokines in serum-free DMEM/F-12 medium. Microglial cells were isolated from mixed glial cultures according to the procedure of Guilian and Baker (Giulian and Baker, 1986). In brief, on days 7-9 the mixed glial cultures were washed three times with DMEM/F-12 and subjected to a shake at 240 rpm for 2 h at 37° C. on a rotary shaker. The floating cells were washed, seeded onto plastic tissue culture flasks, and incubated at 37° C. for 2 h. The attached cells were removed by trypsinization and seeded onto new plates for further studies. 90-95% of this preparation was found to be positive for nonspecific esterase, a marker for macrophages and microglia. For induction of NO production, cells were stimulated with LPS or cytokines in serum-free condition. $C_6$ glial cells obtained from American Type Culture Collection (Rockville, Md.) were also maintained and induced with different stimuli as indicated above.

Isolation of rat macrophages and induction of NO production Resident macrophages were obtained from rat by peritoneal lavage with sterile RPMI 1640 medium containing 1% FBS and 100 µg/ml gentamicin. Cells were washed three times with RPMI 1640 at 4° C., and were maintained at 37° C. in a humidified incubator containing 5% $CO_2$ in air. Macrophages at a concentration of $2 \times 10^6$ ml in RPMI 1640 medium containing L-glutamine and gentamicin were added in volumes of 800 µl to a 35-mm plate. After 1 h, nonadherent cells were removed by washing, and 800 µl of serum-free RPMI 1640 medium with various stimuli was added to the adherent cells. After 24 h the culture supernatants were transferred to measure NO production.

Cell viability Cytotoxic effects of the inhibitors were determined by measuring the cell viability by Trypan blue exclusion.

Assay for NO synthesis Synthesis of NO was determined by assay of culture supernatants for nitrite, a stable reaction product of NO with molecular oxygen. In brief, 400 µl of culture supernatant was allowed to react with 200 µl of Griess reagent (Feinstein et al., 1994), and was incubated at room temperature for 15 min. The optical density of the assay samples was measured spectrophotometrically at 570 nm. Fresh culture media served as the blank in all experiments. Nitrite concentrations were calculated from a standard curve derived from the reaction of $NaNO_2$ in the assay. Protein was measured (Bradford, 1976).

Incorporation of [$^{14}$C]acetate into cholesterol Astrocytes grown in 100-mm plates (~80% confluency) and preincubated in serum-free media with lovastatin or NaPA for 8 h received [2-$^{14}$C]acetate (10 µCi/plate). After 3 h, the cells were washed twice with PBS and scraped off. The lipids were extracted with 1 ml 75% ethanol, and the ethanol extract was saponified with 1 ml of 20% ethanolic KOH at room temperature. To this, 2 ml of water was added, mixed, and extracted twice with 2 ml of hexane. The hexane extracts were dried under nitrogen, dissolved in 50 µl of $CHCl_3$/MeOH (1:1), spotted on a TLC plate along with standard [$^3$H]cholesterol, and run with hexane/ether/acetic acid (70:30:1). The plate was then exposed to a photographic film that was stored at −20° C. and developed after 2 d. The lanes corresponding to standard cholesterol were scraped and counted in 5 ml of scintillation fluid.

Immunoblot analysis for iNOS After a 24 h incubation in the presence or absence of different stimuli, cells were scraped off, washed with Hank's buffer, and homogenized in 50 mM Tris-HCl (pH 7.4) containing protease inhibitors (1 mM PMSF, 5 µg/ml aprotinin, 5 µg/ml pepstatin A, and 5 µg/ml leupeptin). After electrophoresis the proteins were transferred onto a nitrocellulose membrane, and the iNOS band was visualized by immunoblotting with antibodies against mouse macrophage iNOS and [$^{125}$I]-labeled protein A.

RNA isolation and Northern blot analysis Cells were taken out from culture dishes directly by adding Ultraspec-II RNA reagent (Biotecx Laboratories Inc., Houston, Tex.), and total RNA was isolated according to the manufacturer's protocol.

For Northern blot analyses, 20 µg of total RNA was electrophoresed on 1.2% denaturing formal-dehyde-agarose gels, electrotransferred to Hybond-Nylon Membrane (Amersham Corp.), and hybridized at 68° C. with $^{32}$P-labeled cDNA probe using Express Hyb hybridization solution (Clontech, Palo Alto, Calif.) as described by the manufacturer. The cDNA fragment for iNOS was amplified by PCR™ using two primers (forward primer: 5'-CTCCTTCAAAGAG-GCAAAAATA-3' (SEQ ID NO:1); reverse primer: 5'-CACT-TCCTCCAGGATGTTGT-3' (SEQ ID NO:2)), and was cloned in pGEM-T vector (Geller et al., 1993). The clone was confirmed by DNA sequencing, and the insert was used as probe. After hybridization, filters were washed two to three times in solution I (2×SSC, 0.05% SDS) for 1 h at room temperature, followed by solution II (0.1×SSC, 0.1% SDS) at 50° C. for another hour. The membranes were then dried and exposed with x-ray films (Eastman Kodak Co., Rochester, N.Y.). Same filters were stripped and rehybridized with probes for GAPDH. The relative mRNA content for iNOS was measured after scanning the bands with a BioRad Model GS-670; Richmond, Calif.) imaging densitometer.

Nuclear run-on assay For the measurement of gene transcription, nuclei were prepared, and in vitro transcriptional activity was measured with nuclei ($25 \times 106$ nuclei per assay) using 30 µCi of [$\alpha$-$^{32}$P]-UTP (400 Ci/mmol) as described (Caira et al., 1995). In brief, the filters were prehybridized in 1 ml of hybridization buffer (50% formamide, 5×SSC, 1% SDS, 15% dextran sulfate, 1×Denhardt's solution, and 50 µg/ml heparin). After 24 h of prehybridization in the above buffer, hybridization was carried out with the labeled RNAs ($1.3 \times 10^5$ cpm) at 42° C. for 60 h to 3 µg of the immobilized plasmid pGEM-T as a control, or to plasmids containing inserts of rat glyceraldehyde-3-phosphate dehydrogenase, rat actin, and human iNOS cDNAs. The filters were washed twice in 2×SSC, 0.1% SDS for 15 min at SAC, and twice in 0.5×SSC, 0.1% SDS for 15 min. Then the filters were treated with RNase buffer (300 mM NaCl, 10 mM TrisHCl, pH 7.4, 40 mM EDTA, 10 µg/ml RNase A, and 350 U/ml RNase T1) at 37° C. for 30 min, in the same buffer without RNases for another 30 min, and were then autoradiographed.

Determination of TNF-$\alpha$, IL-1$\beta$, and IL-6 in culture supernatants Cells were stimulated with LPS in serum-free media for 24 h in the presence or absence of lovastatin or NaPA, and concentrations of TNF-$\alpha$, IL-1$\beta$, and IL-6 were measured in culture supernatants by using high-sensitivity enzyme-linked immunosorbent assay (R&D Systems, Inc.) according to the manufacturer's instructions.

Preparation of nuclear extracts and electrophoretic mobility shift assay Nuclear extracts from stimulated or unstimulated astrocytes ($1 \times 10^7$ cells) were prepared (Dignam et al., 1983) with slight modifications. Cells were harvested, washed twice with ice-cold PBS, and lysed in 400 µl of buffer A (10 mM Hepes, pH 7.9, 10 mM KCl, 2 mM $MgCl_2$, 0.5 mM DTT, 1 mM PMSF, 5 µg/ml aprotinin, 5 µg/ml pepstatin A, and 5 µg/ml leupeptin) containing 0.1% Nonidet P-40 for 15 min on ice, vortexed vigorously for 15 s, and centrifuged at 14,000 rpm for 30 s. The pelleted nuclei were resuspended in 40 µl of buffer B (20 mM Hepes, pH 7.9, 25% [vol/vol] glycerol, 0.42 M NaCl, 1.5 mM $MgCl_2$, 0.2 mM EDTA, 0.5 mM DTT, 1 mM PMSF, 5 µg/ml aprotinin, 5 µg/ml pepstatin A, and 5 µg/ml leupeptin). After 30 min on ice, lysates were centrifuged at 14,000 rpm for 10 min. Supernatants containing the nuclear proteins were diluted with 20 µl of modified buffer C (20 mM Hepes, pH 7.9, 20% [vol/vol] glycerol, 0.05 M KCl, 0.2 mM EDTA, 0.5 mM DTT, and 0.5 mM PMSF) and stored at −70° C. until use. Nuclear extracts were used for the electrophoretic mobility shift assay using the NF-k$\beta$ DNA binding protein detection system kit (GIBCO/BRL) according to the manufacturer's protocol.

Results

Inhibitors of mevalonate pathway inhibit LPS-induced expression of iNOS in primary astrocytes Both HMG-CoA reductase and mevalonate pyrophosphate decarboxylase are the rate-limiting enzymes of the mevalonate pathway (Goldstein and Brown, 1990; Castillo et al., 1991). The inventor examined the effect of inhibitors of HMG-CoA reductase (lovastatin and mevastatin) and mevalonate pyrophosphate decarboxylase (NaPA) on the induction of iNOS and production of NO. Results in Table 15 show that bacterial LPS at a concentration of 1.0 µg/ml induced the production of NO by about eightfold. Inhibition of NO production by arginase, an enzyme that degrades the substrate (Q-arginine) of NOS and L-NMA, a competitive inhibitor of NOS, indicates that LPS-induced NO production in astrocytes is dependent on NOS-mediated arginine metabolism (Table 15). Lovastatin or mevastatin alone was neither stimulatory nor inhibitory to nitrite production in control astrocytes. Both the inhibitors, however, when added 8 h before the addition of LPS, potentially inhibited LPS-mediated induction of nitrite production in astrocytes. Only 25% inhibition in LPS-induced NO production was found when lovastatin was added to the cells along with LPS, however, the degree of inhibition increased with the increase in time of preincubation, with lovastatin reaching about 90% inhibition of NO production within 8-10 h of preincubation.

To understand the mechanism of inhibitory effect of these inhibitors on LPS-mediated nitrite production, we examined the effect on protein and mRNA levels of iNOS. Rat primary astrocytes were preincubated in serum-free media with different concentrations of lovastatin (5 or 10 µM) or NaPA (2 or 5 mM) or a combination of 2 µM lovastatin and 2 mM NaPA for 8 h received 1.0 µg/ml of LPS. After 24 h, supernatants were used for nitrite assay as described in the Methods section of this example. Data was measured as the mean±SD of three different experiments. Cell homogenates were electrophoresed, transferred onto nitrocellulose membranes, and immunoblotted with antibodies against mouse macrophage iNOS as described in Methods. Samples tested included control, LPS, LPS+lovastatin (5 µM), LPS+lovastatin (10 µM), LPS+NaPA (2 mM), LPS+NaPA (5 mM), and LPS+lovastatin (2 µM)+NaPA (2 mM). After 5 h of incubation, cells were taken out directly by adding ultraspec-II RNA reagent (Biotecx Laboratories Inc.) to the plates for isolation of total RNA, and Northern blot analysis for iNOS mRNA was carried out as described in Methods. Western blot analysis with antibodies against murine macrophage iNOS and Northern blot analysis for iNOS mRNA analysis of LPS-stimulated astrocytes clearly showed that both lovastatin and NaPA significantly inhibited the LPS-mediated induction of iNOS protein and mRNA. A combination of lovastatin and NaPA at a dose lower than the one used individually almost completely inhibited LPS-induced production of NO and expression of iNOS.

To gain further insight into the mechanism of the inhibitory effect of lovastatin and NaPA on LPS-mediated expression of iNOS mRNA, the inventor examined the influence of lovastatin and NaPA on the rate of iNOS gene transcription, as measured by nuclear run-on assays. Rat primary astrocytes preincubated in serum-free media with 10 µM lovastatin or 5 mM NaPA, or a combination of 2 µM lovastatin and 2 mM NaPA for 8 h received 1.0 µg/ml of LPS. After 4 h cells were taken out, and nuclei were collected for nuclear run-on assays. $^{32}$P-labeled mRNA was transcribed in vitro from isolated nuclei, and $1.3 \times 10^5$ cpm of run-on products were hybridized to each blot as described in Methods. The plasmids used were pGEM-T without any insert (negative control) or containing iNOS, glyceraldehyde-3-phosphate dehydrogenase (GAPDH), or actin cDNA inserts. Samples tested included control, LPS, LPS+lovastatin (10 µM), LPS+NaPA (5 mM), and LPS+lovastatin (2 µM)+NaPA (2 mM). LPS induced the transcription of the iNOS gene in astrocytes, and that preincubation of cells with lovastatin or NaPA inhibited the relative rate of LPS-induced nuclear transcription of the iNOS gene. Consistent with the inhibition of LPS-induced expression of mRNA, protein and activity of iNOS by lovastatin and NaPA, the combination of lovastatin and NaPA completely inhibited the transcription of iNOS gene. These results clearly indicate that lovastatin and NaPA inhibit LPS-induced expression of iNOS mRNA, protein and activity by inhibiting transcription of the iNOS gene.

TABLE 15

Inhibition of LPS-induced NO Production in Rat Primary Astrocytes by Lovastatin and Mevastatin

| Stimuli | Nitrite nmol/mg/24 h | % Inhibition |
| --- | --- | --- |
| Control | 2.9 ± 0.5 | — |
| LPS | 25.3 ± 3.2 | — |
| LPS + arginase | 5.9 ± 0.8 | 87 |
| LPS + L-NMA | 5.5 ± 0.7 | 88 |
| Lovastatin | 2.9 ± 0.3 | — |
| Mevastatin | 2.8 ± 0.4 | — |
| LPS + lovastatin | 5.2 ± 0.5 | 90 |
| LPS + mevastatin | 5.5 ± 0.5 | 88 |

Astrocytes were cultured for 24 h in serum-free DMEM/F-12 with the listed reagents; nitrite concentration in the supernatants was measured as described in Methods. Arginase (100 U/ml) and L-NMA (0.1 mM) were added to the cells together with LPS (1.0 µg/ml), however, cells preincubated with lovastatin (10 µM) or mevastatin (10 µM) for 8 h received LPS. Data are mean±SD of three different experiments.

To determine if the synergistic inhibitory effect of lovastatin and NaPA on LPS-induced iNOS expression in astrocytes could be explained solely by inhibition of the mevalonate pathway, the inventor examined the incorporation of [2-$^{14}$C] acetate into cholesterol. Cells preincubated with lovastatin or NaPA for 8 h received [2-$^{14}$C]acetate for 3 h. Lovastatin (10 µM) and NaPA (5 mM) inhibited the synthesis of cholesterol by 73±6.2 and 64±5.3%, respectively. The combination of lovastatin (2 µM) and NaPA (2 mM), however, caused 93±4.2% inhibition, indicating that lovastatin and NaPA affect cholesterol synthesis in an additive fashion. Therefore, absence of complete inhibition of iNOS mRNA or protein by lovastatin or NaPA could be due to the absence of complete inhibition of the mevalonate pathway and depletion of mevalonate metabolites.

Inhibition of LPS- and cytokine-induced production of NO by lovastatin in rat primary astrocytes Similar to LPS, different cytokines and their several combinations are known to induce the expression of iNOS (Jaffrey and Synder, 1995; Mitrovic et al., 1994; Bo et al., 1994; Merrill et al., 1993). To examine whether cytokine-induced NO production is also inhibited by lovastatin, primary astrocytes were stimulated with different combinations of LPS, TNF-α, IL-1β, and IFN-γ for 24 h, and the production of NO was measured. Rat primary astrocytes preincubated in serum-free media with 10 µM lovastatin for 8 h received different combinations of LPS and cytokines. After 24 h of incubation, production of nitrite was measured in supernatants as described earlier. Data was measured as the mean±SD of three different experiments.

Cell homogenates were analyzed for iNOS protein by immunoblotting technique as described before. Concentration of different stimuli were as follows: LPS, 0.5 µg/ml; TNF-α, 20 ng/ml; IL-1β, 50 ng/ml; IFN-γ, 50 U/ml. Samples that were assayed included control, LPS+TNF-α, LPS+IFN-γ, TNF-α+IL-1β, TNF-α+IFN-γ, LPS+TNF-α+lovastatin, LPS+IFN-γ+lovastatin, TNF-α+IL-1β+lovastatin, and TNF-α+IFN-γ+lovastatin. All the combinations of LPS and cytokines significantly induced production of NO, however, addition of 10 µM lovastatin to astrocytes potently inhibited NO production and induction of iNOS protein, indicating that similar to LPS, cytokine-mediated expression of iNOS also involves the mevalonate pathway. Under similar conditions, lovastatin was also found to inhibit LPS- and cytokine-induced NO production in rat $C_6$ glial cells.

Inhibition of LPS-induced activation of NF-kβ and expression of iNOS by lovastatin and NaPA, and its reversal by farnesyl pyrophosphate in rat primary astrocytes. Since activation of NF-kβ is necessary for induction of iNOS (Xie et al., 1994; Kwon et al., 1995), to understand the basis of the inhibition of iNOS, the inventor examined the effect of these inhibitors on LPS-induced activation of NF-kβ in astrocytes by gel-shift DNA-binding assay. Rat primary astrocytes incubated in serum-free media received 1.0 µg/ml of LPS. After 1 h of incubation, cells were taken out to prepare nuclear extracts, and nuclear proteins were used for the electrophoretic mobility shift assay of NF-kβ as described in Methods. Samples tested included control, LPS, LPS-treated nuclear extract with 25-fold excess of unlabeled probe, and LPS-treated nuclear extract with a 50-fold excess of unlabeled probe, respectively. Treatment of astrocytes with 1.0 µg/ml of LPS resulted in activation of NF-kβ. This gel-shift assay detected a specific band in response to LPS that was competed off by an unlabelled probe. Lovastatin or NaPA alone at different concentrations failed to induce NF-kβ.

In an additional experiment, cells preincubated in serum-free media with 10 µM of lovastatin or 5 mM of NaPA for 8 h received 1.0 µg/ml of LPS. Samples tested included control, LPS, LPS+lovastatin (5 µM), LPS+lovastatin (10 µM), LPS+NaPA (2 mM), LPS+NaPA (5 mM). Both lovastatin and NaPA, however, markedly inhibited LPS-induced activation of NF-kβ, indicating that inhibition of iNOS expression by lovastatin and NaPA is possibly due to inhibition of NF-kβ.

The inventor has demonstrated earlier that activation of NF-kβ is necessary for iNOS expression in rat primary astrocytes, and that cAMP derivatives inhibit the expression of iNOS by inhibiting the activation of NF-kβ. To evaluate the possible mechanism of the effect of lovastatin and NaPA, or to determine whether reduced concentrations of end products as opposed to intermediate products of the mevalonate pathway were responsible for the effects of lovastatin and NaPA, the inventor performed rescue experiments with cholesterol, ubiquinone, mevalonate, and FPP. Cells preincubated in serum-free media with 10 µM of lovastatin or 5 mM of NaPA for 8 h received 1.0 µg/ml of LPS along with 100 µM mevalonate or 200 µM farnesyl pyrophosphate. After 24 h, supernatants were used for nitrite assay as described in Methods. Data was measured as the mean±SD of three different experiments. Samples tested included control, LPS, LPS+lovastatin, LPS+lovastatin+mevalonate, LPS+lovastatin+FPP, LPS+NaPA, LPS+NaPA+mevalonate, LPS+NaPA+FPP. After 5 h of incubation, cells were analyzed for iNOS mRNA by Northern blotting technique as described earlier. After 1 h of incubation, cells were taken out to prepare nuclear extracts, and nuclear proteins were used for the electrophoretic mobility shift assay of NF-kβ as described in Methods. The addition of 10 µm ubiquinone or cholesterol to astrocytes did not prevent the inhibitory effect of lovastatin and NaPA. NF-kβ and iNOS were induced in the LPS, LPS+lovastatin+mevalonate, LPS+lovastatin+FPP, and LPS+NaPA+FPP treated cells. These observations support the possibility that depletion of intermediary products rather than end products of mevalonate pathway is responsible for the observed inhibitory effect of lovastatin or NaPA on LPS-induced iNOS expression. On the other hand, mevalonate or FPP substantially reversed the inhibitory effect of lovastatin on iNOS expression and NF-kβ activation. FPP, however, but not mevalonate, reversed the inhibitory effect of NaPA, indicating that the use of mevalonate rather than its synthesis is the prime target of the NaPA.

An inhibitor of Ras farnesyl protein transferase (FPT inhibitor II) inhibits LPS-induced expression of iNOS and activation of NF-kβ in rat primary astrocytes. FPT inhibitor II selectively inhibits ras farnesyl protein transferase with the $IC_{50}$ of 75 nM. In whole cells, however, 25-250 µM of FPT inhibitor II inhibits farnesylation of p21$^{ras}$ by ~90% (Manne et al., 1995). Inhibition of LPS-induced expression of iNOS and activation of NF-kβ by NaPA and its reversal by FPP, but not by mevalonate, indicates a possible involvement of the farnesylation reaction in activation of NF-kβ and induction of iNOS. Since farnesylation is a necessary step for activation of p21$^{ras}$, the central molecule upstream of the Raf/MAP kinase cascade, the inventor examined the effect of FPT inhibitor II, an inhibitor of Ras farnesyl protein transferase, on LPS-mediated expression of iNOS and activation of NF-kβ in rat primary astrocytes. Rat primary astrocytes preincubated in serum-free media with 100 µM or 200 µM FPT inhibitor II for 1 h received 1.0 µg/ml of LPS. After 24 h of incubation, supernatants were used for nitrite assay as described in Methods. Data were determined as the mean±SD of three different experiments. After 5 h of incubation, cells were analyzed for iNOS mRNA by Northern blotting technique as described earlier. After 1 h of incubation, cells were taken out to prepare nuclear extracts, and nuclear proteins were used for the electrophoretic mobility shift assay of NF-kβ as described in Methods. Samples tested included control, LPS, LPS+FPT inhibitor II (100 µM), and LPS+FPT inhibitor II (100 µM). Preincubation of cells for 1 h with 100 or 200 µM FPT inhibitor II potentially inhibited LPS-induced activation of NF-kβ, expression of iNOS, and production of NO, demonstrating the importance of p21$^{ras}$ farnesylation in LPS-mediated activation of NF-kβ and induction of iNOS in astrocytes.

Lovastatin and NaPA inhibit the LPS-induced expression of TNF-α, IL-β, and IL-6 in rat primary astrocytes. Activated astrocytes, the major glial cell population of brain, are reported to secrete TNF-α, IL-1β, and IL-6 (Sharif et al., 1993). Since lovastatin and NaPA inhibited LPS-induced expression of iNOS in astrocytes, the inventor examined the effect of these two inhibitors on LPS-induced expression of TNFα, IL-1β, and IL-6. Rat primary astrocytes preincubated in serum-free media with different concentrations of lovastatin (5 or 10 µM) or NaPA (2 or 5 mM), or a combination of 2 µM of lovastatin and 2 mM of NaPA for 8 h, received 1.0 µg/ml of LPS. Samples tested included control, LPS, LPS+lovastatin (5 µM), LPS+lovastatin (10 µM), NaPA (2 mM), LPS+NaPA (5 mM), and LPS+lovastatin (2 µM)+NaPA (2 mM). After 5 h of incubation, cells were analyzed for TNF-α, IL-1β, and IL-6 mRNAs by Northern blotting technique as described earlier. Astrocytes preincubated with lovastatin or NaPA were stimulated with LPS. Concentrations of TNFα, IL-1β, and IL-6 were measured in the supernatants after 24 h of incubation (Table 16), and the mRNA expression of these cytokines was examined in the cells after 5 h of LPS stimulation. Bacterial LPS markedly induced the mRNA expression and production of respective cytokines in astrocytes.

Although lovastatin or NaPA alone had no effect on the production of cytokines, however, these two compounds strongly inhibited LPS-induced production of TNF-α, IL-1β, and IL-6 in the supernatants (Table 16). The decrease in cytokine production was also accompanied by an inhibition of their mRNA expression, demonstrating that lovastatin and NaPA down-regulate expression of all the inflamatory mediators (iNOS, TNF-α, IL-1β, and IL-6) in astrocytes.

TABLE 16

Inhibition of LPS-induced Production of NO, TNF-α, IL-1β, and IL-6 in Rate Primary Astrocytes, Microglia, and Macrophages by Lovastatin and NaPA

| Cells | Production of NO or cytokines | LPS only | LPS + lovastatin | LPS + NaPA |
|---|---|---|---|---|
| Astrocytes | NO | 25.3 ± 3.2 | 5.2 ± 0.4 | 5.4 ± 0.6 |
| | TNF-α | 5.3 ± 0.8 | 0.3 ± 0.05 | 0.4 ± 0.06 |
| | IL-1β | 10.4 ± 1.5 | 0.8 ± 0.1 | 1.1 ± 0.2 |
| | IL-6 | 136.5 ± 16.8 | 6.9 ± 0.9 | 7.6 ± 0.8 |
| Microglia | NO | 81.2 ± 6.9 | 5.9 ± 0.4 | 6.9 ± 0.9 |
| | TNF-α | 14.5 ± 2.1 | 0.9 ± 0.1 | 1.3 ± 0.2 |
| | IL-1β | 28.2 ± 3.4 | 2.1 ± 0.3 | 2.4 ± 0.2 |
| | IL-6 | 295.6 ± 33.5 | 7.8 ± 1.1 | 9.3 ± 1.2 |
| Macrophages | NO | 118.5 ± 12.5 | 7.2 ± 0.9 | 9.5 ± 0.7 |
| | TNF-α | 18.6 ± 2.3 | 1.2 ± 0.1 | 1.7 ± 0.2 |
| | IL-1β | 34.6 ± 4.5 | 2.3 ± 0.3 | 3.1 ± .4 |
| | IL-6 | 350.0 ± 27.6 | 8.3 ± 0.6 | 10.2 ± 1.4 |

Cells preincubated with 10 μM lovastatin or 5 mM NaPA for 8 h in serum-free condition was stimulated with 1.0 μg/ml of LPS. After 24 h of incubation, concentrations of NO, TNF-α, IL-1β, and IL-6 were measured in supernatants as described in Methods. NO is expressed as nmol/24 h/mg protein whereas TNF-α, IL-1β, and IL-6 are expressed as ng/24 h/mg protein. Data are expressed as the mean±SD of three different experiments.

Inhibition of LPS-induced production of NO, TNF-α, IL-1β, and IL-6 in rat primary microglia and macrophages by lovastatin. Both macrophages and microglia, important sources of NO and cytokines, actively participate in the pathophysiologies of different inflamatory disorders. Since lovastatin and NaPA inhibited the LPS-induced production of NO, TNF-α, IL-1β, and IL-6 in astrocytes, the inventor also examined the effect of these two compounds on LPS-stimulated production of NO, TNF-α, IL-1β, and IL-6 in rat primary microglia and macrophages (Table 16). The rate of production of NO and cytokines after LPS stimulation was much higher in both macrophages and microglia than in astrocytes. Similar to astrocytes, lovastatin or NaPA alone had no effect on the production of NO and cytokines in macrophages and microglia. Both of these compounds, however, strongly inhibited the LPS-induced production of NO, TNF-α, IL-1β, and IL-6 in macrophages and microglia (Table 16). These studies demonstrate the importance of the mevalonate pathway in the LPS induced production of NO, TNF-α, IL-1β, and IL-6 in astrocytes as well as in microglia and macrophages (Table 16). The inhibitors (lovastatin, mevastatin, or NaPA), cytokines (TNF-α, IL-1β, and IFN-γ), or LPS used under these experimental conditions had no effect on the viability of astrocytes, microglia, or macrophages, measured by Trypan blue exclusion. Therefore, the conclusion drawn in this study is not due to any change in viability of the cells.

Discussion

Several lines of evidence presented herein clearly support the conclusion that inhibitors of HMG-CoA reductase (lovastatin or mevastatin) and NaPA reduce the induction of inflammatory mediators (iNOS, TNF-α, IL-1β, and IL-6) in rat astrocytes, microglia, and macrophages, demonstrating the involvement of mevalonate metabolite(s) and farnesyl pyrophosphate in the induction of inflammatory mediators. This conclusion was based on the following observations: first, LPS-induced expression of iNOS, TNF-α, IL-1β, and IL-6, and activation of NF-kβ, was inhibited by lovastatin and NaPA; second, inhibitory effects of lovastatin and NaPA on LPS-mediated induction of iNOS and cytokines was not reversed by cholesterol and ubiquinone, end products of mevalonate pathway, indicating that this inhibitory effect of lovastatin was not due to depletion of end products of mevalonate pathway; third, the reversal of inhibitory effect of lovastatin by mevalonate and FPP and that of NaPA by only FPP, but not by mevalonate, indicates that mevalonate and FPP are necessary compounds for LPS signal transduction; fourth, inhibition of LPS-induced activation of NF-kβ and induction of iNOS by FPT inhibitor II, an inhibitor of Ras farnesyl protein transferase, indicates that farnesylation of $p21^{ras}$ or other proteins is required for signal transduction in the LPS-induced expression of iNOS. Since iNOS, TNF-α, IL-1β, and IL-6 have been implicated in the pathogenesis of demyelinating and neurodegenerative diseases (Mitrovic et al., 1994; Merrill et al., 1993), the inventor's results provide a potentially important mechanism whereby inhibitors of HMG-CoA reductase and mevalonate pyrophosphate decarboxylase may ameliorate neural injury. Inhibition of LPS-induced NF-kβ activation and iNOS expression by lovastatin, NaPA, and FPT inhibitor II indicates that the observed inhibition of iNOS expression is due to inhibition of NF-kβ activation.

Since mevalonate availability regulates the posttranslational isoprenylation of many intracellular signaling proteins including $p21^{ras}$ (Goldstein and Brown, 1990), the observed inhibition of NF-kβ activation and induction of iNOS by lovastatin and NaPA may be due to the decrease or lack of the isoprenylation of $p21^{ras}$, that in turn leads to the lack of or abnormal signal transmission from receptor tyrosine kinase to Raf/MAP kinase cascade, activation of NF-kβ, and induction of iNOS. The prerequisite of Ras farnesylation in transduction of signals from receptor tyrosine kinase to Raf/MAP kinase cascade indicates a possible role of metabolites of mevalonate pathway in the modulation of iNOS induction.

NO, a diffusible free radical, plays many roles as a signaling and as an effector molecule in diverse biological systems including neuronal messenger, vasodilation, and antimicrobial and antitumor activities (Nathan, 1992; Jaffrey and Synder, 1995). In the nervous system, NO appears to have both neurotoxic and neuroprotective effects, and may have a role in the pathogenesis of stroke and other neurodegenerative diseases, and in demyelinating conditions (e.g., multiple sclerosis, experimental allergic encephalopathy, X-adrenoleukodystrophy) associated with infiltrating macrophages and production of proinflamatory cytokines (Mitrovic et al., 1994; Merrill et al., 1993; Dawson et al., 1991). NO and peroxynitrite (reaction product of NO and $O_2$—) are potentially toxic molecules to neurons and oligodendrocytes that may mediate toxicity through the formation of iron-NO complexes of iron-containing enzyme systems (Drapier and Hibbs, 1988), oxidation of protein sulfhydryl groups (Radi et al., 1991), nitration of proteins, and nitrosylation of nucleic acids and DNA strand breaks (Wink et al., 1991). Although monocytes/macrophages are the primary source of iNOS in inflammation, LPS and other cytokines induce a similar response in astrocytes and microglia (Hu et al., 1995; Galea et al., 1992). NO derived from macrophages, microglia, and astrocytes has been implicated in the damage of myelin-producing oligodendrocytes in demyelinating disorders like multiple sclerosis and neuronal death during neuronal degenerating conditions including brain trauma (Hu et al., 1995; Merrill et al., 1993). The studies described herein indicate that lovastatin and NaPA, alone or in combination, may represent a possible avenue of research for therapeutics directed against cytokine- and nitric oxide-mediated brain disorders, particularly in demyelinating conditions.

EXAMPLE 9

Amelioration of Experimental Allergic Encephalomyelitis by Inhibiting the Induction of NOS-2 and Proinflammatory Cytokines Proinflammatory cytokines and inducible nitric oxide synthase (iNOS) are involved in the pathogenesis of experimental allergic encephalomyelitis (EAE), an animal model of multiple sclerosis (MS). In the present study the inventor reports the use of N-acetylcysteine (NAC), NaPA and lovastatin as therapeutic agents for the amelioration of the autoimmune demyelinatory disease in EAE. The development of demyelinating lesions in EAE or MS is the result of a complex chain of events that involves recognition of specific antigen, T cell activation, recruitment of nonspecific cells to the lesion, release of numerous cytokines and inflammatory mediators (e.g., NO) by resident glial cells and infiltrating cells, which in turn leads to demyelination and CNS damage. NAC, a potent antioxidant, blocks the induction of iNOS and TNF-α in rat peritoneal macrophages, astrocytes and $C_6$ glioma. Lovastatin, an inhibitor of the rate limiting enzyme of the mevalonate pathway, has also been shown to block the induction of iNOS and proinflammatory cytokines (TNF-α, IL-1β and IL-6) in rat astrocytes, microglia and macrophages. The inventor provides evidence that NAC, NaPA or lovastatin inhibits the induction of proinflammatory mediators (TNF-α, IFN-γ and iNOS) in EAE central nervous system and also ameliorate the clinical symptoms of the EAE disease.

Materials and Methods

Reagents Female Lewis rats were purchased from Charles River Breeding Laboratories, Wilmington, Mass., USA. Myelin basic protein (MBP), complete Freund's adjuvant (CFA), N-acetylcysteine (NAC) and FITC conjugated anti-mouse IgG were purchased from Sigma Chemical Co., USA. Lovastatin was obtained from Calbiochem, USA.

Induction and clinical assessment of Experimental allergic encephalomyelitis (EAE) Female Lewis rats, 250-300 g, were housed in rat cages and provided with food and water ad libitum. Rats were induced with EAE by injecting intradermally 50 μg of myelin basic protein (MBP) per animal emulsified in complete Freund's adjuvant (CFA) into the medial footpad of each hind leg on day 1 followed by a booster injection on the 7th day under ether anesthesia. Clinical symptoms in these rats manifest as an ascending paralysis resulting in death in most animals. The signs of EAE were scored as: (0) normal; (1) piloerection; (2) loss in tail tonicity; (3) hind leg paralysis; (4) paraplegia; and (5) moribund.

Drug Treatment Regiment Lovastatin, NAC or NaPA therapy was started on the first day of immunization (day 1) and continued daily for the duration of the study. Lovastatin, NAC or NaPA was dissolved in saline and pH was adjusted to 7.0. One group of rats induced for EAE were given i.p. injection of Lovastatin (2 mg/Kg body weight) and another group of rats induced for EAE were given i.p. injection of NAC (150 mg/Kg body weight) or NaPA. One group of animals induced for EAE was left untreated while another group of animals was not induced for EAE and used as the control group.

Immunohistochemistry Brains were fixed in 10% buffered formalin (Stephens Scientific, Riverdale, N.J.). The tissues were embedded in paraffin and sectioned at 4 μm. Sections were then stained for various cytokines and cell markers as described below. For single-label immunohistochemistry, sections were incubated with either anti-iNOS antibody (1:100, rabbit polyclonal, Calbiochem, LaJolla, Calif.) or anti-TNF-α antibody (1:100, rabbit polyclonal, Genzyme, Cambridge, Mass.) or anti-IFN-γ antibody (1:200, rabbit polyclonal, Biosource International, Camarillo, Calif.) essentially as described for other antibodies (Hooper et al., 1997). The tissue sections were further incubated with FITC conjugated anti-rabbit IgG (1:100, Sigma, St. Louis, Mo.), mounted with mounting media (EMS) and analyzed by immunofluorescence microscopy (Olympus) using Adobe photoshop software. For immunofluorescent double-labeling, sections were incubated first with anti-iNOS (1:100) followed by macrophage marker ED1 (1:100, mouse monoclonal, Biosource International, Camarillo, Calif.). Anti-iNOS was visualized using TRITC conjugated anti-rabbit IgG—(1:100, Sigma, St. Louis, Mo.) and ED1 using FITC conjugated anti-mouse IgG (1:100, Sigma, St. Louis, Mo.). Negative control sections were incubated with FITC or TRITC conjugated IgG without the primary antibody.

Results

Expression of iNOS, TNF-α and IFN-γ in Lewis rat brain sections of control, EAE and drug-treated animals iNOS in the CNS of Lewis rats was detection by immunofluorescence. Brain sections of control, EAE, EAE treated with NAC, EAE treated with NaPA or EAE treated with lovastatin were immunostained for iNOS as described under materials and methods. Brain sections of rats with EAE show expression of iNOS protein as green fluorescence in a significant number of cells as compared to control. Moreover, treatment of rats with NAC, lovastatin or NaPA, blocked the ability of MBP to induce the expression of iNOS. NAC treatment seems to be better than lovastatin or NaPA in blocking the induction of iNOS.

TNF-α in the CNS of Lewis rats was detected by immunofluorescence. Brain sections of control, EAE, EAE treated with NAC, EAE treated with NaPA and EAE treated with lovastatin were immunostained for TNF-α as described under materials and methods. Similar to the expression of iNOS, a good number of cells show the expression of TNF-α as green fluorescence in EAE brain as compared to controls. Treatment with NAC, lovastatin or NaPA blocked the induction of TNF-α. In case of TNF-α, better inhibition was observed in brains of rats treated with lovastatin or NaPA.

Lewis rat brain sections were stained immunohistochemically for IFN-γ. Brain sections of control, EAE, EAE treated with NAC, EAE treated with NaPA and EAE treated with lovastatin were immunostained for IFN-γ as described under materials and methods. NAC, lovastatin or NaPA treatments also blocked the induction of IFN-γ in brains of animals challenged with MBP. The demonstration of induction of TNF-α, IFN-γ and iNOS in brains of EAE shows a inflammatory disease process and inhibition of the induction of these cytokines in brains of rats treated with NAC, NaPA or lovastatin indicate that these drugs may be of value in ameliorating the inflammatory disease process in EAE.

Co-localization of iNOS with macrophage/microglial marker ED1 To identify the cell type in the CNS of EAE which express iNOS, the inventor performed immunofluorescence double-labeling study using ED1, a specific marker for macrophage/microglia cells of Lewis rat brain sections. Brain sections of control, EAE, EAE treated with NAC, EAE treated with NaPA and EAE treated with lovastatin were immunostained for iNOS (red) and ED1 (green) as described under materials and methods. Co-expression of iNOS and ED1 that was visualized as yellow/orange was seen only in EAE induced rat brain sections indicating that macrophage/microglia of EAE rat brain express iNOS. Animals induced for EAE and treated with NAC, NaPA or lovastatin showed expression of ED1, however, colocalization of ED1 with iNOS, as seen with EAE sections was not observed. In NAC-, NaPA or lovastatin-treated rat brain sections ED1 expression was observed but not iNOS.

NAC and lovastatin protect against EAE disease in Lewis female rats Since NAC, NaPA and lovastatin inhibited the expression of iNOS and proinflammatory cytokines in activated glial cells (astroglia and microglia) and macrophages and in the CNS of Lewis rats with EAE, the inventor examined the therapeutic potential of NAC, NaPA and/or lovastatin on the disease process of EAE. Administration of Lovastatin in Lewis female rats delays the onset of EAE disease symptoms. Data was taken as average clinical disease scores where 0—normal; 1—piloerection; 2—loss in tail tonicity; 3—hind leg paralysis; 4—paraplegia and 5—moribund. Clinical symptoms of EAE appeared in MBP-treated Lewis female rats (n=9) from 7th day after first immunization. In this model, MBP induced a monophasic acute disease progression resulting in death on 11th day, however, control animals receiving only complete Freund's adjuvant did not show any disease symptoms. On the other hand treatment of MBP-injected rats with NAC (n=9), lovastatin (n=9) or NaPA from first day of immunization protected the rats from the severity of the disease. Both NAC and lovastatin-treated rats received milder clinical symptoms (highest clinical score was between 2 and 3) and specially lovastatin significantly delayed the onset of first of clinical symptom. These results clearly demonstrate that NAC, NaPA and lovastatin provide protection against neuroinflammatory disease of EAE.

Discussion

These studies clearly demonstrate that both NAC, NaPA and lovastatin inhibit the expression of proinflammatory cytokines (TNF-α and IFN-γ) and iNOS in the CNS of Lewis rats with EAE and ameliorate the neuroinflammatory disease process in the central nervous system. Immunohistochemical results show a higher degree of expression of iNOS, tumor necrosis factor-α (TNF-α) and interferon-γ (IFN-γ) in brains of rats with acute monophasic EAE relative to the control animals. Although NAC and lovastatin did not block the clinical symptoms of EAE completely in Lewis rat they significantly reduced the severity of the disease. NAC is a non-toxic drug which has been safely used in humans for more than 30 years. Lovastatin is also approved as an cholesterol-lowering drug for humans. Therefore, inhibition of the expression of proinflammatory cytokines and iNOS in the CNS of EAE rats and amelioration of the EAE disease process by NAC and lovastatin indicates that these drugs may have therapeutic importance in the treatment of neuroinflammatory diseases like MS.

EXAMPLE 10

Proinflammatory Cytokine-Mediated Apoptosis in Demyelinating Diseases

In the present study, the inventor examined the possible involvement of ROS in cytokine-mediated activation of sphingomyelin breakdown and ceramide formation in rat primary glial cells.

Materials and Methods

Reagent DMEM/F-12 and fetal bovine serum (FBS) were from Life Technologies, Inc. Human IL1-β was from Genzyme. Mouse recombinant TNF-α was obtained from Boehringer Mannheim, Germany. Diamide, buthione (SR)-sulfoximine, N-acetylcysteine, and pyrrolidinedithiocarbamate were from Sigma.

Isolation and Maintenance of Rat Primary Microglia, Oligodendrocytes, and Astrocytes Microglial cells were isolated from mixed glial cultures according to the procedure of Guilian and Baker (1986). Briefly, after 7 days the mixed glial cultures were washed 3 times with DMEM/F-12 containing 10% FBS and subjected to a shake at 240 rpm for 4 h at 37° C. on a rotary shaker. The floating cells were washed and seeded onto plastic tissue culture flasks and incubated at 37° C. After 30 min the non-attached cells (mostly oligodendrocytes) were removed by repeated washes, and the attached cells were used as microglia. These cells were seeded onto new plates for further studies. Ninety to ninety-five percent of this preparation was positive for nonspecific esterase, a marker for macrophages and microglia.

After 4 h shaking, the flasks were washed three times to remove the floating cells. Medium with 10% FBS was added, and flasks were subjected to another cycle of shaking for 24 h at 250 rpm. The suspended cells were spun at 200×g and incubated for 30 min in tissue culture dish. The non-attached or weakly attached cells (mostly oligodendrocytes) were removed and seeded onto polylysine-coated dishes and cultured in medium containing 1% FBS. Ninety-five to ninety-seven percent of these cells were positive for galactocerebroside immunostaining.

Astrocytes were prepared from rat cerebral tissue as described by McCarthy and DeVellis (1980). After 10 days of culture astrocytes were separated from microglia and oligodendrocytes by shaking for 24 h in an orbital shaker at 240 rpm. To ensure the complete removal of all oligodendrocytes and microglia, the shaking was repeated twice after a gap of 1 or 2 days. Attached cells were trypsinized (1 mM EDTA and 0.05% trypsin in 10 mM Tris-buffered saline, pH 7.4) and distributed into culture dishes. These cells when checked for the astrocyte marker glial fibrillar acidic protein were found to be 95-100% positive. $C_6$ glial cells obtained from ATCC were also maintained in DMEM/F-12 containing 10% FBS as indicated above.

Brain Tissue Frozen and fixed X-adrenoleukodystrophy and multiple sclerosis brain tissues were obtained from Brain and Tissue Banks for Developmental Disorders, University of Maryland, Baltimore, Md. 21201. Two X-ALD brains were from 7- and 9-year-old males, and two MS brains were from 30- and 33-year old females. Control brain for X-ALD studies was from an 8-year-old male, and control brain for MS studies was from a 30-year-old female.

Lipid Extraction Approximately $1.0 \times 10^6$ cells were exposed to different cytokines in the presence or absence of antioxidants for different periods, and lipids were extracted according to the methods described by Welsh (1996).

Quantification of Sphingomyelin by High Performance TLC and Densitometry Sphingomyelin was separated from total lipid extracts by high performance TLC (LHPK plates from Whatman) as described by Ganser et al. (1988) for phospholipids with the following modification: the plate was overrun for 30 min during its development and was dried overnight in vacuum desiccator. Sphingomyelin was quantitated by densitometric scanning using Imaging Densitometer (model GS-670; Bio-Rad), and software was provided with the instrument by the manufacturer.

Quantification of Ceramide Levels by Diacylglycerol Kinase Assay Ceramide content was quantified essentially according to Priess et al. (1986) using diacylglycerol (DAG) kinase and [γ-$^{32}$P]ATP. Briefly, dried lipids were solubilized in 20 μl of an octyl β-D-glucoside/cardiolipin solution (7.5% octyl β-D-glucoside, 5 mM cardiolipin in 1 mM DTPA) by sonication in a sonicator bath. The reaction was then carried out in a final volume of 100 μl containing the 20-μl sample solution, 50 mM imidazole HCl, pH 6.6, 50 mM NaCl, 12.5 mM MgCl$_2$, 1 mM EGTA, 2 mM dithiothreitol, 6.6 μg of DAG kinase, and 1 mM [γ-$^{32}$P]ATP (specific activity of 1-5× 10$^5$ cpm/nmol) for 30 min at room temperature. The labeled ceramide-1-phosphate was resolved with a solvent system consisting of methyl acetate:n-propyl alcohol:chloroform: methanol, 0.25% KCl in water:acetic acid (100:100:100:40: 36:2). A standard sample of ceramide was phosphorylated under identical conditions and developed in parallel. Both standard and samples had identical $R_F$ values (0.46). Quantification of ceramide-1-phosphate was carried out by autoradiography and densitometric scanning using Imaging Densitometer (model GS-670; Bio-Rad). Values are expressed either as arbitrary units (absorbance) or as percent change.

Measurement of GSH (Reduced Glutathione) and GSSG Oxidized Glutathione Concentration of intracellular reduced GSH was measured using a calorimetric assay kit for GSH from R & D Systems. Briefly, 2×10$^6$ cells were homogenized in 500 μl of ice-cold 5% metaphosphoric acid and centrifuged at 3000×g for 10 min. Supernatants were used to assay GSH using 4-chloro-1-methyl-7-trifluoromethylquinolinium methylsulfate and 30% NaOH at 400 nm. Concentration of GSSG was determined according to the method of Griffith (1980) after derivatization with 2-vinylpyridine for 30 min at room temperature.

Detection of DNA Fragmentation Cells (1×10$^6$) were pelleted in an Eppendorf tube by centrifugation at 1000 rpm for 5 min, washed with phosphate-buffered saline, pH 7.4, resuspended gently in 50 μl of a lysis buffer (200 mM NaCl, 10 mM Tris-HCl, pH 8.0, 40 mM EDTA, pH 8.0, 0.5% SDS, 400 ng of RNase A/μl), and incubated at 37° C. for 1 h. The lysate received 200 μl of the digestion buffer (200 mM NaCl, 10 mM Tris-HCl, pH 8.0, 0.5% SDS, 125 ng of proteinase K/μl). The contents were mixed by inversion several times and then incubated at 50° C. for 2 h. An equal volume of a mixture of phenol, pH 8.0, chloroform, and isoamyl alcohol (25:24:1, v/v) was added, gently mixed for 10 min, and stored at room temperature for 2 min. The two phases were separated by centrifugation at 3000 rpm for 10 min. The viscous aqueous phase was transferred to a fresh tube, and the phenol/chloroform extraction was repeated. The aqueous phase was extracted with an equal volume of chloroform, and 1.0 M MgCl$_2$ was added to the aqueous phase to a final concentration of 10 mM. The total DNA was precipitated by the addition of 2 volumes of absolute ethanol with several inversions. DNA was pelleted by centrifugation at 3000 rpm for 15 min, washed with 70% ethanol, and air-dried. The pellet was dissolved in 25 μl of 10 mM Tris-HCl containing 1.0 mM EDTA, pH 8.0, and electrophoresed in 1.8% agarose gel at 4° C. The gel was stained with ethidium bromide, and DNA-intercalated ethidium fluorescence was photographed on Polaroid film 665 (P/N) using an orange filter. To study DNA fragmentation in banked human brain tissues, brain tissues were gently homogenized in 0.85 M sucrose buffer, and nuclei were purified according to the procedure described previously (Lazo et al., 1991). Total genomic DNA was isolated from the nuclei and electrophoresed as described.

Fragment End Labeling of DNA on Paraffin-embedded Tissue Sections of MS and X-ALD Brains Fragmented DNA was detected in situ by the terminal deoxynucleotidyltransferase-mediated binding of 3'-OH ends of DNA fragments generated in response to apoptotic signals, using a commercially available kit (TdT FragEL™) from Calbiochem. Briefly, paraffin-embedded tissue slides were deparaffinized, rehydrated in graded ethanol, treated with 20 μg/ml proteinase K for 15 min at room temperature, and washed prior to terminal deoxynucleotidyltransferase staining. After terminal deoxynucleotidyltransferase staining, sections were lightly counterstained with methyl green.

Results

NAC and PDTC Block TNF-α- and IL-1β-induced Degradation of Sphingomyelin to Ceramide in Primary Rat Astrocytes Rat primary astrocytes were cultured in serum-free media with TNF-α or IL-1β for different times to quantify the production of ceramide using diacylglycerol (DAG) kinase. Since DAG kinase phosphorylates both DAG and ceramide using [γ-$^{32}$P]ATP as substrate, both lipids can be quantified in the same assay. Rat primary astrocytes were exposed to TNF-α (50 ng/ml) for different time intervals (0, 5, 15, 30, 45 and 60 minutes). Lipids were extracted, and DAG and ceramide contents were determined as described under "Materials and Methods." Results were determined as the mean±S.D. of three different studies. It was found that in astrocytes, the DAG content was much higher than the ceramide content. Stimulation of cells with TNF-α resulted in a time-dependent increase in the production of ceramide (about 3-fold after 45 min). In contrast to induction of ceramide production, the level of DAG, an activator of protein kinase C and acidic sphingomyelinase, was unchanged at different time points of stimulation.

In another experiment, rat primary astrocytes preincubated with either 10 mM NAC or 100 μM PDTC for 1 h in serum-free DMEM/F-12 received TNF-α (50 ng/ml). At different time intervals (0, 15, 30, 45, and 60 minutes), cells were washed with HBSS and scraped off. Lipids were extracted, and levels of ceramide (100% value is 4.51±0.1 nmol/mg protein) and sphingomyelin (100% value is 25.39±6.27 nmol/mg protein) were measured as described under "Materials and Methods-" Results were measured as the mean±S.D. of three different studies. TNF-α-induced degradation of sphingomyelin to ceramide was inhibited by NAC and PDTC.

Similar to TNF-α, stimulation of astrocytes with IL-1β for different times also induced a significant increase in the ceramide content. Rat primary astrocytes preincubated with either 10 mM NAC or 100 μM PDTC for 1 h in serum-free DMEM/F-12 received IL-1β (50 ng/ml). At different time intervals (0, 15. 30, 45, and 60 minutes), cells were washed with HBSS and scraped off. Lipids were extracted, and levels of ceramide (100% value is 4.51±0.1 nmol/mg protein) and sphingomyelin (100% value is 25.39±6.27 nmol/mg protein) were measured as described under "Materials and Methods." Results were measured as the mean±S.D. of three different studies. Almost 3-4-fold increase in ceramide production was found in astrocytes after 30 or 45 min of exposure with TNF-α or IL-1β. This increase in ceramide was paralleled by TNF-α- and IL-1β-induced decrease in sphingomyelin. Sphingomyelin turnover of approximately 18-25% could be observed as early as 15 min following treatment of astrocytes, and maximal effects of up to 45-50% SM hydrolysis were observed after 3045 min of treatment with TNF-α or IL 1β.

These studies indicate that both TNF-α and IL-1β can modulate the degradation of sphingomyelin to produce ceramide, the putative second messenger of the sphingomyelin signal transduction pathway, in rat primary astrocytes within a short time. Interestingly, the inventor found that treatment of astrocytes with antioxidants like NAC (10 mM) 1 h before the addition of TNF-α or IL1β potentially blocked the decrease in sphingomyelin as well as the increase in ceramide, whereas 10 mM acetate had no effect on the degradation of SM to ceramide. Similar to NAC, another antioxidant PDTC also inhibited cytokine-mediated degradation of SM to ceramide. These studies indicate that reactive oxygen species (ROS) are possibly involved in cytokine-induced degradation of SM to ceramide.

TNF-α and IL-1β Decrease Intracellular Level of Reduced Glutathione (GSH) in Rat Primary Astrocytes and NAC Blocks This Decrease Since the intracellular level of GSH is an important regulator of the redox state of a cell, to understand the relationship between induction of ceramide production and intracellular level of GSH in cytokine-stimulated astrocytes, cells were stimulated with TNF-α or IL-1β, and the level of GSH was measured at different times (0, 15, 30, 45, 60, 75, and 90 minutes). Rat primary astrocytes preincubated with 10 mM NAC for 1 h received either TNF-α (50 ng/ml) or IL-1β (50 ng/ml). At different time intervals, cells were scraped off, and GSH concentrations (100% value is 182.5±15.4 nmol/mg protein) were measured as described under "Materials and Methods." Results were measured as the mean±S.D. of three different studies. The stimulation of cells with TNF-α or IL-1β resulted in an immediate decrease in intracellular level of GSH with the maximal decrease (66-70% of control) found within 15-30 min of initiation of stimulation, and with a further increase in time of incubation, the level of GSH was found to be almost normal (88-95% of control at 90 min). These studies indicate that cytokine stimulation apparently induces rapid, short term production of oxidants which transiently deplete GSH. However, the lack of decrease of GSH (FIG. 4) and lack of hydrolysis of SM in the presence of NAC in the cytokine-treated cells indicate that NAC inhibited the cytokine-induced degradation of SM to ceramide by maintaining the normal levels of GSH.

Thiol-depleting Agents Induce the Production of Ceramide in Rat Primary Astrocytes Since NAC, a thiol antioxidant, blocked cytokine-mediated depletion of intracellular levels of GSH and breakdown of SM to ceramide, the inventor investigated the effect of thiol-depleting agents (diamide and buthione-(SR)-sulfoximine) on ceramide production. Diamide reduces the intracellular level of GSH by its oxidation to GSSG, whereas buthione-(SR)-sulfoximine does so by blocking the synthesis of GSH (Shertzer et al., 1995; Akamatsu et al., 1997). Rat primary astrocytes preincubated with 10 mM NAC for 1 h received diamide (0.5 mM). At different time intervals (0, 15, 30, 45, and 60 minutes), cells were washed with HBSS and scraped off. Lipids were extracted, and the level of ceramide (100% value is 4.51±0.1 nmol/mg protein) was measured as described under "Materials and Methods". Results were measured as the mean±S.D. of three different studies. Additionally, at different time intervals (0, 15, 30, 45, and 60 minutes), intracellular level of GSH (100% value is 182.5±15.4 nmol/mg protein) was measured as described under "Materials and Methods." Results were measured as the mean±S.D. of three different studies. Stimulating rat primary astrocytes with diamide resulted in an immediate decrease in intracellular level of GSH due to rapid consumption of intracellular GSH through its nonenzymatic conversion to the oxidized dimer, GSSG (Shertzer et al., 1995), and marked induction of ceramide production (about 7-fold after 30 min of stimulation) indicating that intracellular level of GSH is the important regulator of degradation of SM to ceramide. Consistent with this, treatment of cells with NAC blocked diamide-mediated decrease in GSH level and induction of ceramide production. Similar to diamide, buthione-(SR)-sulfoximine also decreased the level of GSH and induced the production of ceramide.

The inventor investigated the intracellular level of GSSG in astrocytes treated with TNF-α and diamide. Rat primary astrocytes were incubated with TNF-α (50 ng/ml) and diamide (0.5 mM), and at different time intervals (0, 15, 30, 45, and 60 minutes) the intracellular level of GSSG (100% value is 4.9±0.52 nmol/mg protein) was measured as described under "Materials and Methods." Results were measured as the mean±S.D. of three different studies. In contrast to the decrease in intracellular level of GSH, both TNF-α and diamide increased the intracellular level of GSSG. Thus it appears that the low GSH and/or high intracellular oxidant (ROS) levels induced by cytokines and thiol-depleting agents facilitated the induction of ceramide production, whereas the normal levels of GSH and/or low ROS induced or maintained by the addition of NAC under these conditions blocked the hydrolysis of sphingomyelin to ceramide. Taken together, these results demonstrate that the intracellular levels of GSH and/or ROS regulate the extent to which sphingomyelin is degraded to ceramide, and ceramide-mediated signaling cascades are transduced.

Aminotriazole and Hydrogen Peroxide Induce the Production of Ceramide in Rat Primary Astrocytes Inhibition of cytokine-mediated induction of ceramide production by antioxidants and induction of ceramide production by thiol-depleting agents alone indicate the possible involvement of ROS in the induction of ceramide production. Therefore, the inventor examined the effect of exogenous addition of an oxidant like $H_2O_2$ or endogenously produced $H_2O_2$ by inhibition of catalase with aminotriazole (ATZ), which inhibits endogenous catalase to increase the level of $H_2O_2$, on the induction of ceramide production. Rat primary astrocytes were incubated with 5 mM aminotriazole (ATZ) or 0.5 mM $H_2O_2$ in presence or absence of 10 mM NAC. At different time intervals (0, 15, 30, 45, and 60 minutes), cells were washed with HBSS and scraped off. Lipids were extracted, and the level of ceramide (100% value is 4.51±0.1 nmol/mg protein) was measured as described under "Materials and Methods." Results are mean±S.D. of three different studies. Approximately 45 min following the addition of ATZ, ceramide generation increased more than 5-fold over base line. However, pretreatment of cells with NAC blocked the ATZ-mediated increase in ceramide production. Consistent with the increase in ceramide production by ATZ, addition of exogenous $H_2O_2$ to astrocytes also induced the production of ceramide with the maximum increase of about 7-fold after 15 min. These results clearly indicate that intracellular levels of ROS regulate the production of ceramide.

Inhibition of Cytokine-mediated Production of Ceramide in Rat Primary Microglia, Oligodendrocytes, and $C_6$ Glial Cells by NAC Since NAC inhibited the cytokine-mediated production of ceramide in rat primary astrocytes, the inventor examined the effect of NAC on cytokine-mediated induction of ceramide production in rat primary oligodendrocytes, microglia and $C_6$ glial cells. Rat primary microglia, oligodendrocytes, and $C_6$ glial cells preincubated with 10 mM NAC for 1 h in serum-free DMEM/F-12 received TNF-α (50 ng/ml). Cells were washed with HBS and scrapped off at different intervals (0, 5, 30, 45, and 60 minutes). Lipids were extracted, and ceramide content (100% value for microglia, oligodendrocytes, and $C_6$ glial cells are 2.72±0.53, 3.37±0.32, 4.73±0.21 nmol/mg protein, respectively) was measured as described under "Materials and Methods." Results were determined as the mean±SD. of three different studies. The addition of TNF-α to microglia, oligodendrocytes, or $C_6$ glial cells induced the production of ceramide.

The increase in ceramide in these cells ranges from 2.5- to 4-fold with highest increase in glial cells and lowest in oligodendrocytes. The ceramide levels peaked in glial cells at 30 min following stimulation and 45 min of stimulation in oligodendrocyles and $C_6$ glial cells. These observations show that similar to astrocytes, the SM cycle is also present in microglia, oligodendrocytes and $C_6$ glial cells. Consistent with the effect of NAC on the production of ceramides in astrocytes, this antioxidant also potently blocked the TNF-α-induced production of ceramide in microglia, oligodendrocytes, and $C_6$ glial cells indicating that ROS are also involved in cytokine-mediated ceramide production in these cells.

NAC Inhibits TNF-α and Diamide-mediated Apoptosis in Rat Primary Oligodendrocytes by Increasing the Intracellular Level of GSH and Decreasing the Production of Ceramide The inventor investigated the effect of NAC on TNF-α as well as diamide-mediated apoptosis in rat primary oligodendrocytes as evidenced by electrophoretical detection of hydrolyzed DNA fray meets ("laddering"). To understand the role of the intracellular level of GSH in inducing apoptosis, the inventor treated oligodendrocytes with TNF-α or with diamide, a thiol-depleting agent. Rat primary oligodendrocytes preincubated with 10 mM NAC for 1 h received either diamide (0.5 mM) or TNF-α (50 ng/ml). After 12 h of incubation, cells were harvested and washed with phosphate-buffered saline, and genomic DNA was extracted and run on agarose gels as described under "Materials and Methods." Ten micrograms of DNA was loaded in each lane. This study was repeated three times. Levels of ceramide (100% value is $3.37±0.32$ nmol/mg protein) and GSH were measured in homogenates as described under "Methods and Materials." Results were measured as the mean±S.D. of three different studies. Both TNF-α and diamide decreased the intracellular level of GSH, increased the level of ceramide, and induced internucleosomal DNA fragmentation as evident from the typical ladder pattern. Interestingly, blocking of the diamide- and TNF-α-mediated decrease in intracellular levels of GSH by pretreatment with NAC inhibited the induction of ceramide formation and DNA fragmentation indicating that intracellular levels of GSH may regulate apoptosis in oligodendrocytes through ceramide formation. To prove this further, oligodendrocytes were treated with $C_2$-ceramide (a cell-permeable ceramide analog) in the presence or absence of NAC. Rat primary oligodendrocytes preincubated with 10 nM NAC for 1 h received $C_2$-ceramide. After 12 h of incubation, cells were harvested and washed with phosphate-buffered saline, and genomic DNA was extracted and run on agarose gels as described under "Materials and Methods." Ten micrograms of DNA was loaded in each lane. This study was repeated three times. In contrast to the inhibitory effect of NAC on TNF-α-mediated apoptosis, NAC had no effect on $C_2$-ceramide-mediated apoptosis in oligodendrocytes.

DNA Fragmentation in Banked Human Brains with X-ALD and MS To understand the underlying relationship among intracellular levels of GSH, levels of ceramide, and DNA fragmentation in cytokine-inflamed central nervous system of X-ALD and MS, the inventor measured the levels of GSH and ceramide in homogenates and also studied the DNA fragmentation in nuclei from brains of patients with X-ALD and MS. Regions surrounding plaques of human brain white matter were used for DNA laddering and to measure the levels of ceramide and GSH. Controls were age- and sex-matched controls for X-ALD and MS, respectively. Since there was no plaque in control brains, the inventor used white matter of control brain for this study. Genomic DNA isolated from nuclei of banked human brains was run on agarose gel and photographed as described under "Materials and Methods." Ten micrograms of DNA was loaded in each lane. This study was reproduced three times. The same amount of brain material (based on protein concentration) was used to measure the level of ceramide as described under "Materials and Methods-" Results were measured as the mean±S.D. of three different studies. Concentrations of ceramide in the X-ALD and MS controls were $46.6±2.56$ and $61.6±6.69$ nmol/mg protein, respectively. The concentration of GSH was measured in homogenates as described under "Materials and Methods." Results for this experiment was the mean±S.D. of three different studies. In contrast to white matters of control brains, white matters of both X-ALD and MS brains had several plaque regions. In both X-ALD and MS brain homogenates, the level of GSH was lower (55-70% of control), and the level of ceramide was higher (2-3 fold) compared with those found in control brains. Consistent with a lower level of GSH and a higher level of ceramide, genomic DNA isolated from nuclei of X-ALD and MS brains when run on agarose gels formed the typical ladder pattern, an indicator of apoptosis, which was absent in both of the normal brains.

To confirm apoptosis in regions surrounding the plaques of white matters of X-ALD and MS, paraffin-embedded tissue sections of X-ALD and MS were stained with terminal deoxynucleotidyltransferase-mediated fragment end labeling. Terminal deoxynucleotidyltransferase-mediated end labeling of 3'-OH ends of DNA fragments on paraffin-embedded tissue sections (control, X-ALD, and MS) was carried out using a commercially available kit from Calbiochem. Regions surrounding plaques were used for this study. Consistent with increased DNA fragmentation (apoptosis) in isolated nuclei of X-ALD and MS, the inventor observed increased terminal deoxynucleotidyltransferase staining on brain sections of X-ALD and MS compared with those of controls. These biochemical and morphological observations indicate that intracellular level of GSH may be an important factor in cytokine-mediated degradation of SM to ceramide and apoptosis in inflammatory demyelinating diseases like X-ALD and MS.

Discussion

The inventor shows that intracellular GSH plays a crucial role in the breakdown of SM to ceramide, in that low GSH levels are required for ceramide generation and high GSH levels inhibit production of ceramide. Inhibition of cytokine-mediated breakdown of SM to ceramide by antioxidants like N-acetylcysteine (NAC) and pyrrolidinedithiocarbamate (PDTC) and induction of ceramide production by oxidants or pro-oxidants like hydrogen peroxide, aminotriazole, diamide, and L -buthione-(SR)-sulfoximine clearly delineate a novel function of ROS and GSH in regulation of the first step of sphingomyelin signal transduction pathway. Moreover, decreased levels of GSH and increased levels of ceramide correlate with the DNA fragmentation in rat primary oligodendrocytes as well as in the banked human brains from patients with neuroinflammatory diseases (e.g., multiple sclerosis and X-adrenoleukodystrophy).

The present study underlines the importance of reactive oxygen species in cytokine-mediated degradation of sphingomyelin (SM) to ceramide. Treatment of rat primary astrocytes with tumor necrosis factor-α (TNF-α) or interleukin-1β led to marked alteration in cellular redox (decrease in intracellular GSH) and rapid degradation of SM to ceramide. Interestingly, pretreatment of astrocytes with N-acetylcysteine (NAC), an antioxidant and efficient thiol source for glutathione, prevented cytokine-induced decrease in GSH and degradation of sphingomyelin to ceramide, whereas treatment of astrocytes with diamide, a thiol-depleting agent, alone caused degradation of SM to ceramide. Moreover, potent activation of SM hydrolysis and ceramide generation were observed by direct addition of an oxidant like hydrogen peroxide or a prooxidant like aminotriazole. Similar to NAC, pyrrolidinedithiocarbamate, another antioxidant, was also found to be a potent inhibitor of cytokine-induced degradation of SM to ceramide indicating that cytokine-induced hydrolysis of sphingomyelin is redox-sensitive. Besides astrocytes, NAC also blocked cytokine-mediated ceramide production in rat primary oligodendrocytes, microglia, and $C_6$ glial cells. Inhibition of TNF-α- and diamide-mediated depletion of GSH, elevation of ceramide level, and DNA fragmentation (apoptosis) in primary oligodendrocytes by NAC, and observed depletion of GSH, elevation of ceramide level, and apoptosis in banked human brains from patients with neuroinflammatory diseases (e.g., X-adrenoleukodystrophy and multiple sclerosis) indicate that the intracellular level of GSH may play a critical role in the regulation of cytokine-induced generation of ceramide leading to apoptosis of brain cells in these diseases.

Changes in the cellular redox state toward either prooxidant or antioxidant conditions have profound effects on cellular functions. Several lines of evidence presented in this work indicate that the first step of cytokine-induced sphingomyelin signal transduction pathway (i.e. breakdown of sphingomyelin to ceramide and phosphocholine) is redox-sensitive. First, cytokines like TNF-α and IL-1β decreased intracellular GSH and induced the degradation of sphingomyelin to ceramide in rat primary astrocytes, oligodendrocytes, microglia, and rat $C_6$ glial cells, and pretreatment of the cells with antioxidants like NAC restored the levels of GSH and blocked the degradation of sphingomyelin to ceramide. Second, depletion of endogenous glutathione by diamide or buthione sulfoximine alone induces the degradation of sphingomyelin to ceramide which is blocked by NAC. Third, the increase in intracellular $H_2O_2$ by the addition of exogenous $H_2O_2$ or by the inhibition of endogenous catalase by aminotriazole induced the degradation of sphingomyelin to ceramide which is also blocked by NAC. Fourth, besides NAC, PDTC, an antioxidant but not the precursor of GSH (Laight et al., 1997), also inhibited the TNF-α and IL-1β-induced hydrolysis of sphingomyelin to ceramide.

Over the years a number of sphingomyelinase activities have been observed in the cell. The major activities are the acid sphingomyelinase present in lysosomes, an enzyme with deficient activity in Niemann-Pick disease (Spence, 1993), and plasma membrane-associated magnesium-dependent neutral pH optimal sphingomyelinase (Chatterjee, 1993). In addition, a cytosolic magnesium-independent (Okazaki et al., 1994) and zinc-dependent acidic (Schissel et al., 1996) sphingomyelinase have also been reported. The lysosomal acidic sphingomyelinase is believed to be responsible for degradation of sphingomyelin associated with turnover of membrane. The membrane-associated neutral sphingomyelinase is known to be activated in serum deprivation, TNF-α, and Fas-associated growth suppression and apoptosis (Tepper et al., 1995; Weigman et al., 1994). Although the studies reported here do not identify the sphingomyelinase that is redox-sensitive, it is likely that the observed redox-sensitive hydrolysis of sphingomyelin in cytokine-induced production of ceramide is mediated by the plasma membrane-associated neutral sphingomyelinase.

The inventor's studies showing DNA fragmentation and increase in ceramide and decrease in GSH in primary oligodendrocytes and banked human brains with X-ALD and MS clearly indicate that intracellular redox (level of GSH) is an important regulator of apoptosis via controlling the generation of ceramide. The inventor's conclusion is based on the following observations. First, treatment of oligodendrocytes with TNF-α decreased intracellular level of GSH, increased degradation of SM to ceramide, and induced DNA fragmentation; however, pretreatment of oligodendrocytes with NAC blocked the TNF-α-mediated decrease in GSH level, increase in ceramide level, and increase in DNA fragmentation. In contrast, NAC had no effect on ceramide-mediated DNA fragmentation. Second, treatment of oligodendrocytes only with diamide, a thiol-depleting agent, decreased intracellular level of GSH, increased level of ceramide, and induced DNA fragmentations which are prevented by pretreatment of NAC, a thiol-replenishing agent. Third, the inventor observed increased fragmentation of DNA in the white matter region surrounding plaques from patients with X-ALD and MS where the levels of GSH and ceramide were lower and higher, respectively, compared with those found in white matters of control human brains. These observations indicate that maintenance of the thiol/oxidant balance is crucial for protection against cytokine-mediated ceramide production and thereby against ceramide-induced cytotoxicity.

Observations described herein have demonstrated that ceramide potentiates the cytokine-mediated induction of inducible nitric oxide synthase in astrocytes and $C_6$ glial cells. Although ceramide by itself did not induce the expression of inducible nitric oxide synthase and production of NO, it markedly stimulated the cytokine-induced expression of inducible nitric oxide synthase and production of NO indicating that sphingomyelin-derived ceramide generation may be an important factor in cytokine-mediated cytotoxicity in neurons and oligodendrocytes in neuroinflammatory diseases. The NAC, which has been used to block the cytokine-induced ceramide production in this study and to inhibit cytokine-mediated induction of inducible nitric oxide synthase, is a nontoxic pharmaceutical drug that enters the cell readily and serves both as a scavenger of ROS and a precursor of GSH, the major intracellular thiol (Smilkstein et al., 1988). Therefore, the use of reductants such as NAC or other thiol compounds may be beneficial in restoring cellular redox and in inhibition of cytokine-mediated induction of inducible nitric oxide synthase and breakdown of sphingomyelin thus reducing NO-mediated cytotoxicity as well as ceramide-mediated apoptosis in neuroinflammatory diseases.

EXAMPLE 11

Lovastatin and Sodium Phenylacetate Normalize the Levels of Very Long Chain Fatty Acids in Skin Fibroblasts of X-Adrenoleukodystrophy The inventor has observed that lovastatin and NaPA inhibit the induction of nitric oxide synthase and proinflammatory cytokines (TNF-α, IL-1β and IL-6) in rat primary astrocytes, microglia and macrophages indicating that these drugs, alone or in combination, may represent a possible avenue of research for therapeutics directed against cytokine- and NO-mediated brain disorders, particularly in demyelinating conditions. Lovastatin and NaPA have already been approved for medication/drug trials for human diseases. In the current work the inventor provides evidence for the therapeutic intervention against pathognomonic accumulation of VLCFA in X-ALD with these drugs.

Materials and Methods

Reagents DMEM, bovine calf serum and Hanks' buffered salt solution (HBSS) were from Gibco. [1-$^{14}$C]Lignoceric acid was synthesized by treatment of n-tricosanoyl bromide with K$^{14}$CN as described previously (Hoshi and Kishimoto, 1973).

Enzyme assay for β-oxidation of lignoceric acid The enzyme activity of [1-$^{14}$C]lignoceric acid β-oxidation to acetate was measured in intact cells suspended in HBSS. Briefly, the reaction mixture in 0.25 ml of HBSS contained 50-60 µg of protein and 6 µM 1-$^{14}$C]lignoceric acid. Fatty acids were solubilized with α-cyclodextrin and β-oxidation of [1-$^{14}$C]lignoceric acid was carried out as described previously (Singh et al., 1984; Lazo et al., 1988).

Measurement of VLCFA in fibroblasts Fatty acid methyl ester (FAME) was prepared as described previously by Lepage and Roy (1986) with modifications. Fibroblast cells, suspended in HBSS, were disrupted by sonication to form a homogeneous solution. An aliquot (200 µl) of this solution was transferred to a glass tube and 5 µg heptacosanoic (27:0) acid was added as internal standard and lipids were extracted by Folch partition. Fatty acids were transesterified with acetyl chloride (200 µl) in the presence of methanol and benzene (4:1) for 2 h at 100° C. The solution was cooled down to room temperature followed by addition of 5 ml 6% potassium carbonate solution at ice-cooled temperature Isolation and purification of FAME were carried out as detailed by Dacremont et al. (1995). Purified FAME, suspended in chloroform, was analyzed by gas chromatograph GC-15A attached with chromatopac C-R3A integrator from Shimadzu Corporation.

Preparation of post-nuclear membrane and Western blot analysis The Membranes were prepared as described previously (Contreras et al., 1996). Briefly, the post-nuclear fraction was diluted with an ice-cold solution of 0.1 M sodium carbonate, 30 mM iodoacetamide, pH 11.5. After 30 min of incubation at 4° C., the membranes were sedimented by ultracentrifugation The sedimented membranes were electrophoresed in 7.5% sodium dodecylsulfate-polyacrylamide gel, transferred to PVDF membranes and immunoblotted with antibodies against ALDP as described (Contreras et al., 1996).

RNA isolation and Northern blot analysis Cultured skin fibroblasts were taken out from culture flasks directly by adding Ultraspec-II RNA reagent (Biotecx) and total RNA was isolated according to the manufacturer's protocol. 20 µg of RNA from each sample was electrophoretically resolved on 1.2% denaturing formaldehyde-agarose gel, transferred to nylon membrane, and crosslinked using UV Stratalinker (Stratagene, La Jolla, Calif.). Full length ALDP cDNA was kindly provided by Dr. Patrick Aubourg, INSEAM, Hospital Saint-Vincent-de-Paul, Paris, France. $^{32}$P-labeled cDNA probes were prepared according to the instructions provided with Ready-To-Go DNA labeling kit (Pharmacia Biotech). Northern blot analysis was performed essentially as described for Express Hyb Hybridization solution (Clontech, Palo Alto, Calif.) at 68° C. GAPDH cDNA probe was used as standard for comparing hybridization signals.

Results

Inhibitors of mevalonate pathway stimulate the β-oxidation of lignoceric acid in X-ALD fibroblasts. First, the inventor studied the effect of mevalonate inhibitors (lovastatin, mevastatin and NaPA) on the β-oxidation of lignoceric acid in control human skin fibroblasts. It is apparent from Table 17 that lovastatin, mevastatin and NaPA stimulated the β-oxidation of lignoceric acid in control human skin fibroblasts. Since the β-oxidation of lignoceric acid is impaired in X-ALD patients, the inventor studied the effect of these compounds on lignoceric acid β-oxidation in cultured skin fibroblasts of X-ALD. Cultured skin X-ALD fibroblasts were incubated in serum-containing DMEM with different concentrations of lovastatin (0, 2, 4, 6, 8, and 10 µM) or NaPA (0, 1, 2, 3, 4, and 5 mM) in the presence or absence of 2 µM lovastatin. After every 24 h, medium was replaced with the addition of fresh reagents. Lignoceric acid β-oxidation was measured after 72 h in cell suspension as described above. Values were measured as the mean±S.D. of three different studies. Similar to control fibroblasts, these compounds also stimulated lignoceric acid β-oxidation in X-ALD fibroblasts. Both lovastatin and NaPA stimulated lignoceric acid β-oxidation in X-ALD fibroblasts in a dose-dependent manner. The highest dose of lovastatin found to stimulate lignoceric acid β-oxidation (by 70%) was 5 µM whereas the highest dose of NaPA found to stimulate lignoceric acid β-oxidation (by 40%) was 5 mM. However, a greater degree of stimulation (more than two-fold) was observed by a combination of lovastatin and NaPA even at a dose lower than the one used individually. Higher doses of lovastatin (10-20 µM) or NaPA (1-20 mM) were cytotoxic to the X-ALD fibroblasts and did not result in further significant stimulation. In the cell fatty acids are oxidized by mitochondrial and peroxisomal β-oxidation enzyme systems. The inventor examined the effect of etomoxir, an inhibitor of mitochondrial β-oxidation, on the β-oxidation of fatty acids (Mannaerts et al., 1979). Etomoxir had no effect on lovastatin- or NaPA-mediated stimulation of lignoceric acid β-oxidation indicating that the observed stimulation of lignoceric acid β-oxidation was a peroxisomal function.

Modulation of cellular content of VLCFA in X-ALD fibroblasts by lovastatin and NaPA Since mevalonate inhibitors increased β-oxidation of lignoceric acid in control as well as X-ALD fibroblasts, the inventor examined the effect of these compounds on the in situ levels of VLCFA in X-ALD fibroblasts. Cultured skin X-ALD fibroblasts were incubated in serum-containing DMEM with 5 µm lovastatin, 5 mM NaPA or the combination of 2 µm lovastatin and 2 mM NaPA for different days (0, 3, 6, 9, 12, and 15 days), and the ratios of $C_{26:0}/C_{22:0}$ (A) and $C_{24:0}/C_{22:0}$ (B) were measured as described. Values were determined as the mean of two different experiments. Treatment of X-ALD fibroblasts with 5 µm of lovastatin for different time periods (days) resulted in a time-dependent decrease in the ratios of $C_{26:0}/C_{22:0}$ and $C_{24:0}/C_{22:0}$. Within 12-15 days of treatment, the ratios of $C_{26:0}/C_{22:0}$ and $C_{24:0}/C_{22:0}$ in X-ALD fibroblasts decreased to the normal level. Similar to lovastatin, NaPA also lowered the ratios of $C_{26:0}/C_{22:0}$ and $C_{24:0}/C_{22:0}$ in X-ALD fibroblasts almost to the normal level after 15 days of treatment. However, consistent with the higher degree of stimulation of lignoceric acid β-oxidation by a combination of lovastatin and NaPA, the same combination lowered the ratios of $C_{26:0}/C_{22:0}$ and $C_{24:0}/C_{22:0}$ to normal levels within 7 days. This decrease in the ratios of $C_{26:0}/C_{22:0}$ and $C_{24:0}/C_{22:0}$ was also associated with a decrease in the absolute amounts of $C_{24:0}$ and $C_{26:0}$ whereas no significant change was observed in the levels of $C_{22:0}$ (behenoic acid).

Normalization of the levels of VLCFA by lovastatin or NaPA in different X-ALD cells with or without deletion of the X-ALD gene. Although the precise function of ALDP, X-ALD gene product, in the metabolism of VLCFA is not known at the present time, however, accumulation of VLCFA in X-ALD cells with loss or mutations in ALDP and their normalization following transfection of cDNA of ALDP indicate a role of ALDP in the metabolism of VLCFA (Cartier et al., 1995). Therefore, the inventor next attempted to examine whether lovastatin or NaPA were able to lower the levels of VLCFA in X-ALD fibroblast cell lines with mutation or deletion of the X-ALD gene. Western blot analysis of post-nuclear membrane fraction of X-ALD skin fibroblasts with antibodies against ALDP and Northern blot analysis of X-ALD skin fibroblasts for ALDP mRNA were carried out as described.

ALDS2, ALDS3 and ALDS4 are X-ALD skin fibroblasts with mutation of the X-ALD gene, whereas ALDS5 and ALDS6 are X-ALD skin fibroblasts with deletion of the X-ALD gene. The status of ALDP mRNA or protein and the rate of β-oxidation of lignoceric acid (Table 18) in different X-ALD dibroblasts indicates that ALDS2, ALDS3 and ALDS4 are X-ALD skin fibroblasts with mutation of the X-ALD gene, whereas ALDS5 and ALDS6 are X-ALD skin fibroblasts with deletion of the X-ALD gene. It is apparent from Table 18 that the treatment of X-ALD fibroblasts with lovastatin or NaPA or a combination of these stimulated the β-oxidation of lignoceric acid (55-80%) and normalized the ratios of $C_{26:0}/C_{22:0}$ indicating that these drugs are capable of lowering the level of VLCFA in X-ALD fibroblasts to the normal levels, irrespective of mutation or deletion of the X-ALD gene, the candidate gene for X-ALD.

TABLE 17

Lovastatin and NaPA stimulate the β-oxidation of lignoceric acid in control human skin fibroblasts

| Treatment | Lignoceric acid β-oxidation (pmol/h/mg protein) |
|---|---|
| Control | 570.2 ± 52.3 |
| Lovastatin (5 μM) | 945.7 ± 105.6 |
| Mevastatin (5 μM) | 889.6 ± 78.4 |
| NaPA (5 mM) | 826.2 ± 87.2 |

Cells were treated for 72 h in serum-containing DMEM with the listed reagents; β-oxidation, of lignoceric acid was measured as described in Section 2. Medium was replaced after every 24 h with the addition of fresh reagents. Data are mean±S.D. of three different studies.

Discussion

The present study underlines the importance of lovastatin, an inhibitor of 3-hydroxy-3-methyl-glutaryl-coenzyme A (HMG-CoA) reductase, and the sodium salt of phenylacetic acid (NaPA), an inhibitor of mevalonate pyrophosphate decarboxylase, alone or in combination, in stimulating the β-oxidation of lignoceric acid ($C_{24:0}$) and in normalizing the pathognomonic accumulation of saturated very long chain fatty acids (VLCFA) in cultured skin fibroblasts of adrenoleukodystrophy (X-ALD) in which the ALD gene is either mutated or deleted. The detailed mechanism leading to the decrease in the accumulation of VLCFA in X-ALD fibroblasts is not known, but is likely through the stimulation of peroxisomal β-oxidation of VLCFA. In light of the fact that these compounds also inhibit the induction of proinflammatory cytokines and nitric oxide synthase in astrocytes and microglia, the ability of lovastatin and NaPA to normalize the pathognomonic accumulation of VLCFA in skin fibroblasts of X-ALD identify these drugs as possible therapeutics for the neuroinflammatory disease process in X-ALD.

EXAMPLE 12

Lovastatin for X-Linked Adrenoleukodystrophy in Humans

The inventor has shown in animal studies that lovastatin, a 3-hydroxy-3-methylglutaryl coenzyme A reductase inhibitor, and sodium phenylacetate, an inhibitor of mevalonate pyrophosphate decarboxylase, inhibit the induction of inducible nitric oxide synthase and proinflammatory cytokines (tumor necrosis factor (alpha), interleukin-1(beta), and interleukin-6) involved in the pathogenesis of neurologic damage in

TABLE 18

Effect of lovastatin and NaPA on (A) β-oxidation of lignoceric acid and (B) the ratios of $C_{26:0}/C_{22:0}$ and $C_{24:0}/C_{22:0}$ in cultured skin fibroblasts of X-ALD

A.

| | Lignoceric acid β-oxidation (pmol/h/mg protein) | | | |
|---|---|---|---|---|
| Cell line | Control | Lovastatin | NaPA | Lovastatin + NaPA |
| ALDS2 | 142.7 ± 15.7 | 223.5 ± 24.1 | 202.5 ± 17.4 | 274.6 ± 30.5 |
| ALDS5 | 154.2 ± 14.2 | 248.2 ± 26.2 | 211.5 ± 22.6 | 296.2 ± 25.6 |
| ALDS6 | 132.4 ± 15.9 | 218.3 ± 19.8 | 189.7 ± 21.2 | 250.1 ± 28.3 |
| ALDS3 | 122.3 ± 11.7 | 201.3 ± 22.3 | 183.2 ± 17.3 | 248.6 ± 29.6 |
| ALDS4 | 118.5 ± 12.6 | 192.8 ± 20.5 | 178.9 ± 18.3 | 238.7 ± 21.1 |

B.

| | $C_{26:0}/C_{22:0}$ | | | $C_{26:0}/C_{22:0}$ | | |
|---|---|---|---|---|---|---|
| | Control | Lovastatin | Lovastatin + NaPA | Control | Lovastatin | Lovastatin + NaPA |
| ALDS2 | 0.17 ± 0.022 | 0.049 ± 0.01 | 0.04 ± 0.008 | 1.84 ± 0.25 | 1.25 ± 0.15 | 1.14 ± 0.15 |
| ALDS5 | 0.18 ± 0.025 | 0.055 ± 0.008 | 0.04 ± 0.007 | 1.94 ± 0.29 | 1.28 ± 0.21 | 1.18 ± 0.12 |
| ALDS6 | 0.22 ± 0.034 | 0.058 ± 0.01 | 0.045 ± 0.008 | 2.01 ± 0.3 | 1.31 ± 0.18 | 1.21 ± 0.14 |
| ALDS3 | 0.16 ± 0.024 | 0.045 ± 0.06 | 0.03 ± 0.005 | 1.88 ± 0.21 | 1.26 ± 0.16 | 1.19 ± 0.25 |
| ALDS4 | 0.19 ± 0.028 | 0.052 ± 0.07 | 0.036 ± 0.006 | 1.96 ± 0.23 | 1.29 ± 0.02 | 1.22 ± 0.15 |

Cells were incubated in serum containing DMEM with 5 μM lovastatin, 5 mM NaPA or the combination of 2 μM lovastatin and 2 mM NaPA for 15 days, and the β-oxidation of lignoceric acid (A) and the ratios of $C_{26:0}/C_{22:0}$ and $C_{24.0}/C_{22.0}$ (B) were measured as described in Section 2. Results are mean±S.D. of three different studies. ALDS2, ALDS3 and ALDS4 are X-ALD skin fibroblasts with mutation of the X-ALD gene, whereas ALDS5 and ALDS6 are X-ALD skin fibroblasts with deletion of the X-ALD gene.

X-linked adrenoleukodystrophy. The inventor has also shown that lovastatin, sodium phenylacetate, and compounds that increase intracellular cyclic AMP and protein kinase A activity normalize the levels of very-long-chain fatty acids in cultured skin fibroblasts from patients with childhood adrenoleukodystrophy and adrenomyeloneuropathy.

To demonstrate lovastatin's effectiveness in treating elevated VLCFAs in human patients, the inventor has treated seven patients from three families with lovastatin for two to six months. The study was approved by the institutional review board at the inventor's medical school, and the patients provided informed consent. The diagnosis was established in each case by clinical findings and documentation of elevated plasma levels of very-long-chain fatty acids (C26:0) by two different laboratories. Each patient was treated with 20 mg of lovastatin per day for two weeks; the dose was increased to 40 mg per day if no adverse effects were noted. Plasma very-long-chain fatty acids (C26:0) were measured periodically throughout the study. Adverse events and compliance were assessed on the basis of the patients' reports and by periodic measurement of plasma total cholesterol, creatine kinase, aspartate aminotransferase, and alanine aminotransferase.

One patient (Patient 4) was withdrawn from the study because of persistent diarrhea and a marked elevation of serum creatine kinase levels. Another (Patient 5) discontinued treatment. The inventor's results (Table 19) show that plasma levels of very-long-chain fatty acids (C26:0) declined from their pretreatment values within one month after the initiation of lovastatin therapy in each patient and remained low and within the normal range for up to six months in the five patients who continued the treatment. Their lower post-treatment cholesterol values (Table 19) provide evidence of compliance with therapy. The short duration and small size of the study did not allow the inventor to assess whether there was a clinical benefit.

humans. These suppressors may be used to reduce the induction of iNOS and proinflammatory cytokines, reduce the accumulation of VLCFAs, and treat neuroinflammatory diseases such as X-linked adrenoleukodystrophy and multiple sclerosis. As described in Example 12, lovastatin shows effectiveness in reducing the accumulation of very-long-chain fatty acids in human X-ALD patients. Any of the various inhibitors and/or induction suppressors described herein can be used in a human to treat any disease or disorder wherein a undesirable amount of iNOS and/or proinflammatory cytokines is acting to promote tissue damage. Dosages and combinations of inhibitors, suppressors, and/or other pharmaceuticals that may be used can be determined first through an animal model of a particular disease or disorder, and then tested in a human population. Dosages may be optimized on an individual basis, with routine experimentation by those of skill in the art.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be sub-

TABLE 19

Effect of Lovastatin Therapy on Plasma Levels of Very-Long-Chain Fatty Acids in Patients with X-Linked Adrenoleukodystrophy

| | | | | | Plasma Very-Long-Chain Fatty Acids† | | | | | | Plasma Total Cholesterol | |
|---|---|---|---|---|---|---|---|---|---|---|---|---|
| Patient No. | Age | Age at Onset years | Clinical Phenotype* | Before Treatment | AT 1 MO | AT 2 MO | AT 3 MO | AT 4 MO | AT 5 MO | AT 6 MO | Before Treatment | After Treatment‡ |
| | | | | | | micrograms per milliliter | | | | | mg/dl | |
| 1 | 42 | 28 | Cerebral AMN | 0.8 | 0.44 | 0.42 | 0.36 | 0.37 | 0.21 | 0.21 | 109 | 96 |
| 2 | 52 | 35 | AMN and Addison's disease§ | 0.72 | 0.42 | 0.41 | 0.56 | 0.35 | 0.17 | 0.17 | 222 | 158 |
| 3 | 55 | 45 | AMN | 0.97 | 0.37 | 0.5 | 0.3 | 0.34 | 0.41 | 0.17 | 236 | 204 |
| 4 | 21 | 14 | Adolescent cerebral ALD | 1.14 | 0.5 | 0.42 | — | 0.42 | — | — | 165 | 167 |
| 5 | 25 | — | Presymptomatic AMN¶ | 0.75 | 0.43 | 0.41 | 0.43 | — | — | — | 140 | 149 |
| 6 | 44 | — | Heterozygous‖ | 0.37 | 0.24 | 0.21 | 0.21 | 0.22 | 0.26 | 0.16 | 280 | 230 |
| 7 | 70 | 45 | Heterozygous‖ | 0.44 | 0.3 | 0.34 | 0.32 | 0.34 | 0.41 | 0.17 | 239 | 183 |

*AMN denotes adrenomyeloneuropathy, and ALD adrenoleukodystrophy.
†The value in 50 normal control subjects was 0.24 ± 0.13 μg per milliliter.
‡Post-treatment total cholesterol levels were obtained at six months for the patients who continued treatment (Patients 1, 2, 3, 6, and 7), at four months for Patient 4, and at three months for Patient 5. Patients 4 and 5 discontinued treatment.
§Addison's disease is part of the spectrum of ALD.
¶Patient 5 had nerve-conduction abnormalities consistent with AMN but no symptoms when last examined.
‖Patients 6 and 7 were women who carried one copy of the mutant X gene. Patient 6 had no symptoms when last examined; patient 7 had mild spasticity and paresthesia of both legs.

These results indicate that lovastatin treatment may represent a simple, safe, and effective way to reduce the accumulated plasma very-long-chain fatty acids in adult patients with X-linked adrenoleukodystrophy.

EXAMPLE 13

Treatment of Humans with Inhibitors of iNOS and Cytokines

The inhibitors, induction suppressors, induction enhancers, and stimulators or iNOS and/or proinflammatory cytokines of the present invention may be used in the treatment of cells and organisms such as mammals, including rodents and stituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbas, A. K., et al., *Cellular and Molecular Immunology*, W. B. Saunders Co., Publisher, Philadelphia, Pa., 1991.

Abbondanzo et al., Breast Cancer Res. Treat., 16:182(#151), 1990.

Akamatsu, Ohno, Hirota, Kegoshima, Yodoi, Shigesada, "Redox regulation of the DNA binding activity in transcription factor PEBP2. The roles of two conserved cysteine residues," *J. Biol. Chem.* 272:14497-14500, 1997.

Allred et al., Breast Cancer Res. Treat., 16:182(#149), 1990.

Aruoma, O. I., et al., "The antioxidant action of N-acetyl cysteine: its reaction with hydrogen peroxide, hydroxyl radical, superoxide, and hypochlorous acid," *Free Rad. Biol. Med.*, 6:593-597, 1989.

Bagasra, Michaels, Zheng, Bobroski, Spitsin, Fu, Tawadros, Koprowski, "Activation of the inducible form of nitric oxide synthase in the brains of patients with multiple sclerosis," *Proc. Natl. Acad. Sci.*, 92:12041-12045, 1995.

Beasley and Brenner, "Role of nitric oxide in hemodialysis hypotension," *Kidney Int.*, 42, Suppl., 38:S96-S100, 1992.

Beckman et al. "Apparent hydroxyl radical production by peroxynitrite: implications for endothelial injury from nitric oxide and superoxide," *Proc. Natl. Acad. Sci. U.S.A.*, 87:1620-1624, 1990.

Beg, Ruben, Scheinman, Haskil, Rosen, Baldwin Jr., "I kappa B interacts with the nuclear localization sequences of the subunits of NF-kappa B: a mechanism for cytoplasmic retention," *Genes de Dev.*, 6:1899-1913, 1992.

Begum and Ragolia, "cAMP counter-regulates insulin-mediated protein phosphatase-2A inactivation in rat skeletal muscle cells," *J. Biol. Chem.*, 271:31166-31171, 1996.

Berisha et al., "Nitric oxide as a mediator of oxidant lung injury due to paraquat," Proc. Natl. Acad. Sci. U.S.A., 91:744-749, 1994.

Blenis, "Signal transduction via the MAP kinases: proceed at your own RSK," *Proc. Natl. Acad. Sci. USA.*, 90:5889-5892, 1993.

Bo, Dawson, Wesselingh, Mork, Choi, Kong, Hanley, Trapp, "Induction of nitric oxide synthase in demyelinating regions of multiple sclerosis brains," *Ann. Neurol.* 36:778-786, 1994.

Bonfoco, E., et al., "Apoptosis and necrosis: two distinct events induced, respectively, by mild and intense insults with N-methyl-D-aspartate on nitric oxide/superoxide in cortical cell cultures," *Proc. Natl. Acad. Sci. USA.*, 92:7162-7166, 1995.

Boughton-Smith et al., "Nitric oxide synthase activity in ulcerative colitis and Crohn's disease," *Lancet* 342:338-340, 1993.

Bradford, M., "A rapid and sensitive method for the quantitation of microgram quantities of protein utilizing the principle of protein-dye binding," *Anal. Biochem.*, 72:248-254, 1976.

Bredesen, "Neural apoptosis," *Ann. Neurol.*, 38:839-851, 1995.

Brown et al., Breast Cancer Res. Treat., 16:192(#1191), 1990.

Brugg, Mitchel, Agid, Ruberg, "Ceramide induces apoptosis in cultured mesencephalic neurons," *J. Neurochem.*, 66:733-739, 1996.

Buisson et al., "The neuroprotective effect of a nitric oxide inhibitor in a rat model of focal cerebral ischaemia," *Br. J. Pharmacol.*, 106:766-767, 1992.

Bull et al., *J. Invest. Derm.*, 103:435, 1994.

Busse, R., et al., "Induction of nitric oxide synthase by cytokines in vascular smooth muscle cells," *FEBS Lett.*, 275:87-90, 1990.

Caira, Pacot, Bardot, Malki, Latruffe, "Transcriptional and post-transcriptional analysis of peroxisomal protein encoding genes from rat treated with an hypolipemic agent, ciprofibrate," *Biochem. Pharmacol.*, 49:611-619, 1995.

Cartier, N., J. Lopez, P. Moullier, F. Rocchiccioli, M. O. Rolland, P. Jorge, J. Mosser, J. L. Mandel, P. F. Bougneres, O. Danos, and P. Aubourg. "Retroviral-mediated gene transfer corrects very-long-chain fatty acid metabolism in adrenoleukodystrophy fibroblasts," *Proc. Natl. Acad. Sci. USA.* 92:1674-1678, 1995.

Casey, P. J., et al., "P21 ras is modified by a farnesyl isoprenoid," *Proc. Natl. Acad. Sci. USA*, 86:8323-8327, 1989.

Castillo, Martinez-Cayuela, Zafra, Garcia-Peregrin, "Effect of phenylalanine derivatives on the main regulatory enzymes of cholesterogenesis," *Mol. Cell. Biochem.*, 105: 21-25, 1991.

Chatterjee, "Neutral sphingomyelinase," *Adv. Lipid Res.*, 26:25-47, 1993.

Chen, Y and Rosazza, J. P. N., "A bacterial nitric oxide synthase from a *Nocardia* species. Biochem Biophys Res Commun," 203:1251-1258, 1994.

Chiueh et al. "Enhanced hydroxyl radical generation by 2'-methyl analog of MPTP: suppression by clorgyline and deprenyl," *Synapse* 11:346-348, 1992.

Contreras, M., J. Mosser, J. L. Mandel, P. Aubourg, and I. Singh. "The protein coded by the X-adrenoleukodystrophy gene is a peroxisomal integral membrane protein," *FEBS Lett.* 344:211-215, 1994.

Contreras, M., T. K. Sengupta, F. Sheilh, P. Aubourg, and I. Singh. "Topology of ATP-binding domain of adrenoleukodystrophy gene product in peroxisomes," *Arch. Biochem. Biophys.* 334:369-379, 1996.

Corbett and McDaniel, "Selective inhibition of inducible nitric oxide synthase by aminoguanidine," *Methods Enzymol.*, 268:398-408, 1996.

Cornell, N. W. "Rapid fractionation of cell suspensions with the use of brominated hydrocarbons," *Anal. Biochem.* 102: 326-331, 1980.

Cross, Misko, Lin, Hickey, Trotter, Tilton, "Aminoguanidine, an inhibitor of inducible nitric oxide synthase, ameliorates experimental autoimmune encephalomyelitis in SJL mice," *J. Clin. Invest.*, 93:2684-2690, 1994.

Dacrement, G., G. Cocquyt, and G. Vincent. "Measurement of very long chain fatty acids, phytanic acid and pristanic acid in plasma and cultured fibroblasts by gas chromatography," *J. Inher. Metab. Dis.* 18 Suppl. 1:76-83, 1995.

Dawson, Dawson, London, Bredt, Snyder, "Nitric oxide mediates glutamate neurotoxicity in primary cortical cultures," *Proc. Natl. Acad. Sci. USA*, 88:6368-6371, 1991.

Dbaio, Perry, Gamard, Platt, Poirier, Obeid, Hannun, "Cytokine response modifier A (CrmA) inhibits ceramide formation in response to tumor necrosis factor (TNF)-alpha: CrmA and Bcl-2 target distinct components in the apoptotic pathway," *J. Exp. Med.*, 185:481-490, 1997.

Decrement, Cocquyt, Vincent, "Measurement of very long-chain fatty acids, phytanic and pristanic acid in plasma and cultured fibroblasts by gas chromatography," *J. Inher. Metabl. Dis.*, 18(Suppl. 1):76-83, 1995.

Devary, Gottleib, Lau, Karin, "Rapid and preferential activation of the c-jun gene during the mammalian UV response," *Mol. Cell. Biol.*, 11:2804-2811, 1991.

Devlin, J. et al., "Nitric oxide generation. A predictive parameter of acute allograft rejection," *Transplantation*, 58:592-595, 1994.

Dignam, J. D., et al., "Accurate transcription initiation by RNA polymerase II in a soluble extract from isolated mammalian nuclei," *Nucleic Acids Res.*, 11:1475-1489, 1983.

Dobashi, Pahan, Chahal, Singh, "Modulation of endogenous antioxidant enzymes by nitric oxide in rat C6 glial cells," *J. Neurochem.*, 68:1896-1903, 1997.

Drapier, J-C., et al., "Differentiation of murine macrophages to express nonspecific cytotoxicity for tumor cells results in L-arginine-dependent inhibition of mitochondrial ironsulfur enzymes in the macrophages effector cells," *J. Immunol*, 140:2829-2838, 1988.

Eberhardt et al., "Molecular cloning of the rat inducible nitric oxide synthase gene promoter," *Biochem. Biophys. Res. Commun.*, 223:752-756, 1996.

Eisieik & Leijersfam, "The inducible form of nitric oxide synthase (iNOS) in insulin-producing cells," *Diabetes & Metabolism*, 20:116-122, 1994.

Evans et al., "Differential effects of monoclonal antibodies to tumor necrosis factor alpha and gamma interferon on induction of hepatic nitric oxide synthase in experimental gram-negative sepsis," *Infec. Imm.*, 60:4133-4139, 1992.

Feinstein, Galea, Cermak, Chugh, Lyandvert, Reis, "Nitric oxide synthase expression in glial cells: suppression by tyrosine kinase inhibitors," *J. Neurochem.*, 62:811-814, 1994b.

Feinstein, Galea, Roberts, Berquist, Wang, Reis, "Induction of nitric oxide synthase in rat $C_6$ glial cells," *J. Neurochem.*, 62:315-321, 1994a.

Fenyk-Melody, Garrison, Brunnert, Weidner, Shen, Shelton, Mudgett, "Experimental autoimmune encephalomyelitis is exacerbated in mice lacking the NOS2 gene," *J. Immunol.*, 160:2940-2946, 1998.

Frohman, In: PCR™ Protocols: A Guide to Methods and Applications, Academic Press, NY, 1990

Galea, Feinstein, Reis, "Induction of calcium-independent nitric oxide synthase activity in primary rat glial cultures," *Proc. Natl. Acad. Sci. USA*, 89:10945-10949, 1992.

Ganser, Kemer, Brown, Davisson, Kirschner, "A survey of neurological mutant mice. I. Lipid composition of myelinated tissue in known myelin mutants," *Dev. Neurosci.*, 10:99-122, 1988.

Geller, D. A., et al., "A central role for IL-1 beta in the in vitro and in vivo regulation of hepatic inducible nitric oxide synthase: IL-1 beta induces hepatic nitric oxide synthesis," *J. Immunol.*, 155:4890-4898, 1995.

Geller, Lowenstein, Shapiro, Nussler, Di Silvio, Wang, Nakayama, Simmons, Snyder, Billiar, "Molecular cloning and expression of inducible nitric oxide synthase from human hepatocytes," *Proc. Natl. Acad. Sci. USA*, 90:3491-3495, 1993.

Geng, Y., et al., "Tyrosine kinases are involved with the expression of inducible nitric oxide synthase in human articular chondrocytes," *J. Cell. Physiol.*, 163:545-554, 1995.

Giulian, D., and T. J. Baker. "Characterization of amoebid microglia isolated from developing mammalian brain," *J. Neurosci.* 6:2163-2178, 1986.

Goldstein, J. L., et al., "Regulation of the mevalonate pathway," *Nature*, 343:425-430, 1990.

Goureau et al., "Lipopolysaccharide and cytokines induce a macrophage-type of nitric oxide synthase in bovine retinal pigmented epithelial cells," *Biochem. Biophys. Res. Commun.*, 186:854-859, 1992.

Graves, L. M., K. E. Bornfeildt, E. W. Raines, B. C. Potts, S. G. Macdonald, R. Ross, and E. G. Krebs. 1993. "Protein kinase A antagonizes platelet-derived growth factor-induced signaling by mitogen-activated protein kinase in human arterial smooth muscle cells," *Proc. Natl. Acad. Sci. USA*. 90:10300-10304.

Griffith, "Determination of glutathione and glutathione disulfide using glutathione reductase and 2-vinylpyridine," *Anal. Biochem.*, 106:207-212, 1980.

Guilian and Baker, "Characterization of ameboid microglia isolated from developing mammalian brain," *J. Neurosci.*, 6:2163-2178, 1986.

Haga et al., "Synthetic Alzheimer amyloid beta/A4 peptides enhance production of complement C3 component by cultured microglial cells," *Brain Res.*, 601:88-94, 1993.

Hamid et al., "Induction of nitric oxide synthase in asthma," *Lancet*, 342:1510-1513, 1993.

Hancock, J. F., et al., "Methylation and proteolysis are essential for efficient membrane binding of prenylated $p21^{k-ras}$ (B)," *EMBO J.*, 10:641-646, 1991.

Hannun and Bell, "Functions of sphingolipids and sphingolipid breakdown products in cellular regulation," *Science*, 243:500-507, 1989.

Hannun, "Functions of ceramide in coordinating cellular responses to stress," *Science*, 274:1855-1858, 1996.

Hannun, "The sphingomyelin cycle and the second messenger function of ceramide," *J. Biol. Chem.*, 269:3125-3127, 1994.

Hardy, S. J., A. Ferranta, A. Poulos, B. S. Robinson, D. W. Johnson, and A. W. Murray. "Effect of exogenous fatty acids with greater than 22 carbon atoms (very long chain fatty acids) on superoxide production by human neutrophils," *J. Immunol.* 153:1754-1761, 1994.

Hashmi, M., W. Stanley, and I. Singh. "Lignoceroyl-CoASH ligase: enzyme defect in fatty acid β-oxidation system in X-linked childhood adrenoleukodystrophy," *FEBS Lett.* 196:247-250, 1986.

Henin et al., "Inhibition of fatty acid and cholesterol synthesis by stimulation of AMP-activated protein kinase," *FASEB J.*, 9:541-546, 1995.

Henkel, T., et al., "Rapid proteolysis of IkB-alpha is necessary for activation of transcription factor NF-kB," *Nature*, 365:182-185, 1993.

Her, Lakhani, Zu, "Dual phosphorylation and autophosphorylation in mitogen-activated protein (MAP) kinase activation," *Blochem. J.*, 296:25-31, 1993.

Hibbs et al., "Evidence for cytokine-inducible nitric oxide synthesis from L-arginine in patients receiving interleukin-2 therapy," *J. Clin. Invest.*, 89:867-877, 1992.

Hooper, Bagsra, Marini, Zborek, Ohnishi, Kean, Champion, Sarker, Bobroski, Farber, Akaike, Maeda, Koprosky, "Prevention of experimental allergic encephalomyelitis by targeting nitric oxide and peroxynitrite: implications for the treatment of multiple sclerosis," *Proc. Natl. Acad. Sci. USA.*, 94:2528-2533, 1997.

Hooper, Spitsin, Kean, Champion, Dickson, Chaudhry, Koprowski, "Uric acid, a natural scavenger of peroxynitrite, in experimental allergic encephalomyelitis and multiple sclerosis," *Proc. Natl. Acad. Sci. USA*, 95:675-680, 1998.

Hoshi, M., and Y. Kishimoto. "Synthesis of cerebronic acid from lignoceric acid by rat brain preparation. Some properties and distribution of the hydroxylation system," *J. Biol. Chem.* 248:4123-4130, 1973.

Hu, S. X., et al., "Differential regulation by cytokines of human astrocyte nitric oxide production," *Glia*, 15:491-494, 1995.

Ialenti et al., "Modulation of adjuvant arthritis by endogenous nitric oxide," *Br. J. Pharmacol.*, 110:701-706, 1993.

Issazadeh, Mustafa, Ljungdahl, Hojeberg, Dagerlind, Elde, Olsson, "Interferon-γ, interleukin 4 and transforming growth factor β in experimental autoimmune encephalomyelitis in Lewis rats: dynamics of cellular mRNA expression in the central nervous system and lymphoid cells," *J. Neurosci. Res.*, 40:579-590, 1995.

Jaffrey, S. R. et al., "Nitric oxide: a neural messenger," *Annu. Rev. Cell Dev. Biol.*, 11:417-440, 1995.

Jayadev, Lincardic, Hannun, "Identification of arachidonic acid as a mediator of sphingomyelin hydrolysis in response to tumor necrosis factor alpha," *J. Biol. Chem.*, 269:5757-5763, 1994.

Jelinek, T., et al., "Ras-induced activation of Raf-1 is dependent on tyrosine phosphorylation;" *Mol. Cell. Biol.*, 16:1027-1034, 1996.

Joshi et al., "Effect of aminoguanidine on in vivo expression of cytokines and inducible nitric oxide synthase in the lungs of endotoxemic rats," *Res. Commun. Mol. Pathol. Pharmacol. Mar.*, 91:339-346, 1996.

Kantey, Feinstein, Papa, Hemi, Karasik, "Tumor necrosis factor alpha-induced phosphorylation of insulin receptor substrate-1 (IRS-1). Possible mechanism for suppression of insulin-stimulated tyrosine phosphorylation of IRS-1," *J. Biol. Chem.*, 270:23780-23784, 1995.

Kaurs & Halliwell, "Evidence for nitric oxide-mediated oxidative damage in chronic inflammation. Nitrotyrosine in serum and synovial fluid from rheumatoid patients," *FEBS Lett.*, 350:9-12, 1994.

Kharitonov et al., "Increased nitric oxide in exhaled air of asthmatic patients," *Lancet*, 343:133-135, 1994.

Kikuchi, A., et al., "The post-translational modification of ras p21 is important for Raf-1 activation," *J. Biol. Chem.*, 269:20054-20059, 1994.

Kilbourn et al., "NG-methyl-L-arginine inhibits tumor necrosis factor-induced hypotension: implications for the involvement of nitric oxide," *Proc. Natl. Acad. Sci. U.S.A.*, 87:3629-3632, 1990.

Klinkert, Kojima, Lesslauer, Rinner, Lassmann, Wekerle, "TNF-alpha receptor fusion protein prevents experimental auto-immune encephalomyelitis and demyelination in Lewis rats: an overview," *J. Neuroimmunol.*, 72(2)163-168, 1997.

Kolb-Bachofen et al., "Epidermal keratinocyte expression of inducible nitric oxide synthase in skin lesions of psoriasis vulgaris," *Lancet*, 344:139 1994.

Kolesnick and Golde, "The sphingomyelin pathway in tumor necrosis factor and interleukin-1 signaling," *Cell*, 77:325-328, 1994.

Koprowski, Zheng, Heber-Katz, Fraser, Rorke, Fu, Hanlon, Dietzscold, "In vivo expression of inducible nitric oxide synthase in experimentally induced neurologic diseases," *Proc. Natl. Acad. Sci.*, 90:3024-3027, 1993.

Krasemann, E. W., V. Meier, G. C. Korenke, D. H. Hunneman, and F. Hanefeld. "Identification of mutations in the ALD-gene of 20 families with adrenoleukodystrophy/adrenomyeloneuropathy," *Hum. Genet.* 97:194-197, 1996.

Kroncke et al., "Activated macrophages kill pancreatic syngeneic islet cells via arginine-dependent nitric oxide generation," *Biochem. Biophys. Res. Commun.*, 175:752-758, 1991.

Kubes, P., et al., "Nitric oxide: an endogenous modulator of leukocyte adhesion," *Proc. Natl. Acad. Sci. USA*, 88:4651-4655, 1991.

Kwon, Corbett, Rodi, Sullivan, McDaniel, "Interleukin-1 beta-induced nitric oxide synthase expression by rat pancreatic beta-cells: evidence for the involvement of NF-k$\beta$ in the signaling mechanism," *Endocrinology*, 136:4790-4795, 1995.

Lageweg, W., J. E. C. Sykes, M. Lopes-Cardozo, and R. J. A. Wanders. "Oxidation of very long chain fatty acids in rat brain:cerotic acid is -oxidized exclusively in rat brain peroxisomes," *Biochim. Biophys. Acta* 1085:381-384, 1991.

Laight, Carrier, Anggard, "Investigation of role for oxidant stress in vascular tolerance development to glyceryl trinitrate in vitro," *Br. J. Pharmacol.*, 120:1477-1482, 1997.

Lander, H. M., et al., "Activation of human peripheral blood mononuclear cells by nitric oxide generating compounds," *J. Immunol.*, 150:1509-1516, 1993.

Lander, H. M., et al., "p21$^{ras}$ as a common signaling target of reactive free radicals and cellular redox stress," *J. Biol. Chem.*, 270:21195-21198, 1995.

Latinis and Koretzky, "Fas ligation induces apoptosis and Jun kinase activation independently of CD45 and Lck in human T cells," *Blood*, 87:871-875, 1996.

Law, Stimmel, Damore, Carter, Clarke, Wall, "Lipopolysaccharide-induced NF-k$\beta$ activation in mouse 70Z/3 pre-B lymphocytes is inhibited by mevilonin and 5'-methyladenosine: roles of protein isoprenylation and carboxylation reactions," *Mol. Cell. Biol.*, 12:103-111, 1992.

Lazo, O., M. Contreras, A. Bhusan, W. Stanley, and I. Singh. "Adrenoleukodystrophy: Impaired oxidation of fatty acids due to peroxisomal lignoceroyl-CoA ligase deficiency," *Arch. Biochem. Biophys.* 270:722-728, 1989.

Lazo, O., M. Contreras, M. Hashmi, W. Stanley, C. Irazu, and I. Singh. "Peroxisomal lignoceroyl-CoA ligase deficiency in childhood adrenoleukodystrophy and adrenomyeloneuropathy," *Proc. Natl. Acad. Sci. USA.* 85:7647-7651, 1988.

Lazo, Singh, Singh, "Postnatal development and isolation of peroxisomes from brain," *J. Neurochem.*, 56:1343-1353 22, 1991.

Lee et al., "Nitric oxide mediates Fos expression in the spinal cord induced by mechanical noxious stimulation," *Neuro Report*, 3:841-844, 1992.

Lepage, G. and C. C. Roy. "Direct transesterification of all classes of lipids in one-step reaction," *J. Lipid Res.* 27:114-120, 1986.

Li, S., et al., "Raf-1 protein kinase activates the NF-k$\beta$ transcription factor by dissociating the cytoplasmic NF-k$\beta$-Ik$\beta$ complex," *Proc. Natl. Acad. Sci. USA*, 90:9247-9251, 1993.

Ligtenberg, M., S. Kemp, C. O, Sarde, B. M. van Geel, W. J. Kleijer, P. G. Barth, J. L. Mandel, B. A. van Oost, and P. A. Bolhuis. "Spectrum of mutations in the gene encoding the adrenoleukodystrophy protein," *Am. J. Hum. Gen.* 56:44-50, 1995.

Linardic, Jayadev, Hannun, "Activation of the sphingomyelin cycle by brefeldin A: effects of brefeldin A on differentiation and implications for a role for ceramide in regulation of protein trafficking," *Cell Grow. Different.*, 7:765-774, 1996.

Lipton, S. A., Choi, Y. B., Pan, Z. H., Lei, S. Z., Chen, H. S., Sucher, N. J., Loscalzo, J., Singel, D. J., and Stamler, J. S. "A redox-based mechanism for the neuroprotective and neurodestructive effects of nitric oxide and related nitrosocompounds," *Nature* 364:626-632, 1993.

Liu, Hannun, "Inhibition of the neutral magnesium-dependent sphingomyelinase by glutathione," *J. Biol. Chem.*, 272:16281-16287, 1997.

Lo and Cruz, "Involvement of reactive oxygen species in cytokine and growth factor induction of c-fos expression in chondrocytes," *J. Biol. Chem.*, 270:11727-11730, 1995.

Lowenstein, C. J., et al., "Cloned and expressed macrophage nitric oxide synthase contrasts with the brain enzyme," *Proc. Natl. Acad. Sci. USA*, 89:6711-6715, 1993.

Lowick et al., "Inducible production of nitric oxide in osteoblast-like cells and in fetal mouse bone explants is associated with suppression of osteoclastic bone resorption," *J. Clin. Invest.*, 93:1465-1472, 1994.

Lozano, Berra, Munico, Diaz-Meco, Dominguez, Sanz, Moscat, "Protein kinase C zeta isoform is critical for kappa B-dependent promoter activation by sphingomyelinase," *J. Biol. Chem.*, 269:19200-19202, 1994.

Maimone, Gregory, Amason, Reder, "Cytokine levels in the cerebrospinal fluid and serum of patients with multiple sclerosis," *J. Neurolmmunol.*, 32:67-74, 1991.

Mandia et al., *Invest Opthalmol.*, 35:3673-3689, 1994.

Mannaerts, G. P., L. J. Debeer, J. Thomas, and P. J. De Schepper. "Mitochondrial and peroxisomal fatty acid oxidation in liver homogenates and isolated hepatocytes from control and clofibrate-treated rats," *J. Biol. Chem.* 254:4585-4595, 1979.

Manne, Ricca, Brown, Tuomori, Yan, et al., "Ras farnesylation as a target for novel antitumor agent: potent and selective farnesyl diphosphate analog inhibitors of farnesyl transferase," *Drug Dev. Res.*, 34:121-137, 1995.

Marietta, M. *Trends Biochem. Sci.* 14:488, 1989.

Marietta, M. A., "Nitric oxide synthase: aspects concerning structure and catalysis," *Cell*, 78:927-930, 1994.

Martin, O'Brien, Nishioka, McGahon, Mahboubi, Saido, Green, "Proteolysis of fodrin (non-erythroid spectrin) during apoptosis," *J. Biol. Chem.*, 270:6425-6428, 1995.

McCarthy, K., et al., "Preparation of separate astroglial and oligodendroglial cultures from rat cerebral tissue," *J. Cell Biol.*, 85:890-902, 1980.

McCartney-Francis, N., et al., "Suppression of arthritis by an inhibitor of nitric oxide synthase," *J. Exp. Med.*, 178:749-754, 1993.

McGuiness, Powers, Bias, Schmeckpeper, Segal, Gowda, Wesselingh, Berger, Griffin, Smith, "Human leukocyte antigens and cytokine expression in cerebral inflammatory demyelinative lesions of X-linked adrenoleukodystrophy and multiple sclerosis," *J. Neuroimmunol.*, 75:174-182, 1997.

McGuinness, M. C., D. E. Griffin, G. V. Raymond, C. A. Washington, H. W. Moser, and K. D. Smith. "Tumor necrosis factor- and X-linked adrenoleukodystrophy," *J. Neuroimmunol.* 61:161-169, 1995.

Mehta, K., et al., "Inhibition by all-trans-retinoic acid of tumor necrosis factor and nitric oxide production by peritoneal macrophages," *J. Leukocyte Biol.*, 55:336-342, 1994.

Meller et al., "Production of endogenous nitric oxide and activation of soluble guanylate cyclase are required for N-methyl-D-aspartate-produced facilitation of the nociceptive tail-flick reflex," *Europ. J. Pharmacol.*, 214:93-96, 1992.

Menon, S. D., et al., "Differential induction of nuclear NF-kB by protein phosphatase inhibitors in primary and transformed human cells," *J. Biol. Chem.*, 268:26804-26812, 1993.

Merrill and Benveniste, "Cytokines in inflammatory brain lesions: helpful and harmful," *Trends Neurosci.*, 19:331-338, 1996.

Merrill, J. E., Ignarro, Sherman, Melinck, Lane., "Microglial cell cytotoxicity of oligodendrocytes is mediated through nitric oxide," *J. Immunol.*, 151:2132-2141, 1993.

Michel, von Echten-Deckert, Rother, Sandoff, Wang, Merrill Jr., "Characterization of ceramide synthesis. A dihydroceramide desaturase introduces the 4,5-trans-double bond of sphingosine at the level of dihydroceramide," *J. Biol. Chem.*, 272:22432-22437, 1997.

Miller et al., "Amelioration of chronic ileitis by nitric oxide synthase inhibition," *J. Pharmacol. Exp. Ther.*, 264:11-16, 1993.

Miller et al., *Lancet*, 34:465-466, 1993.

Mitrovic, B., Ignarro, Montestruque, Smoll, Merrill., "Nitric oxide as a potential pathological mechanism in demyelination: its differential effects on primary glial cells in vivo," *Neurosci.*, 61:575-585, 1994.

Mittal, C. K., "Nitric oxide synthase: involvement of oxygen radicals in conversion of L-arginine to nitric oxide," *Biochem. Biophys. Res. Commun.*, 193:126-132, 1993.

Moncada et al. "Biosynthesis of nitric oxide from L-arginine. A pathway for the regulation of cell function and communication," *Biochem. Pharmacol.*, 38:1709-1715, 1989.

Moore et al, "7-Nitro indazole, an inhibitor of nitric oxide synthase, exhibits anti-nociceptive activity in the mouse without increasing blood pressure," *Brit. J. Pharmacol.*, 108:296-297, 1992.

Moore et al., "L-NG-nitro arginine methyl ester exhibits anti-nociceptive activity in the mouse," *Brit. J. Pharmacol.*, 102:198-202, 1991.

Moser, H. W. "Clinical and therapeutic aspects of adrenoleukodystrophy and adrenomyeloneuropathy," *J. Neuropathol. Expt. Neurol.* 54:740-744, 1995.

Moser, H. W., A. E. Moser, I. Singh, and B. P. O'Neill. "Adrenoleukodystrophy: survey of 303 cases-biochemistry, diagnosis, and therapy," *Ann. Neurol.* 16:628-641, 1984.

Moser, Smith, Moser, "X-linked adrenoleukodystrophy. In: *The metabolic and molecular bases of inherited disease*, 7th ed., Scriver O R, Beaudet A L, Sly W S, Valle D, eds., New York: McGraw-Hill, Vol. 2, 232549, 1995.

Mosser, J., A. M. Douar, C. O, Sarde, P. Kioschis, R. Feil, H. Moser, A. M. Poustka, J. L. Mandel, and P. Aubourg. P. "Putative X-linked adrenoleukodystrophy gene shares unexpected homology with ABC transporters," *Nature* 361:726-730, 1993.

Muhl et al., "Expression of nitric oxide synthase in rat glomerular mesangial cells mediated by cyclic AMP," *Br. J. Pharmcol.*, 112:1-8, 1994.

Mulligan et al., "Protective effects of inhibitors of nitric oxide synthase in immune complex-induced vasculitis," *Br. J. Pharmacol.*, 107:1159-1162, 1992.

Nagafuji et al., "Blockade of nitric oxide formation by N omega-nitro-L-arginine mitigates ischemic brain edema and subsequent cerebral infarction in rats," *Neurosci.*, 147:159-162, 1992.

Nakamura et al., In: Enzyme Immunoassays: Heterogeneous and Homogeneous Systems, Chapter 27, 1987.

Nathan, C., "Nitric oxide as a secretory product of mammalian cells," *FASEB J.*, 6:3051-3064, 1992.

Nathan, C. F., "Secretory products of macrophages," *J. Clin. Invest.*, 79:319-326, 1987.

Nishiya, T., Uehara, Nomura, "Herbimycin A suppresses NF-k$\beta$ activation and tyrosine phosphorylation of JAK2 and the subsequent induction of nitric oxide synthase in C6 glioma cells," *FEBS Lett.*, 371:333-336, 1995.

Okazaki, Bielawska, Domae, Bell, Hannun, "Characteristics and partial purification of a novel cytosolic, magnesium-independent, neutral sphingomyelinase activated in the early signal transduction of 1 alpha,25-dihydroxyvitamin D3-induced HL-60 cell differentiation," *J. Biol. Chem.*, 269:4070-4077, 1994.

Olesen et al., "Nitric oxide is a key molecule in migraine and other vascular headaches," *Trends Pharmacol Sci.*, 15:149-153, 1994.

Petros et al., "Effect of nitric oxide synthase inhibitors on hypotension in patients with septic shock," *Lancet*, 338:1557-1558, 1991.

Physicians' Desk Reference, Medical Economics Company, Inc., Montvale, N.J., 1998.

Powers, J. M. "The pathology of peroxisomal disorders with pathogenetic considerations," *J. Neuropathol. Expt. Neurol.* 54:710-719, 1995.

Powers, J. M., Y. Liu, A. B. Moser, and H. W. Moser. "The inflammatory myelinopathy of adrenoleukodystrophy: cells, effector molecules, and pathogenetic implications," *J. Neuropathol. Expt. Neurol.* 51:630-643, 1992.

Priess, Loomis, Bishop, Stein, Niedel, Bell, "Quantitative measurement of sn-1,2-diacylglycerols present in platelets, hepatocytes, and ras- and sis-transformed normal rat kidney cells," *J. Biol. Chem.,* 261:8597-8600, 1986.

Radi, R., et al., "Peroxynitrite oxidation of sulfhydryls. The cytotoxic potential of superoxide and nitric oxide," *J. Biol. Chem.,* 266:4244-4250, 1991.

Reimann et al., "Lipopolysaccharide induces activation of the Raf-1/MAP kinase pathway. A putative role for Raf-1 in the induction of the IL-1 beta and the TNF-alpha genes," *J. Immunol.,* 153:5740-5749, 1994.

Remington's Pharmaceutical Sciences" 8th and 15th Editions

Repko and Maltese, "Post-translational isoprenylational of cellular proteins is altered in response to mevalonate availability," *J. Biol. Chem.,* 264:9945-9952, 1989.

Rizo, W. B., P. A. Watkins, M. W. Philips, D. Cranin, B. Campbell, and J. Avigan, J. "Adrenoleukodystrophy: Oleic acid lowers fibroblasts saturated C22-26 fatty acids," *Neurology* 36:357-361, 1986.

Rizzo, W. B., R. T. Leshne, A. Odone, A. L. Dammann, D. A. Craft, M. E. Jensen, S. S. Jennings, S. Davis, R. Jaitly, and J. A. Sgro. "Dietery erucic acid therapy for X-linked adrenoleukodystrophy," *Neurology* 39:1415-1422, 1989.

Rogers et al., "Complement activation by beta-amyloid in Alzheimer disease," *Proc. Natl. Acad. Sci. U.S.A.* 89(21): 10016-10020, 1992.

Rossomando, Dent, Sturgill, Marshak, "Mitogen-activated protein kinase kinase 1 (MKK1) is negatively regulated by threonine phosphorylation," *Mol. Cell. Biol.,* 14:1594-1602, 1994.

Rudick and Ransohoff, "Cytokine secretion by multiple sclerosis monocytes. Relationship to disease activity," *Arch. Neurol.,* 49:265-270, 1992.

Ruuls, Van der Linden, Sontrop, Huitinga, Dijkstra, "Aggravation of experimental allergic encephalomyelitis (EAE) by administration of nitric oxide (NO) synthase inhibitors," *Clin. Exp. Immunol.,* 103:467-474, 1996.

Ruzicka et al., *J. Invest. Derm.,* 103:397, 1994.

Samid, D., et al., "Phenylacetate: A novel nontoxic inducer of tumor cell differentiation," *Cancer Res.,* 52:1988-1992, 1992.

Samid, D., et al., "Selective activity of phenylacetate against malignant gliomas: Resemblance to fetal brain damage in phenylketonuria," *Cancer Res.,* 54:891-895, 1994.

Saran et al., "Reaction of NO with O2-. implications for the action of endothelium-derived relaxing factor (EDRF)," *Free Rad. Res. Commun.* 10:221-226, 1990.

Schiessel, Schuchman, Williams, Tabas, "Zn2+-stimulated sphingomyelinase is secreted by many cell types and is a product of the acid sphingomyelinase gene," *J. Biol. Chem.,* 271:18431-18436, 1996.

Schilling-et al., "A new approach in the treatment of hypotension in human septic shock by NG-monomethyl-L-arginine, an inhibitor of the nitric oxide synthetase," *Intensive Care Med.,* 19:227-231, 1993.

Schmidt, Traenckner, Meier, Baeuerle, "Induction of oxidative stress by okadaic acid is required for activation of transcription factor NF-kappa B," *J. Biol. Chem.,* 270: 27136-27142, 1995.

Schreck, R., et al., "Nuclear factor kB: An oxidative stress responsive transcription factor of eukaryotic cells," *Free Rad. Res. Commun.,* 17:221-237, 1992.

Schreck, Rieber, Baeuerle, "Reactive oxygen intermediates as apparently widely used messengers in the activation of the NF-kappa B transcription factor and HIV-1," *EMBO J.,* 10:2247-2258, 1991.

Sen and Packer, "Antioxidant and redox regulation of gene transcription. *FASEB J.,* 10:709-720, 1996. Antioxidant and redox regulation of gene transcription," *FASEB J.* May; 10(7):709-720, 1996.

Shafer and Murphy, "Activated astrocytes induce nitric oxide synthase-2 in cerebral endothelium via tumor necrosis factor-α," *Glia,* 21:370-379, 1997.

Sharif, S. F., et al., "Human astrocyte production of tumor necrosis factor-alpha, interleukin-1 beta, and interleukin-6 following exposure to lipopolysaccharide endotoxin," *Neurological Res.,* 15:109-112, 1993.

Shertzer, Vasilion, Liu, Tabor, Nebert, "Enzyme induction by L-buthionine (S,R)-sulfoximine in cultured mouse hepatoma cells," *Chem. Res. Toxicol.,* 8:431-436, 1995.

Shin, Drysdale, Shin, Noble, Fisher, Paznekas, "Definition of a lipopolysaccharide-responsive element in the 5'-flanking regions of MuRantes and crg-2," *Mol. Cell. Biol.,* 14:2914-2925, 1994.

Sinensky, Beck, Leonard, Evans, "Differential inhibitory effects of lovastatin on protein isoprenylation and sterol synthesis," *J. Biol. Chem.,* 265:19937-19941, 1991.

Singh, I. "Biochemistry of peroxisomes in health and disease," *Mol. Cell. Biochem.* 167:1-29, 1997.

Singh, I., A. E. Moser, S. Goldfischer, and H. W. Moser. "Lignoceric acid is oxidized in peroxisome: Implication for the Zellweger cerebro-hepato-renal syndrome and adrenoleukodystrophy," *Proc. Natl. Acad. Sci. USA* 81:4203-4207, 1984.

Singh, I., et al., "Acyl-CoA ligases from rat brain microsomes. An immunochemical study," *Biochim. Biophys. Acta.,* 963:509-514, 1988.

Smilkstein, M. J., et al., "Efficacy of oral N-acetyl cystein in the treatment of acetaminophen overdose. Analysis of the national multicenter study," *N. Engl. J. Med.,* 319:1557-1562, 1988.

Sommer, N., P. A. Loschmann, G. H. Northoff, M. Weller, A. Steinbrecher, J. P. Steinbach, R. Lichtenfels, R. Meyermann, A. Riethmuller, A. Fontana, J. Dichgans, and R. Martin. "The antidepressant rolipram suppresses cytokine production and prevents autoimmune encephalomyelitis," *Nature Med.* 1:244-248, 1995.

Spence, *Adv. Lipid Res.,* "Sphingomyelinases," 26:3-23, 1993.

Stadler et al., "Articular chondrocytes synthesize nitric oxide in response to cytokines and lipopolysaccharide," *J. Immunol.,* 147:3915-3920, 1991

Stefanova, I., Corcoran, Horak, Wahl, Bolen, Horak, "Lipopolysaccharide induces activation of CD14-associated protein tyrosine kinase p53/56lyn," *J. Biol. Chem.,* 268:20725-20728, 1993.

Stevanovic-Racic et al., *Arth. & Rheum.,* 37, 1062-1069, 1994.

Stites, D. P., and Terr, A. I., *Basic and Clinical Immunology,* 7th Ed., Appleton & Lange, Publisher, Norwalk, Conn., 1991.

Stuehr, D. J., et al., "Nitric oxide: a macrophage product responsible for cytostasis and respiratory inhibition in tumor target cells," *J. Expt. Med.,* 169:1543-1555, 1989.

Sun, Maggirwar, Harhaj, "Molecular cloning of mouse tissue inhibitor of metalloproteinases-3 and its promoter. Specific lack of expression in neoplastic JB6 cells may reflect altered gene methylation," *J. Biol. Chem.*, 270:18347-18351, 1995.

Suzuki, Mizuno, Packer, "Signal transduction for nuclear factor-kappa B activation. Proposed location of antioxidant-inhibitable step," *J. Immunol.*, 153:5008-5015, 1994.

Taupin, Renno, Bourbonniere, Peterson, Rodriguez, Owens, "Increased severity of experimental autoimmune encephalomyelitis, chronic macrophage/microglial reactivity, and demyelination in transgenic mice producing tumor necrosis factor-α in the central nervous system," *Eur. J. Immunol.*, 27:905-913, 1997.

Tepper, Jaydev, Liu, Bielawska, Wolff, Yonchara, Hannun, Seldin, "Role for ceramide as an endogenous mediator of Fas-induced cytotoxicity," *Proc. Natl. Acad. Sci. U.S.A.*, 92:8443-8447, 1995.

The Merck Index, 11th Edition, Susan Budavari, Ed., Merck & Co., Inc., Rahway, N.J. U.S.A., 1989.

Thibault, Samid, Cooper, Figg, Tompkins, Patronas, Headlee, Kohler, Venzon, Myers, "Phase I study of phenylacetate administration twice daily to patients with cancer," *Cancer*, 75:2932-2938, 1995.

Thiemermann & Vane, *Eur. J. Pharmacol.*, 211:172-182, 1992.

Thompson, "Apoptosis in the pathogenesis and treatment of disease," *Science*, 267:1456-1462, 1995.

Tiku, Liesch, Robertson, "Production of hydrogen peroxide by rabbit articular chondrocytes. Enhancement by cytokines," *J. Immunol.*, 145:690-696, 1990.

Trifiletti et al., "Neuroprotective effects of NG-nitro-L-arginine in focal stroke in the 7-day old rat," *Europ. J. Pharmacol.*, 218:197-198, 1992.

Tsuji, S., T. Ohno, T. Miyatake, A. Suzuki, and T. Yamakawa. "Fatty acid elongation activity in fibroblasts from patients with adrenoleukodystrophy (ALD)," *J. Biochem.* 96:1241-1247, 1984.

Tsukada, Miyagi, Matsuda, Yanagisawa, Yone, "Tumor necrosis factor and interleukin-1 in the CSF and sera of patients with multiple sclerosis," *J. Neurol Sci.*, 104:230-234, 1991.

van der Veen, Hinton, Incardonna, Hofman, "Extensive 14 peroxynitrite activity during progressive stages of central nervous system inflammation," *J. Neuroimmunol.*, 77:1-7, 1997.

Verheij, Bose, Lin, Yao, Jarvis, Grant, et al., "Requirement for ceramide-initiated SAPK/JNK signalling in stress-induced apoptosis," *Nature*, 380:75-79, 1996.

Villarroya, Violleau, Younes-Chennoufi, Baumann, "Myelin-induced experimental allergic encephalomylitis in Lewis rats: tumor necrosis factor-a levels in serum and cerebrospinal fluid immunohistochemical expression in glial cells and macrophages of optic nerve and spinal cord," *J. Neuroimmunol.*, 64:55-61, 1996.

Wang, M-H., et al., "Macrophage stimulating protein inhibits induction of nitric oxide production by endotoxin or cytokine-stimulated mouse macrophages," *J. Biol. Chem.*, 269: 14027-14031, 1995.

Watkins, P. A., S. J. Gould, M. A. Smith, L. T. Braiterman, H. M. Wei, F. Kok, A. B. Moser, H. W. Moser, and K. D. Smith. "Altered expression of ALDP in X-linked adrenoleukodystrophy," *Am. J. Hum. Genet.* 57:292-301, 1995.

Weigman, Schutze, Machleidt, Witte, Kronke, "Functional dichotomy of neutral and acidic sphingomyelinases in tumor necrosis factor signaling," *Cell*, 78:1005-1015, 1994.

Welsh el at., "Interleukin-1 beta-induced nitric oxide production in isolated rat pancreatic islets requires gene transcription and may lead to inhibition of the Krebs cycle enzyme aconitase," *Endocrinol.*, 129:3167-3173, 1991.

Welsh, "Interleukin-1 beta-induced ceramide and diacylglycerol generation may lead to activation of the c-Jun NH2-terminal kinase and the transcription factor ATF2 in the insulin-producing cell line RINm5F," *J. Biol. Chem.*, 271: 8307-8312, 1996.

White et al., "Superoxide and peroxynitrite in atherosclerosis," *Proc. Natl. Acad. Sci. U.S.A.*, 91:1044-1048, 1994.

Wiesner and Dawson, "Staurosporine induces programmed cell death in embryonic neurons and activation of the ceramide pathway," *J. Neurochem.* 66:1418-1425, 1996.

Wink, Kasprazak, Maragos, Elespuru, Misra, Dunams, Cebula, Koch, "DNA deaminating ability and genotoxicity of nitric oxide and its progenitors," *Science*, 254:1001-1003, 1991.

Winlaw et al., "Increased nitric oxide production in heart failure," *Lancet*, 344:373-374, 1994.

Xie, Q-W., Kashiwabara, Nathan, "Role of transcription factor NF-kβ/Rel in induction of nitric oxide synthase," *J. Biol. Chem.*, 269:4705-4708, 1994.

Xie, Q-W., et al., "Promoter of the mouse gene encoding calcium-independent nitric oxide synthase confers inducibility by interferon-gamma and bacterial lipopolysaccharides," *J. Expt. Med.*, 177:1779-1784, 1993.

Yao, Zhang, Delikat, Mathias, Basu, Kolesnick, "Phosphorylation of Raf by ceramide-activated protein kinase," *Nature*, 378:307-310, 1995.

Zang, X., et al., "Lipopolysaccharide-induced selective priming effects on tumor necrosis factor alpha and nitric oxide production in mouse peritoneal macrophages," *J. Exp. Med.*, 177:511-516, 1993.

Zembowicz & Vane, "Induction of nitric oxide synthase activity by toxic shock syndrome toxin 1 in a macrophage-monocyte cell line," *Proc. Natl. Acad. Sci. U.S.A.*, 89:2051-2055, 1992.

Zhang and Kolesnick, "Signaling through the sphingomyelin pathway," *Endocrinology*, 136:4157-4160, 1995.

Zhang, Alter, Reed, Bomer, Obeid, Hannun, "Bcl-2 interrupts the ceramide-mediated pathway of cell death," *Proc. Natl. Acad. Sci. U.S.A.*, 93:5325-5328, 1996.

The invention claimed is:

1. A method of treating inflammation in cells of a subject that does not have an elevated cholesterol level, to reduce the risk of cardiovascular disease or stroke, the method comprising:
   a) determining the level of inflammation in a subject, or in cells of the subject, which subject does not have an elevated cholesterol level, by testing for an indicator of inflammation;
   b) administering to cells of those subjects determined in step a) to have elevated level of inflammation by virtue of such testing, an amount of an inhibitor of 3-hydroxy-3-methylglutaryl coenzyme A (HMG-CoA) reductase that is effective to reduce said inflammation and reduce the risk of cardiovascular disease or stroke in said subject.

2. The method of claim 1, wherein said inhibitor HMG-CoA reductase is a statin.

3. The method of claim 2, wherein said statin is lovastatin or mevastatin.

4. The method of claim 1, wherein the effective amount of said inhibitor is between about 0.25 mg/kg/day and 0.55 mg/kg/day.

5. The method of claim 1, wherein the inhibitor is comprised in a tablet.

6. The method of claim 1, further defined as a method of treating inflammation in cells of a subject determined to have elevated inflammation to reduce the risk of stroke in said subject.

7. The method of claim 1, further defined as a method of treating inflammation in cells of a subject determined to have elevated inflammation to reduce the risk of cardiovascular disease in said subject.

8. The method of claim 7, wherein the cardiovascular disease is ischemia reperfusion.

9. The method of claim 1, wherein the cells or the subject has been determined to have elevated inflammation by virtue of the presence of an indicator of NF-κβ activation.

10. The method of claim 9, wherein the indicator of NF-κβ activation is elevated iNOS.

11. The method of claim 9, wherein the indicator of NF-κβ activation is elevated proinflammatory cytokines.

12. The method of claim 6, wherein the cells or the subject has been determined to have elevated inflammation by virtue of the presence of an indicator of NF-κβ activation.

13. The method of claim 12, wherein the indicator of NF-κβ activation is elevated iNOS.

14. The method of claim 12, wherein the indicator of NF-κβ activation is elevated proinflammatory cytokines.

15. The method of any one of claims 1 through 14, wherein said subject is a human and the cells are human cells.

16. The method of claim 1, wherein the subject is a rodent and the cells are rodent cells.

17. The method of any one of claims 1 through 14, wherein the subject does not have an elevated lipid level.

* * * * *